US011166976B2

(12) United States Patent
Beigelman et al.

(10) Patent No.: US 11,166,976 B2
(45) Date of Patent: *Nov. 9, 2021

(54) S-ANTIGEN TRANSPORT INHIBITING OLIGONUCLEOTIDE POLYMERS AND METHODS

(71) Applicant: ALIGOS THERAPEUTICS, INC., South San Francisco, CA (US)

(72) Inventors: Leonid Beigelman, San Mateo, CA (US); Rajendra Pandey, South San Francisco, CA (US); Vivek Kumar Rajwanshi, Cupertino, CA (US); David Bernard Smith, San Mateo, CA (US); Lawrence M. Blatt, Healdsburg, CA (US); Jin Hong, Brisbane, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/018,822

(22) Filed: Sep. 11, 2020

(65) Prior Publication Data

US 2020/0405743 A1     Dec. 31, 2020

Related U.S. Application Data

(63) Continuation-in-part of application No. 16/676,929, filed on Nov. 7, 2019.

(60) Provisional application No. 62/907,845, filed on Sep. 30, 2019, provisional application No. 62/855,323, filed on May 31, 2019, provisional application No. 62/757,632, filed on Nov. 8, 2018.

(51) Int. Cl.
| | |
|---|---|
| *A61K 31/7125* | (2006.01) |
| *A61K 9/00* | (2006.01) |
| *A61P 31/20* | (2006.01) |
| *C12N 15/113* | (2010.01) |
| *C07H 21/02* | (2006.01) |

(52) U.S. Cl.
CPC ........ *A61K 31/7125* (2013.01); *A61K 9/0019* (2013.01); *A61P 31/20* (2018.01); *C07H 21/02* (2013.01); *C12N 15/1131* (2013.01)

(58) Field of Classification Search
CPC ............ A61K 31/7125; A61K 31/7225; C12N 15/1131
See application file for complete search history.

(56) References Cited

U.S. PATENT DOCUMENTS

| | | | |
|---|---|---|---|
| 5,830,658 A | 11/1998 | Gryaznov | |
| 6,180,777 B1 | 1/2001 | Horn | |
| 6,187,545 B1 | 2/2001 | McKay et al. | |
| 7,358,068 B2 | 4/2008 | Vaillant et al. | |
| 8,008,269 B2 | 8/2011 | Vaillant et al. | |
| 8,008,270 B2 | 8/2011 | Vaillant et al. | |
| 8,067,385 B2 | 11/2011 | Vaillant et al. | |
| 8,513,211 B2 | 8/2013 | Vaillant et al. | |
| 8,716,359 B2 | 5/2014 | Vaillant et al. | |
| 8,987,435 B2 | 3/2015 | Swayze et al. | |
| 8,993,738 B2 | 3/2015 | Prakash et al. | |
| 9,127,033 B2 | 9/2015 | Prakash et al. | |
| 9,133,458 B2 | 9/2015 | Bazinet et al. | |
| 9,200,283 B2 | 12/2015 | Bazinet et al. | |
| 9,533,003 B2 | 1/2017 | Bazinet et al. | |
| 9,603,865 B2 | 3/2017 | Vaillant | |
| 9,738,895 B2 | 8/2017 | Swayze et al. | |
| 9,976,138 B2 | 5/2018 | Prakash et al. | |
| 10,087,210 B2 | 10/2018 | Prakash et al. | |
| 2002/0009713 A1 | 1/2002 | Mi

(56) References Cited

FOREIGN PATENT DOCUMENTS

| WO | WO 2002020543 | 3/2002 | | |
|----|---------------|--------|---|---|
| WO | WO 2004024919 | 3/2004 | | |
| WO | WO 2004028458 | 4/2004 | | |
| WO | WO 2005025487 | 3/2005 | | |
| WO | WO 2005063300 | 7/2005 | | |
| WO | WO 2005082921 | 9/2005 | | |
| WO | WO 2006001931 | 1/2006 | | |
| WO | WO 2006002540 | 1/2006 | | |
| WO | WO 2006042418 | 4/2006 | | |
| WO | WO 2006096995 | 11/2006 | | |
| WO | WO 2006119619 | 11/2006 | | |
| WO | WO 2006119643 | 11/2006 | | |
| WO | WO 2006122409 | 11/2006 | | |
| WO | WO 2006130949 | 12/2006 | | |
| WO | WO 2007022642 | 3/2007 | | |
| WO | WO 2007036016 | 4/2007 | | |
| WO | WO 2010048585 | 4/2010 | | |
| WO | WO 2011139702 | 11/2011 | | |
| WO | WO 2012021985 | 2/2012 | | |
| WO | WO 2013033223 | 3/2013 | | |
| WO | WO 2013170385 | 11/2013 | | |
| WO | WO 2013170386 | 11/2013 | | |
| WO | WO 2014032176 | 3/2014 | | |
| WO | WO 2015172128 | 11/2015 | | |
| WO | WO 2016004525 | 1/2016 | | |
| WO | WO-2016004525 A1 * | 1/2016 | ........... | A61K 31/675 |
| WO | WO 2016030863 | 3/2016 | | |
| WO | WO 2016164619 | 10/2016 | | |
| WO | WO 2017079983 | 5/2017 | | |
| WO | WO 2017223421 | 12/2017 | | |
| WO | WO 2020097342 | 5/2020 | | |

OTHER PUBLICATIONS

Ai-Mahtab, Mamun, et al., "Safety and Efficacy of Nucleic Acid Polymers in Monotherapy and Combined with Immunotherapy in Treatment-Naive Bangladeshi Patients with HBeAg+ Chronic Hepatitis B Infection" PLOS ONE (2016) 11 (6), 26 pages.

Bazinet, Michel, et al., "Update on safety and efficacy in the REP 401 protocol: REP 2139-Mg or REP 2165-Mg used in combination with tenofovir disoproxil fumarate and pegylated Interferon alpha-2a in treatment naïve caucasian patients with chronic HBeAg negative HBV infection" The International Liver Congress, EASL 2017, Amsterdam, The Netherlands, Apr. 19-23.

Beilstein, Frank, et al., "Nucleic acid polymers are active against hepatitis delta virus infection in vitro" Journal of Virology (2018), 92(4).

Bernstein, et al., "Amphipathic DNA polymers exhibit antiherpetic activity in vitro and in vivo", Antimicrobial Agents and Chemotherapy (2008), 52(8), 2727-2733.

Clark, C.L., et al., "CD, absorption and thermodynamic analysis of repeating dinucleotide DNA, RNA and hybrid duplexes [d/r(AC)]12-[d/r(GT/U)]12 and the influence of phosphorothioate substitution" Nucleic Acids Research (1997), 25(20), 4098-4105.

Deleavey, G. F. et al., "Designing Chemically Modified Oligonucleotides for Targeted Gene Silencing", Chemistry & Biology, 2012, vol. 19, pp. 937-954.

Fennewald, Susan M. and Robert F. Rando, "Inhibition of High Affinity Basic Fibroblast Growth Factor Binding by Oligonucleotides" The Journal of Biological Chemistry (1995) vol. 270, No. 37, pp. 21718-21721.

Guvakova, Marina A., et al., Phosphorothioate Oligodeoxynucleotides Bind to Basic Fibroblast.

Growth Factor, Inhibit Its Binding to Cell Surface Receptors, and Remove It from Low Affinity Binding Sites on Extracellular Matrix The Journal of Biological Chemistry (1995) vol. 270, No. 6, pp. 2620-2627.

Hashem, Gihan M., et al., "Hybrid Oligomer Duplexes Formed with Phosphorothioate DNAs: CD Spectra and Melting Temperatures of S-DNA-RNA Hybrids Are Sequence-Dependent but Consistent with Similar Heteronomous Conformations" Biochemistry (1998), 37(1), 61-72.

Heil, Florian, et al., "Species-Specific Recognition of Single-Stranded RNA via Toll-like Receptor 7 and 8" Science, (Mar. 5, 2004) vol. 303, 1526-1529.

Krieg, Arthur M., et al., "CpG motifs in bacterial DNA trigger direct B-cell activation" Nature (Apr. 1995) vol. 374, pp. 546-549.

Lee, Andrew M., et al., "Inhibition of cellular entry of lymphocytic choriomeningitis virus by amphipathic DNA polymers" Virology (2008), 372(1), 107-117.

Noordeen, Faseeha, et al., "Nucleic acid polymers prevent the establishment of duck hepatitis B virus infection in vivo" Antimicrobial Agents and Chemotherapy (2013), 57(11), 5299-5306.

Noordeen, Faseeha, et al., "Therapeutic antiviral effect of the nucleic acid polymer REP 2055 against persistent duck hepatitis B virus infection" PLoS One (2015), 10(11).

Prakash, Thazha P., et al., Synergistic effect of phosphorothioate, 50-vinylphosphonate and.

Khvorova, A. et al., "The Chemical Evolution of Oligonucleotide Therapies of Clinical Utility", Nature Biotechnology, 2017, vol. 35 (3), pp. 238-248.

GalNAc modifications for enhancing activity of synthetic siRNA Bioorganic & Medicinal Chemistry Letters 26 (2016) pp. 2817-2820.

Real, C. I. et al., "Nucleic acid-based polymers effective against hepatitis B Virus infection in patients don't harbor immunostimulatory properties in primary isolated liver cells" Sci. Rep. (2017) 7, 43838.

Rizzetto, "Investigational drugs in development for Hepatitis D", Expert Opinion on Investigational Drugs (2017) 26:9, 999-1005.

Roehl, I, et al., "Nucleic Acid Polymers with Accelerated Plasma and Tissue Clearance for Chronic Hepatitis B Therapy" Molecular Therapy: Nucleic Acids, (2017) vol. 8, pp. 1-12.

Schoeneweis, et al., "Activity of nucleic acid polymers in rodent models of HBV infection" Antiviral Research (Nov. 2017) vol. 149, pp. 26-33.

Soriano, et al., "New antivirals for the treatment of chronic hepatitis B" Expert Opinion on Investigational Drugs (2017), 26(7), 843-851.

Vaillant, Andrew, "Nucleic acid polymers: Broad spectrum antiviral activity, antiviral mechanisms and optimization for the treatment of hepatitis B and hepatitis D infection" Antiviral Research (2016) vol. 133, pp. 32-40.

Vaillant, Andrew, "REP 2139: Antiviral Mechanisms and Applications in Achieving Functional Control of HBV and HDV Infection" American Chemical Society, Infectious Diseases (2018).

Search Report and Written Opinion dated Feb. 17, 2020 in PCT Application No. PCT/US2019/060283 filed Nov. 7, 2019.

Written Opinion dated May 18, 2020 in PCT Application No. PCT/US2019/060283 filed Nov. 7, 2019.

International Preliminary Report on Patentability dated Feb. 23, 2021 in PCT Application No. PCT/US2019/060283 filed Nov. 7, 2019.

* cited by examiner

5'-Cholesterol attached via TEG Linker

3'-Cholesterol attached via TEG Linker

5'-Vitamin E attached via TEG linker

3'-Vitamin E attached via TEG linker

FIGURE 6A

| No. | Compound Structure (5' to 3') | EC$_{50}$ (μM) | CC$_{50}$ (μM) | Comments |
|---|---|---|---|---|
| 282 | 5'-mApsm(5m)CpsmApsm(5m)CpsmApsm(5m)CpsmAps m(5m)CsmApsm(5m)CpsmApsm(5m)CpsmApsm(5m)Cps mApsm(5m)CsmApsm(5m)CpsmApsm(5m)CpsmApsm(5m) CpsmApsm(5m)CsmApsm(5m)CpsmApsm(5m)CpsmApsm(5m)Cps mApsm(5m)CpsmApsm(5m)C 3' | Control | A | PS 40mer All 2'-OMe |
| 283 | 5'lnApsln(5m)CpslnApsln(5m)CpslnApsln(5m)Cps lnApsln(5m)CpslnApsln(5m)CpslnApsln(5m)Cps lnApsln(5m)CpslnApsln(5m)CpslnApsln(5m)Cps lnApsln(5m)CpslnApsln(5m)CpslnApsln(5m)Cps lnApsln(5m)CpslnApsln(5m)CpslnApsln(5m)C 3' | AAAA | A | PS 40mer All LNA PS |
| 284 | 5'-mApsln(5m)CpsmApsln(5m)CpsmApsln(5m)Cps mApsln(5m)CpsmApsln(5m)CpsmApsln(5m)Cps mApsln(5m)CpsmApsln(5m)CpsmApsln(5m)Cps mApsln(5m)CpsmApsln(5m)CpsmApsln(5m)Cps mApsln(5m)CpsmApsln(5m)CpsmApsln(5m)C 3' | AAAA | A | PS 40mer Alternating 2'-OMe/LNA |
| 285 | 5'VPmApsln(5m)CpsmApsln(5m)CpsmApsln(5m)Cps mApsln(5m)CpsmApsln(5m)CpsmApsln(5m)Cps mApsln(5m)CpsmApsln(5m)CpsmApsln(5m)Cps mApsln(5m)CpsmApsln(5m)CpsmApsln(5m)Cps mApsln(5m)CpsmApsln(5m)CpsmApsln(5m)C 3' | AAAA | | PS 40mer Alternating 2'-OMe/LNA 5'-VP endcap |

FIGURE 6A (continued)

| No. | Compound Structure (5' to 3') | EC$_{50}$ (µM) | CC$_{50}$ (µM) | Comments |
|---|---|---|---|---|
| 286 | 5' mApsm(5m)CpslnApsm(5m)CpsmApsm(5m)Cps lnApsm(5m)CpslnApsm(5m)CpsmApsm(5m)CpslnApsm(5m)Cps mApsln(5m)CpslnApsm(5m)CpsmApsm(5m)CpsmApsm(5m)Cps mApsm(5m)CpslnApsm(5m)CpsmApsm(5m)CpsmApsm(5m)Cps lnApsm(5m)CpsmApsm(5m)CpslnApsm(5m)C 3' | AAA |  | PS 40mer<br>2'-OMe; 13 LNA (every 3$^{rd}$ base) |
| 287 | 5' VPmApsm(5m)CpslnApsm(5m)CpsmApsm(5m)Cps lnApsm(5m)CpsmApsm(5m)CpsmApsm(5m)CpslnApsm(5m)Cps mApsln(5m)CpslnApsm(5m)CpsmApsm(5m)CpsmApsm(5m)Cps mApsm(5m)CpslnApsm(5m)CpsmApsm(5m)CpsmApsm(5m)Cps lnApsm(5m)CpsmApsm(5m)CpslnApsm(5m)C 3' | AAAA | A | PS 40mer<br>2'-OMe; 13 LNA (every 3$^{rd}$ base)<br>5'-VP endcap |
| 288 | 5' mApsm(5m)CpsmApsm(5m)CpsmApsln(5m)Cps mApsm(5m)CpsmApsm(5m)CpsmApsm(5m)CpslnApsm(5m)Cps mApsm(5m)CpsmApsm(5m)CpsmApsm(5m)CpsmApsm(5m)Cps mApsm(5m)CpsmApsln(5m)CpsmApsm(5m)CpsmApsm(5m)Cps mApsm(5m)CpsmApsm(5m)CpslnApsm(5m)C 3' | AAAA | A | PS 40mer<br>2'-OMe; 10 LNA (every 4$^{th}$ base) |
| 289 | 5'-VP-mApsm(5m)CpsmApsm(5m)CpsmApsln(5m)Cps mApsm(5m)CpsmApsm(5m)CpsmApsm(5m)CpslnApsm(5m)Cps mApsm(5m)CpsmApsm(5m)CpsmApsm(5m)CpsmApsm(5m)Cps mApsm(5m)CpsmApsln(5m)CpsmApsm(5m)CpsmApsm(5m)Cps mApsm(5m)CpsmApsm(5m)CpslnApsm(5m)C 3' | AAAA | A | PS 40mer<br>2'-OMe; 10 LNA (every 4$^{th}$ base)<br>5'-VP endcap |

FIGURE 6A (continued)

| No. | Compound Structure (5' to 3') | EC$_{50}$ (µM) | CC$_{50}$ (µM) | Comments |
|---|---|---|---|---|
| 290 | 5' mApsRm(5m)CpsmApsRm(5m)CpsmApsRm(5m)CpsmApsRm(5m)CpsmApsRm(5m)CpsmA psRm(5m)CpsmApsRm(5m)CpsmApsRm(5m)CpsmApsRm(5m)CpsmApsRm(5m)CpsmApsR m(5m)CpsmApsRm(5m)CpsmApsRm(5m)CpsmApsRm(5m)CpsmApsRm(5m)CpsmApsR m(5m)CpsmApsRm(5m)CpsmApsRm(5m)CpsmApsRm(5m)C 3' | AA | A | PS 40mer<br>20 R isomer dimer blocks |
| 291 | 5' VPmApsm(5m)CpsmApsRm(5m)CpsmApsRm(5m)CpsmApsRm(5m)CpsmApsRm(5m)Cps mApsRm(5m)CpsmApsRm(5m)CpsmApsRm(5m)CpsmApsRm(5m)CpsmApsRm(5m)CpsmA psRm(5m)CpsmApsRm(5m)CpsmApsRm(5m)CpsmApsRm(5m)CpsmApsRm(5m)CpsmApsR m(5m)CpsmApsRm(5m)CpsmApsRm(5m)CpsmApsRm(5m)C 3' | AAAA | A | PS 40mer<br>19 R isomer dimer blocks; 1 m(5m)C<br>5'-VP endcap |
| 292 | 5' mApsm(5m)CpslnApsm(5m)CpsmApsm(5m)CpsmApsm(5m)CpslnApsm(5m)CpsmApsm (5m)CpslnApsm(5m)CpsmApsm(5m)CpslnApsm(5m)CpsmApsm(5m)CpsmApsm (5m)CpslnApsm(5m)CpsmApsm(5m)CpsmApsm(5m)CpslnApsm(5m)CpsmAps m(5m)CpsmApsm(5m)C 3' | AAA | A | PS 40mer<br>2'-OMe; 5 LNA |
| 293 | 5' VPmApsm(5m)CpslnApsm(5m)CpsmApsm(5m)CpsmApsm(5m)CpslnApsm(5m)CpsmAps m(5m)CpslnApsm(5m)CpsmApsm(5m)CpslnApsm(5m)CpsmApsm(5m)CpslnApsm(5m)Cps mApsm(5m)CpslnApsm(5m)CpsmApsm(5m)CpslnApsm(5m)CpsmApsm(5m)CpslnApsm(5m)Cps mApsm(5m)CpsmApsm(5m)C 3' | AAAA | A | PS 40mer<br>2'-OMe; 5 LNA<br>5'-VP endcap |

FIGURE 6A (continued)

| No. | Compound Structure (5' to 3'') | EC$_{50}$ (µM) | CC$_{50}$ (µM) | Comments |
|---|---|---|---|---|
| 294 | 5'VPmApsmA(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)C 3' | AAA | A | PS 41mer<br>20 R isomer dimer blocks<br>5'-VP endcap |
| 295 | 5'VPmApsm(5m)CpsmApsln(5m)CpsmApsm(5m)CpsmApsln(5m)CpsmApsm(5m)CpsmApsln(5m)CpsmApsm(5m)CpsmApsln(5m)CpsmApsm(5m)CpsmApsln(5m)CpsmApsm(5m)CpsmApsln(5m)CpsmApsm(5m)CpsmApsln(5m)CpsmApsm(5m)CpsmApsln(5m)CpsmApsm(5m)C 3' | AAA | B | PS 40mer<br>2'-OMe; 10 LNA<br>5'-VP endcap |
| 314 | 5'EPmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)C 3' | AAAA | A | PS 40mer<br>Alternating 2'-OMe / LNA<br>5'-EP endcap |
| 315 | 5'EPmApsm(5m)CpsmRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)CpsmApsRm(5m)C 3' | A | A | PS 40mer<br>19 R isomer dimer blocks; 1 (5m)mC<br>5'-EP endcap |

FIGURE 6A (continued)

| No. | Compound Structure (5' to 3') | EC$_{50}$ (μM) | CC$_{50}$ (μM) | Comments |
|---|---|---|---|---|
| 316, 281 | 5'EPmApsm(5m)CpsmApsm(5m)CpsmApsm(5m)CpsmApsm(5m)CpsmApsm(5m)CpslnApsm(5m)CpslnApsm(5m)CpsmApsm(5m)CpslnApsm(5m)CpsmApsm(5m)CpsmAps m(5m)CpslnApsm(5m)CpsmApsm(5m)CpslnApslnApsln(5m)Cps mApsm(5m)CpsmApsm(5m)C 3' | AAA | A | PS 40mer<br>5 LNA<br>5'-EP endcap |

Potency: AAAA: ≥ 25-fold more potent than Control (reference compound no. 282); AAA: ≥ 10-fold more potent than Control and < 25-fold more potent than Control; AA: ≥ 5-fold more potent than Control and < 10-fold more potent than Control; A: ≥ 2-fold more potent than Control and < 5-fold more potent than Control Cytotoxicity: A: ≥ 2 μM; B: < 2 μM

FIGURE 6B

| No. | Compound Structure (5' to 3') | EC50 (μM) | CC50 (μM) |
|---|---|---|---|
| 6, 274, 283 (SEQ ID NO: 71) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)CpslnApsln(5m)CpslnApsln(5m)C 3' | A | B |
| 376 (SEQ ID NO: 7) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)C 3' | D | A |
| 371 (SEQ ID NO: 5) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnA 3' | D | A |
| 372 (SEQ ID NO: 1) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)C 3' | D | A |
| 273, 282 (SEQ ID NO: 72) | 5' mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmApsm( 5m)CpsmApsm(5m)C-3' | D | A |
| 367 (SEQ ID NO: 73) | 5' mApsmCpsmApsmCpsmApsmCpsmApsmCpsmApsmCpsmApsmCpsmA psmCpsmApsmCpsmApsmCpsmApsmCpsmApsmCpsmApsmCpsmApsmCpsmAps mCpsmApsmCpsmApsmCpsmApsmCpsmApsmC-3' | C | A |
| 368 (SEQ ID NO: 2) | 5' lnApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)C 3' | D | A |

FIGURE 6B (continued)

| No. | Compound Structure (5' to 3') | EC$_{50}$ (μM) | CC$_{50}$ (μM) |
|---|---|---|---|
| 369 (SEQ ID NO: 6) | 5' mApsm(5m)CpsmApsm(5m)CpsmApsm(5m)CpsmAps m(5m)CpsmApsm(5m)CpsmApsm(5m)CpsmApsm(5m)CpsmA 3' | D | A |
| 370 (SEQ ID NO: 8) | 5' mApsm(5m)CpsmApsm(5m)CpsmApsm(5m)CpsmAps m(5m)CpsmApsm(5m)CpsmApsm(5m)CpsmApsm(5m)CpsmApsm(5m)C 3' | D | A |
| 345 (SEQ ID NO: 74) | 5' unApsun(5m)CpsunApsun(5m)CpsunApsun(5m)CpsunApsun(5m)C psunApsun(5m)CpsunApsun(5m)CpsunApsun(5m)CpsunAps un(5m)CpsunApsun(5m)CpsunApsun(5m)CpsunApsun(5m)CpsunAps un(5m)CpsunApsun(5m)CpsunApsun(5m)CpsunApsun(5m)CpsunAps un(5m)CpsunApsun(5m)CpsunApsun(5m)C 3' | B | A |
| 346 (SEQ ID NO: 45) | 5' mApsun(5m)CpsmApsun(5m)CpsmApsun(5m)CpsmApsun(5m)CpsmAps un(5m)CpsmApsun(5m)CpsmApsun(5m)CpsmApsun(5m)CpsmApsun(5m)CpsmApsun(5m)CpsmApsun(5m)CpsmApsun(5m)CpsmApsun(5m)CpsmAps un(5m)CpsmApsun(5m)CpsmApsun(5m)CpsmApsun(5m)CpsmApsun(5m)CpsmAps un(5m)C 3' | A | A |
| 351 (SEQ ID NO: 75) | 5' lnApspr(5m)CpslnApspr(5m)CpslnApspr(5m)CpslnApspr (5m)CpslnApspr(5m)CpslnApspr(5m)CpslnApspr(5m)Cps lnApspr(5m)CpslnApspr(5m)CpslnApspr(5m)CpslnApspr (5m)CpslnApspr(5m)CpslnApspr(5m)CpslnApspr(5m)Cps lnApspr(5m)CpslnApspr(5m)C-Cholesterol 3' | D | B |

FIGURE 6B (continued)

| No. | Compound Structure (5' to 3') | EC$_{50}$ (μM) | CC$_{50}$ (μM) |
|---|---|---|---|
| 352 (SEQ ID NO: 76) | 5' lnApspr(5m)CpslnApspr(5m)CpslnApspr(5m)CpslnApspr (5m)CpslnApspr(5m)CpslnApspr(5m)CpslnApspr(5m)Cps lnApspr(5m)CpslnApspr(5m)CpslnApspr(5m)CpslnApspr (5m)CpslnApspr(5m)CpslnApspr(5m)CpslnApspr(5m)Cps lnApspr(5m)CpslnApspr(5m)C-Palmitoyl 3' | D | B |
| 373 (SEQ ID NO: 11) | 5' lnApsln(5m)CpslnApsln(5m)CpslnApsln(5m)CpslnAps ln(5m)CpslnApsln(5m)CpslnApsln(5m)CpslnApsln(5m)Cps lnApsln(5m)CpslnApsln(5m)CpslnApsln(5m)CpslnApsln(5m)CpslnAps ln(5m)CpslnApsln(5m)C 3' | B | B |
| 308 (SEQ ID NO: 12) | 5' lnApsln(5m)CpslnApsln(5m)CpslnApoln(5m)CpslnApsln(5m)CpslnAps ln(5m)CpolnApsln(5m)CpslnApsln(5m)CpolnApsln(5m)CpslnApsln(5m)CpslnApsln( 5m)CpolnApsln(5m)CpslnApoln(5m)CpslnApsln ln(5m)CpslnApsln(5m)C 3' | C | A |
| 239 (SEQ ID NO: 22) | 5' mApsm(5m)CpsmApsm(5m)CpsmApsm(5m)CpsmApsm(5m)CpsmAps DBLR-ps-c4-CONH-c2-psm(5m)C 3' mApsm(5m)CpsmApsm(5m)CpsmApsm(5m)CpsmApsm(5m)CpsmA 5' | D | A |
| 235 (SEQ ID NO: 3) | 5' lnApsln(5m)CpslnApsln(5m)CpslnApsln(5m)CpslnApsln(5m)CpslnAps ln(5m)CpslnApsln(5m)CpslnApsln(5m)CpslnAps-DBLR-ps-c4-CONH-c2-psln(5m)C 3' lnApsln(5m)CpslnApsln(5m)CpslnApsln(5m)CpslnApsln(5m)CpslnApsln(5m)CpslnA 5' | D | B |
| 236 (SEQ ID NO: 23) | 5' lnApsln(5m)CpslnApsln(5m)CpslnApsln(5m)CpslnApsln(5m)CpslnAps ln(5m)CpslnApsln(5m)CpslnApsln(5m)CpslnAps-DBLR-ps-c4-CONH-c2-psm(5m)C 3' lnApsln(5m)CpslnApsln(5m)CpslnApsln(5m)CpslnApsln(5m)CpslnAps 5' | D | B |

FIGURE 6B (continued)

| No. | Compound Structure (5' to 3') | EC$_{50}$ (μM) | CC$_{50}$ (μM) |
|---|---|---|---|
| 237 (SEQ ID NO: 166) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)Cps-DBLR-ps-c4-CONH-c2-psm(5m)C 3' 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)C 5' | A | B |
| 301 (SEQ ID NO: 77) | 5' lnApsln(5m)CpslnApsln(5m)CpsrApsln(5m)CpslnApsln(5m)CpslnApsrCps lnApsln(5m)CpslnApsln(5m)CpsrApsln(5m)CpslnApsln(5m)CpslnApsrCps lnApsln(5m)CpslnApsln(5m)CpsrApsln(5m)CpslnApsln(5m)CpslnApsrCps lnApsln(5m)CpslnApsln(5m)CpsrApsln(5m)CpslnApsln(5m)CpslnAps ln(5m)C 3' | A | B |
| 303 (SEQ ID NO: 13) | 5' lnApsln(5m)CpslnApsln(5m)CpsrApsln(5m)CpslnApsln(5m)CpslnApsrCps lnApsln(5m)CpslnApsln(5m)CpsrApsln(5m)CpslnApsln(5m)CpslnApsrCps lnApsln(5m)CpslnApsln(5m)CpsrApsln(5m)CpslnApsln(5m)CpslnApsrCps lnApsln(5m)CpslnApsln(5m)CpsrApsln(5m)CpslnApsln(5m)CpslnAps ln(5m)C 3' | B | B |
| 305 (SEQ ID NO: 78) | 5' lnApsln(5m)CpolnApsln(5m)CpolnApsln(5m)CpolnApsln(5m)CpolnAps ln(5m)CpolnApsln(5m)CpolnApsln(5m)CpolnApsln(5m)CpolnApsln(5m)C polnApsln(5m)CpolnApsln(5m)CpolnApsln(5m)CpolnApsln(5m)CpolnAps ln(5m)CpolnApsln(5m)CpolnApsln(5m)CpolnApsln(5m)CpolnApsln(5m)C polnApsln(5m)CpolnApsln(5m)C 3' | C | A |
| 309 (SEQ ID NO: 144) | 5' lnApsln(5m)CpolnApoln(5m)CpslnApsln(5m)CpolnApsln(5m)CpslnAps ln(5m)CpolnApoln(5m)CpslnApsln(5m)CpolnApoln(5m)CpslnApsln(5m)C pslnApsln(5m)CpolnApoln(5m)CpslnApoln(5m)CpslnApoln(5m)CpolnAps ln(5m)CpslnApsln(5m)C 3' | D | B |
| 297 (SEQ ID NO: 14) | 5' mApsm(5m)CpsmApsm(5m)CpsrApsm(5m)CpsmApsm(5m)CpsmApsrCps mApsm(5m)CpsmApsm(5m)CpsrApsm(5m)CpsmApsm(5m)CpsmApsrCps mApsm(5m)CpsmApsm(5m)CpsrApsm(5m)CpsmApsm(5m)CpsmApsrCps mApsm(5m)CpsmApsm(5m)CpsrApsm(5m)CpsmApsm(5m)CpsmAps m(5m)C 3' | C | A |

FIGURE 6B (continued)

| No. | Compound Structure (5' to 3') | EC$_{50}$ (μM) | CC$_{50}$ (μM) |
|---|---|---|---|
| 298 (SEQ ID NO: 79) | 5' mApsm(5m)CpsmApsm(5m)CpsrApsrCpsmApsm(5m)CpsrApsm(5m)CpsrApsm(5m)CpsmApsm(5m)CpsrApsrCpsmApsm(5m)CpsmApsrCpsrAps m(5m)CpsrApsm(5m)CpsrApsrCpsmApsm(5m)CpsmApsrCporApsm(5m)CpsmAps m(5m)CpsrApsrCpsmApsm(5m)CpsmApsm(5m)C 3' | D | A |
| 300 (SEQ ID NO: 80) | 5' mApsm(5m)CpsmApsm(5m)CpsrApsrCpsmApsm(5m)CpsmApsrCpsrAps m(5m)CpsmApsm(5m)CpsrApsrCpsmApsm(5m)CpsmApsrCpsrApsm(5m)CpsmAps m(5m)CpsrApsrCpsmApsm(5m)CpsmApsm(5m)C 3' | D | A |
| 312 (SEQ ID NO: 15) | 5' mApsm(5m)CpsmApom(5m)CpsmApom(5m)CpsmApsm(5m)CpsmAps m(5m)CpomApsm(5m)CpsmApsm(5m)CpsmApom(5m)CpsmApsm(5m)CpsmApsm( 5m)CpomApsm(5m)CpsmApsm(5m)CpsmApom(5m)CpsmAps m(5m)CpsmApsm(5m)C 3' | D | A |
| 313 (SEQ ID NO: 16) | 5' mApsm(5m)CpsmApsm(5m)CpomApsm(5m)CpomApsm(5m)CpsmAps m(5m)CpomApom(5m)CpsmApsm(5m)CpomApom(5m)CpomApsm(5m)C psmApsm(5m)CpomApom(5m)CpsmApsm(5m)CpsmApom(5m)CpomAps m(5m)CpsmApsm(5m)C 3' | D | A |
| 299 (SEQ ID NO: 17) | 5' mApsm(5m)CpsmApsm(5m)CpsrApsm(5m)CpsmApsm(5m)CpsmApsrCps mApsm(5m)CpsmApsm(5m)CpsrApsm(5m)CpsmApsm(5m)CpsmApsrCps mApsm(5m)CpsmApsm(5m)CpsrApsm(5m)CpsmApsm(5m)CpsmAps m(5m)C 3' | D | A |
| 304 (SEQ ID NO: 18) | 5' lnApsln(5m)CpslnApsln(5m)CpsrApsrCpslnApsln(5m)CpslnApsrCpsrAps ln(5m)CpslnApsln(5m)CpsrApsrCpslnApsln(5m)CpslnApsrCpsrApsln(5m)CpslnApsl n(5m)CpsrApsrCpslnApsln(5m)CpslnApsln(5m)C 3' | D | A |
| 302 (SEQ ID NO: 19) | 5' lnApsln(5m)CpslnApsln(5m)CpsrApsrCpslnApsln(5m)CpslnApsr Apsln(5m)CpslnApsln(5m)CpsrApsrCpslnApsln(5m)CpslnApsrCpsrAps ln(5m)CpslnApsln(5m)CpsrApsrCpslnApsrCpsrApsln(5m)CpslnApsl n(5m)CpsrApsrCpslnApsln(5m)CpslnApsln(5m)C 3' | D | A |

FIGURE 6B (continued)

| No. | Compound Structure (5' to 3') | EC$_{50}$ (µM) | CC$_{50}$ (µM) |
|---|---|---|---|
| 307 (SEQ ID NO: 81) | 5' lnApsln(5m)CpslnApsln(5m)CpolnApsln(5m)CpslnAps ln(5m)CpolnApoln(5m)CpslnApsln(5m)CpolnApsln(5m)C pslnApsln(5m)CpolnApoln(5m)CpslnApsln(5m)CpolnAps ln(5m)CpslnApsln(5m)CpolnApoln(5m)CpslnApoln(5m)C polnApsln(5m)CpslnApsln(5m)C 3' | D | A |
| 375 (SEQ ID NO: 82) | 5' mApsSm(5m)CpsmApsm(5m)CpsmApsm(5m)CpsmAps m(5m)CpsmApsm(5m)CpsmApsm(5m)CpsmApsSm(5m)C psmApsm(5m)CpsmApsm(5m)CpsmApsSm(5m)CpsmApsSm(5m)CpsmApsm(5m)C psmApsm(5m)CpsmApsm(5m)CpsmApsm(5m)C psmApsm(5m)CpsmApsm(5m)C 3' | B | A |
| 201 (SEQ ID NO: 62) | 5' mApsSm(5m)CpsmApsm(5m)CpsmApsm(5m)CpsmAps m(5m)CpsmApsSm(5m)CpsmApsm(5m)CpsmApsSm(5m)CpsmAps m(5m)CpsmApsm(5m)CpsmApsSm(5m)CpsmApsSm(5m)CpsmApsm(5m)CpsmApsSm(5m)CpsmAps m(5m)CpsmApsm(5m)CpsmApsm(5m)CpsmApsSm(5m)C psmApsm(5m)CpsmApsm(5m)C 3' | C | A |
| 202 (SEQ ID NO: 58) | 5' mApsSm(5m)CpsmApsm(5m)CpsmApsSm(5m)CpsmApsm(5m)CpsmAps m(5m)CpsmApsSm(5m)CpsmApsm(5m)CpsmApsm(5m)CpsmApsSm(5m)CpsmApsSm(5m)CpsmApsm(5m)CpsmAps m(5m)CpsmApsm(5m)CpsmApsm(5m)CpsmApsm(5m)CpsmAps m(5m)CpsmApsm(5m)CpsmApsm(5m)CpsmApsm(5m)CpsmAps m(5m)CpsmApsm(5m)C 3' | C | A |
| 203 (SEQ ID NO: 66) | 5' mApsSm(5m)CpsmApsm(5m)CpsmApsSm(5m)CpsmApsm(5m)CpsmAps m(5m)CpsmApsSm(5m)CpsmApsm(5m)CpsmApsSm(5m)CpsmApsSm(5m)CpsmApsm(5m)CpsmApsSm(5m)CpsmApsm(5m)CpsmApsSm(5m)CpsmAps m(5m)CpsmApsSm(5m)CpsmApsm(5m)CpsmApsm(5m)CpsmAps m(5m)CpsmApsm(5m)CpsmApsm(5m)CpsmApsm(5m)CpsmAps m(5m)CpsmApsm(5m)C 3' | B | A |

FIGURE 6B (continued)

| No. | Compound Structure (5' to 3') | EC$_{50}$ (μM) | CC$_{50}$ (μM) |
|---|---|---|---|
| 204 (SEQ ID NO: 56) | 5' mApsSm(5m)CpsmApsSm(5m)CpsmApsSm(5m)CpsmApsm(5m)Cp smApsSm(5m)CpsmApsSm(5m)CpsmApsm(5m)CpsmApsS m(5m)CpsmApsSm(5m)CpsmApsm(5m)CpsmApsSm(5m)CpsmApsS m(5m)CpsmApsm(5m)CpsmApsSm(5m)CpsmApsm(5m)C psmApsSm(5m)CpsmApsSm(5m)CpsmApsm(5m)C 3' | D | A |
| 205 (SEQ ID NO: 54) | 5' mApsSm(5m)CpsmApsSm(5m)CpsmApsSm(5m)CpsmApsSm(5m) CpsmApsSm(5m)CpsmApsSm(5m)CpsmApsSm(5m)CpsmApsS m(5m)CpsmApsSm(5m)CpsmApsSm(5m)CpsmApsSm(5m)CpsmApsS m(5m)CpsmApsSm(5m)CpsmApsSm(5m)CpsmApsSm(5m)C 3' | D | A |
| 353 (SEQ ID NO: 51) | 5' 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)C 3' | B | A |
| 351 (SEQ ID NO: 83) | 5' 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)C-Cholesterol 3' | D | A |
| 352 (SEQ ID NO: 84) | 5' 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)Cps 3mAps3m(5m)Cps3mAps3m(5m)Cps3mAps3m(5m)C-Tocopherol 3' | D | A |

FIGURE 6B (continued)

| No. | Compound Structure (5' to 3') | EC$_{50}$ (μM) | CC$_{50}$ (μM) |
|---|---|---|---|
| 178 (SEQ ID NO: 85) | 5' mApsRm(5m)CpsmApsm(5m)CpsmApsm(5m)CpsmApsm(5m)CpsmAps m(5m)CpsmApsm(5m)CpsmApsm(5m)CpsmApsm(5m)CpsmApsRm(5m)C psmApsm(5m)CpsmApsm(5m)CpsmApsSm(5m)CpsmApsRm(5m)CpsmApsm(5m)C psmApsm(5m)CpsmApsm(5m)CpsmApsm(5m)CpsmApsRm(5m)C psmApsm(5m)CpsmApsm(5m)C 3' | A | A |
| 179 (SEQ ID NO: 63) | 5' mApsm(5m)CpsmApsm(5m)CpsmApsm(5m)CpsmApsm(5m)CpsmAps m(5m)CpsmApsRm(5m)CpsmApsm(5m)CpsmApsm(5m)CpsmApsR m(5m)CpsmApsm(5m)CpsmApsm(5m)CpsmApsRm(5m)CpsmApsR m(5m)CpsmApsm(5m)CpsmApsm(5m)CpsmApsm(5m)CpsmApsR psmApsm(5m)CpsmApsm(5m)C 3' | A | A |
| 180 (SEQ ID NO: 59) | 5' mApsm(5m)CpsmApsRm(5m)CpsmApsm(5m)CpsmApsm(5m)CpsmAps m(5m)CpsmApsRm(5m)CpsmApsm(5m)CpsmApsm(5m)CpsmApsR m(5m)CpsmApsm(5m)CpsmApsm(5m)CpsmApsm(5m)CpsmApsm(5m)C psmApsm(5m)CpsmApsm(5m)CpsmApsm(5m)CpsmApsRm(5m)C psmApsm(5m)CpsmApsm(5m)C 3' | C | A |
| 182 (SEQ ID NO: 67) | 5' mApsRm(5m)CpsmApsRm(5m)CpsmApsm(5m)CpsmApsm(5m)CpsmAps m(5m)CpsmApsRm(5m)CpsmApsm(5m)CpsmApsm(5m)CpsmApsR m(5m)CpsmApsm(5m)CpsmApsm(5m)CpsmApsm(5m)CpsmApsm(5m)C psmApsm(5m)CpsmApsm(5m)CpsmApsm(5m)CpsmApsRm(5m)C psmApsm(5m)CpsmApsm(5m)C 3' | A | A |
| 183 (SEQ ID NO: 57) | 5' mApsRm(5m)CpsmApsRm(5m)CpsmApsm(5m)CpsmApsm(5m)CpsmApsm(5m)C psmApsRm(5m)CpsmApsRm(5m)CpsmApsm(5m)CpsmApsm(5m)CpsmApsR m(5m)CpsmApsm(5m)CpsmApsm(5m)CpsmApsRm(5m)CpsmApsR psmApsm(5m)CpsmApsm(5m)CpsmApsm(5m)CpsmApsm(5m)C psmApsRm(5m)CpsmApsm(5m)CpsmApsm(5m)C 3' | D | A |

FIGURE 6B (continued)

| No. | Compound Structure (5' to 3') | EC$_{50}$ (μM) | CC$_{50}$ (μM) |
|---|---|---|---|
| 184, 290 (SEQ ID NO: 55) | 5' mApsRm(5m)CpsmApsRm(5m)CpsmApsRm(5m)CpsmApsRm(5m)CpsmA psRm(5m)CpsmApsRm(5m)CpsmApsRm(5m)CpsmApsRm(5m)CpsmApsRm(5m)C psmApsRm(5m)CpsmApsRm(5m)CpsmApsRm(5m)CpsmApsR m(5m)CpsmApsRm(5m)CpsmApsRm(5m)CpsmApsRm(5m)CpsmApsR m(5m)CpsmApsRm(5m)CpsmApsRm(5m)CpsmApsRm(5m)C 3' | A | A |
| 177 (SEQ ID NO: 52) | 5' mApsRm(5m)CpsmApsm(5m)CpsmApsm(5m)CpsmApsm(5m)CpsmAps m(5m)CpsmApsm(5m)CpsmApsm(5m)CpsmApsm(5m)CpsmApsRm(5m)C psmApsm(5m)CpsmApsm(5m)CpsmApsSm(5m)CpsmApsRm(5m)CpsmApsm(5m)C psmApsm(5m)CpsmApsm(5m)CpsmApsm(5m)CpsmApsRm(5m)C psmApsm(5m)C 3' | B | A |
| 374 (SEQ ID NO: 44) | 5' mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmA 3' | D | A |
| 363 (SEQ ID NO: 9) | 5' mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmApsm(5m)CpsmApsm(5m)CpsmApsm-3' | D | A |
| 364 (SEQ ID NO: 10) | 5' mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmApsm(5m)CpsmApsm(5m)CpsmAps | D | A |
| 365 (SEQ ID NO: 24) | 5' mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmApsm(5m)C 3' | D | A |
| 366 (SEQ ID NO: 27) | 5' mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmAps m(5m)CpsmApsm(5m)CpsmApsm(5m)CpsmApsm(5m)CpsmA 3' | D | A |

FIGURE 6B (continued)

| No. | Compound Structure (5' to 3') | EC$_{50}$ (μM) | CC$_{50}$ (μM) |
|---|---|---|---|
| 13 (SEQ ID NO: 42) | 5' mApsmoe(5m)CpsmApsmoe(5m)CpsmApsmoe(5m)CpsmApsmoe(5m)CpsmApsmoe(5m)CpsmApsmoe(5m)CpsmApsmoe(5m)CpsmApsmoe(5m)CpsmApsmoe(5m)CpsmApsmoe(5m)Cp 3' | D | A |
| 238 (SEQ ID NO: 86) | 5' mApsm(5m)CpsmApsm(5m)CpsmApsm(5m)CpsmApsm(5m)CpsmAps-DBLR-ps-c4-CONH-c2-psm(5m)C 3'-5' mApsm(5m)CpsmApsm(5m)CpsmApsm(5m)CpsmApsm(5m)CpsmApsm(5m)C 5' | D | A |
| 240 (SEQ ID NO: 4) | 5' mApsm(5m)CpsmApsm(5m)CpsmApsm(5m)CpsmApsm(5m)CpsmApsm(5m)CpsmAps 5m)Cps-DBLR-ps-c4-CONH-c2-ps(5m)mC 3'-5' mApsm(5m)CpsmApsm(5m)CpsmApsm(5m)CpsmApsm(5m)CpsmApsm(5m)CpsmApsm(5m)C 5' | B | A |
| 241 (SEQ ID NO: 167) | 5' lnApsln(5m)CpslnApsln(5m)CpslnApsln(5m)CpslnApsln(5m)CpslnApsln(5m)Cps-TREB-ps-c3-O-C3-ps(5m)mC 3' lnApsln(5m)CpslnApsln(5m)CpslnApsln(5m)CpslnApsln(5m)CpslnApsln(5m)CpslnApsln(5m)Cps lnApsln(5m)Cps 5' | B | A |
| 242 (SEQ ID NO: 25) | 5' lnApsln(5m)CpslnApsln(5m)CpslnApsln(5m)CpslnApsln(5m)CpslnApsln(5m)CpslnAps-TREB-ps-c3-O-C3-psm(5m)C 3' lnApsln(5m)CpslnApsln(5m)CpslnApsln(5m)CpslnApsln(5m)CpslnApsln(5m)CpslnApsln(5m)CpslnAps 5' lnApsln(5m)CpslnApsln(5m)CpslnAps 5' | A | A |

FIGURE 6B (continued)

| No. | Compound Structure (5' to 3') | EC$_{50}$ (µM) | CC$_{50}$ (µM) |
|---|---|---|---|
| 243 (SEQ ID NO: 164) | 5' lnApslnApsln(5m)CpslnApsln(5m)CpslnApsln(5m)CpslnAps ln(5m)CpslnApsln(5m)CpslnApsln(5m)CpslnA-TREB-ps-c3-O-C3-psm(5m)C 3'-5' lnApsln(5m)CpslnApsln(5m)CpslnApsln(5m)CpslnApsln(5m)CpslnAps ln(5m)CpslnApsln(5m)CpslnApsln(5m)CpslnAln(5m)CpslnApsln(5m)Cps lnApsln(5m)CpslnApsln(5m)CpslnApsln(5m)CpslnApsln(5m)CpslnAps ln(5m)CpslnApsln(5m)CpslnA 5' | | A |
| 130 (SEQ ID NO: 169) | 5' VP-mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)C 3' | A | A |
| 380 (SEQ ID NO: 153) | 5' mApsm(5m)CpsmApsm(5m)CpsunApsun(5m)CpsunApsun(5m)CpsmAps m(5m)CpsmApsm(5m)CpsunApsun(5m)CpsunApsun(5m)CpsmApsm(5m)CpsmAps m(5m)CpsunApsun(5m)CpsunApsun(5m)CpsmApsm(5m)CpsmApsm(5m)CpsmAps un(5m)CpsunApsun(5m)CpsmApsm(5m)CpsmApsm(5m)CpsunApsun(5m)CpsunAps un(5m)C 3' | D | A |
| 310 (SEQ ID NO: 87) | 5' mApsm(5m)CpsmApsm(5m)CpomApom(5m)CpsmApsm(5m)CpsmAps m(5m)CpomApom(5m)CpomApom(5m)CpsmApsm(5m)CpsmApsm(5m)CpsmApsm( 5m)CpomApom(5m)CpomApom(5m)CpsmApsm(5m)CpsmApsm(5m)CpsmAps m(5m)CpsmApsm(5m)CpomApom(5m)CpsmApsm(5m)CpsmApsm(5m)CpsmApsm( 5m)CpsmApsm(5m)C 3' | D | A |
| 311 (SEQ ID NO: 88) | 5' mApsm(5m)CpsmApom(5m)CpomApom(5m)CpomApom(5m)CpsmAps m(5m)CpsmApom(5m)CpomApom(5m)CpomApom(5m)CpomApsm(5m)CpomApsm(5m)C psmApsm(5m)CpomApom(5m)CpomApom(5m)CpsmApom(5m)CpomApsm(5m)CpomAps m(5m)CpsmApsm(5m)CpomApom(5m)CpsmApom(5m)CpsmApom(5m)C pomApsm(5m)CpsmApsm(5m)C 3' | D | A |

FIGURE 6B (continued)

| No. | Compound Structure (5' to 3') | EC$_{50}$ (μM) | CC$_{50}$ (μM) |
|---|---|---|---|
| 254 (SEQ ID NO: 89) | 5' mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmApsm( 5m)CpsmApsm(5m)Cpo-CHOL 3' | D | A |
| 324 (SEQ ID NO: 90) | 5' P-mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmApsm( 5m)CpsmApsm(5m)C 3' | D | A |
| 323 (SEQ ID NO: 91) | 5' P-lnApsln(5m)CpslnApsln(5m)CpslnApsln(5m)CpslnApsln(5m)CpslnAps lnApsln(5m)CpslnApsln(5m)CpslnApsln(5m)CpslnApsln(5m)CpslnApsln(5m)Cps lnApsln(5m)CpslnApsln(5m)CpslnApsln(5m)CpslnApsln(5m)CpslnApsln(5m)Cps lnApsln(5m)CpslnApsln(5m)C-3' | D | A |
| 306 (SEQ ID NO: 92) | 5' lnApsln(5m)CpolnApsln(5m)CpslnApsln(5m)CpslnApoln(5m)CpslnAps lnApsln(5m)CpolnApsln(5m)CpslnApsln(5m)CpslnApoln(5m)CpslnApsln(5m)CpslnApsln( 5m)CpolnApsln(5m)CpslnApsln(5m)CpolnApsln(5m)CpslnApoln(5m)CpslnApsln( 5m)CpslnApsln(5m)C 3' | D | A |
| 325 (SEQ ID NO: 93) | 5' mApsm(5m)CpslnApsln(5m)CpslnApsln(5m)CpslnApsln(5m)CpsmAps m(5m)CpsmApsm(5m)CpslnApsln(5m)CpslnApsln(5m)CpslnApsln(5m)CpsmApsm( 5m)CpsmApsm(5m)CpslnApsln(5m)CpslnApsln(5m)CpslnApsln(5m)CpsmApsm( 5m)CpsmApsm(5m)C 3' | D | A |
| 326 (SEQ ID NO: 94) | 5' lnApsln(5m)CpslnApsln(5m)CpslnApsln(5m)CpsmApsm(5m)CpsmAps lnApsln(5m)CpslnApsln(5m)CpslnApsln(5m)CpsmApsm(5m)CpslnApsln(5m)Cps lnApsln(5m)CpsmApsm(5m)CpsmApsm(5m)CpslnApsln(5m)CpslnApsln(5m)CpsmApsm( 5m)CpsmApsm(5m)C 3' | D | A |

FIGURE 6B (continued)

| No. | Compound Structure (5' to 3') | EC$_{50}$ (µM) | CC$_{50}$ (µM) |
|---|---|---|---|
| 327 (SEQ ID NO: 95) | 5' moeApsmoeApsmoeApsmoe(5m)CpsmoeApsmoe(5m)CpsmoeApsmoeApsmoe(5m)CpsmoeApsmoe(5m)CpsmoeApsmoe(5m)CpslnApsln(5m)CpslnAps moe(5m)CpsmoeApsmoe(5m)CpsmoeApsmoe(5m)CpsmoeApsmoe(5m)CpsmoeAps moe(5m)CpsmoeApsln(5m)CpslnApsln(5m)Cps moeApsmoe(5m)CpsmoeApsmoe(5m)CpsmoeApsmoe(5m)CpsmoeAps moe(5m)CpsmoeApsmoe(5m)C 3' | D | A |
| 328 (SEQ ID NO: 96) | 5' lnApsln(5m)CpslnApsln(5m)CpslnApsmoe(5m)CpsmoeApsmoe(5m)Cps moeApsmoe(5m)CpsmoeApsmoe(5m)CpsmoeApsmoe(5m)CpsmoeAps ln(5m)CpslnApsln(5m)CpslnApsmoe(5m)CpsmoeApsmoe(5m)CpsmoeAps moe(5m)CpsmoeApsmoe(5m)CpsmoeApsmoe(5m)CpsmoeApsmoe(5m)Cps lnApsln(5m)CpslnApsln(5m)CpslnApsmoe(5m)CpsmoeApsmoe(5m)Cps moeApsmoe(5m)C 3' | D | A |
| 158 (SEQ ID NO: 97) | 5' lnApsun(5m)CpslnApsun(5m)CpslnApsun(5m)CpslnApsmoe(5m)CpslnAps un(5m)CpslnApsun(5m)CpslnApsun(5m)CpslnApsun(5m)CpslnApsun(5m)CpslnAps un(5m)CpslnApsun(5m)CpslnApsun(5m)CpslnApsun(5m)CpslnAps un(5m)CpslnApsun(5m)CpslnApsun(5m)CpslnApsun(5m)CpslnApsun(5m)CpslnAps un(5m)CpslnApsun(5m)C 3' | B | A |
| 150 (SEQ ID NO: 98) | 5' unApsln(5m)CpsunApsln(5m)CpsunApsln(5m)CpsunApsln(5m)CpsunAps ln(5m)CpsunApsln(5m)CpsunApsln(5m)CpsunApsln(5m)CpsunApsln(5m)CpsunAps n(5m)CpsunApsln(5m)CpsunApsln(5m)CpsunApsln(5m)CpsunAps ln(5m)CpsunApsln(5m)CpsunApsln(5m)CpsunApsln(5m)CpsunApsln(5m)CpsunApsl n(5m)CpsunApsln(5m)C 3' | A | A |
| 159 (SEQ ID NO: 99) | 5' lnApsln(5m)CpslnApsln(5m)CpsunApsun(5m)CpsunApsun(5m)CpslnApsln(5m)CpslnAps ln(5m)CpslnApsln(5m)CpsunApsun(5m)CpsunApsun(5m)CpslnApsln(5m)CpslnApsl n(5m)CpsunApsun(5m)CpsunApsun(5m)CpslnApsln(5m)CpslnAps ln(5m)CpslnApsln(5m)CpsunApsun(5m)CpsunApsun(5m)CpslnApsln(5m)CpsunAps un(5m)CpsunApsun(5m)C 3' | C | A |

FIGURE 6B (continued)

| No. | Compound Structure (5' to 3') | EC₅₀ (μM) | CC₅₀ (μM) |
|---|---|---|---|
| 341 (SEQ ID NO: 100) | 5' lnApsgn(5m)CpslnApsgn(5m)CpslnApsgn(5m)CpslnApsgn(5m)CpslnAps gn(5m)CpslnApsgn(5m)CpslnApsgn(5m)CpslnApsgn(5m)CpslnApsgn(5m)CpslnAps gn(5m)CpslnApsgn(5m)CpslnApsgn(5m)CpslnApsgn(5m)CpslnApsgn(5m)CpslnAps gn(5m)CpslnApsgn(5m)C 3' | D | A |
| 342 (SEQ ID NO: 101) | 5' gnApsm(5m)CgnApsm(5m)CgnApsm(5m)CgnApsm(5m)CgnApsm(5m)CgnApsm(5m)C gnApsm(5m)CgnApsm(5m)CgnApsm(5m)CgnApsm(5m)CgnApsm(5m)CgnApsm(5m)C gnApsm(5m)CgnApsm(5m)CgnApsm(5m)CgnApsm(5m)CgnApsm(5m)CgnApsm(5m)C 3' | B | A |
| 244 (SEQ ID NO: 102) | 5' mApsm(5m)CpsmApsm(5m)CpsmApsm(5m)CpsmApsm(5m)CpsmApsm(5m)CpsmAps m(5m)Cps-TREB-ps-c3-O-C3-psm(5m)C 3' mApsm(5m)CpsmApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)Cps 5' | C | A |
| 245 (SEQ ID NO: 26) | 5' mApsm(5m)CpsmApsm(5m)CpsmApsm(5m)CpsmApsm(5m)CpsmApsm(5m)CpsmAps m(5m)CpsmApsm(5m)CpsmAps-TREB-ps-c3-O-C3-ps(5m)mC 3' mApsm(5m)CpsmApsm(5m)CpsmApsm(5m)CpsmApsm(5m)CpsmApsm(5m)CpsmAps m(5m)CpsmApsm(5m)CpsmApsm(5m)CpsmAps 5' | C | A |
| 343 (SEQ ID NO: 165) | 5' mApsgn(5m)CpslnApsgn(5m)CpsmApsm(5m)CpsmApsm(5m)CpsmApsm(5m)CpsmAps gn(5m)CpsmApsgn(5m)CpsmApsgn(5m)CpsmApsgn(5m)CpsmApsgn(5m)CpsmAps gn(5m)CpsmApsgn(5m)CpsmApsgn(5m)CpsmApsgn(5m)CpsmApsgn(5m)CpsmAps gn(5m)CpsmApsgn(5m)C 3' | B | A |
| 329 (SEQ ID NO: 103) | 5' lnApsln(5m)CpslnApsln(5m)CpslnApsln(5m)CpslnApsln(5m)CpslnAps ln(5m)CpsmApsm(5m)CpsmApsm(5m)CpsmApsm(5m)CpsmApsm(5m)CpsmApsm( 5m)CpslnApsln(5m)CpslnApsln(5m)CpsmApsm(5m)CpsmApsm(5m)CpsmApsm( 5m)CpsmApsm(5m)C 3' | C | A |

FIGURE 6B (continued)

| No. | Compound Structure (5' to 3') | EC$_{50}$ (μM) | CC$_{50}$ (μM) |
|---|---|---|---|
| 330 (SEQ ID NO: 104) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)C 3' | B | B |
| 331 (SEQ ID NO: 105) | 5' lnApsln(5m)CpslnApsln(5m)CpslnApsln(5m)CpslnApsln(5m)CpslnAps ln(5m)CpsmoeApsmoe(5m)CpsmoeApsmoe(5m)CpsmoeApsmoe(5m)Cps moeApsmoe(5m)CpsmoeApsmoe(5m)CpslnApsln(5m)CpslnApsln(5m)Cps lnApsln(5m)CpslnApsln(5m)CpsmoeApsmoe(5m)CpsmoeApsmoe(5 m)CpsmoeApsmoe(5m)CpsmoeApsmoe(5m)C 3' | D | A |
| 332 (SEQ ID NO: 106) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)CpsmoeApsmoe(5m)CpsmoeApsmoe(5m)CpsmoeAps moe(5m)CpsmoeApsmoe(5m)CpsmoeApsmoe(5m)CpsmoeApsmoeAps moe(5m)CpsmoeApsmoe(5m)CpsmoeApsmoe(5m)CpsmoeAps moe(5m)C 3' | D | A |
| 333 (SEQ ID NO: 107) | 5' lnApsln(5m)CpslnApsln(5m)CpsApsln(5m)CpslnApsln(5m)CpslnAps(5m)CpslnApsl n(5m)CpslnApsln(5m)CpsApsln(5m)CpslnApsln(5m)CpslnApsln(5m)CpslnAps (5m)CpslnApsln(5m)CpsApsln(5m)CpslnApsln(5m)CpslnApsln(5m)CpslnAps(5m)C pslnApsln(5m)CpslnApsln(5m)CpsApsln(5m)CpslnApsln(5m)Cps lnApsln(5m)C 3' | B | A |
| 334 (SEQ ID NO: 108) | 5' lnApsln(5m)CpslnApsln(5m)CpsAps(5m)CpslnApsln(5m)CpslnApsln(5m)CpsApsln(5 m)CpslnApsln(5m)CpsAps(5m)CpslnApsln(5m)CpslnAps(5m)CpsApsln(5m)CpslnA psln(5m)CpsAps(5m)CpslnApsln(5m)CpsApsln(5m)CpslnAps(5m)CpsApsln(5m)C psrAps(5m)CpslnApsln(5m)CpslnApsln(5m)C 3' | B | A |

FIGURE 6B (continued)

| No. | Compound Structure (5' to 3') | EC$_{50}$ (μM) | CC$_{50}$ (μM) |
|---|---|---|---|
| 335 (SEQ ID NO: 109) | 5' lnApsln(5m)CpslnApsln(5m)CpsApsln(5m)CpslnApsln(5m)CpslnApsl n(5m)CpslnApsln(5m)CpsApsln(5m)CpslnApsln(5m)CpslnAps (5m)CpolnApsln(5m)CpslnApsln(5m)CpsApsln(5m)CpslnApsln(5m)CpslnApsln(5m) C 3' | C | A |
| 336 (SEQ ID NO: 20) | 5' lnApsln(5m)CpslnApsln(5m)CpsAps(5m)CpslnApsln(5m)CpslnApsln(5m)CpsApsln(5 m)CpslnApsln(5m)CpsAps(5m)CpslnApsln(5m)CpslnApsln(5m)CpsApsln(5m)CpslnA psln(5m)CpsAps(5m)CpslnApsln(5m)C 3' | C | A |
| 337 (SEQ ID NO: 21) | 5' lnApsln(5m)CpslnApsln(5m)CpslnApsln(5m)CpslnApsln(5m)CpslnAps ln(5m)CpsAps(5m)CpsAps(5m)CpsAps(5m)CpslnApsln(5m)CpslnApsln(5m )CpslnApsln(5m)CpslnApsln(5m)CpslnApsln(5m)CpsAps(5m)CpsA ps(5m)CpsAps(5m)CpsAps(5m)C 3' | A | B |
| 338 (SEQ ID NO: 110) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)CpsAps(5m)CpslnApsln(5m)CpsAps(5m)CpsAps(5m)CpsAps(5 m)CpsAps(5m)CpsAps(5m)CpsAps(5m)C 3' | B | B |
| 117 (SEQ ID NO: 111) | 5' lnApsln(5m)CpslnApsln(5m)CpslnApsln(5m)CpslnApsln(5m)CpslnAps lnApsln(5m)CpslnApsln(5m)CpslnApsln(5m)CpslnApsln(5m)CpslnApsln(5m)Cps lnApsln(5m)CpslnApsln(5m)CpslnApsln(5m)CpslnApsln(5m)CpslnAps ln(5m)CpslnApsln(5m)CpslnApsln(5m)CpslnApsln(5m)C 3' | B | A |
| 118 (SEQ ID NO: 28) | 5' lnApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)CpslnApsln(5m)CpslnApsln(5m)CpslnApsln(5m)Cps lnA 3' | B | A |

FIGURE 6B (continued)

| No. | Compound Structure (5' to 3') | EC$_{50}$ (μM) | CC$_{50}$ (μM) |
|---|---|---|---|
| 134, 277, 284 (SEQ ID NO: 43) | 5' mApsln(5m)CpsmApsln(5m)CpsmApsln(5m)CpsmApsln(5m)CpsmAps ln(5m)CpsmApsln(5m)CpsmApsln(5m)CpsmApsln(5m)CpsmApsln(5m)CpsmApsln( 5m)CpsmApsln(5m)CpsmApsln(5m)CpsmAps ln(5m)CpsmApsln(5m)CpsmApsln(5m)CpsmApsln(5m)CpsmApsln(5m)CpsmApsln( 5m)CpsmApsln(5m)C 3' | A | A |
| 142 (SEQ ID NO: 112) | 5' lnApsln(5m)CpsmApsm(5m)CpslnApsm(5m)CpslnApsm(5m)CpslnAps m(5m)CpslnApsm(5m)CpslnApsm(5m)CpslnApsm(5m)CpslnApsm(5m)Cps lnApsm(5m)CpslnApsm(5m)CpslnApsm(5m)CpslnApsm(5m)CpslnAps m(5m)CpslnApsm(5m)CpslnApsm(5m)CpslnApsm(5m)Cps lnApsm(5m)CpslnApsm(5m)CpslnApsm(5m)CpslnA m(5m)C 3' | C | A |
| 190 (SEQ ID NO: 168) | 5' lnApsRm(5m)CpslnApsln(5m)CpslnApsln(5m)CpslnApsln(5m)CpslnAps ln(5m)CpslnApsln(5m)CpslnApsln(5m)CpslnApsln(5m)CpsmApsRm(5m)C pslnApsln(5m)CpslnApsln(5m)CpslnApsSln(5m)CpsmApsRm(5m)CpslnApsln(5m)C pslnApsln(5m)CpslnApsln(5m)CpslnApsln(5m)CpsmApsRm(5m)C pslnApsln(5m)CpslnApsm(5m)C 3' | B | A |
| 191 (SEQ ID NO: 64) | 5' mApsRm(5m)CpslnApsln(5m)CpslnApsln(5m)CpslnApsln(5m)CpslnAps ln(5m)CpsmApsRm(5m)CpslnApsln(5m)CpslnApsln(5m)CpsmApsR m(5m)CpslnApsln(5m)CpslnApsln(5m)CpsmApsRm(5m)CpslnAps ln(5m)CpslnApsln(5m)CpslnApsln(5m)CpsmApsRm(5m)CpslnApsl n(5m)CpslnApsm(5m)C 3' | B | A |
| 192 (SEQ ID NO: 60) | 5' lnApsln(5m)CpslnApsln(5m)CpsmApsRm(5m)CpslnApsln(5m)CpslnAps ln(5m)CpsmApsRln(5m)CpslnApsln(5m)CpslnApsln(5m)CpsmApsR ln(5m)CpslnApsln(5m)CpsmApsRln(5m)CpslnApsln(5m)CpslnApsln(5m)C pslnApsln(5m)CpsmApsRln(5m)CpslnApsln(5m)CpsmApsRln(5m)C pslnApsln(5m)CpslnApsm(5m)C 3' | B | A |

FIGURE 6B (continued)

| No. | Compound Structure (5' to 3') | EC$_{50}$ (μM) | CC$_{50}$ (μM) |
|---|---|---|---|
| 210 (SEQ ID NO: 68) | 5' mApsSm(5m)CpslnApsln(5m)CpslnApsln(5m)CpslnApsln(5m)CpslnAps ln(5m)CpslnApsln(5m)CpslnApsln(5m)CpsmApsSm(5m)C pslnApsln(5m)CpslnApsln(5m)CpslnApsln(5m)CpslnAps ln(5m)CpslnApsln(5m)CpslnApsln(5m)CpsmApsSm(5m)C pslnApsln(5m)CpslnApsln(5m)C 3' | B | A |
| 211 (SEQ ID NO: 65) | 5' mApsSm(5m)CpsmApsSm(5m)CpslnApsln(5m)CpslnApsln(5m)CpslnAps ln(5m)CpsmApsSm(5m)CpslnApsln(5m)CpslnApsln(5m)CpsmApsSm(5m)CpslnAps ln(5m)CpslnApsln(5m)CpslnApsln(5m)CpsmApsSm(5m)C pslnApsln(5m)CpslnApsln(5m)C 3' | B | A |
| 212 (SEQ ID NO: 61) | 5' lnApsln(5m)CpslnApsln(5m)CpsmApsSm(5m)CpslnApsln(5m)CpslnAps ln(5m)CpsmApsSm(5m)CpslnApsln(5m)CpslnApsln(5m)CpsmApsSm(5m)CpslnAps ln(5m)CpsmApsSm(5m)CpslnApsln(5m)CpslnApsln(5m)CpsmApsSm(5m)CpslnAps ln(5m)CpslnApsln(5m)C 3' | B | A |
| 218 (SEQ ID NO: 69) | 5' mApsm(5m)CpsmApsRln(5m)CpsmApsm(5m)CpsmApsm(5m)CpsmApsR ln(5m)CpsmApsm(5m)CpsmApsm(5m)CpsmApsRln(5m)CpsmApsm(5m)C psmApsm(5m)CpsmApsRln(5m)CpsmApsm(5m)CpsmApsm(5m)CpsmApsRln(5m)C psmApsm(5m)CpsmApsm(5m)C 3' | C | A |
| 223 (SEQ ID NO: 70) | 5' VP-mApsm(5m)CpsmApsRln(5m)CpsmApsm(5m)CpsmApsm(5m)CpsmAps m(5m)CpsmApsRln(5m)CpsmApsm(5m)CpsmApsm(5m)CpsmApsRln(5m)CpsmApsR ln(5m)CpsmApsm(5m)CpsmApsm(5m)CpsmApsRln(5m)CpsmApsm(5m)C psmApsm(5m)CpsmApsRln(5m)CpsmApsm(5m)CpsmApsm(5m)CpsmApsRln(5m)C psmApsm(5m)CpsmApsm(5m)C 3' | C | A |
| 221 (SEQ ID NO: 151) | 5' mApsmApsRln(5m)CpsmApsRln(5m)CpsmApsRln(5m)CpsmApsRln(5m)CpsmA psRln(5m)CpsmApsRln(5m)CpsmApsRln(5m)CpsmApsRln(5m)CpsmApsR ln(5m)CpsmApsRln(5m)CpsmApsRln(5m)CpsmApsRln(5m)CpsmApsR ln(5m)CpsmApsRln(5m)CpsmApsRln(5m)CpsmApsR ln(5m)CpsmApsRln(5m)CpsmApsRln(5m)C 3' | A | A |

FIGURE 6B (continued)

| No. | Compound Structure (5' to 3') | EC$_{50}$ (μM) | CC$_{50}$ (μM) |
|---|---|---|---|
| 127 (SEQ ID NO: 53) | 5' VP-mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)C 3' | D | A |
| 128 (SEQ ID NO: 30) | 5' VP-mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmAps m(5m)CpsmApsm(5m)CpsmApsm(5m)CpsmApsm(5m)C 3' | C | A |
| 129 (SEQ ID NO: 38) | 5' VP-mApsm(5m)CpsmApsm(5m)CpsmApsm(5m)CpsmApsm(5m)CpsmAps m(5m)CpsmApsm(5m)CpsmApsm(5m)CpsmApsm(5m)CpsmApsm(5m)CpsmApsm( 5m)CpsmApsm(5m)CpsmApsm(5m)CpsmApsm(5m)CpsmApsm(5m)CpsmApsm( 5m)C 3' | C | A |
| 120 (SEQ ID NO: 47) | 5' VP-mApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)CpslnApsln(5m)CpslnApsln(5m)CpslnApsln(5m)CpslnAps ln(5m)CpslnApsln(5m)CpslnApsln(5m)C 3' | B | A |
| 121 (SEQ ID NO: 31) | 5' VP-mApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)CpslnApsln(5m)CpslnApsln(5m)CpslnApsln(5m)CpslnAps ln(5m)CpslnApsln(5m)CpslnApsln(5m)C 3' | B | A |
| 122 (SEQ ID NO: 39) | 5' VP-mApsln(5m)CpslnApsln(5m)CpslnApsln(5m)CpslnApsln(5m)CpslnAps ln(5m)CpslnApsln(5m)CpslnApsln(5m)CpslnApsln(5m)CpslnApsln(5m)Cps lnApsln(5m)CpslnApsln(5m)CpslnApsln(5m)CpslnApsln(5m)CpslnAps lnApsln(5m)C 3' | A | A |

FIGURE 6B (continued)

| No. | Compound Structure (5' to 3') | EC$_{50}$ (μM) | CC$_{50}$ (μM) |
|---|---|---|---|
| 181 (SEQ ID NO: 48) | 5' VP-mApsm(5m)CpsmApsm(5m)CpsmApsRm(5m)CpsmApsm(5m)CpsmAps m(5m)CpsmApsRm(5m)CpsmApsm(5m)CpsmApsm(5m)CpsmApsR m(5m)CpsmApsm(5m)CpsmApsm(5m)CpsmApsRm(5m)CpsmApsm(5m)C psmApsm(5m)CpsmApsRm(5m)CpsmApsm(5m)CpsmApsRm(5m)C psmApsm(5m)CpsmApsm(5m)C 3' | C | A |
| 147 (SEQ ID NO: 152) | 5' unApsln(5m)CpsunApsln(5m)CpsunApsln(5m)CpsunApsln(5m)CpsunAps ln(5m)CpsunApsln(5m)CpsunApsln(5m)CpsunApsln(5m)CpsunApsl n(5m)CpsunApsln(5m)CpsunApsln(5m)CpsunApsln(5m)CpsunAps ln(5m)CpsunApsln(5m)CpsunApsln(5m)CpsunApsln(5m)Cps 3' | D | A |
| 148 (SEQ ID NO: 29) | 5' unApsln(5m)CpsunApsln(5m)CpsunApsln(5m)CpsunApsln(5m)CpsunAps ln(5m)CpsunApsln(5m)CpsunApsln(5m)CpsunApsln(5m)CpsunApsl n(5m)CpsunApsln(5m)CpsunApsln(5m)CpsunApsln(5m)CpsunAps ln(5m)CpsunApsln(5m)CpsunApsln(5m)CpsunApsln(5m)C 3' | D | A |
| 149 (SEQ ID NO: 34) | 5' unApsln(5m)CpsunApsln(5m)CpsunApsln(5m)CpsunApsln(5m)CpsunAps ln(5m)CpsunApsln(5m)CpsunApsln(5m)CpsunApsln(5m)CpsunApsl n(5m)CpsunApsln(5m)CpsunApsln(5m)CpsunApsln(5m)CpsunAps ln(5m)CpsunApsln(5m)CpsunApsln(5m)CpsunApsln(5m)CpsunApsl n(5m)C 3' | B | A |
| 151 (SEQ ID NO: 46) | 5' VP-mApsln(5m)CpsunApsln(5m)CpsunApsln(5m)CpsunApsln(5m)CpsunAps ln(5m)CpsunApsln(5m)CpsunApsln(5m)CpsunApsln(5m)CpsunApsl n(5m)CpsunApsln(5m)CpsunApsln(5m)CpsunApsln(5m)CpsunAps ln(5m)CpsunApsln(5m)CpsunApsln(5m)CpsunApsln(5m)Cps 3' | D | A |
| 152 (SEQ ID NO: 32) | 5' VP-mApsln(5m)CpsunApsln(5m)CpsunApsln(5m)CpsunApsln(5m)CpsunAps ln(5m)CpsunApsln(5m)CpsunApsln(5m)CpsunApsln(5m)CpsunApsl n(5m)CpsunApsln(5m)CpsunApsln(5m)CpsunApsln(5m)CpsunAps ln(5m)CpsunApsln(5m)CpsunApsln(5m)CpsunApsln(5m)C 3' | D | A |

FIGURE 6B (continued)

| No. | Compound Structure (5' to 3') | EC$_{50}$ (μM) | CC$_{50}$ (μM) |
|---|---|---|---|
| 153 (SEQ ID NO: 40) | 5' VP-mApsln(5m)CpsunApsln(5m)CpsunApsln(5m)CpsunAps ln(5m)CpsunApsln(5m)CpsunApsln(5m)CpsunApsln(5m)CpsunApsl n(5m)CpsunApsln(5m)CpsunApsln(5m)CpsunApsln(5m)CpsunAps ln(5m)CpsunApsln(5m)CpsunApsln(5m)CpsunApsln(5m)CpsunApsl n(5m)C 3' | B | A |
| 168 (SEQ ID NO: 49) | 5' VP-mApsm(5m)CpsmApsln(5m)CpsmApsln(5m)CpsmApsln(5m)CpsmAps m(5m)CpsmApsln(5m)CpsmApsln(5m)CpsmApsln(5m)CpsmApsln(5m)CpsmApsm( 5m)CpsmApsm(5m)CpsmApsln(5m)CpsmApsm(5m)CpsmAps m(5m)CpsmApsln(5m)CpsmApsm(5m)CpsmApsm(5m)C 3' | | |
| 169 (SEQ ID NO: 33) | 5' VP-mApsm(5m)CpsmApsln(5m)CpsmApsln(5m)CpsmApsln(5m)CpsmAps m(5m)CpsmApsln(5m)CpsmApsln(5m)CpsmApsln(5m)CpsmApsln(5m)CpsmApsm( 5m)CpsmApsm(5m)CpsmApsln(5m)CpsmApsm(5m)CpsmApsln(5m)C 3' | | |
| 170 (SEQ ID NO: 41) | 5' VP-mApsm(5m)CpsmApsln(5m)CpsmApsln(5m)CpsmApsln(5m)CpsmAps m(5m)CpsmApsln(5m)CpsmApsln(5m)CpsmApsln(5m)CpsmApsln(5m)CpsmApsm( 5m)CpsmApsm(5m)CpsmApsln(5m)CpsmApsm(5m)CpsmAps m(5m)CpsmApsln(5m)CpsmApsln(5m)CpsmApsln(5m)CpsmApsm( 5m)C 3' | | |
| 294 (SEQ ID NO: 50) | 5' VP-mApsmApsRm(5m)CpsmApsRm(5m)CpsmApsRm(5m)C psmApsRm(5m)CpsmApsRm(5m)CpsmApsRm(5m)CpsmApsRm(5m)Cps mApsRm(5m)CpsmApsRm(5m)CpsmApsRm(5m)CpsmApsRm(5m)CpsmA psRm(5m)CpsmApsRm(5m)CpsmApsRm(5m)CpsmApsRm(5m)C psmApsRm(5m)CpsmApsRm(5m)C 3' | B | A |
| 276, 291 (SEQ ID NO: 163) | 5' VP-mApsm(5m)CpsmApsRm(5m)CpsmApsRm(5m)CpsmApsRm(5m) CpsmApsRm(5m)CpsmApsRm(5m)CpsmApsRm(5m)CpsmApsR m(5m)CpsmApsRm(5m)CpsmApsRm(5m)CpsmApsRm(5m)CpsmApsR m(5m)CpsmApsRm(5m)CpsmApsRm(5m)CpsmApsRm(5m)CpsmApsR m(5m)CpsmApsRm(5m)CpsmApsRm(5m)C 3' | A | A |

FIGURE 6B (continued)

| No. | Compound Structure (5' to 3') | EC$_{50}$ (μM) | CC$_{50}$ (μM) |
|---|---|---|---|
| 275, 295 (SEQ ID NO: 150) | 5' VP-mApsm(5m)CpsmApsm(5m)CpslnApsm(5m)CpsmApsm(5m)CpsmAps m(5m)CpslnApsm(5m)CpslnApsm(5m)CpsmApsm(5m)CpslnApsm(5m)CpsmApsm( 5m)CpslnApsm(5m)CpslnApsm(5m)CpsmApsm(5m)CpslnApsm(5m)CpsmAps m(5m)CpslnApsm(5m)CpsmApsm(5m)CpsmApsm(5m)CpslnApsm(5m)CpsmApsm( 5m)CpsmApsm(5m)C 3' | A | B |
| 173, 293 (SEQ ID NO: 154) | 5' VP-mApsm(5m)CpsmApsm(5m)CpslnApsm(5m)CpsmApsm(5m)CpsmAps m(5m)CpslnApsm(5m)CpsmApsm(5m)CpsmApsm(5m)CpslnApsm(5m)CpsmApsm( 5m)CpsmApsm(5m)CpslnApsm(5m)CpsmApsm(5m)CpslnApsm(5m)CpsmAps m(5m)CpslnApsm(5m)CpsmApsm(5m)CpsmApsm(5m)CpslnApsm(5m)CpsmApsm( 5m)CpsmApsm(5m)C 3' | A | A |
| 165, 287 (SEQ ID NO: 155) | 5' VP-mApsm(5m)CpslnApsm(5m)CpsmApsm(5m)CpsmApsln(5m)CpslnAps m(5m)CpsmApsln(5m)CpsmApsm(5m)CpslnApsm(5m)CpslnApsm(5m)CpsmApsm( 5m)CpslnApsm(5m)CpsmApsln(5m)CpslnApsm(5m)CpsmApsm(5m)CpslnAps m(5m)CpslnApsm(5m)CpsmApsm(5m)CpsmApsm(5m)CpsmApsm(5m)CpsmApsm( 5m)CpslnApsm(5m)C 3' | B | A |
| 167, 289 (SEQ ID NO: 156) | 5' VP-mApsm(5m)CpsmApsln(5m)CpsmApsm(5m)CpsmApsm(5m)CpslnApsm(5m)CpslnAps m(5m)CpsmApsln(5m)CpsmApsln(5m)CpslnApsm(5m)CpsmApsm(5m)CpsmApsln( 5m)CpsmApsm(5m)CpsmApsln(5m)CpsmApsln(5m)CpsmApsm(5m)CpsmAps ln(5m)CpsmApsm(5m)CpsmApsln(5m)CpsmApsln(5m)CpsmApsm(5m)CpsmApsm( 5m)CpsmApsln(5m)C 3' | B | A |
| 164, 286 (SEQ ID NO: 157) | 5' mApsm(5m)CpslnApsm(5m)CpsmApsln(5m)CpsmApsm(5m)CpsmApsm(5m)CpslnAps m(5m)CpslnApsm(5m)CpsmApsm(5m)CpsmApsln(5m)CpsmApsm(5m)CpsmApsln( 5m)CpslnApsm(5m)CpslnApsm(5m)CpslnApsm(5m)CpsmApsm(5m)CpslnAps m(5m)CpsmApsm(5m)CpslnApsm(5m)CpsmApsm(5m)CpslnApsm(5m)CpsmApsm( 5m)CpslnApsln(5m)C 3' | C | A |
| 166, 288 (SEQ ID NO: 113) | 5' mApsm(5m)CpslnApsm(5m)CpsmApsln(5m)CpsmApsm(5m)CpsmApsln(5m)CpsmAps ln(5m)CpsmApsm(5m)CpslnApsm(5m)CpsmApsln(5m)CpsmApsm(5m)CpsmApsln( 5m)CpsmApsm(5m)CpsmApsln(5m)CpsmApsm(5m)CpsmApsm(5m)CpsmApsln ln(5m)CpsmApsm(5m)CpsmApsm(5m)CpsmApsln(5m)CpsmApsm(5m)CpsmApsm( 5m)CpsmApsln(5m)C 3' | A | A |

FIGURE 6B (continued)

| No. | Compound Structure (5' to 3') | EC$_{50}$ (μM) | CC$_{50}$ (μM) |
|---|---|---|---|
| 171, 280, 292 (SEQ ID NO: 114) | 5' mApsm(5m)CpslnApsm(5m)CpsmApsm(5m)CpsmApsm(5m)CpsmAps m(5m)CpslnApsm(5m)CpsmApsm(5m)CpsmApsm(5m)CpsmApsm(5m)CpsmApsm( 5m)CpsmApsm(5m)CpslnApsm(5m)CpsmApsm(5m)CpsmAps m(5m)CpslnApsm(5m)CpsmApsm(5m)CpslnApsm(5m)CpsmApsm( 5m)CpsmApsm(5m)C 3' | B | A |
| 172 (SEQ ID NO: 115) | 5' mApsm(5m)CpsmApsm(5m)CpsmApsm(5m)CpsmApsm(5m)CpsmAps m(5m)CpslnApsm(5m)CpsmApsm(5m)CpsmApsm(5m)CpsmApsm(5m)CpsmApsm( 5m)CpslnApsm(5m)CpslnApsm(5m)CpsmApsm(5m)CpsmAps m(5m)CpslnApsm(5m)CpsmApsm(5m)CpslnApsm(5m)CpsmApsm( 5m)CpsmApsm(5m)C 3' | | |
| 314 (SEQ ID NO: 116) | 5' EP-mApsln(5m)CpsmApsln(5m)CpsmApsln(5m)CpsmApsln(5m)CpsmAps ln(5m)CpsmApsln(5m)CpsmApsln(5m)CpsmApsln(5m)CpsmApsln(5m)CpsmApsln( 5m)CpsmApsln(5m)CpsmApsln(5m)CpsmApsln(5m)CpsmAps ln(5m)CpsmApsln(5m)CpsmApsln(5m)CpslnApsln(5m)CpsmApsln( 5m)CpsmApsln(5m)C 3' | A | B |
| 281, 316 (SEQ ID NO: 145) | 5' EP-mApsm(5m)CpsmApsln(5m)CpsmApsm(5m)CpsmApsm(5m)CpsmAps m(5m)CpslnApsm(5m)CpsmApsm(5m)CpslnApsm(5m)CpsmApsm(5m)CpslnApsm( 5m)CpsmApsm(5m)CpslnApsm(5m)CpsmApsm(5m)CpsmAps m(5m)CpslnApsm(5m)CpsmApsm(5m)CpslnApsln(5m)CpsmApsm( 5m)CpsmApsm(5m)C 3' | A | A |
| 296 (SEQ ID NO: 146) | 5' mApsln(5m)CpsmApsln(5m)CpsmApsln(5m)CpsmApsln(5m)CpsmAps ln(5m)CpsrApsln(5m)CpsmApsln(5m)CpsmApsln(5m)CpsrApsln(5m)Cps mApsln(5m)CpsmApsln(5m)CpsrApsln(5m)CpsmApsln(5m)CpsmAps ln(5m)CpsrApsln(5m)CpsmApsln(5m)CpsmApsln(5m)CpsrApsln(5m)Cps mApsln(5m)CpsmApsm(5m)C 3' | A | A |
| 285 (SEQ ID NO: 117) | 5' VP-mApsln(5m)CpsmApsln(5m)CpsmApsln(5m)CpsmApsln(5m)CpsmAps ln(5m)CpsmApsln(5m)CpsmApsln(5m)CpsmApsln(5m)CpsmApsln(5m)CpsmApsln( 5m)CpsmApsln(5m)CpsmApsln(5m)CpsmApsln(5m)CpsmAps ln(5m)CpsmApsln(5m)CpsmApsln(5m)CpsmApsln(5m)CpsmApsln( 5m)CpsmApsln(5m)C 3' | A | B |

FIGURE 6B (continued)

| No. | Compound Structure (5' to 3') | EC$_{50}$ (μM) | CC$_{50}$ (μM) |
|---|---|---|---|
| 251 (SEQ ID NO: 158) | 5' cpApsm(5m)CpsmApsm(5m)CpsmAps(5m)CpsmAps m(5m)CpsmApsm(5m)CpsmApsm(5m)CpsmApsm(5m)CpsmApsm( 5m)CpsmApsm(5m)CpsmApsm(5m)CpsmApsm(5m)CpsmAps m(5m)CpsmApsm(5m)CpsmApsm(5m)CpsmApsm(5m)CpsmApsm( 5m)CpsmApsm(5m)C 3' | A | A |
| 356 (SEQ ID NO: 118) | 5' 4'-Me-mApsln(5m)CpsmApsln(5m)CpsmApsln(5m)CpsmAps ln(5m)CpsmApsln(5m)CpsmApsln(5m)CpsmApsln(5m)CpsmApsln( 5m)CpsmApsln(5m)CpsmApsln(5m)CpsmApsln(5m)CpsmAps ln(5m)CpsmApsln(5m)CpsmApsln(5m)CpsmApsln(5m)CpsmApsln( 5m)CpsmApsln(5m)C 3' | A | A |
| 320 (SEQ ID NO: 119) | 5' mApsln(5m)CpsmApsln(5m)CpsmApsln(5m)CpsmApsln(5m)CpsmAps ln(5m)CpsmApsln(5m)CpsmApsln(5m)CpsmApsln(5m)CpsmApsln( 5m)CpsmApsln(5m)CpsmApsln(5m)CpsmApsln(5m)CpsmAps ln(5m)CpsmApsln(5m)CpsmApsln(5m)CpsmApsln(5m)CpsmApsln(5m)C 3' | A | A |
| 357 (SEQ ID NO: 35) | 5' mApsln(5m)CpsmApsm(5m)CpslnApsm(5m)CpsmApsm(5m)CpsmAps m(5m)CpslnApsm(5m)CpsmApsm(5m)CpslnApsm(5m)CpsmApsln( 5m)CpsmApsm(5m)CpslnApsm(5m)CpsmApsm(5m)CpsmAps m(5m)CpslnApsm(5m)CpsmApsm(5m)CpslnApsm(5m)C 3' | A | B |
| 322 (SEQ ID NO: 36) | 5' mApsm(5m)CpsmApsln(5m)CpsmApsm(5m)CpsmApsln(5m)CpsmAps m(5m)CpsmApsln(5m)CpsmApsm(5m)CpsmApsm(5m)CpsmApsln( 5m)CpsmApsm(5m)CpsmApsln(5m)CpsmApsm(5m)CpsmAps ln(5m)CpsmApsm(5m)CpsmApsln(5m)CpsmApsm(5m)C 3' | B | A |
| 317 (SEQ ID NO: 37) | 5' EP-mApsm(5m)CpsmApsln(5m)CpsmApsm(5m)CpsmApsln(5m)CpsmAps m(5m)CpsmApsln(5m)CpsmApsm(5m)CpsmApsln(5m)CpsmApsln( 5m)CpsmApsm(5m)CpsmApsln(5m)CpsmApsm(5m)CpsmAps ln(5m)CpsmApsm(5m)CpsmApsln(5m)CpsmApsm(5m)CpsmApsm( 5m)CpsmApsln(5m)C 3' | A | B |

FIGURE 6B (continued)

| No. | Compound Structure (5' to 3') | EC$_{50}$ (μM) | CC$_{50}$ (μM) |
|---|---|---|---|
| 318 (SEQ ID NO: 147) | 5' EP-mApsm(5m)CpslnApsln(5m)CpsmApsm(5m)CpslnAps m(5m)CpslnApsln(5m)CpsmApsm(5m)CpslnApsm(5m)CpsmApsm( 5m)CpslnApsm(5m)CpsmApsln(5m)CpsmApsm(5m)CpslnAps m(5m)CpsmApsln(5m)CpsmApsm(5m)CpslnApsln(5m)CpsmApsm( 5m)CpslnApsm(5m)C 3' | B | B |
| 319 (SEQ ID NO: 148) | 5' EP-mApsm(5m)CpsmApsm(5m)CpsmApsm(5m)CpsmAps m(5m)CpsmApsm(5m)CpsmApsm(5m)CpsmApsm(5m)CpsmApsm( 5m)CpsmApsm(5m)CpsmApsm(5m)CpsmApsm(5m)CpsmAps m(5m)CpsmApsm(5m)CpsmApsm(5m)CpsmApsm(5m)CpsmApsm( 5m)CpsmApsm(5m)C 3' | A | B |
| 315 (SEQ ID NO: 149) | 5' EP-mApsm(5m)CpsmApsRm(5m)CpsmApsRm(5m)CpsmApsRm(5m) CpsmApsRm(5m)CpsmApsRm(5m)CpsmApsRm(5m)CpsmApsR m(5m)CpsmApsRm(5m)CpsmApsRm(5m)CpsmApsRm(5m)CpsmApsR m(5m)CpsmApsRm(5m)CpsmApsRm(5m)CpsmApsRm(5m)CpsmApsR m(5m)CpsmApsRm(5m)CpsmApsRm(5m)CpsmApsRm(5m)C 3' | C | A |
| 357 (SEQ ID NO: 120) | 5' mApsln(5m)Cps3calApsln(5m)CpsmApsln(5m)CpsmApsln(5m)CpsmAps ln(5m)Cps3calApsln(5m)CpsmApsln(5m)CpsmApsln(5m)Cps3calAps ln(5m)CpsmApsln(5m)CpsmApsln(5m)Cps3calApsln(5m)CpsmApsln(5m)CpsmApsl n(5m)Cps3calApsln(5m)CpsmApsln(5m)CpsmApsln(5m)Cps3calA psln(5m)CpsmApsln(5m)CpsmApsln(5m)C 3' | A | A |
| 347 (SEQ ID NO: 121) | 5'GalNAc5mApsln(5m)CpsmApsln(5m)CpsmAps ln(5m)CpsmApsln(5m)CpsmApsln(5m)CpsmApsln(5m)CpsmApsln( 5m)CpsmApsln(5m)CpsmApsln(5m)CpsmApsln(5m)CpsmAps ln(5m)CpsmApsln(5m)CpsmApsln(5m)CpsmApsln(5m)CpsmApsln( 5m)CpsmApsln(5m)CpsmApsln(5m)C 3' | | |

FIGURE 6B (continued)

| No. | Compound Structure (5' to 3') | EC$_{50}$ (μM) | CC$_{50}$ (μM) |
|---|---|---|---|
| 348 (SEQ ID NO: 122) | 5' GalNAc5mApsm(5m)CpsmApsln(5m)CpsmAps m(5m)CpsmApsln(5m)CpsmApsm(5m)CpsmApsln(5m)CpsmApsln( 5m)CpsmApsm(5m)CpsmApsln(5m)CpsmApsm(5m)CpsmAps ln(5m)CpsmApsm(5m)CpsmApsln(5m)CpsmApsm(5m)CpsmApsm( 5m)CpsmApsln(5m)CpsmApsm(5m)CpsmApsln(5m)C 3' | | |
| 350 (SEQ ID NO: 123) | 5' GalNAc5mApsln(5m)CpsmApsln(5m)CpsmAps ln(5m)CpsmApsln(5m)CpsmApsln(5m)CpsrApsln(5m)CpsmApsln(5m)Cps mApsln(5m)CpsrApsln(5m)CpsmApsln(5m)CpsmApsln(5m)CpsrAps ln(5m)CpsmApsln(5m)CpsrApsln(5m)CpsmApsln(5m)CpsmApsln(5m)Cps mApsln(5m)CpsrApsln(5m)CpsmApsln(5m)CpsmApsln(5m)C 3' | | |
| 349 (SEQ ID NO: 124) | 5' GalNAc5mApsm(5m)CpsmApsm(5m)CpsmAps m(5m)CpsmApsm(5m)CpslnApsm(5m)CpsmApsm(5m)CpsmApsm( 5m)CpslnApsm(5m)CpsmApsm(5m)CpsmApsm(5m)CpslnAps m(5m)CpsmApsm(5m)CpsmApsm(5m)CpslnApsm(5m)CpsmApsm( 5m)CpslnApsm(5m)CpsmApsm(5m)CpsmApsm(5m)C 3' | | |
| 339 (SEQ ID NO: 125) | 5' mApsln(5m)CpsmApsln(5m)CpsmApsln(5m)CpsmApsln(5m)CpsmAps ln(5m)CpsmApsln(5m)CpslnApsln(5m)CpsmApsln(5m)CpsmApsln( 5m)CpsmApsln(5m)CpsmApsln(5m)CpsmApsln(5m)CpsmAps ln(5m)CpsmApsln(5m)CpscpApsln(5m)CpsmApsln(5m)CpsmApsln( 5m)CpscpApsln(5m)C 3' | A | A |
| 252 (SEQ ID NO: 126) | 5' mApsln(5m)CpsmApsln(5m)CpsmApsln(5m)CpsmApsln(5m)CpsmAps ln(5m)CpsmApsln(5m)CpsmApsln(5m)CpsmApsln(5m)CpsmApsln( 5m)CpsmApsln(5m)CpsmApsln(5m)CpsmApsln(5m)CpsmAps ln(5m)CpsmApsln(5m)CpsmApscp(5m)CpsmApsln(5m)CpsmApsln( 5m)CpsmApscp(5m)C 3' | A | A |
| 340 (SEQ ID NO: 127) | 5' mApsln(5m)CpsmApsln(5m)CpsmApsln(5m)CpsmApsln(5m)CpsmAps ln(5m)CpsmApsln(5m)CpsmApsln(5m)CpsmApsln(5m)CpsmApsln( 5m)CpsmApsln(5m)CpsmApsln(5m)CpsmApsln(5m)CpsmAps ln(5m)CpsmApsln(5m)CpsamApsln(5m)CpsmApsln(5m)CpsmApsln( 5m)CpsamApsln(5m)C 3' | A | A |

FIGURE 6B (continued)

| No. | Compound Structure (5' to 3') | EC$_{50}$ (μM) | CC$_{50}$ (μM) |
|---|---|---|---|
| 250 (SEQ ID NO: 128) | 5' mApsIn(5m)CpsmApsIn(5m)CpsmApsIn(5m)CpsmAps ln(5m)CpsmApsIn(5m)CpsmApsIn(5m)CpsmApsIn(5m)CpsmApsIn( 5m)CpsmApsIn(5m)CpsmApsIn(5m)CpsmApsIn(5m)CpsmAps ln(5m)CpsmApsIn(5m)CpsmApsIn(5m)CpsmApsIn(5m)CpsmApsIn( 5m)CpsmApsm(5m)C 3' | A | A |
| 359 (SEQ ID NO: 129) | 5' mApsmGpsmApsmGpsmApsmGpsmApsmGpsmApsmGpsm ApsmGpsmApsmGpsmApsmGpsmApsmGpsmApsmGpsmApsmGpsmAp smGpsmApsmGpsmApsmGpsmApsmApsmGpsmApsmGpsmApsmG 3' | D | A |
| 360 (SEQ ID NO: 130) | 5' mGpsmApsmGpsmApsmGpsmApsmGpsmApsmGpsmApsm GpsmApsmGpsmApsmGpsmApsmGpsmApsmGpsmApsmGpsmApsmGp smApsmGpsmApsmGpsmApsmGpsmApsmGpsmA 3' | D | A |
| 361 (SEQ ID NO: 159) | 5' mCpsmApsmCpsmApsmCpsmApsmCpsmApsmCpsmApsmC psmApsmCpsmApsmCpsmApsmCpsmApsmCpsmApsmCpsmApsmCps mApsmCpsmApsmCpsmApsmCpsmAps mCpsmApsmCpsmA 3' | D | A |
| 362 (SEQ ID NO: 162) | 5' mApsmUpsmApsmUpsmApsmUpsmApsmUpsmApsmUpsm ApsmUpsmApsmUpsmApsmUpsmApsmUpsmApsmUpsmApsmUpsmAp smUpsmApsmUpsmApsmUpsmApsmUpsmApsmU 3' | D | A |
| 377 (SEQ ID NO: 161) | 5' mApsIn(5m)CpsmApsIn(5m)CpsmApsIn(5m)CpsmApsIn(5m)Cpsr ApsIn(5m)CpsrApsIn(5m)CpsmApsIn(5m)CpsrApsIn(5m)CpsmAps ln(5m)CpsrApsIn(5m)CpsmApsIn(5m)CpsrApsIn(5m)CpsmApsIn(5 m)CpsmApsIn(5m)CpsmApsIn(5m)CpsmApsIn(5m)C 3' | A | A |

FIGURE 6B (continued)

| No. | Compound Structure (5' to 3') | EC$_{50}$ (μM) | CC$_{50}$ (μM) |
|---|---|---|---|
| 378 (SEQ ID NO: 160) | 5' mApsln(5m)CpsmApsln(5m)CpsmApsln(5m)CpsrApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsrApsln(5m)CpsrApsln(5m)CpsmApsln(5m)CpsmApsln(5m)C 3' | A | A |
| 379 (SEQ ID NO: 131) | 5' mApsln(5m)CpsmApsln(5m)CpsmApsln(5m)CpsrApsln(5m)CpsmApsln(5m)CpsmApsln(5m)CpsmApsln(5m)CpsmApsln(5m)CpsmApsln(5m)CpsmApsln(5m)CpsrApsln(5m)CpsmApsln(5m)CpsmApsln(5m)C 3' | A | A |
| 381 (SEQ ID NO: 132) | 5' 4etlAps4etl(5m)Cps4etlAps4etl(5m)Cps4etlAps4etl(5m)Cps4etlAps4etl(5m)Cps4etlAps4etl(5m)Cps4etlAps4etl(5m)Cps4etlAps4etl(5m)Cps4etlAps4etl(5m)Cps4etlAps4etl(5m)Cps4etlAps4etl(5m)Cps4etlAps4etl(5m)Cps4etlAps4etl(5m)Cps4etlAps4etl(5m)Cps4etlAps4etl(5m)C 3' | A | A |
| 382 (SEQ ID NO: 133) | 5' mAps4etl(5m)CpsmAps4etl(5m)CpsmAps4etl(5m)CpsmAps4etl(5m)CpsmAps4etl(5m)CpsmAps4etl(5m)CpsmAps4etl(5m)CpsmAps4etl(5m)CpsmAps4etl(5m)CpsmAps4etl(5m)CpsmAps4etl(5m)CpsmAps4etl(5m)CpsmAps4etl(5m)CpsmAps4etl(5m)CpsmAps4etl(5m)C 3' | A | A |
| 383 (SEQ ID NO: 134) | 5' mApsm(5m)CpsmApsm(5m)CpsmApsm(5m)CpsmApsm(5m)CpsmAps4etl(5m)CpsmAps4etl(5m)CpsmAps4etl(5m)CpsmAps4etl(5m)CpsmAps4etl(5m)CpsmAps4etl(5m)CpsmApsm(5m)CpsmApsm(5m)CpsmAps4etl(5m)CpsmApsm(5m)CpsmAps4etl(5m)C 3' | B | A |
| 384 (SEQ ID NO: 135) | 5' mApsln(5m)CpsmApsln(5m)CpsmApsln(5m)CpsmApsln(5m)CpsmApsln(5m)CpsmApsln(5m)CpsrApslnApsln(5m)CpsmApsln(5m)CpsmApsln(5m)CpsmApsln(5m)CpsmApsln(5m)CpsmApsln(5m)CpsmApsln(5m)CpsmApsln(5m)C 3' | A | A |

FIGURE 6B (continued)

| No. | Compound Structure (5' to 3') | EC$_{50}$ (μM) | CC$_{50}$ (μM) |
|---|---|---|---|
| 385 (SEQ ID NO: 136) | 5'nmlnApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)C 3' | A | A |
| 386 (SEQ ID NO: 137) | 5'nmlnApsnmlnApsln(5m)CpsnmlnApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)C 3' | A | A |
| 387 (SEQ ID NO: 138) | 5'nmlnApsnmlnApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)C 3' | A | A |
| 388 (SEQ ID NO: 139) | 5'ApsnmlnApsln(5m)CpsmApsnmlnApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m | A | A |
| 389 (SEQ ID NO: 140) | 5'nmlnApsnmlnApsnmlnApsnmln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m)CpsmApsln(5m) C 3' | A | A |
| 390 (SEQ ID NO: 141) | 5'mApsam(5m)CpsmApsam(5m)CpsmApsam(5m)CpsmApsam(5m)CpsmApsam(5m)CpsmApsam(5m)CpsmApsam(5m)CpsmApsam(5m)CpsmApsam(5m)CpsmApsam(5m)CpsmApsam(5m)CpsmApsa m(5m)CpsmApsam(5m)CpsmApsam(5m)CpsmApsam(5m)CpsmApsam(5m)Cpsmapsam(5m)C-3' | A | B |

FIGURE 6B (continued)

| No. | Compound Structure (5' to 3') | EC$_{50}$ (μM) | CC$_{50}$ (μM) |
|---|---|---|---|
| 391 (SEQ ID NO: 142) | 5'-mApsm(5m)CpsmApscp(5m)CpsmApscp(5m)CpsmApsm(5m)Cpsm Apscp(5m)CpsmApsm(5m)Cpsm Apscp(5m)CpsmApscp(5m)CpsmA psm(5m)CpsmApscp(5m)CpsmApsm(5m)CpsmApsm(5m)CpsmAps cp(5m)CpsmApsm(5m)CpsmApscp(5m)CpsmApscp(5m)C-3' | A | B |
| 392 (SEQ ID NO: 143) | 5'-mApsm(5m)CpsmApsm(5m)CpsmApsm(5m)CpsmApsm(5m)Cpscp Apsm(5m)CpsmApsm(5m)CpsmApsm(5m)CpscpApsm(5m)CpsmAp sm(5m)CpscpApsm(5m)CpsmApsm(5m)CpscpApsm(5m)CpsmAps m(5m)CpsmApsm(5m)CpscpApsm(5m)CpsmApsm(5m)C-3' | B | B |

Potency: A: EC$_{50}$ < 30 nM; B: EC$_{50}$ ≥ 30 nM and EC$_{50}$ < 100 nM; C: EC$_{50}$ ≥ 100 nM and EC$_{50}$ < 300 nM; D: EC$_{50}$ ≥ 300 nM Cytotoxicity: A: CC$_{50}$ > 1000 nM; B: CC$_{50}$ ≤ 1000 nM

FIGURE 6B (continued)
In Figure 6B, the following abbreviations are used, and each is described in Table A.
TABLE A
| Abbreviation | Name | Structure |
|---|---|---|
| A | Adenine | 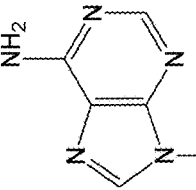 |
| C | Cytosine | 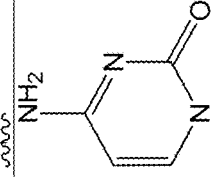 |
| (5m)C | 5-methyl-cytosine | 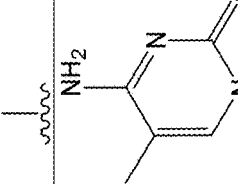 |
| G | Guanine | 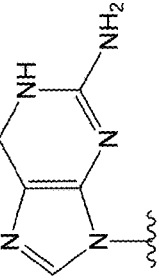 |

FIGURE 6B (continued)
| Abbreviation | Name | Structure |
|---|---|---|
| U | Uracil | 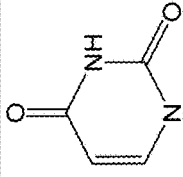 |
| am | AmNA | 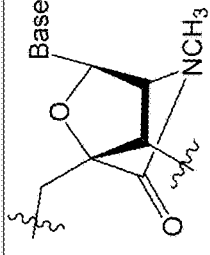 |
| ln | LNA | 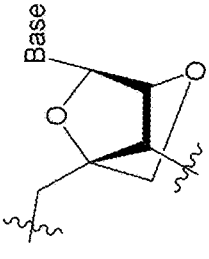 |
| m | 2'-OMe | 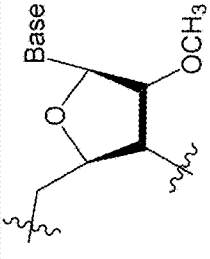 |
| moe | 2'-MOE | 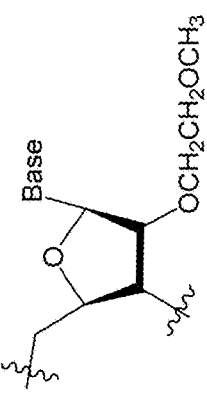 |

FIGURE 6B (continued)

| Abbreviation | Name | Structure |
|---|---|---|
| 3m | 3'-OMe | 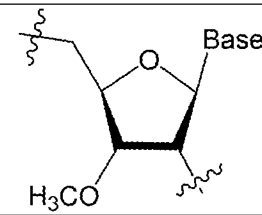 |
| cp | scp-BNA | 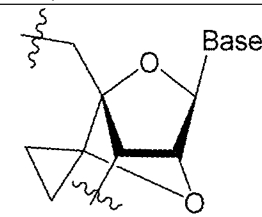 |
| r | RNA | 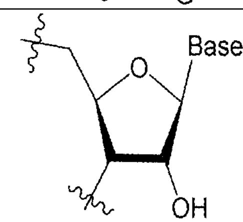 |
| un | acyclic | 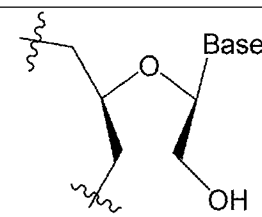 |

FIGURE 6B (continued)

| Abbreviation | Name | Structure |
|---|---|---|
| gn | GNA | 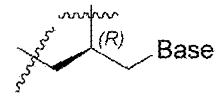 |
| po | Phosphate | |
| ps | Phosphorothioate | |
| psR | Phosphorothioate with (R)-stereochemistry | |
| psS | Phosphorothioate with (S)-stereochemistry | |
| 3'-cholesterol (CHOL) | | 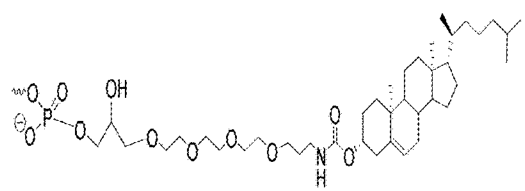 |

FIGURE 6B (continued)

| Abbreviation | Name | Structure |
|---|---|---|
| Cy5 | | 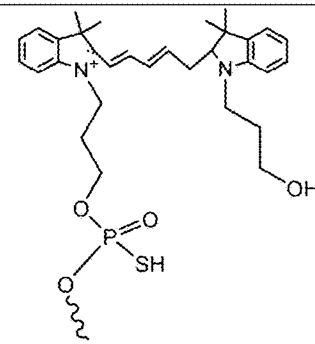 |
| DBLR-ps-c4-CONH-c2 | | 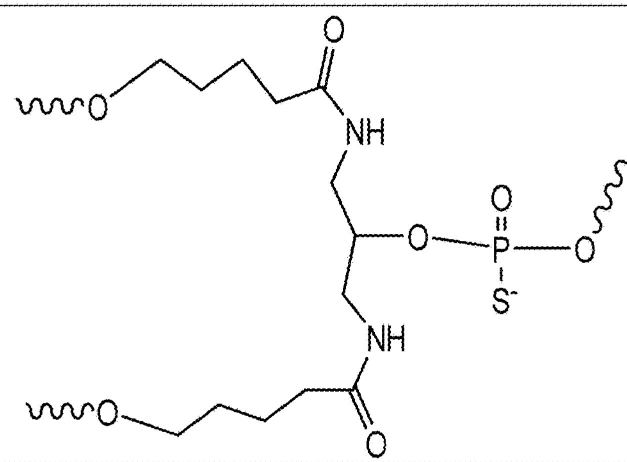 |
| Palmitoyl | | 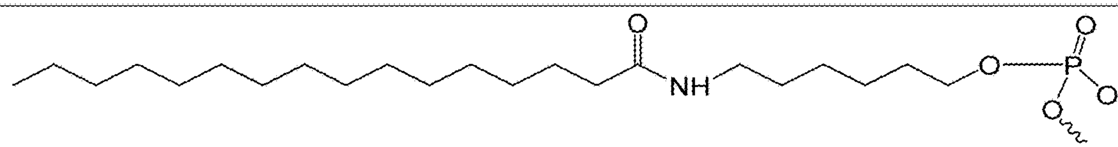 |
| Tocopherol | | 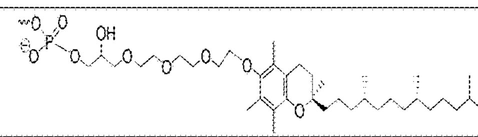 |

FIGURE 6B (continued)

| Abbreviation | Name | Structure |
|---|---|---|
| TREB-ps-c3-O-C3 | | 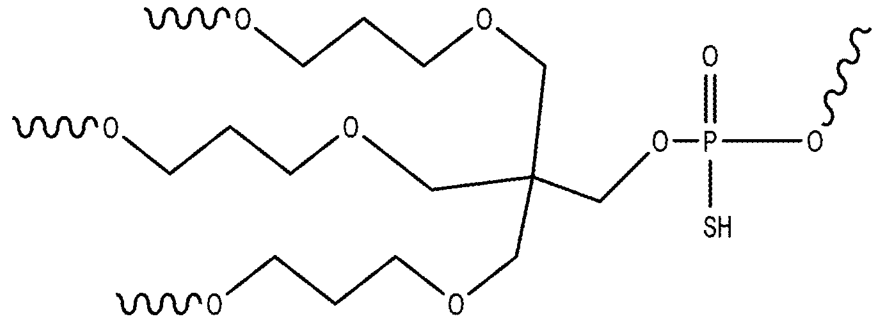 |
| GalNAc5 | | 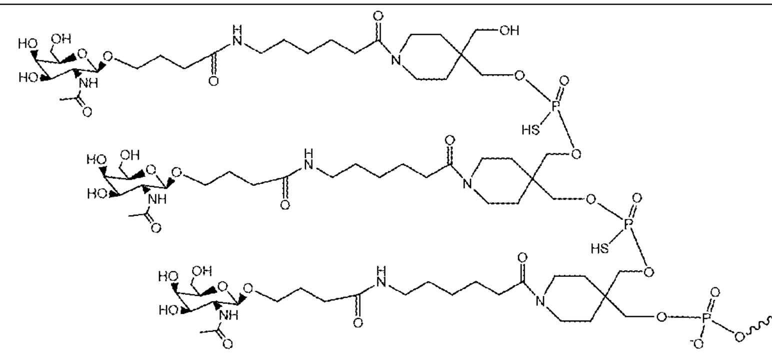 |
| EP | 5'-Ethyl phosphonate endcap | 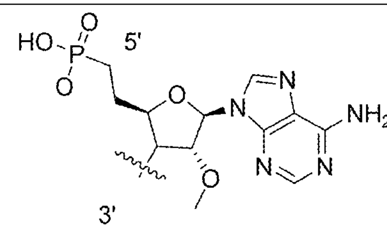 |
| P | | |

FIGURE 6B (continued)

| Abbreviation | Name | Structure |
|---|---|---|
| VP | | 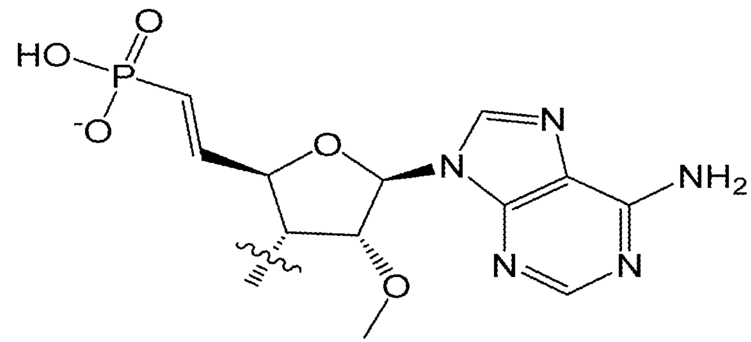 |
| 4'-Me | 4'-Me-2-OMe-A | 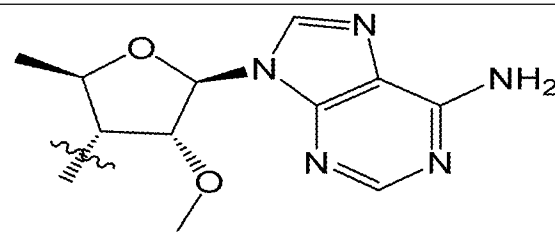 |
| 3cal | 3'-C-allyl-A | 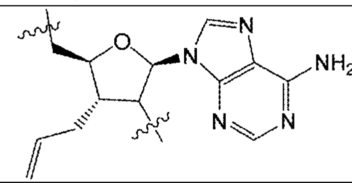 |
| 4etl | | 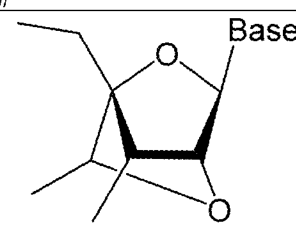 |

For example, using the abbreviations and structures from Table A, one skilled in the art understands that the abbreviation "ln(5m)C" represents the following:

Preparation of ((((E)-2-((2R,3R,4R,5R)-5-(6-benzamido-9H-purin-9-yl)-3-(((2-cyanoethoxy)(diisopropylamino)phosphino)oxy)-4-methoxytetrahydrofuran-2-yl)vinyl)phosphoryl)bis(oxy))bis(methylene) bis(2,2-dimethylpropanoate) (5VP)

FIGURE 9A

Preparation of (2R,3R,4R,5R)-5-(4-benzamido-5-methyl-2-oxopyrimidin-1(2H)-yl)-2-((((R)-(((2R,3R,4R,5R)-5-(6-benzamido-9H-purin-9-yl)-2-((bis(4-methoxyphenyl)(phenyl)methoxy)methyl)-4-methoxytetrahydrofuran-3-yl)oxy)(2-cyanoethoxy)phosphorothioyl)oxy)methyl)-4-methoxytetrahydrofuran-3-yl(2-cyanoethyl)diisopropylphosphoramidite (9R)

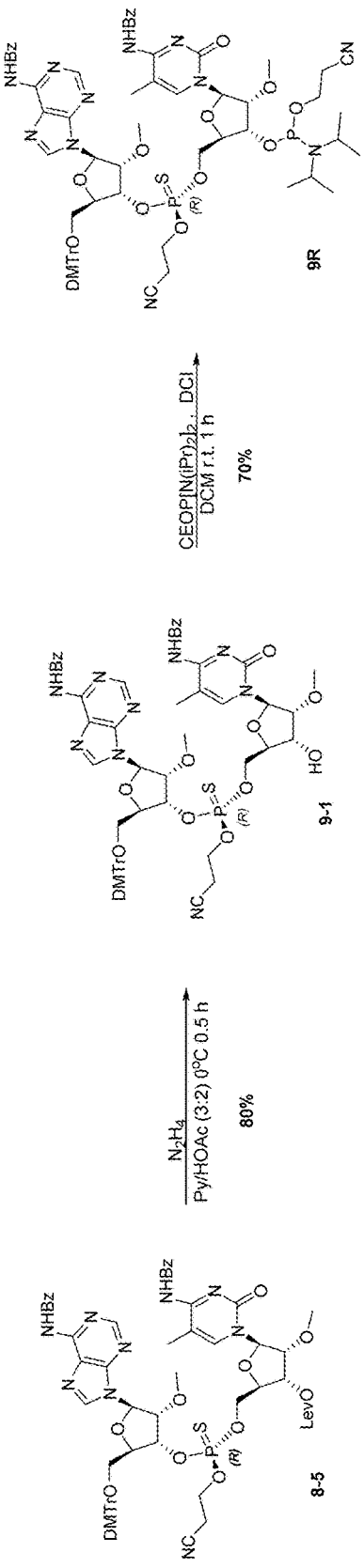

FIGURE 9B

Preparation of (2R,3R,4R,5R)-5-(4-benzamido-5-methyl-2-oxopyrimidin-1(2H)-yl)-2-((((S)-(((2R,3R,4R,5R)-5-(6-benzamido-9H-purin-9-yl)-2-((bis(4-methoxyphenyl)(phenyl)methoxy)methyl)-4-methoxytetrahydrofuran-3-yl)oxy)(2-cyanoethoxy)phosphorothioyl)oxy)methyl)-4-methoxytetrahydrofuran-3-yl(2-cyanoethyl)diisopropylphosphoramidite (9S)

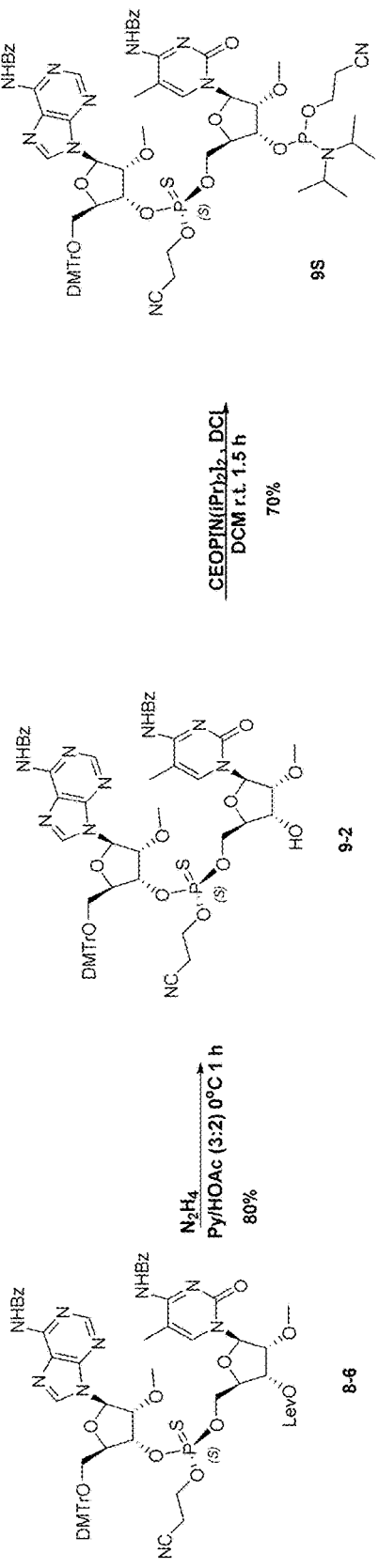

FIGURE 11A

Preparation of (1R,3R,4R,7S)-3-(4-benzamido-5-methyl-2-oxopyrimidin-1(2H)-yl)-1-((((R)-(((2R,3R,4R,5R)-5-(6-benzamido-9H-purin-9-yl)-2-((bis(4-methoxyphenyl)(phenyl)methoxy)methyl)-4-methoxytetrahydrofuran-3-yl)oxy)(2-cyanoethoxy)phosphorothioyl)oxy)methyl)-2,5-dioxabicyclo[2.2.1]heptan-7-yl (2-cyanoethyl) diisopropylphosphoramidite (11R)

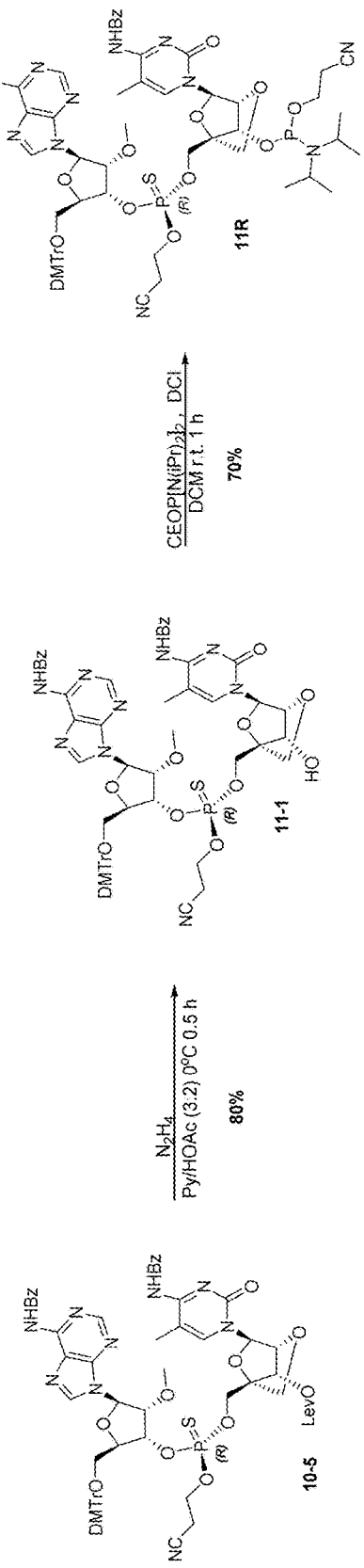

FIGURE 11B

Preparation of (1R,3R,4R,7S)-3-(4-benzamido-5-methyl-2-oxopyrimidin-1(2H)-yl)-1-((((S)-(((2R,3R,4R,5R)-5-(6-benzamido-9H-purin-9-yl)-2-((bis(4-methoxyphenyl)(phenyl)methoxy)methyl)-4-methoxytetrahydrofuran-3-yl)oxy)(2-cyanoethoxy)phosphorothioyl)oxy)methyl)-2,5-dioxabicyclo[2.2.1]heptan-7-yl (2-cyanoethyl) diisopropylphosphoramidite (11S)

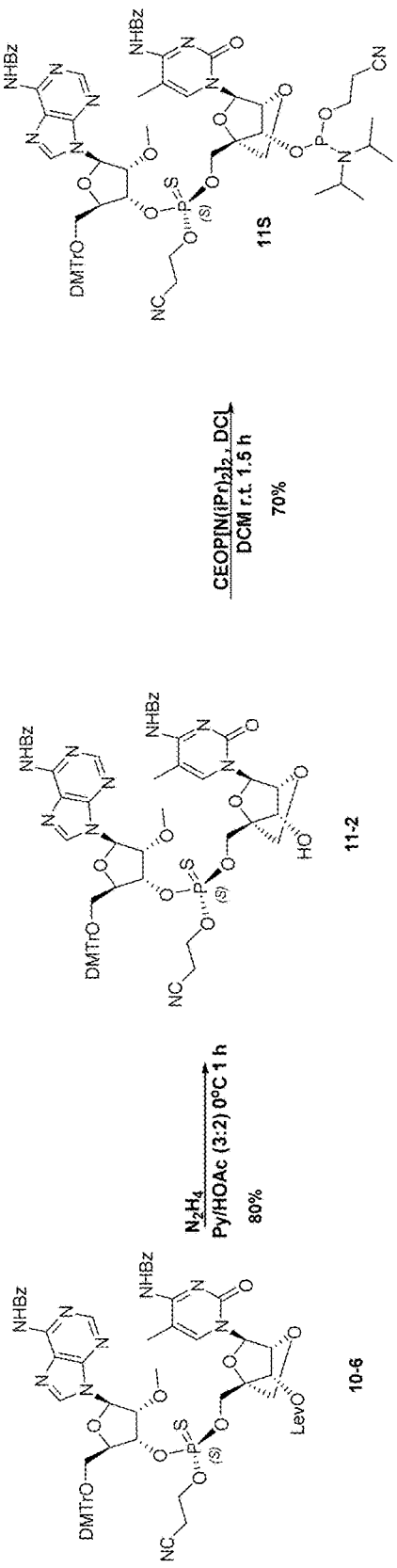

Compound No. 296

Compound Nos. 134, 277, 284

Compound Nos. 167, 289

FIGURE 21 — Compound No. 294

Compound Nos. 276, 291

S-ANTIGEN TRANSPORT INHIBITING OLIGONUCLEOTIDE POLYMERS AND METHODS

RELATED APPLICATION INFORMATION

This application is a continuation-in-part of U.S. Ser. No. 16/676,929, filed Nov. 7, 2019, which claims priority to U.S. Ser. No. 62/757,632, filed Nov. 8, 2018; U.S. Ser. No. 62/855,323, filed May 31, 2019; and to U.S. Ser. No. 62/907,845, filed Sep. 30, 2019. Each of the foregoing is incorporated herein by reference in its entirety.

REFERENCE TO SEQUENCE LISTING

The present application is being filed along with a Sequence Listing in electronic format. The Sequence Listing is provided as a file entitled ALIG008SeqListing2.TXT, which was created and last modified on Jun. 21, 2021 and is 35,293 bytes in size. The information in the electronic Sequence Listing is hereby incorporated by reference in its entirety.

BACKGROUND

Field

This application relates to STOPS™ antiviral compounds that are S-antigen transport inhibiting oligonucleotide polymers, processes for making them and methods of using them to treat diseases and conditions.

Description

The STOPS™ compounds described herein are antiviral oligonucleotides that can be at least partially phosphorothioated and exert their antiviral activity by a non-sequence dependent mode of action. See A. Vaillant, "Nucleic acid polymers: Broad spectrum antiviral activity, antiviral mechanisms and optimization for the treatment of hepatitis B and hepatitis D infection", Antiviral Research 133, 32-40 (2016). The term "Nucleic Acid Polymer" (NAP) has been used in the literature to refer to such oligonucleotides, although that term does not necessarily connote antiviral activity. A number of patent applications filed in the early 2000s disclosed the structures of certain specific compounds and identified various structural options as potential areas for future experimentation. See, e.g., U.S. Pat. Nos. 7,358,068; 8,008,269; 8,008,270 and 8,067,385. These efforts resulted in the identification of the compound known to those skilled in the art as REP 2139, a phosphorothioated 40-mer having repeating adenosine-cytidine (AC) units with 5-methylation of all cytosines and 2'-O methyl modification of all riboses, along with the compound known as its clinical progenitor, REP 2055. See I. Roehl et al., "Nucleic Acid Polymers with Accelerated Plasma and Tissue Clearance for Chronic Hepatitis B Therapy", Molecular Therapy: Nucleic Acids Vol. 8, 1-12 (2017). The authors of that publication indicated that the structural features of these compounds had been optimized for the treatment of hepatitis B (HBV) and hepatitis D (HBD). See also A. Vaillant, "Nucleic acid polymers: Broad spectrum antiviral activity, antiviral mechanisms and optimization for the treatment of hepatitis B and hepatitis D infection", Antiviral Research 133 (2016) 32-40. According to these authors and related literature, such compounds preserve antiviral activity against HBV while preventing recognition by the innate immune response to allow their safe use with immunotherapies such as pegylated interferon. However, there remains a long-felt need for more effective compounds in this class.

SUMMARY

It has now been discovered that, contrary to the teachings in the art regarding the optimum combination of desirable structural features for antiviral compounds, significantly improved properties can be obtained by modifying them to provide STOPS™ compounds as described herein. For example, in some embodiments the sequence independent antiviral activity of the new STOPS™ compounds against HBV, as determined by HBsAg Secretion Assay, is greater than that of a reference compound. In view of the many years of research culminating in the art-recognized optimized structure of REP 2139, there had been little expectation by those skilled in the art that embodiments of the modified STOPS™ compounds described herein would be reasonably likely to display such improvements in potency. Thus, the structures of the new STOPS™ compounds and methods of using them to treat HBV and HBD are surprising and unexpected.

Some embodiments described herein relate to a modified oligonucleotide or complex thereof having sequence independent antiviral activity against hepatitis B, that can include an at least partially phosphorothioated sequence of alternating A and C units, wherein:

the A units comprise one or more selected from:

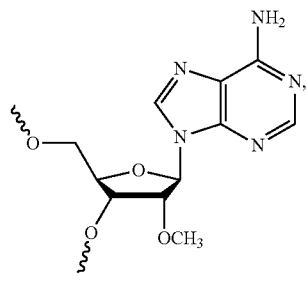

2'-OMe-A

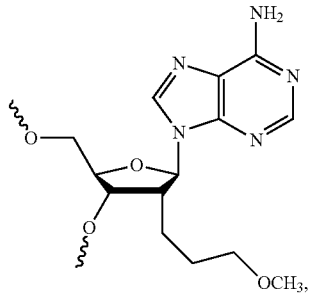

2'-O-MOE-A

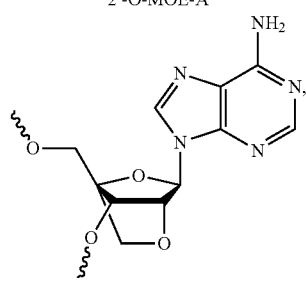

LNA-A

-continued
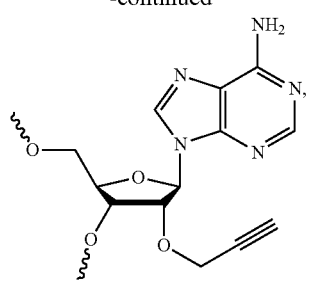
2'-O-Propargyl-A
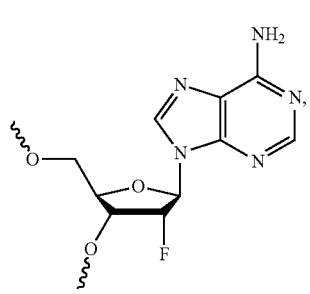
2'-F-A
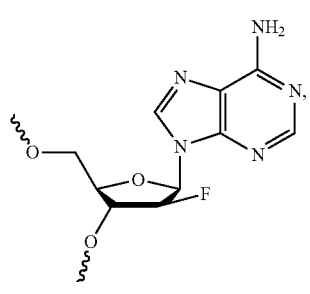
2'-araF-A
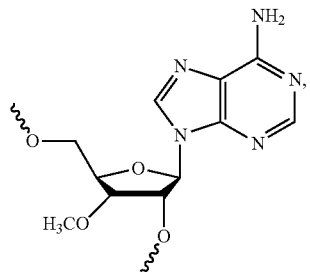
3'-OMe-A
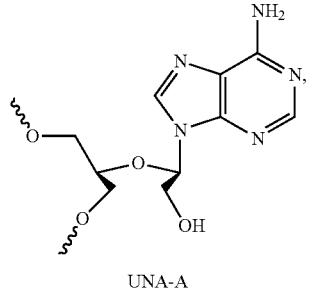
UNA-A
-continued
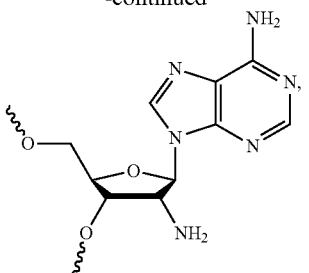
2'-NH$_2$-A
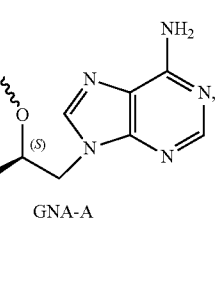
GNA-A
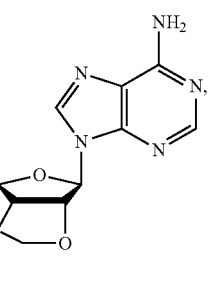
ENA-A
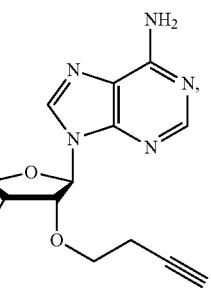
2'-O-Butynyl-A
scp-BNA-A -continued
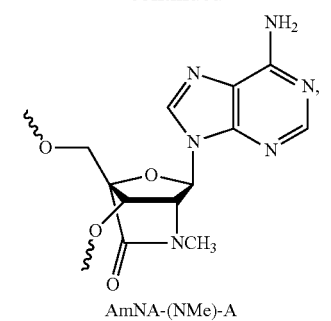
AmNA-(NMe)-A
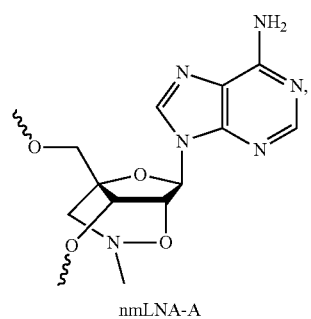
nmLNA-A
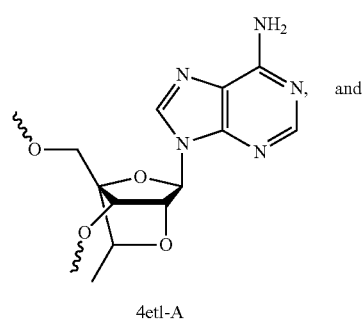
4etl-A
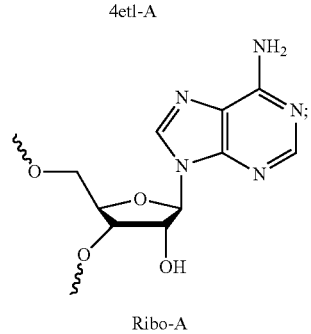
Ribo-A
the C units comprise one or more selected from
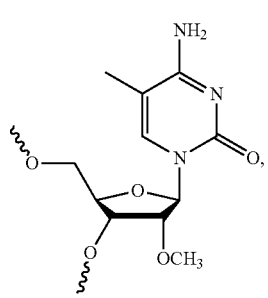
2'-OMe-(5m)C
-continued
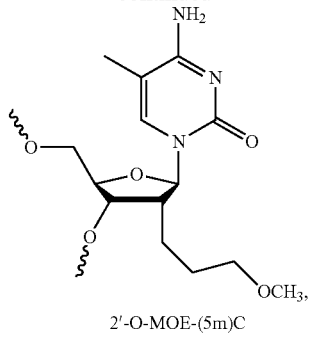
2'-O-MOE-(5m)C
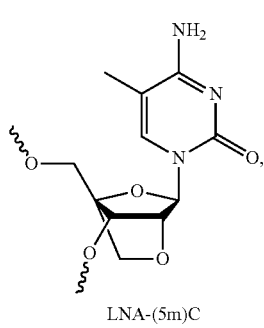
LNA-(5m)C
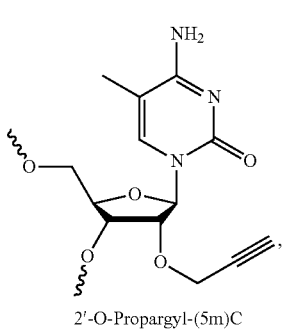
2'-O-Propargyl-(5m)C
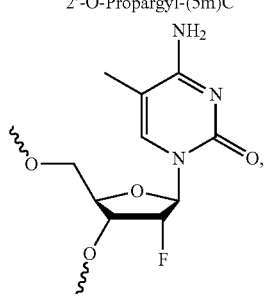
2'-F-(5m)C
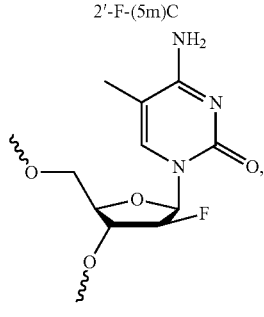
2'-araF-(5m)C

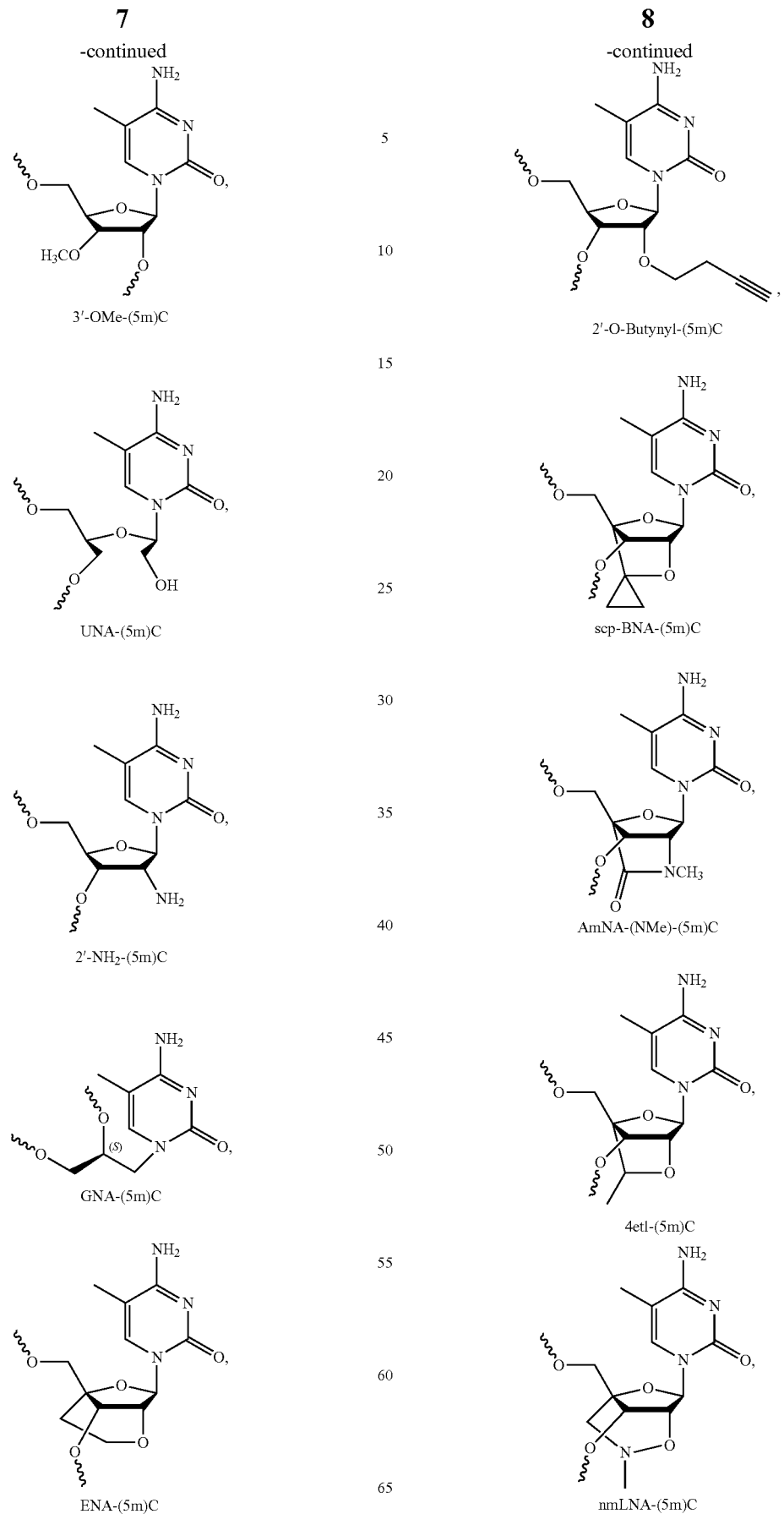

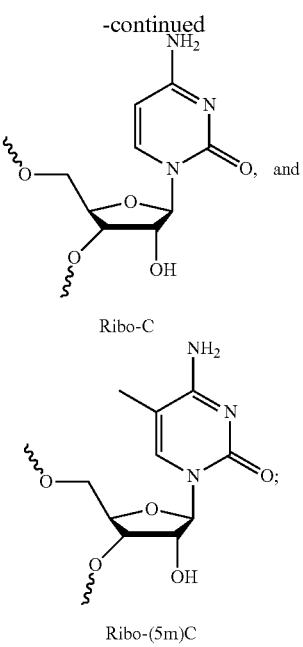

each terminal

is independently hydroxyl, an O,O-dihydrogen phosphorothioate, a dihydrogen phosphate, an endcap or a linking group;

each internal

is a phosphorus-containing linkage to a neighboring A or C unit, the phosphorus-containing linkage being a phosphorothioate linkage or a modified linkage selected from phosphodiester, phosphorodithioate, methylphosphonate, diphosphorothioate, 5'-phosphoramidate, 3',5'-phosphordiamidate, 5'-thiophosphoramidate, 3',5'-thiophosphordiamidate or diphosphodiester; and the sequence independent antiviral activity against hepatitis B, as determined by HBsAg Secretion Assay, is greater than that of a reference compound;

with the proviso that, when the sequence of alternating A and C units comprises a Ribo-A unit, the sequence further comprises at least one A unit that is not a Ribo-A unit; and with the proviso that, when the sequence of alternating A and C units comprises a Ribo-C unit, the sequence further comprises at least one C unit that is not a Ribo-C unit.

Some embodiments described herein relate to a method of treating a HBV and/or HDV infection that can include administering to a subject identified as suffering from the HBV and/or HDV infection an effective amount of a modified oligonucleotide modified oligonucleotide as described herein, or a pharmaceutical composition that includes an effective amount of a modified oligonucleotide as described herein.

Some embodiments disclosed herein relate to a method of inhibiting replication of HBV and/or HDV that can include contacting a cell infected with the HBV and/or HDV with an effective amount of a modified oligonucleotide modified oligonucleotide as described herein, or a pharmaceutical composition that includes an effective amount of a modified oligonucleotide as described herein.

These are other embodiments are described in greater detail below

BRIEF DESCRIPTION OF THE DRAWINGS

FIG. 6A illustrates embodiments of modified oligonucleotides and corresponding values of sequence independent antiviral activity against hepatitis B (as determined by HBsAg Secretion Assay) and cytotoxicity.

FIG. 9A illustrates an embodiment of a reaction scheme for preparing compound 9R.

FIG. 9B illustrates an embodiment of a reaction scheme for preparing compound 9S.

FIG. 11A illustrates an embodiment of a reaction scheme for preparing compound 11R.

FIG. 11B illustrates an embodiment of a reaction scheme for preparing compound 11S.

DETAILED DESCRIPTION

Definitions

Figure 1:
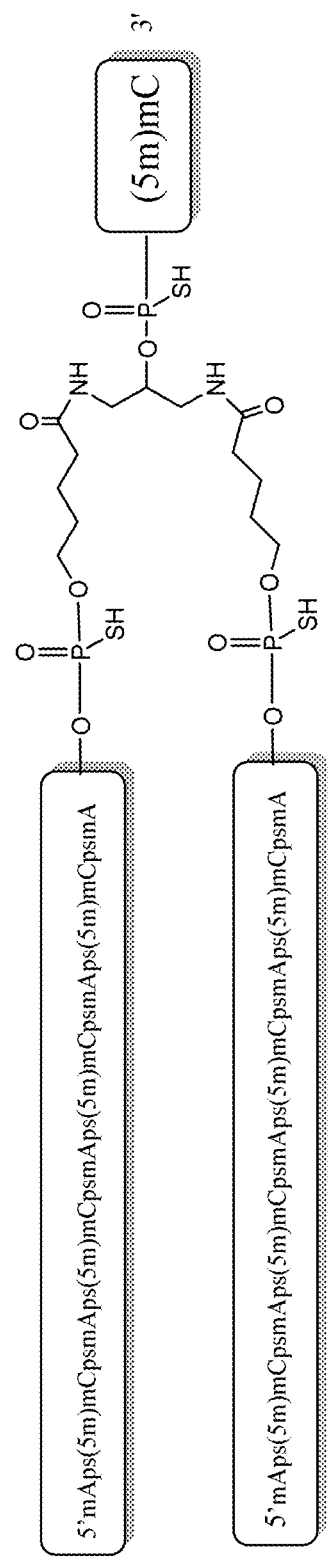
FIG. 1 illustrates an embodiment of a modified oligonucleotide that comprises a $C_{2-6}$alkylene linkage.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The hepatitis B virus (HBV) is a DNA virus and a member of the Hepadnaviridae family. HBV infects more than 300 million worldwide and is a causative agent of liver cancer and liver disease such as chronic hepatitis, cirrhosis, and hepatocellular carcinoma. HBV can be acute and/or chronic. Acute HBV infection can be either asymptomatic or present with symptomatic acute hepatitis. HBV is classified into eight genotypes, A to H.

HBV is a partially double-stranded circular DNA of about 3.2 kilobase (kb) pairs. The HBV replication pathway has been studied in great detail. T. J. Liang, *Heptaology* (2009) 49(5 Suppl): S13-S21. One part of replication includes the formation of the covalently closed circular (cccDNA) form. The presence of the cccDNA gives rise to the risk of viral reemergence throughout the life of the host organism. HBV carriers can transmit the disease for many years. An estimated 257 million people are living with hepatitis B virus infection, and it is estimated that over 750,000 people worldwide die of hepatitis B each year. In addition, immunosuppressed individuals or individuals undergoing chemotherapy are especially at risk for reactivation of an HBV infection.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure an HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

As used herein in the context of oligonucleotides or other materials, the term "antiviral" has its usual meaning as understood by those skilled in the art and thus includes an effect of the presence of the oligonucleotides or other material that inhibits production of viral particles, typically by reducing the number of infectious viral particles formed in a system otherwise suitable for formation of infectious viral particles for at least one virus. In certain embodiments, the antiviral oligonucleotide has antiviral activity against multiple different virus, e.g., both HBV and HDV.

As used herein the term "oligonucleotide" (or "oligo") has its usual meaning as understood by those skilled in the art and thus refers to a class of compounds that includes oligodeoxynucleotides, oligodeoxyribonucleotides and oligoribonucleotides. Thus, "oligonucleotide" refers to an oligomer or polymer of ribonucleic acid (RNA) or deoxyribonucleic acid (DNA) or mimetics thereof, including reference to oligonucleotides composed of naturally-occurring nucleobases, sugars and phosphodiester (PO) internucleoside (backbone) linkages as well as "modified" or substituted oligonucleotides having non-naturally-occurring portions which function similarly. Thus, the term "modified" (or "substituted") oligonucleotide has its usual meaning as understood by those skilled in the art and includes oligonucleotides having one or more of various modifications, e.g., stabilizing modifications, and thus can include at least one modification in the internucleoside linkage and/or on the ribose, and/or on the base. For example, a modified oligonucleotide can include modifications at the 2'-position of the ribose, acyclic nucleotide analogs, methylation of the base, phosphorothioated (PS) linkages, phosphorodithioate linkages, methylphosphonate linkages, linkages that connect to the sugar ring via sulfur or nitrogen, and/or other modifications as described elsewhere herein. Thus, a modified oligonucleotide can include one or more phosphorothioated (PS) linkages, instead of or in addition to PO linkages. Like unmodified oligonucleotides, modified oligonucleotides that include such PS linkages are considered to be in the same class of compounds because even though the PS linkage contains a phosphorous-sulfur double bond instead of the phosphorous-oxygen double bond of a PO linkage, both PS and PO linkages connect to the sugar rings through oxygen atoms.

As used herein in the context of modified oligonucleotides, the term "phosphorothioated" oligonucleotide has its usual meaning as understood by those skilled in the art and thus refers to a modified oligonucleotide in which all of the phosphodiester internucleoside linkages have been replaced by phosphorothioate linkages. Those skilled in the art thus understand that the term "phosphorothioated" oligonucleotide is synonymous with "fully phosphorothioated" oligonucleotide. A phosphorothioated oligonucleotide (or a sequence of phosphorothioated oligonucleotides within a partially phosphorothioated oligonucleotide) can be modified analogously, including (for example) by replacing one or more phosphorothioated internucleoside linkages by phosphodiester linkages. Thus, the term "modified phosphorothioated" oligonucleotide refers to a phosphorothioated oligonucleotide that has been modified in the manner analogous to that described herein with respect to oligonucleotides, e.g., by replacing a phosphorothioated linkage with a modified linkage such as phosphodiester, phosphorodithioate, methylphosphonate, diphosphorothioate, 5'-phosphoramidate, 3',5'-phosphordiamidate, 5'-thiophosphoramidate, 3',5'-thiophosphordiamidate or diphosphodiester. An at least partially phosphorothioated sequence of a modified oligonucleotide can be modified similarly, and thus, for example, can be modified to contain a non-phosphorothioated linkage such as phosphodiester, phosphorodithioate, methylphosphonate, diphosphorothioate 5'-phosphoramidate, 3',5'-phosphordiamidate, 5'-thiophosphoramidate, 3',5'-thiophosphordiamidate or diphosphodiester. In the context of describing modifications to a phosphorothioated oligonucleotide, or to an at least partially phosphorothioated sequence of a modified oligonucleotide, modification by inclusion of a phosphodiester linkage may be considered to result in a modified phosphorothioated oligonucleotide, or to a modified phosphorothioated sequence, respectively. Analogously, in the context of describing modifications to an oligonucleotide, or to an at least partially phosphodiesterified sequence of a modified oligonucleotide, the inclusion of a phosphorothioated linkage may be considered to result in a modified oligonucleotide or a modified phosphodiesterified sequence, respectively.

As used herein in the context of dinucleotides or oligonucleotides, the term "stereochemically defined phosphorothioate linkage" has its usual meaning as understood by those skilled in the art and thus refers to a phosphorothioate linkage having a phosphorus stereocenter with a selected chirality (R or S configuration). A composition containing such a dinucleotide or oligonucleotide can be enriched in molecules having the selected chirality. The stereopurity of such a composition can vary over a broad range, e.g. from about 51% to about 100% stereopure. In various embodiments, the stereopurity is greater than 55%, 65%, 75%, 85%, 90%, 91%, 92%, 93%, 94%, 95%, 96%, 97%, 98%, or 99%; or in a range defined as having any two of the foregoing stereopurity values as endpoints.

The term "sequence independent" antiviral activity has its usual meaning as understood by those skilled in the art and thus refers to an antiviral activity of an oligonucleotide (e.g., a modified oligonucleotide) that is independent of the sequence of the oligonucleotide. Methods for determining whether the antiviral activity of an oligonucleotide is sequence independent are known to those skilled in the art and include the tests for determining if an oligonucleotide acts predominantly by a non-sequence complementary mode of action as disclosed in Example 10 of U.S. Pat. Nos. 7,358,068; 8,008,269; 8,008,270 and 8,067,385, which is hereby incorporated herein by reference and particularly for the purpose of describing such tests.

In the context of describing modified oligonucleotides having sequence independent antiviral activity and comprising a sequence (e.g., an at least partially phosphorothioated sequence) of A and C units (e.g., alternating A and C units, or AC units), the terms "A" and "C" refer to the modified adenosine-containing (A) units and modified cystosine-containing (C) units set forth in Tables 1 and 2 below, respectively.

TABLE 1

"A" UNITS

| Abbreviation (A Unit) | Structure (A Unit) |
|---|---|
| 2'-OMe-A | |
| 2'-O-MOE-A | |
| LNA-A | |
| 2'-O-Propargyl-A | |
| 2'-F-A | |

TABLE 1-continued
"A" UNITS
| Abbreviation (A Unit) | Structure (A Unit) |
|---|---|
| 2'-araF-A | 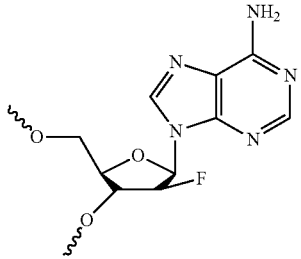 |
| 3'-OMe-A | 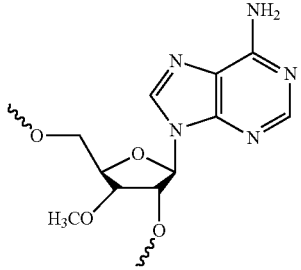 |
| UNA-A | 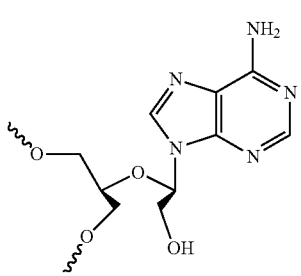 |
| 2'-NH$_2$-A | 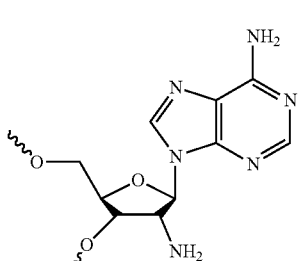 |
| GNA-A | 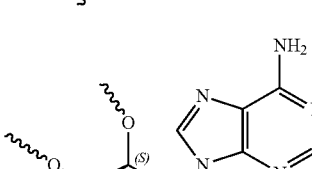 |
| ENA-A | 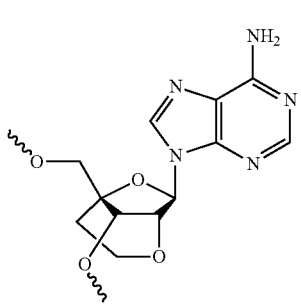 |
| 2'-O-Butynyl-A | 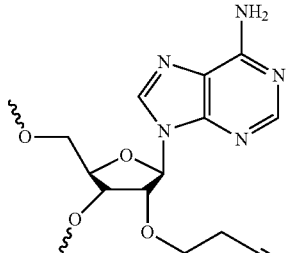 |
| scp-BNA-A | 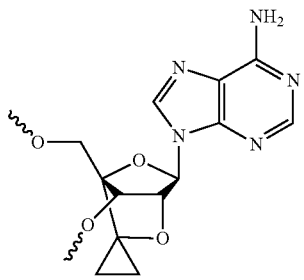 |
| AmNA(NMe)-A | 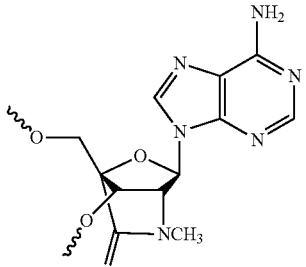 |
| nmLNA-A | 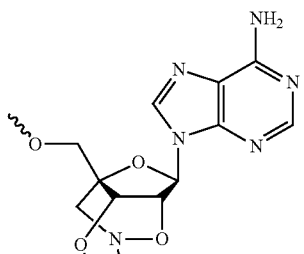 |
| 4etl-A | 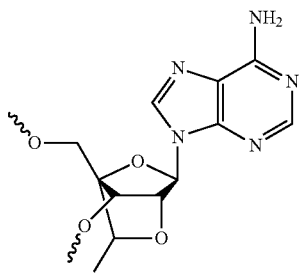 |

TABLE 1-continued
| "A" UNITS | |
|---|---|
| Abbreviation (A Unit) | Structure (A Unit) |
| Ribo-A | 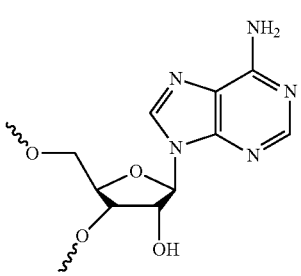 |
TABLE 2
| "C" UNITS | |
|---|---|
| Abbreviation (C Unit) | Structure (C Unit) |
| 2'-OMe-(5m)C | 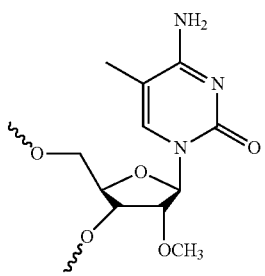 |
| 2'-O-MOE-(5m)C | 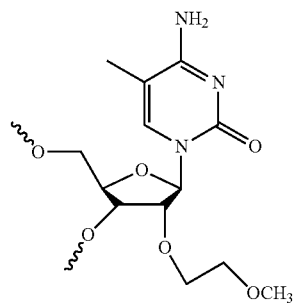 |
| LNA-(5m)C | 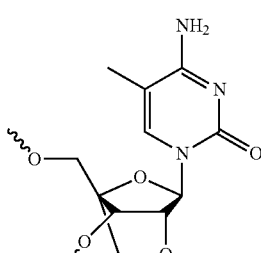 LNA-5mC |
TABLE 2-continued
| "C" UNITS | |
|---|---|
| Abbreviation (C Unit) | Structure (C Unit) |
| 2'-O-Propargyl-(5m)C | 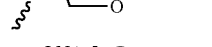 |
| 2'-F-(5m)C | 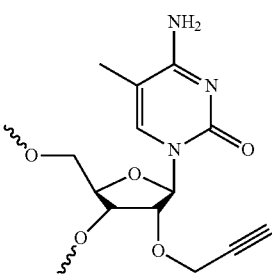 |
| 2'-araF-(5m)C | 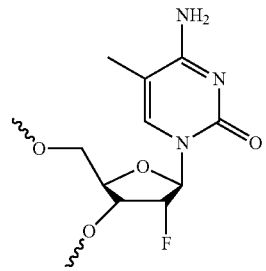 |
| 3'-OMe-(5m)C | 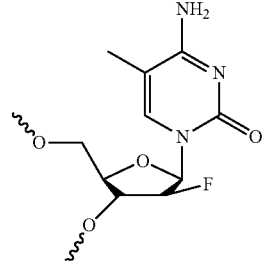 |
| UNA-(5m)C | 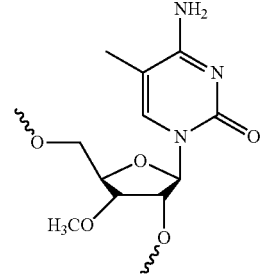 |

TABLE 2-continued
"C" UNITS
| Abbreviation (C Unit) | Structure (C Unit) |
|---|---|
| 2'-NH$_2$-(5m)C | 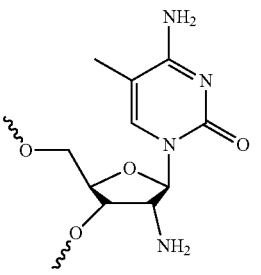 |
| GNA-(5m)C | 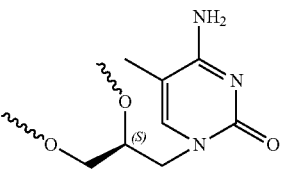 |
| ENA-(5m)C | 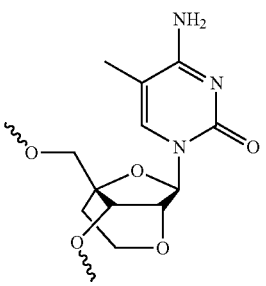 |
| 2'-O-Butynyl-(5m)C | 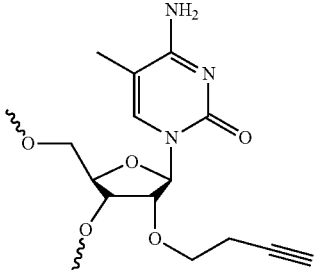 |
| scp-BNA-(5m)C | 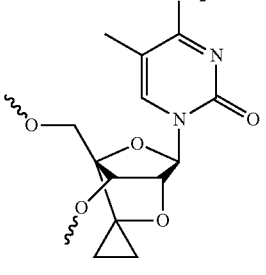 |
| AmNA-(NMe)-(5m)C | 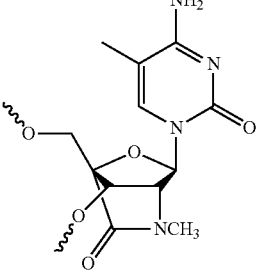 |
| 4etl-(5m)C | 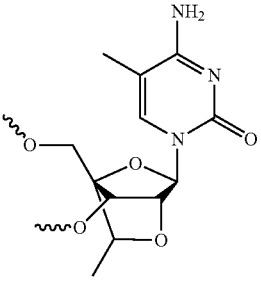 |
| nmLNA-(5m)C | 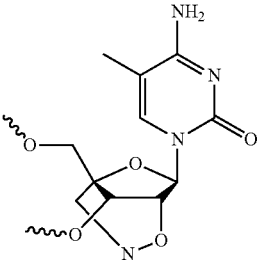 |
| Ribo-C | 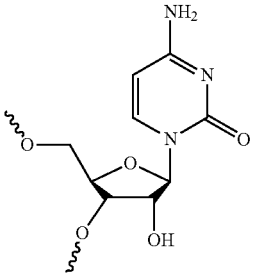 |
| Ribo-(5m)C | 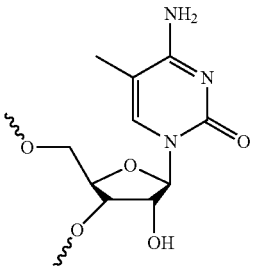 |
Modified Oligonucleotide Compounds
An embodiment provides a STOPS™ modified oligonucleotide compound having sequence independent antiviral activity against hepatitis B, comprising an at least partially phosphorothioated sequence of alternating A and C units, wherein the A units are any one or more selected from those set forth in Table 1 and the C units are any one or more selected from those set forth in Table 2. Various combinations of A and C units can be included in the at least partially phosphorothioated AC sequence, including the combinations described in Table 3 below.

TABLE 3

EXAMPLES OF AC UNITS

| No. | A Unit | C Unit |
|---|---|---|
| 1 | 2'-OMe-A | 2'-OMe-(5m)C |
| 2 | 2'-OMe-A | 2'-O-MOE-(5m)C |
| 3 | 2'-OMe-A | LNA-(5m)C |
| 4 | 2'-OMe-A | ENA-(5m)C |
| 5 | 2'-OMe-A | scp-BNA-(5m)C |
| 6 | 2'-OMe-A | AmNA-(NMe)-(5m)C |
| 7 | 2'-OMe-A | 2'-O-Propargyl-(5m)C |
| 8 | 2'-OMe-A | 2'-O-Butynyl-(5m)C |
| 9 | 2'-OMe-A | 2'-F-(5m)C |
| 10 | 2'-OMe-A | 2'-araF-(5m)C |
| 11 | 2'-OMe-A | 3'-OMe-(5m)C |
| 12 | 2'-OMe-A | UNA-(5m)C |
| 13 | 2'-OMe-A | 2'-NH$_2$-(5m)C |
| 14 | 2'-OMe-A | GNA-(5m)C |
| 15 | 2'-OMe-A | 4etl-(5m)C |
| 16 | 2'-OMe-A | nmLNA-(5m)C |
| 17 | 2'-O-MOE-A | 2'-OMe-(5m)C |
| 18 | 2'-O-MOE-A | 2'-O-MOE-(5m)C |
| 19 | 2'-O-MOE-A | LNA-(5m)C |
| 20 | 2'-O-MOE-A | ENA-(5m)C |
| 21 | 2'-O-MOE-A | scp-BNA-(5m)C |
| 22 | 2'-O-MOE-A | AmNA-(NMe)-(5m)C |
| 23 | 2'-O-MOE-A | 2'-O-Propargyl-(5m)C |
| 24 | 2'-O-MOE-A | 2'-O-Butynyl-(5m)C |
| 25 | 2'-O-MOE-A | 2'-F-(5m)C |
| 26 | 2'-O-MOE-A | 2'-araF-(5m)C |
| 27 | 2'-O-MOE-A | 3'-OMe-(5m)C |
| 28 | 2'-O-MOE-A | UNA-(5m)C |
| 29 | 2'-O-MOE-A | 2'-NH$_2$-(5m)C |
| 30 | 2'-O-MOE-A | GNA-(5m)C |
| 31 | 2'-O-MOE-A | 4etl-(5m)C |
| 32 | 2'-O-MOE-A | nmLNA-(5m)C |
| 33 | LNA-A | 2'-OMe-(5m)C |
| 34 | LNA-A | 2'-O-MOE-(5m)C |
| 35 | LNA-A | LNA-(5m)C |
| 36 | LNA-A | ENA-(5m)C |
| 37 | LNA-A | scp-BNA-(5m)C |
| 38 | LNA-A | AmNA-(NMe)-(5m)C |
| 39 | LNA-A | 2'-O-Propargyl-(5m)C |
| 40 | LNA-A | 2'-O-Butynyl-(5m)C |
| 41 | LNA-A | 2'-F-(5m)C |
| 42 | LNA-A | 2'-araF-(5m)C |
| 43 | LNA-A | 3'-OMe-(5m)C |
| 44 | LNA-A | UNA-(5m)C |
| 45 | LNA-A | 2'-NH$_2$-(5m)C |
| 46 | LNA-A | GNA-(5m)C |
| 47 | LNA-A | 4etl-(5m)C |
| 48 | LNA-A | nmLNA-(5m)C |
| 49 | ENA-A | 2'-OMe-(5m)C |
| 50 | ENA-A | 2'-O-MOE-(5m)C |
| 51 | ENA-A | LNA-(5m)C |
| 52 | ENA-A | ENA-(5m)C |
| 53 | ENA-A | scp-BNA-(5m)C |
| 54 | ENA-A | AmNA-(NMe)-(5m)C |
| 55 | ENA-A | 2'-O-Propargyl-(5m)C |
| 56 | ENA-A | 2'-O-Butynyl-(5m)C |
| 57 | ENA-A | 2'-F-(5m)C |
| 58 | ENA-A | 2'-araF-(5m)C |
| 59 | ENA-A | 3'-OMe-(5m)C |
| 60 | ENA-A | UNA-(5m)C |
| 61 | ENA-A | 2'-NH$_2$-(5m)C |
| 62 | ENA-A | GNA-(5m)C |
| 63 | ENA-A | 4etl-(5m)C |
| 64 | ENA-A | nmLNA-(5m)C |
| 65 | scp-BNA-A | 2'-OMe-(5m)C |
| 66 | scp-BNA-A | 2'-O-MOE-(5m)C |
| 67 | scp-BNA-A | LNA-(5m)C |
| 68 | scp-BNA-A | ENA-(5m)C |
| 69 | scp-BNA-A | scp-BNA-(5m)C |
| 70 | scp-BNA-A | AmNA-(NMe)-(5m)C |
| 71 | scp-BNA-A | 2'-O-Propargyl-(5m)C |
| 72 | scp-BNA-A | 2'-O-Butynyl-(5m)C |
| 73 | scp-BNA-A | 2'-F-(5m)C |
| 74 | scp-BNA-A | 2'-araF-(5m)C |
| 75 | scp-BNA-A | 3'-OMe-(5m)C |
| 76 | scp-BNA-A | UNA-(5m)C |
| 77 | scp-BNA-A | 2'-NH$_2$-(5m)C |
| 78 | scp-BNA-A | GNA-(5m)C |
| 79 | scp-BNA-A | 4etl-(5m)C |
| 80 | scp-BNA-A | nmLNA-(5m)C |
| 81 | AmNA(N-Me)-A | 2'-OMe-(5m)C |
| 82 | AmNA(N-Me)-A | 2'-O-MOE-(5m)C |
| 83 | AmNA(N-Me)-A | LNA-(5m)C |
| 84 | AmNA(N-Me)-A | ENA-(5m)C |
| 85 | AmNA(N-Me)-A | scp-BNA-(5m)C |
| 86 | AmNA(N-Me)-A | AmNA-(NMe)-(5m)C |
| 87 | AmNA(N-Me)-A | 2'-O-Propargyl-(5m)C |
| 88 | AmNA(N-Me)-A | 2'-O-Butynyl-(5m)C |
| 89 | AmNA(N-Me)-A | 2'-F-(5m)C |
| 90 | AmNA(N-Me)-A | 2'-ara-F-(5m)C |
| 91 | AmNA(N-Me)-A | 3'-OMe-(5m)C |
| 92 | AmNA(N-Me)-A | UNA-(5m)C |
| 93 | AmNA(N-Me)-A | 2'-NH$_2$-(5m)C |
| 94 | AmNA(N-Me)-A | GNA-(5m)C |
| 95 | AmNA(N-Me)-A | 4etl-(5m)C |
| 96 | AmNA(N-Me)-A | nmLNA-(5m)C |
| 97 | 2'-O-Propargyl-A | 2'-OMe-(5m)C |
| 98 | 2'-O-Propargyl-A | 2'-O-MOE-(5m)C |
| 99 | 2'-O-Propargyl-A | LNA-(5m)C |
| 100 | 2'-O-Propargyl-A | ENA-(5m)C |
| 101 | 2'-O-Propargyl-A | scp-BNA-(5m)C |
| 102 | 2'-O-Propargyl-A | AmNA-(NMe)-(5m)C |
| 103 | 2'-O-Propargyl-A | 2'-O-Propargyl-(5m)C |
| 104 | 2'-O-Propargyl-A | 2'-O-Butyne-(5m)C |
| 105 | 2'-O-Propargyl-A | 2'-F-(5m)C |
| 106 | 2'-O-Propargyl-A | 2'-araF-(5m)C |
| 107 | 2'-O-Propargyl-A | 3'-OMe-(5m)C |
| 108 | 2'-O-Propargyl-A | UNA-(5m)C |
| 109 | 2'-O-Propargyl-A | 2'-NH$_2$-(5m)C |
| 110 | 2'-O-Propargyl-A | GNA-(5m)C |
| 111 | 2'-O-Propargyl-A | 4etl-(5m)C |
| 112 | 2'-O-Propargyl-A | nmLNA-(5m)C |
| 113 | 2'-O-Butynyl-A | 2'-OMe-(5m)C |
| 114 | 2'-O-Butynyl-A | 2'-O-MOE-(5m)C |
| 115 | 2'-O-Butynyl-A | LNA-(5m)C |
| 116 | 2'-O-Butynyl-A | ENA-(5m)C |
| 117 | 2'-O-Butynyl-A | scp-BNA-(5m)C |
| 118 | 2'-O-Butynyl-A | AmNA-(NMe)-(5m)C |
| 119 | 2'-O-Butynyl-A | 2'-O-Propargyl-(5m)C |
| 120 | 2'-O-Butynyl-A | 2'-O-Butynyl-(5m)C |
| 121 | 2'-O-Butynyl-A | 2'-F-(5m)C |
| 122 | 2'-O-Butynyl-A | 2'-araF-(5m)C |
| 123 | 2'-O-Butynyl-A | 3'-OMe-(5m)C |
| 124 | 2'-O-Butynyl-A | UNA-(5m)C |
| 125 | 2'-O-Butynyl-A | 2'-NH$_2$-(5m)C |
| 126 | 2'-O-Butynyl-A | GNA-(5m)C |
| 127 | 2'-O-Butynyl-A | 4etl-(5m)C |
| 128 | 2'-O-Butynyl-A | nmLNA-(5m)C |
| 129 | 2'-F A | 2'-OMe-(5m)C |
| 130 | 2'-F A | 2'-O-MOE-(5m)C |
| 131 | 2'-F A | LNA-(5m)C |
| 132 | 2'-F A | ENA-(5m)C |
| 133 | 2'-F A | scp-BNA-(5m)C |
| 134 | 2'-F A | AmNA-(NMe)-(5m)C |
| 135 | 2'-F A | 2'-O-Propargyl-(5m)C |
| 136 | 2'-F A | 2'-O-Butynyl-(5m)C |
| 137 | 2'-F A | 2'-F-(5m)C |
| 138 | 2'-F A | 2'-ara-F-(5m)C |
| 139 | 2'-F A | 3'-OMe-(5m)C |
| 140 | 2'-F A | UNA-(5m)C |
| 141 | 2'-F A | 2'-NH$_2$-(5m)C |
| 142 | 2'-F A | GNA-(5m)C |

TABLE 3-continued

EXAMPLES OF AC UNITS

| No. | A Unit | C Unit |
|---|---|---|
| 143 | 2'-F A | 4etl-(5m)C |
| 144 | 2'-F A | nmLNA-(5m)C |
| 145 | 2'-araF A | 2'-OMe-(5m)C |
| 146 | 2'-araF A | 2'-O-MOE-(5m)C |
| 147 | 2'-araF A | LNA-(5m)C |
| 148 | 2'-araF A | ENA-(5m)C |
| 149 | 2'-araF A | scp-BNA-(5m)C |
| 150 | 2'-araF A | AmNA-(NMe)-(5m)C |
| 151 | 2'-araF A | 2'-O-Propargyl-(5m)C |
| 152 | 2'-araF A | 2'-O-Butynyl-(5m)C |
| 153 | 2'-araF A | 2'-F-(5m)C |
| 154 | 2'-araF A | 2'-araF-(5m)C |
| 155 | 2'-araF A | 3'-OMe-(5m)C |
| 159 | 2'-araF A | UNA-(5m)C |
| 157 | 2'-araF A | 2'-NH$_2$-(5m)C |
| 158 | 2'-araF A | GNA-(5m)C |
| 159 | 2'-araF A | 4etl-(5m)C |
| 160 | 2'-araF A | nmLNA-(5m)C |
| 161 | 3'-OMe-A | 2'-OMe-(5m)C |
| 162 | 3'-OMe-A | 2'-O-MOE-(5m)C |
| 163 | 3'-OMe-A | LNA-(5m)C |
| 164 | 3'-OMe-A | ENA-(5m)C |
| 165 | 3'-OMe-A | scp-BNA-(5m)C |
| 166 | 3'-OMe-A | AmNA-(NMe)-(5m)C |
| 167 | 3'-OMe-A | 2'-O-Propargyl-(5m)C |
| 168 | 3'-OMe-A | 2'-O-Butynyl-(5m)C |
| 169 | 3'-OMe-A | 2'-F-(5m)C |
| 170 | 3'-OMe-A | 2'-ara-F-(5m)C |
| 171 | 3'-OMe-A | 3'-OMe-(5m)C |
| 172 | 3'-OMe-A | UNA-(5m)C |
| 173 | 3'-OMe-A | 2'-NH$_2$-(5m)C |
| 174 | 3'-OMe-A | GNA-(5m)C |
| 175 | 3'-OMe-A | 4etl-(5m)C |
| 176 | 3'-OMe-A | nmLNA-(5m)C |
| 177 | UNA-A | 2'-OMe-(5m)C |
| 178 | UNA-A | 2'-O-MOE-(5m)C |
| 179 | UNA-A | LNA-(5m)C |
| 180 | UNA-A | ENA-(5m)C |
| 181 | UNA-A | scp-BNA-(5m)C |
| 182 | UNA-A | AmNA-(NMe)-(5m)C |
| 183 | UNA-A | 2'-O-Propargyl-(5m)C |
| 184 | UNA-A | 2'-O-Butynyl-(5m)C |
| 185 | UNA-A | 2'-F-(5m)C |
| 186 | UNA-A | 2'-araF-(5m)C |
| 187 | UNA-A | 3'-OMe-(5m)C |
| 188 | UNA-A | UNA-(5m)C |
| 189 | UNA-A | 2'-NH$_2$-(5m)C |
| 190 | UNA-A | GNA-(5m)C |
| 191 | UNA-A | 4etl-(5m)C |
| 192 | UNA-A | nmLNA-(5m)C |
| 193 | 2'-NH$_2$-A | 2'-OMe-(5m)C |
| 194 | 2'-NH$_2$-A | 2'-O-MOE-(5m)C |
| 195 | 2'-NH$_2$-A | LNA-(5m)C |
| 196 | 2'-NH$_2$-A | ENA-(5m)C |
| 197 | 2'-NH$_2$-A | scp-BNA-(5m)C |
| 198 | 2'-NH$_2$-A | AmNA-(NMe)-(5m)C |
| 199 | 2'-NH$_2$-A | 2'-O-Propargyl-(5m)C |
| 200 | 2'-NH$_2$-A | 2'-O-Butynyl-(5m)C |
| 201 | 2'-NH$_2$-A | 2'-F-(5m)C |
| 202 | 2'-NH$_2$-A | 2'-ara-F-(5m)C |
| 203 | 2'-NH$_2$-A | 3'-OMe-(5m)C |
| 204 | 2'-NH$_2$-A | UNA-(5m)C |
| 205 | 2'-NH$_2$-A | 2'-NH$_2$-(5m)C |
| 206 | 2'-NH$_2$-A | GNA-(5m)C |
| 207 | 2'-NH$_2$-A | 4etl-(5m)C |
| 208 | 2'-NH$_2$-A | nmLNA-(5m)C |
| 209 | GNA-A | 2'-OMe-(5m)C |
| 210 | GNA-A | 2'-O-MOE-(5m)C |
| 211 | GNA-A | LNA-(5m)C |
| 212 | GNA-A | ENA-(5m)C |
| 213 | GNA-A | scp-BNA-(5m)C |
| 214 | GNA-A | AmNA-(NMe)-(5m)C |
| 215 | GNA-A | 2'-O-Propargyl-(5m)C |
| 216 | GNA-A | 2'-O-Butynyl-(5m)C |
| 217 | GNA-A | 2'-F-(5m)C |
| 218 | GNA-A | 2'-ara-F-(5m)C |
| 219 | GNA-A | 3'-OMe-(5m)C |
| 220 | GNA-A | UNA-(5m)C |
| 221 | GNA-A | 2'-NH$_2$-(5m)C |
| 222 | GNA-A | GNA-(5m)C |
| 223 | GNA-A | 4etl-(5m)C |
| 224 | GNA-A | nmLNA-(5m)C |
| 225 | nmLNA-A | 2'-OMe-(5m)C |
| 226 | nmLNA-A | 2'-O-MOE-(5m)C |
| 227 | nmLNA-A | LNA-(5m)C |
| 228 | nmLNA-A | ENA-(5m)C |
| 229 | nmLNA-A | scp-BNA-(5m)C |
| 230 | nmLNA-A | AmNA-(NMe)-(5m)C |
| 231 | nmLNA-A | 2'-O-Propargyl-(5m)C |
| 232 | nmLNA-A | 2'-O-Butynyl-(5m)C |
| 233 | nmLNA-A | 2'-F-(5m)C |
| 234 | nmLNA-A | 2'-ara-F-(5m)C |
| 235 | nmLNA-A | 3'-OMe-(5m)C |
| 236 | nmLNA-A | UNA-(5m)C |
| 237 | nmLNA-A | 2'-NH$_2$-(5m)C |
| 238 | nmLNA-A | GNA-(5m)C |
| 239 | nmLNA-A | 4etl-(5m)C |
| 240 | nmLNA-A | nmLNA-(5m)C |
| 241 | 4etl-A | 2'-OMe-(5m)C |
| 242 | 4etl-A | 2'-O-MOE-(5m)C |
| 243 | 4etl-A | LNA-(5m)C |
| 244 | 4etl-A | ENA-(5m)C |
| 245 | 4etl-A | scp-BNA-(5m)C |
| 246 | 4etl-A | AmNA-(NMe)-(5m)C |
| 247 | 4etl-A | 2'-O-Propargyl-(5m)C |
| 248 | 4etl-A | 2'-O-Butynyl-(5m)C |
| 249 | 4etl-A | 2'-F-(5m)C |
| 250 | 4etl-A | 2'-ara-F-(5m)C |
| 251 | 4etl-A | 3'-OMe-(5m)C |
| 252 | 4etl-A | UNA-(5m)C |
| 253 | 4etl-A | 2'-NH$_2$-(5m)C |
| 254 | 4etl-A | GNA-(5m)C |
| 255 | 4etl-A | 4etl-(5m)C |
| 256 | 4etl-A | nmLNA-(5m)C |

The length of a modified oligonucleotide as described herein can vary over a broad range. In various embodiments, a modified oligonucleotide as described herein comprises an at least partially phosphorothioated sequence of alternating A and C units that has a sequence length of about 8 units, about 10 units, about 12 units, about 14 units, about 16 units, about 18 units, about 20 units, about 24 units, about 30 units, about 34 units, about 36 units, about 38 units, about 40 units, about 44 units, about 50 units, about 60 units, about 76 units, about 100 units, about 122 units, about 124 units, about 150 units, about 172 units, about 200 units, or a sequence length in a range between any two of the aforementioned values. For example, in an embodiment, the at least partially phosphorothioated sequence of alternating A and C units has a sequence length in the range of 8 units to 200 units. In another embodiment, the at least partially phosphorothioated sequence of alternating A and C units has a sequence length that is in any one or more (as applicable) of the following ranges: about 8 units to about 36 units; about 16 units to about 36 units; 20 units to 36 units; 16 units to 30 units; 18 units to 60 units; 20 units to 30 units; 30 units to 50 units; 34 units to 46 units, 36 units to 44 units; 44 units to 200 units; 44 units to 150 units; 44 units to 120 units; 50 units to 200 units; 50 units to 150 units; 50 units to 120 units; 60 units to 200 units; 60 units to 150 units; and/or 60 units to 120 units.

As described elsewhere herein, a modified oligonucleotide can comprise a single at least partially phosphorothioated sequence of alternating A and C units in some embodiments, or in other embodiments the modified oligonucleotide can comprise a plurality of at least partially phosphorothioated sequences of alternating A and C units that are linked together. Thus, a modified oligonucleotide that contains a single at least partially phosphorothioated sequence of alternating A and C units can have the same sequence length as that sequence. Examples of such sequence lengths are described elsewhere herein. Similarly, a modified oligonucleotide that contains a plurality of at least partially phosphorothioated sequences of alternating A and C units can have sequence length that is the result of linking those sequences as described elsewhere herein. Examples of sequence lengths for a modified oligonucleotide that contains a plurality of at least partially phosphorothioated sequences of alternating A and C units are expressed elsewhere herein in terms of the lengths of the individual sequences, and also taking into account the length of the linking group.

A modified oligonucleotide as described herein can comprises a plurality of at least partially phosphorothioated sequences of alternating A and C units. In an embodiment, when the sequence of alternating A and C units comprises a Ribo-A unit, the sequence further comprises at least one A unit that is not a Ribo-A unit. Similarly, in an embodiment, when the sequence of alternating A and C units comprises a Ribo-C unit, the sequence further comprises at least one C unit that is not a Ribo-C unit. In an embodiment, the modified oligonucleotide can contain one or more of various nucleotide units (known to those skilled in the art, e.g., thymine, cytosine, adenine, guanine and modified versions thereof) that are not A or C units, e.g., as an end group(s) and/or as a linking group(s) between two or more at least partially phosphorothioated sequences of alternating A and C units. For example, in an embodiment, the modified oligonucleotide comprises one or more cytosine units that link together at least two or more of the at least partially phosphorothioated sequences of alternating A and C units. In an embodiment, the two or more at least partially phosphorothioated sequences of alternating A and C units, which are linked together by a non-A/non-C linking group, are identical to one another. An example of such a modified oligonucleotide is $(AC)_8$-cytosine-$(AC)_8$. Such a modified oligonucleotide that comprises a plurality of identical sequences that are joined together may be referred to herein as a concatemer. The two or more at least partially phosphorothioated sequences of alternating A and C units that are linked together can also be different from one another. An example of such a modified oligonucleotide is $(AC)_8$-cytosine-$(AC)_{16}$.

The modified oligonucleotide can contain two or more different A groups and/or two or more different C groups. When an A or C group is replaced by a different A or C group, such a replacement is not ordinarily considered to interrupt the alternating sequence of A and C units. For example, in an embodiment, at least some of the A units are not 2'O-methylated on the ribose ring and/or at least some of the C units are not 2'O-methylated on the ribose ring. However, in some embodiments the group linking the two at least partially phosphorothioated sequences of alternating A and C units is itself an A or C unit that interrupts the alternating sequence of A and C units. For example, an at least partially phosphorothioated 16-mer of alternating A and C units may be linked by an A unit to another such 16-mer to form $(AC)_8$-A-$(AC)_8$. Similarly, such a 16-mer may be linked by a C unit to another such 16-mer to form $(AC)_8$-C-$(AC)_8$. As noted above, when a plurality of at least partially phosphorothioated sequences of alternating A and C units that are identical to one another are joined together by a linking group, the modified oligonucleotide may be referred to herein as a concatemer. As noted above, the two or more at least partially phosphorothioated sequences of alternating A and C units that are linked together can also be different from one another. Examples of such modified oligonucleotides include $(AC)_8$-A-$(AC)_{16}$ and $(AC)_8$-C-$(AC)_{16}$.

In an embodiment, the modified oligonucleotide comprises a 5' endcap. In various embodiments, the 5' endcap is selected from

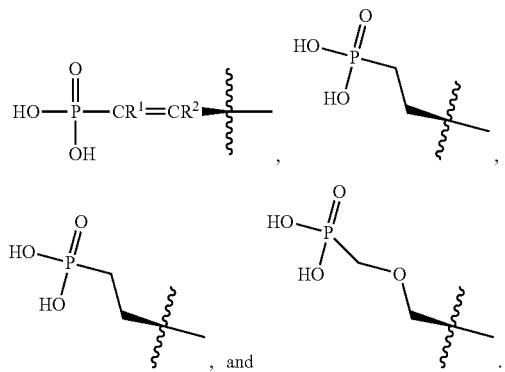

In an embodiment, $R^1$ and $R^2$ are each individually selected from hydrogen, deuterium, phosphate, thio$C_{1-6}$alkyl, and cyano. For example, in an embodiment, $R^1$ and $R^2$ are both hydrogen and the modified oligonucleotide comprises a vinyl phosphonate endcap. In other embodiments, $R^1$ and $R^2$ are not both hydrogen. In some embodiments, the 5' endcap is selected from

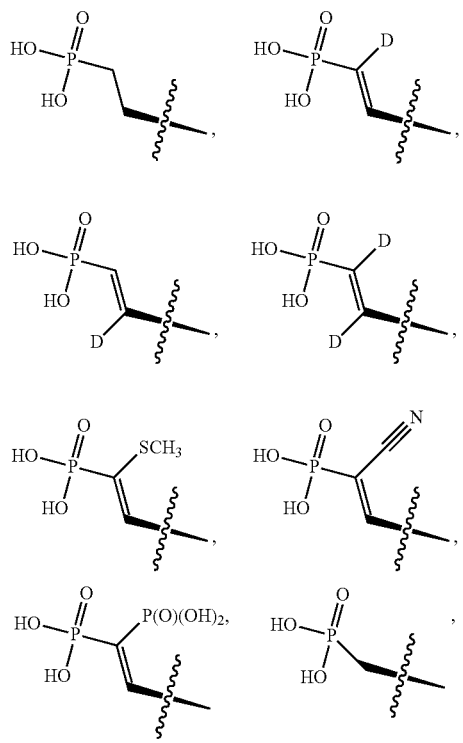

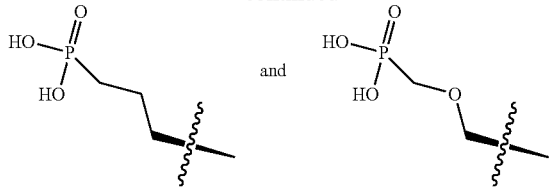

In other embodiments, the modified oligonucleotide comprises a 3' and/or 5' linking group. For example, with respect to modified oligonucleotide compounds comprising A and C units as described herein, such as the A and C units of Tables 1 and 2, respectively, at least one terminal

∿∿O can be a linking group. Various linking groups known to those skilled in the art can be used to link the modified oligonucleotide to another moiety (such as one or more second oligonucleotides and/or targeting ligands). In an embodiment, the linking group comprises a non-A/non-C linking group or an A or C unit that interrupts the alternating sequence of A and C units as discussed above, or the linking group comprises a $C_{2-6}$alkylene linkage (FIG. 1), a $C_{2-6}$alkylene oxide linkage, such as a propylene oxide linkage (FIG. 2), or a tetraethylene glycol (TEG) linkage (FIGS. 3A-D).

Figure 2:
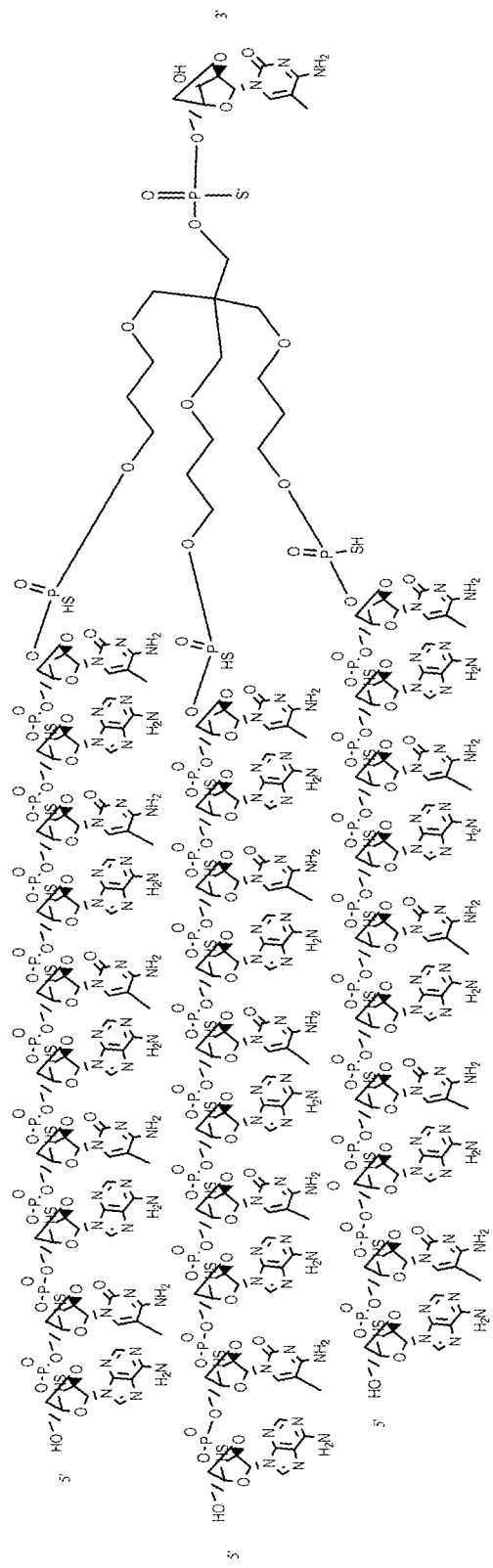
FIG. 2 illustrates an embodiment of a modified oligonucleotide that comprises a propylene oxide linkage.

In various embodiments, two, three, four or more of the modified oligonucleotides can be connected to each other in various ways. For example, the modified oligonucleotides can be connected end-to-end via 3' and/or 5' linking groups, and/or a linking group can be connected to a one 3' or 5' end of multiple modified oligonucleotides, e.g., as illustrated in FIGS. 1 and 2.

Figure 3A:
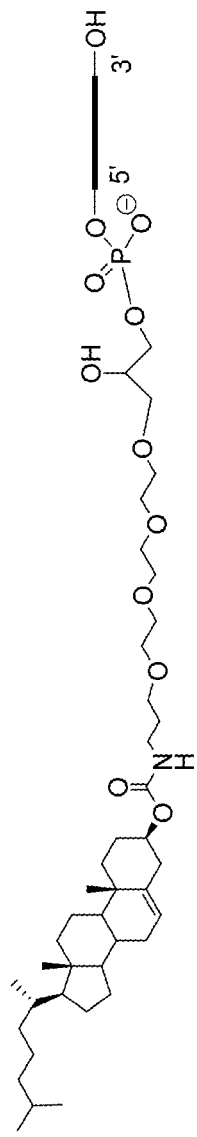
FIG. 3A illustrates an embodiment of a modified oligonucleotide having cholesterol attached via a 5' tetraethylene glycol (TEG) linkage.
Figure 3B:
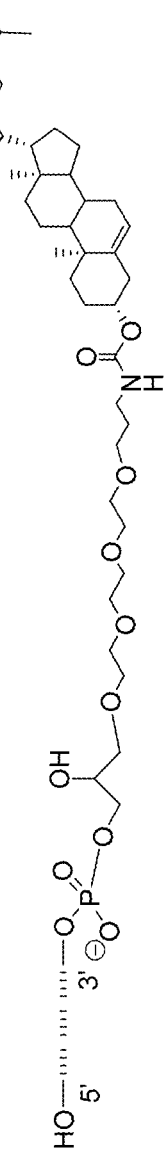
FIG. 3B illustrates an embodiment of a modified oligonucleotide having cholesterol attached via a 3' TEG linkage.
Figure 3C:
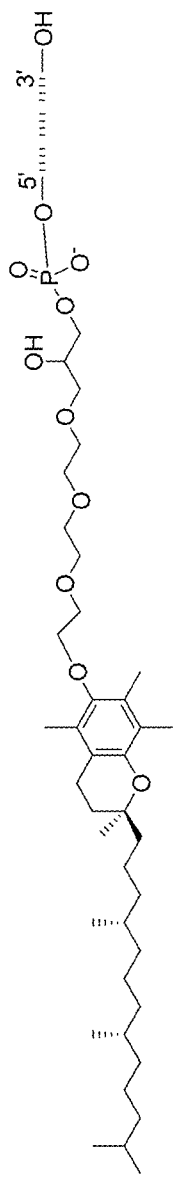
FIG. 3C illustrates an embodiment of a modified oligonucleotide having a tocopherol (Vitamin E) attached via a 5' TEG linkage.
Figure 3D:
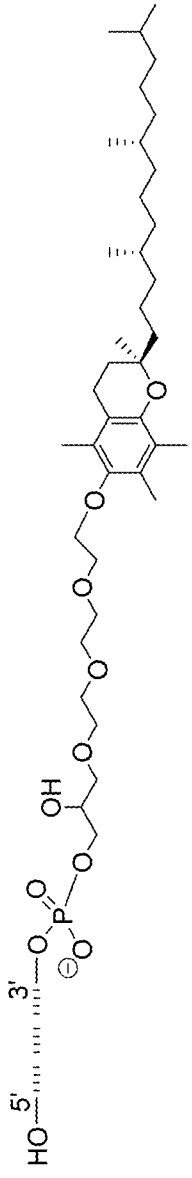
FIG. 3D illustrates an embodiment of a modified oligonucleotide having a tocopherol (Vitamin E) attached via a 3' TEG linkage.
Figure 4A:
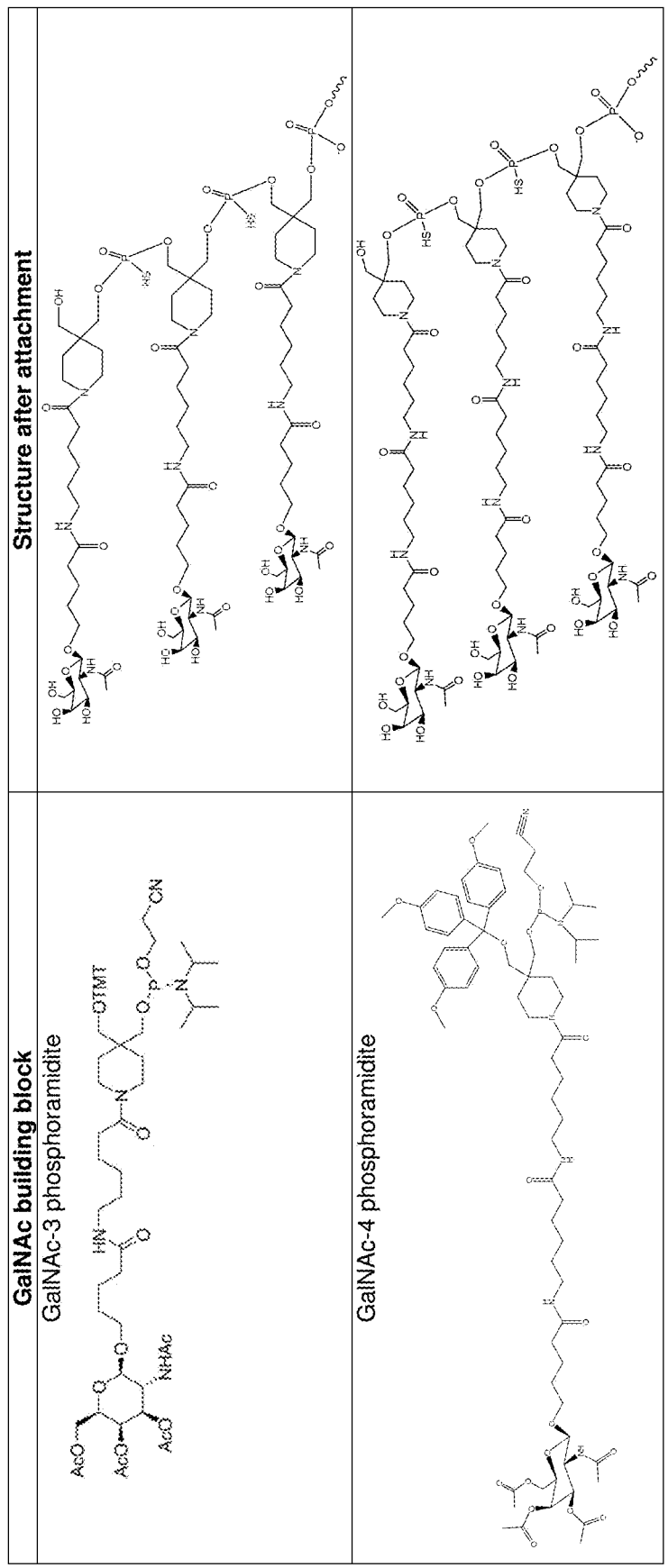
FIGS. 4A and 4B illustrate embodiments of modified oligonucleotides having GalNac attached via a linking group.
Figure 4A:
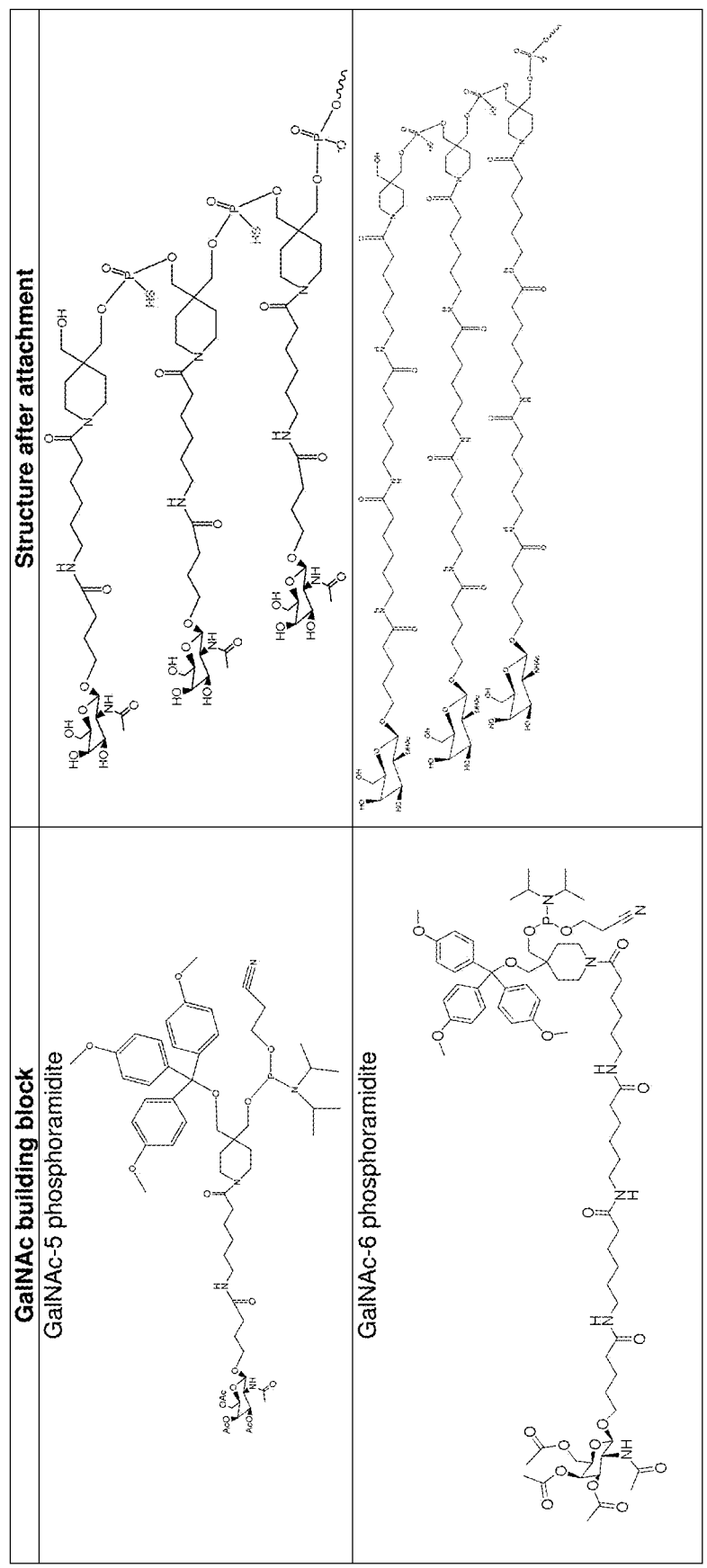
Figure 4B:
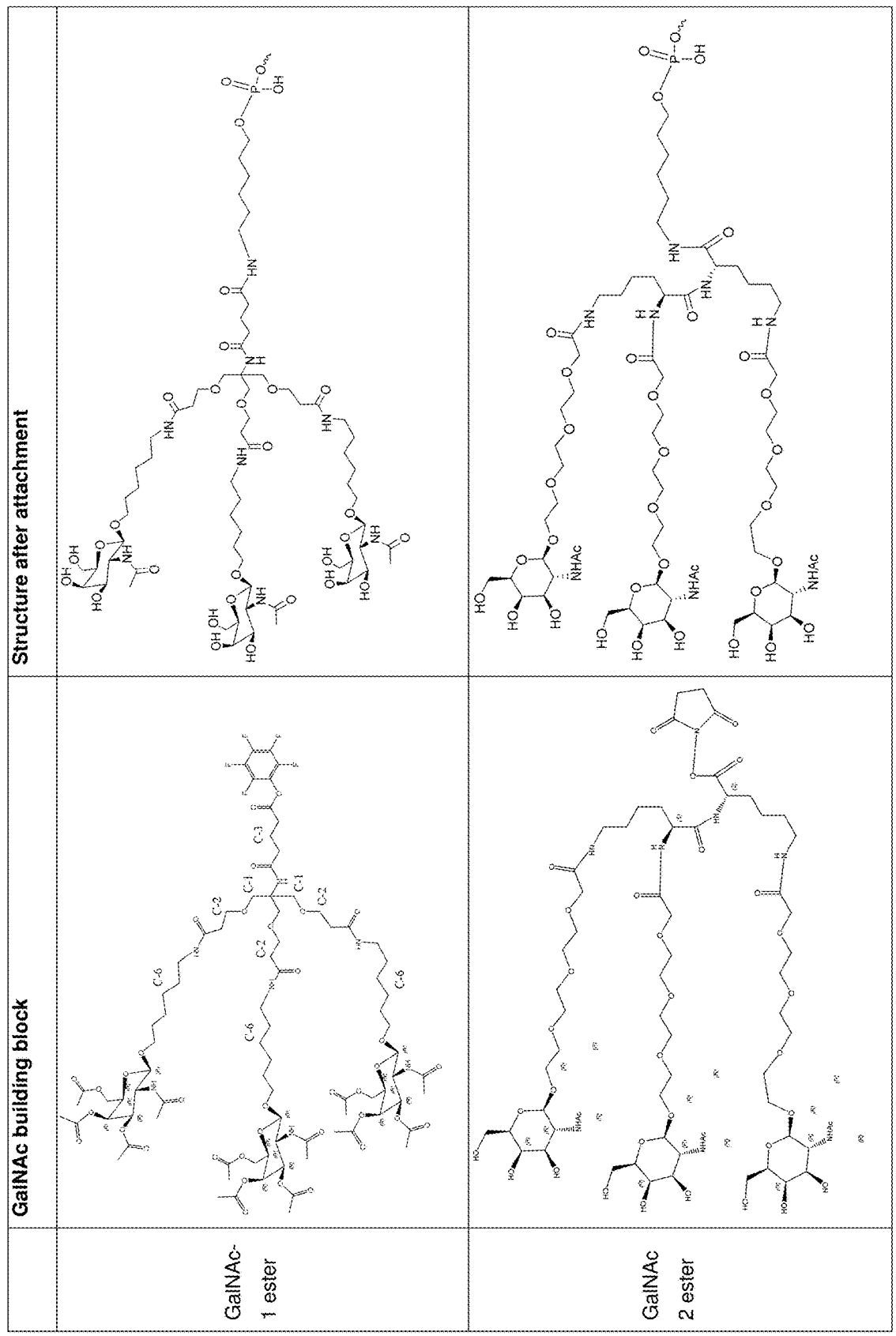

In various embodiments, the modified oligonucleotide further comprises a targeting ligand that is attached to the modified oligonucleotide via the linking group. For example, in various embodiments the targeting ligand is, or comprises, a N-acetylgalactosamine (GalNac) (e.g., triantennary-GalNAc), a tocopherol or cholesterol. FIGS. 3A and 3B illustrate embodiments of modified oligonucleotides having cholesterol attached via a 5' TEG linking group and a 3'TEG linking group, respectively. FIGS. 3C and 3D illustrate embodiments of modified oligonucleotides having a tocopherol (Vitamin E) attached via a 5' TEG linking group and a 3'TEG linking group, respectively. FIGS. 4A and 4B illustrate embodiments of modified oligonucleotides having GalNac attached via a linking group. In an embodiment, the GalNac is a triantennary GalNac.

In various embodiments, the at least partially phosphorothioated sequence of alternating A and C units can include modification(s) to one or more phosphorothioated linkages. The inclusion of such a modified linkage is not ordinarily considered to interrupt the alternating sequence of A and C units because those skilled in the art understand that such a sequence may be only partially phosphorothioated and thus may comprise one or more modifications to a phosphorothioate linkage. In various embodiments, the modification to the phosphorothioate linkage is a modified linkage selected from phosphodiester, phosphorodithioate, methylphosphonate, diphosphorothioate and diphosphodiester. For example, in an embodiment, the modified linkage is a phosphodiester linkage.

In various embodiments, the at least partially phosphorothioated sequence of alternating A and C units can have various degrees of phosphorothioation. For example, in an embodiment, the at least partially phosphorothioated sequence of alternating A and C units is at least 50%, 55%, 60%, 65%, 70%, 75%, 80%, 85%, 90%, or 95% phosphorothioated. In an embodiment, the at least partially phosphorothioated sequence of alternating A and C units is at least 85% phosphorothioated. In an embodiment, the at least partially phosphorothioated sequence of alternating A and C units is fully phosphorothioated.

In various embodiments, the at least partially phosphorothioated sequence of alternating A and C units can include stereochemical modification(s) to one or more phosphorothioated linkages. In an embodiment, the modified oligonucleotides described herein can comprise at least one stereochemically defined phosphorothioate linkage. In various embodiments, the stereochemically defined phosphorothioate linkage has an R configuration. In various embodiments, the stereochemically defined phosphorothioate linkage has an S configuration.

Those skilled in the art will recognize that modified oligonucleotide compounds comprising A and C units as described herein, such as the A and C units of Tables 1 and 2, respectively, contain internal linkages between the A and C units as well as terminal groups at the 3' and 5' ends. Thus, with respect to the A and C units described herein, such as the A and C units of Tables 1 and 2, respectively, each

∿∿O represents an internal

∿∿O or a terminal

∿∿O.

In various embodiments, each terminal

∿∿O is independently hydroxyl, an O,O-dihydrogen phosphorothioate, a dihydrogen phosphate, an endcap or a linking group. In various embodiments, each internal

∿∿O is a phosphorus-containing linkage to a neighboring A or C unit, the phosphorus-containing linkage being a phosphorothioate linkage or a modified linkage selected from phosphodiester, phosphorodithioate, methylphosphonate, diphosphorothioate 5'-phosphoramidate, 3',5'-phosphordiamidate, 5'-thiophosphoramidate, 3',5'-thiophosphordiamidate or diphosphodiester.

As noted above, the STOPS™ compounds described herein are antiviral oligonucleotides. In various embodiments, a modified oligonucleotide as described herein, comprising an at least partially phosphorothioated sequence of alternating A and C units, has sequence independent antiviral activity against hepatitis B, as determined by HBsAg Secretion Assay, that is greater than that of a reference compound. For example, in an embodiment, the sequence independent antiviral activity against hepatitis B is at least 2-fold greater than a reference compound. In another embodiment, the sequence independent antiviral activity against hepatitis B is in the range of from 2-fold greater than a reference compound to 5-fold greater than a reference compound. In another embodiment, the sequence independent antiviral activity against hepatitis B is at least 5-fold greater than a reference compound. In another embodiment, the sequence independent antiviral activity against hepatitis B is in the range of from 5-fold greater than a reference compound to 10-fold greater than a reference compound. In another embodiment, the sequence independent antiviral activity against hepatitis B is at least 10-fold greater than a reference compound. In another embodiment, the sequence independent antiviral activity against hepatitis B is in the range of from 10-fold greater than a reference compound to 25-fold greater than a reference compound. In another embodiment, the sequence independent antiviral activity against hepatitis B is at least 25-fold greater than a reference compound. In this context, the aforementioned terms 2-fold, 5-fold, 10-fold and 25-fold refer to the increased potency of a modified oligonucleotide as described herein as compared to another compound in HBsAg Secretion Assay, as indicated by an $EC_{50}$ value that is one-half, one-fifth, one-tenth or one-twenty-fifth that of a reference compound, respectively. For example, a modified oligonucleotide having a potency that is two-fold greater than a reference compound has an $EC_{50}$ value in HBsAg Secretion Assay that is one-half that of the $EC_{50}$ value of a reference compound. Likewise, a modified oligonucleotide having a potency that is five-fold greater than a reference compound has an $EC_{50}$ value in HBsAg Secretion Assay that is one-fifth that of a reference compound. Similarly, a modified oligonucleotide having a potency that is ten-fold greater than a reference compound has an $EC_{50}$ value in HBsAg Secretion Assay that is one-tenth that of a reference compound. Likewise, a modified oligonucleotide having a potency that is twenty five-fold greater than a reference compound has an $EC_{50}$ value in HBsAg Secretion Assay that is one-twenty-fifth that of a reference compound. In some embodiments, the reference compound can be the phosphorothioated AC 40-mer oligonucleotide known as REP 2139 discussed above. In some embodiments, the reference compound can be the AC 40-mer oligonucleotide having the structure 5' mApsmCps-mApsmCpsmApsmCpsmApsmCpsmApsmCpsmApsmCps-mApsmCpsmApsm CpsmApsmCpsmApsmCps-mApsmCpsmApsmCpsmApsmCpsmApsmCpsmApsmCpsmAps mCpsmApsmCpsmApsmCpsmApsmCpsmApsmC 3' (2'-OMe-A, 2'-OMe-C).

In various embodiments, a modified oligonucleotide as described herein, comprising an at least partially phosphorothioated sequence of alternating A and C units, has sequence independent antiviral activity against hepatitis B, as determined by HBsAg Secretion Assay, that is in an "A" activity range of less than 30 nanomolar (nM); in a "B" activity range of 30 nM to less than 100 nM; in a "C" activity range of 100 nM to less than 300 nM; or in a "D" activity range of greater than 300 nM. In some embodiments, a modified oligonucleotide as described herein, comprising an at least partially phosphorothioated sequence of alternating A and C units, has sequence independent antiviral activity against hepatitis B, as determined by HBsAg Secretion Assay, that is less than 50 nM.

The modified oligonucleotides described herein can be prepared in the form of various complexes. Thus, an embodiment provides a chelate complex of a modified oligonucleotide as described herein. For example, in an embodiment such a chelate complex comprises a calcium, magnesium or zinc chelate complex of the modified oligonucleotide. The modified oligonucleotides described herein can also be prepared in the form of various monovalent counterion complexes. For example, in an embodiment such a counterion complex comprises a lithium, sodium or potassium complex of the modified oligonucleotide.

An embodiment provides a modified oligonucleotide or complex thereof having sequence independent antiviral activity against hepatitis B, comprising an at least partially phosphorothioated sequence of alternating A and C units as described herein, wherein;

the at least partially phosphorothioated sequence of alternating A and C units is at least 85% phosphorothioated;

the at least partially phosphorothioated sequence of alternating A and C units has a sequence length in the range of 36 units to 44 units;

the A units comprise at least 12 2'-OMe-A units (e.g., at least 15 2'-OMe-A units) and at least 1 Ribo-A unit (e.g., at least 2 Ribo-A units);

the C units comprise at least 15 LNA-5mC units; and the modified oligonucleotide has an $EC_{50}$ value, as determined by HBsAg Secretion Assay, that is less than 100 nM (e.g., less than 50 nM or less than 30 nM).

An embodiment provides a modified oligonucleotide or complex thereof having sequence independent antiviral activity against hepatitis B, comprising an at least partially phosphorothioated sequence of alternating A and C units as described herein, wherein;

the at least partially phosphorothioated sequence of alternating A and C units is at least 85% phosphorothioated;

the at least partially phosphorothioated sequence of alternating A and C units has a sequence length in the range of 36 units to 44 units;

the A units comprise at least 15 2'-OMe-A units;

the C units comprise at least 7 LNA-5mC units; and the modified oligonucleotide has an $EC_{50}$ value, as determined by HBsAg Secretion Assay, that is less than 100 nM (e.g., less than 50 nM or less than 30 nM).

An embodiment provides a modified oligonucleotide or complex thereof having sequence independent antiviral activity against hepatitis B, comprising an at least partially phosphorothioated sequence of alternating A and C units as described herein, wherein;

the at least partially phosphorothioated sequence of alternating A and C units is at least 85% phosphorothioated;

the at least partially phosphorothioated sequence of alternating A and C units has a sequence length in the range of 36 units to 44 units;

the A units comprise at least 15 2'-OMe-A units;

the C units comprise at least 3 LNA-5mC units; and the modified oligonucleotide has an $EC_{50}$ value, as determined by HBsAg Secretion Assay, that is less than 100 nM (e.g., less than 50 nM or less than 30 nM).

An embodiment provides a modified oligonucleotide or complex thereof having sequence independent antiviral activity against hepatitis B, comprising an at least partially phosphorothioated sequence of alternating A and C units as described herein, wherein;

the at least partially phosphorothioated sequence of alternating A and C units is at least 85% phosphorothioated;

the at least partially phosphorothioated sequence of alternating A and C units has a sequence length in the range of 36 units to 44 units;

the A units comprise at least 18 2'-OMe-A units;

the C units comprise at least 15 LNA-5mC units; and the modified oligonucleotide has an $EC_{50}$ value, as determined by HBsAg Secretion Assay, that is less than 100 nM (e.g., less than 50 nM or less than 30 nM).

Synthesis

The modified oligonucleotides described herein can be prepared in various ways. In an embodiment, the building block monomers described in Tables 4 and 5 are employed to make the modified oligonucleotides described herein by applying standard phosphoramidite chemistry. The building blocks described in Tables 4 and 5 and other building block phosphoramidite monomers can be prepared by known methods or obtained from commercial sources (Thermo Fischer Scientific US, Hongene Biotechnology USA Inc., Chemgenes Corporation). Exemplary procedures for making modified oligonucleotides are set forth in the Examples below.

TABLE 4

| BUILDING BLOCKS FOR "A" UNITS | |
|---|---|
| Abbreviation | Structure |
| 2'-OMe-A PHOSPHORAMIDITE | 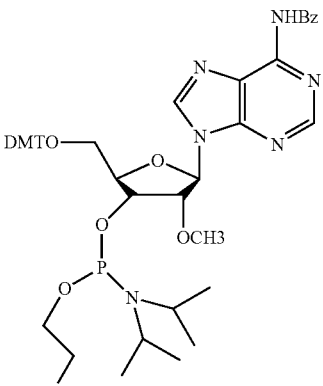 |
| 2'-F-A PHOSPHORAMIDITE | 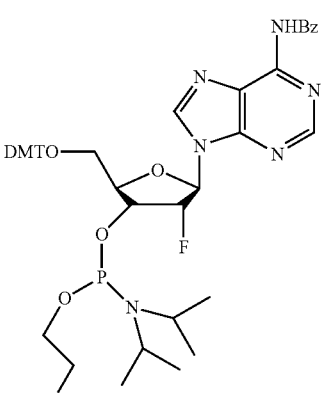 |

TABLE 4-continued

| BUILDING BLOCKS FOR "A" UNITS | |
|---|---|
| Abbreviation | Structure |
| 2'-O-MOE-A PHOSPHORAMIDITE | 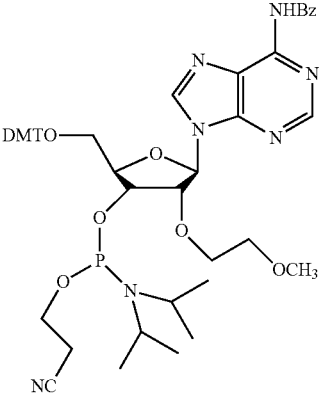 |
| LNA-A PHOSPHORAMIDITE | 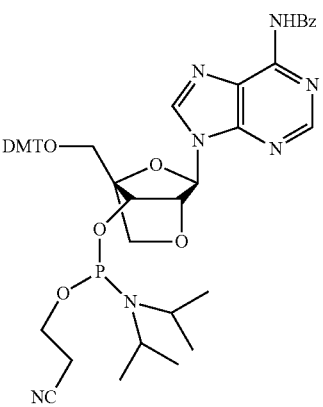 |
| ENA-A PHOSPHORAMIDITE | 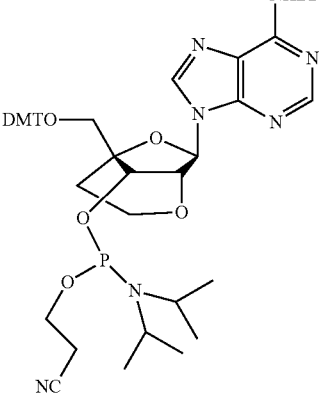 |

TABLE 4-continued

BUILDING BLOCKS FOR "A" UNITS

| Abbreviation | Structure |
|---|---|
| 2'-O-Butyne-A PHOSPHORAMIDITE | |
| 2'-NH$_2$-A PHOSPHORAMIDITE | |
| 2'-F-Ara-A PHOSPHORAMIDITE | |
| 2'-O-Propargyl-A PHOSPHORAMIDITE | 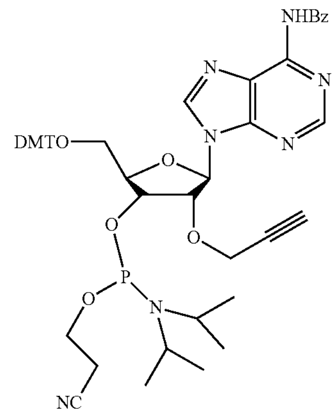 |
| UNA-A PHOSPHORAMIDITE | 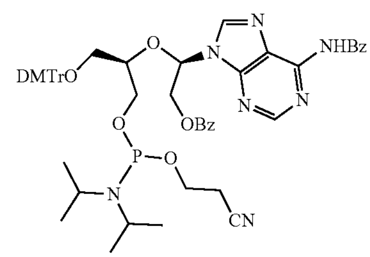 |
| GNA-A PHOSPHORAMIDITE | 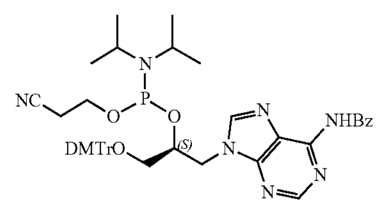 |
| 3'-O-Methyl-A PHOSPHORAMIDITE | 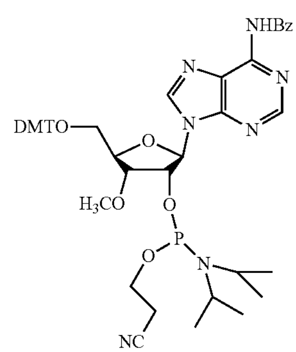 |
| scp-BNA-A PHOSPHORAMIDITE | 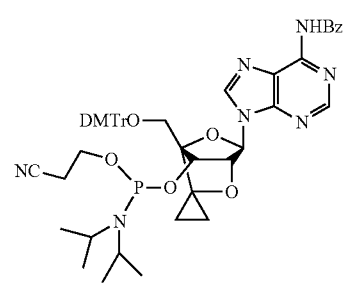 |

TABLE 4-continued

BUILDING BLOCKS FOR "A" UNITS

| Abbreviation | Structure |
| --- | --- |
| AmNA-(N-Me)-A PHOSPHORAMIDITE | 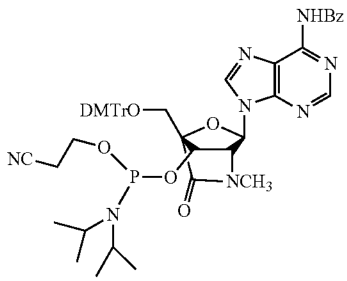 |
| nmLNA-A PHOSPHORAMIDITE | 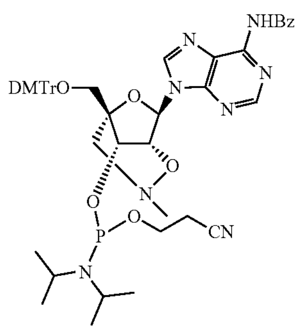 |
| 4etl-A PHOSPHORAMIDITE | 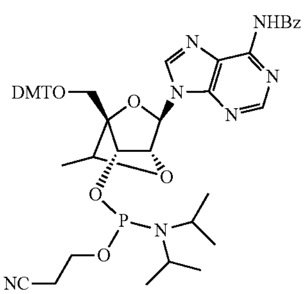 |
| Ribo-A PHOSPHORAMIDITE | 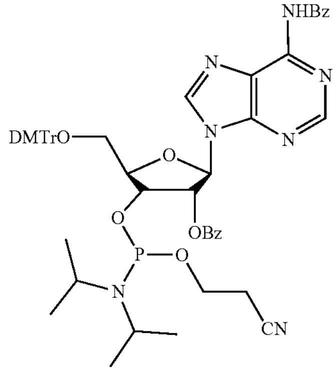 |

TABLE 5

BUILDING BLOCKS FOR "C" UNITS

| Abbreviation | Structure |
| --- | --- |
| 2'-OMe-(5m)C PHOSPHORAMIDITE | 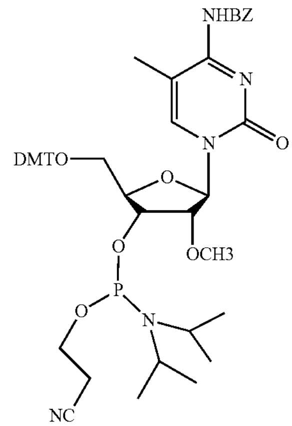 |
| 2'-F-(5m)C PHOSPHORAMIDITE | 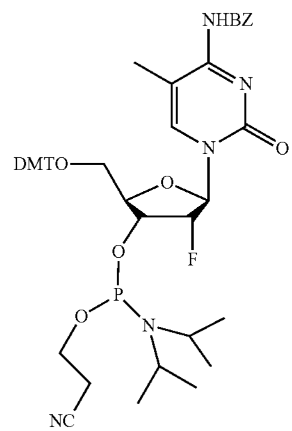 |
| 2'-O-MOE-(5m)C PHOSPHORAMIDITE | 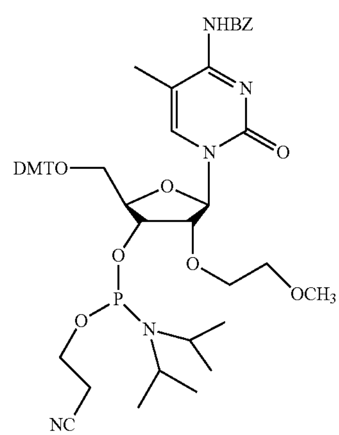 |

TABLE 5-continued

BUILDING BLOCKS FOR "C" UNITS

| Abbreviation | Structure |
|---|---|
| LNA-(5m)C PHOSPHORAMIDITE | |
| ENA-(5m)C PHOSPHORAMIDITE | |
| 2'-O-Butyne-(5m)C PHOSPHORAMIDITE | |
| 2'-NH$_2$-(5m)C PHOSPHORAMIDITE | 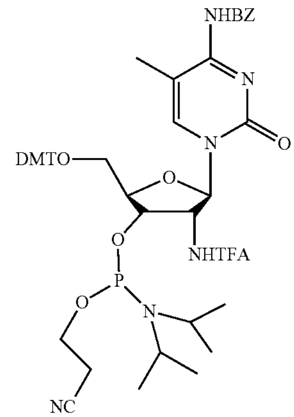 |
| 2'-F-Ara-(5m)C PHOSPHORAMIDITE | 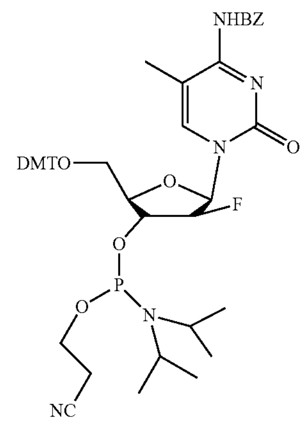 |
| 2'-O-Propargyl-(5m)C PHOSPHORAMIDITE | 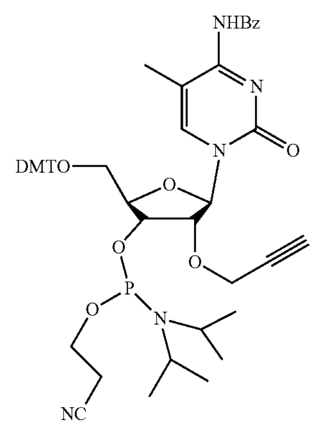 |
| UNA-(5m)C PHOSPHORAMIDITE | 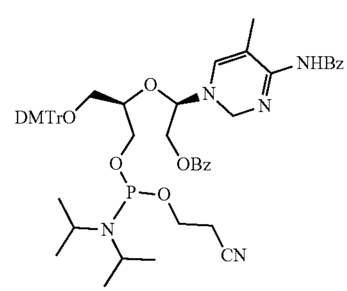 |

TABLE 5-continued

BUILDING BLOCKS FOR "C" UNITS

| Abbreviation | Structure |
| --- | --- |
| GNA-(5m)C PHOSPHORAMIDITE | (structure) |
| 3'-O-Methyl-(5m)C PHOSPHORAMIDITE | (structure) |
| scp-BNA-(5m)C PHOSPHORAMIDITE | (structure) |
| AmNA-(NMe)-(5m)C PHOSPHORAMIDITE | (structure) |
| 4etl-(5m)C PHOSPHORAMIDITE | (structure) |
| nmLNA-(5m)C PHOSPHORAMIDITE | (structure) |
| Ribo-C PHOSPHORAMIDITE | (structure) |

TABLE 5-continued

BUILDING BLOCKS FOR "C" UNITS

| Abbreviation | Structure |
|---|---|
| Ribo-(5m)C PHOSPHORAMIDITE | 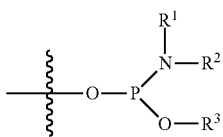 |

In various embodiments, the STOPS™ modified oligonucleotides described herein can also be prepared using dinucleotides that comprise or consist of any two of the building block monomers described in Tables 4 and 5. Exemplary procedures for making dinucleotides and the corresponding modified oligonucleotides are set forth in the Examples below.

An embodiment provides a dinucleotide comprising, or consisting of, an A unit and a C unit connected by a stereochemically defined phosphorothioate linkage, wherein the A unit is selected from any of the building block monomers described in Table 4 and the C unit is selected from any of the building block monomers described in Table 5, and wherein each

∿∿O is independently hydroxyl, an O,O-dihydrogen phosphorothioate, an O,O-dihydrogen phosphate, a phosphoramidite, a dimethoxytrityl ether, or the stereochemically defined phosphorothioate linkage. In an embodiment, the

∿∿O is a phosphoramidite of the following formula (A):

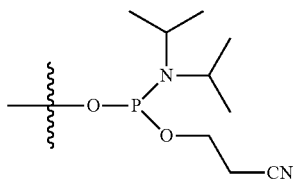

(A)

In various embodiments $R^1$ and $R^2$ of formula (A) are each individually a $C_{1-6}$alkyl, and $R^3$ is a $C_{1-6}$alkyl or a cyano$C_{1-6}$alkyl. For example, in an embodiment the phosphoramidite of the formula (A) is a phosphoramidite of the following formula (A1):

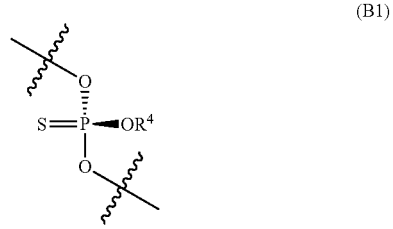

(A1)

In another embodiment, the

∿∿O is a stereochemically defined phosphorothioate linkage that is a phosphorothioate. For example, in an embodiment, the stereochemically defined phosphorothioate linkage is a phosphorothioate of the following Formula (B1) or (B2):

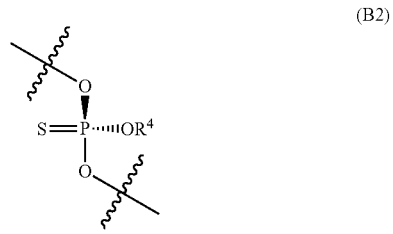

(B1)

(B2)

In various embodiments $R^4$ of formulae (B1) and (B2) is a $C_{1-6}$ alkyl or a cyano$C_{1-6}$ alkyl. For example, in an embodiment, the phosphorothioates of the formulae (B1) and (B2) are phosphorothioates of the following Formulae (B3) or (B4), respectively:

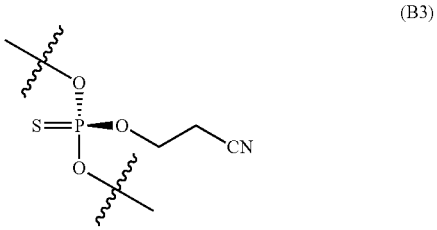

(B3)

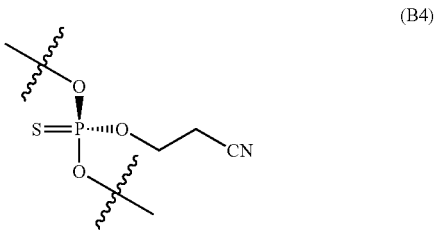

(B4)

Various embodiments provide methods of making a modified oligonucleotide as described herein, comprising coupling one or more dinucleotides as described herein. Exemplary methods of carrying out such coupling are illustrated in the Examples below.

Pharmaceutical Compositions

Some embodiments described herein relate to a pharmaceutical composition, that can include an effective amount of a compound described herein (e.g., a STOPS™ modified oligonucleotide compound or complex thereof as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, optionally in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a modified oligonucleotide or complex thereof as described herein, or a pharmaceutical composition that includes an effective amount of a modified oligonucleotide or complex thereof as described herein. Other embodiments described herein relate to using a modified oligonucleotide or complex thereof as described herein in the manufacture of a medicament for treating a HBV and/or HDV infection. Still other embodiments described herein relate to the use of a modified oligonucleotide or complex thereof as described herein or a pharmaceutical composition that includes a modified oligonucleotide as described herein for treating a HBV and/or HDV infection.

Various routes may be used to administer a modified oligonucleotide or complex thereof to a subject in need thereof as indicated elsewhere herein. In an embodiment, the modified oligonucleotide or complex thereof is administered to the subject by a parenteral route. For example, in an embodiment, the modified oligonucleotide or complex thereof is administered to the subject intravenously. In another embodiment, the modified oligonucleotide or complex thereof is administered to the subject subcutaneously. Surprisingly, it has now been found that embodiments of a modified oligonucleotide or complex thereof as described herein can be subcutaneously administered to a primate in an amount that is both safe and effective for treatment. Previously, subcutaneous administration of a modified oligonucleotide or complex thereof (such as REP 2139, REP 2055 or those described in U.S. Pat. Nos. 7,358,068; 8,008,269; 8,008,270 and 8,067,385) to a primate was considered unlikely to be safe and effective because of the relatively high dosages believed required to achieve efficacy and the concomitant increase in the potential risk of safety concerns such as undesirable injection site reactions. Thus, for example, prior clinical studies involving the administration of REP 2139 to humans are believed to have utilized only intravenous routes. At the dosage levels that were believed to be necessary for efficacy, it is believed that safety concerns such as undesirable injection site reactions would have precluded subcutaneous administration.

Figure 12:
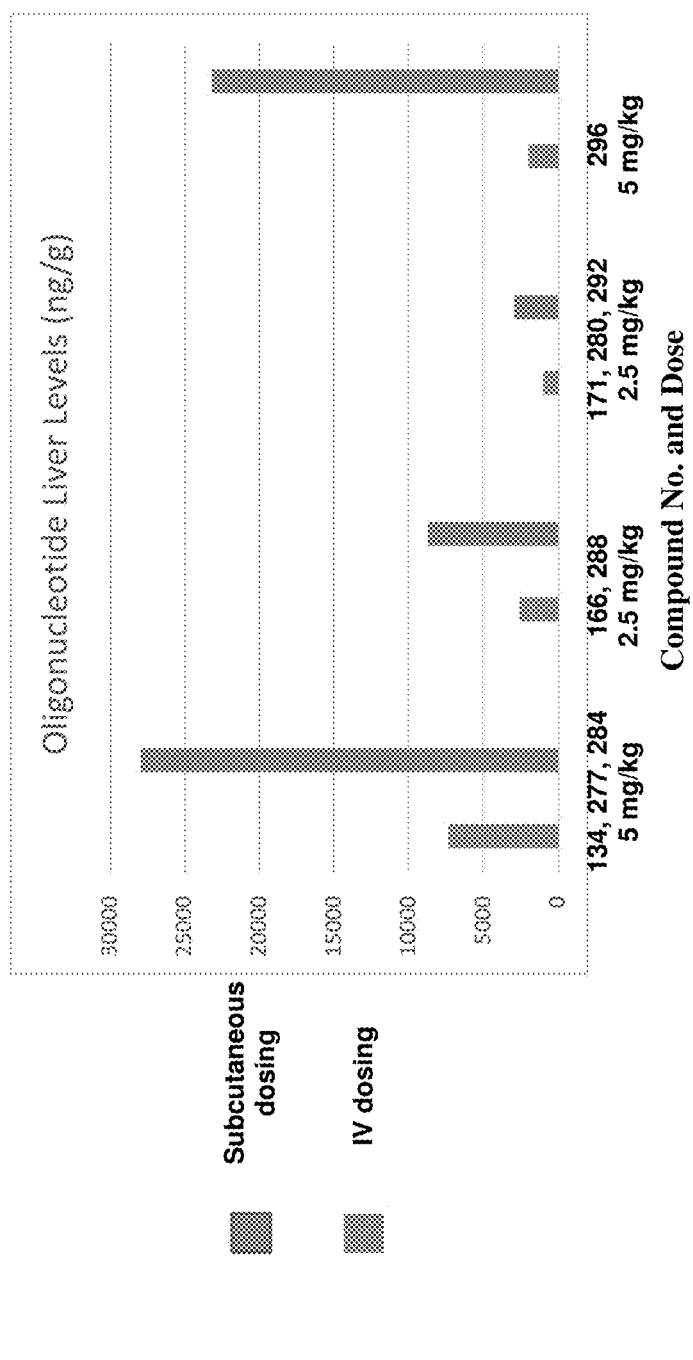
FIG. 12 illustrates liver exposure results following subcutaneous administration to non-human primates of embodiments of modified oligonucleotide compounds.
Figure 13:
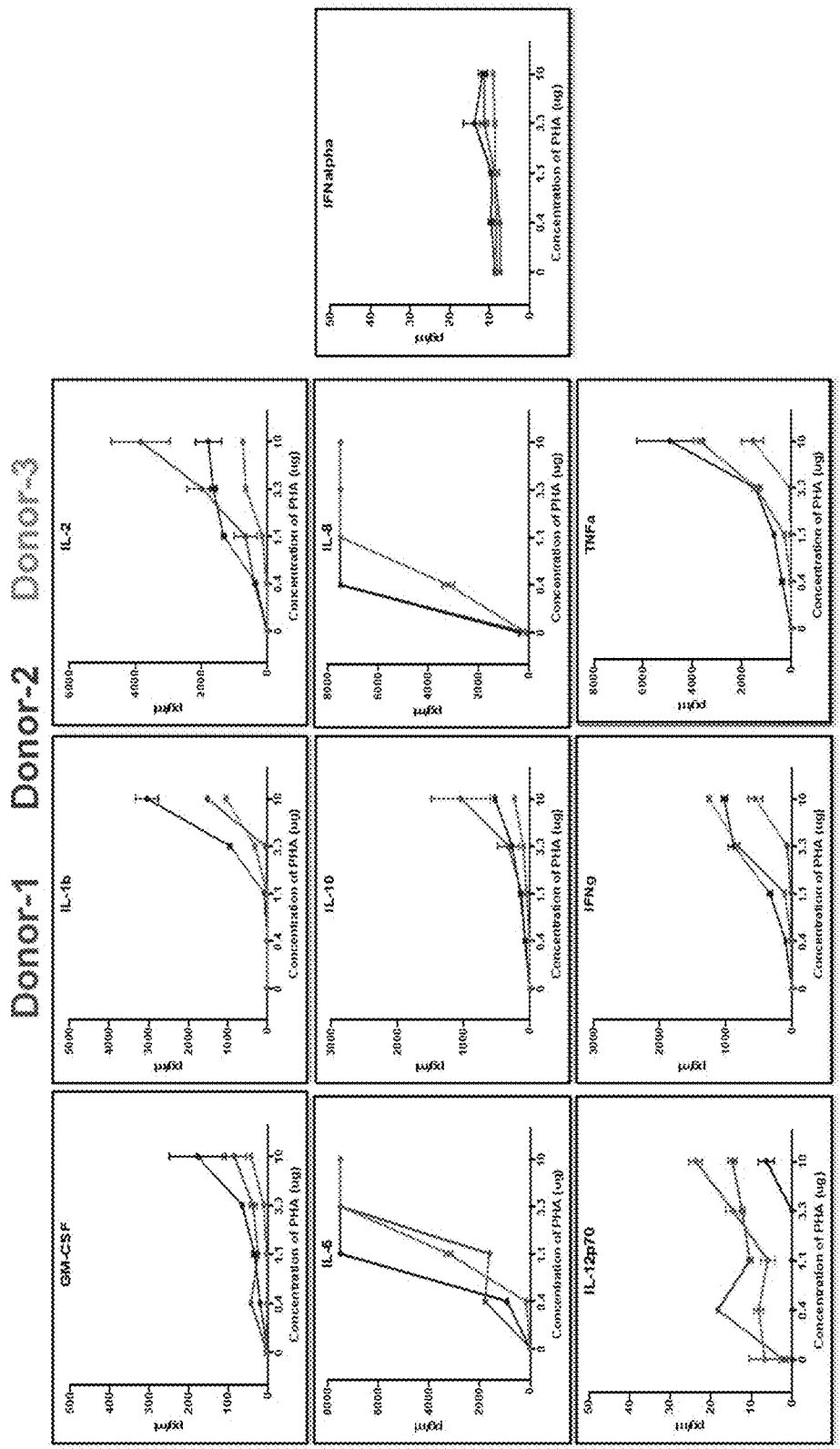
FIG. 13 illustrates PBMC assay results illustrating the immune reaction of embodiments of modified oligonucleotide compounds.
Figure 14:
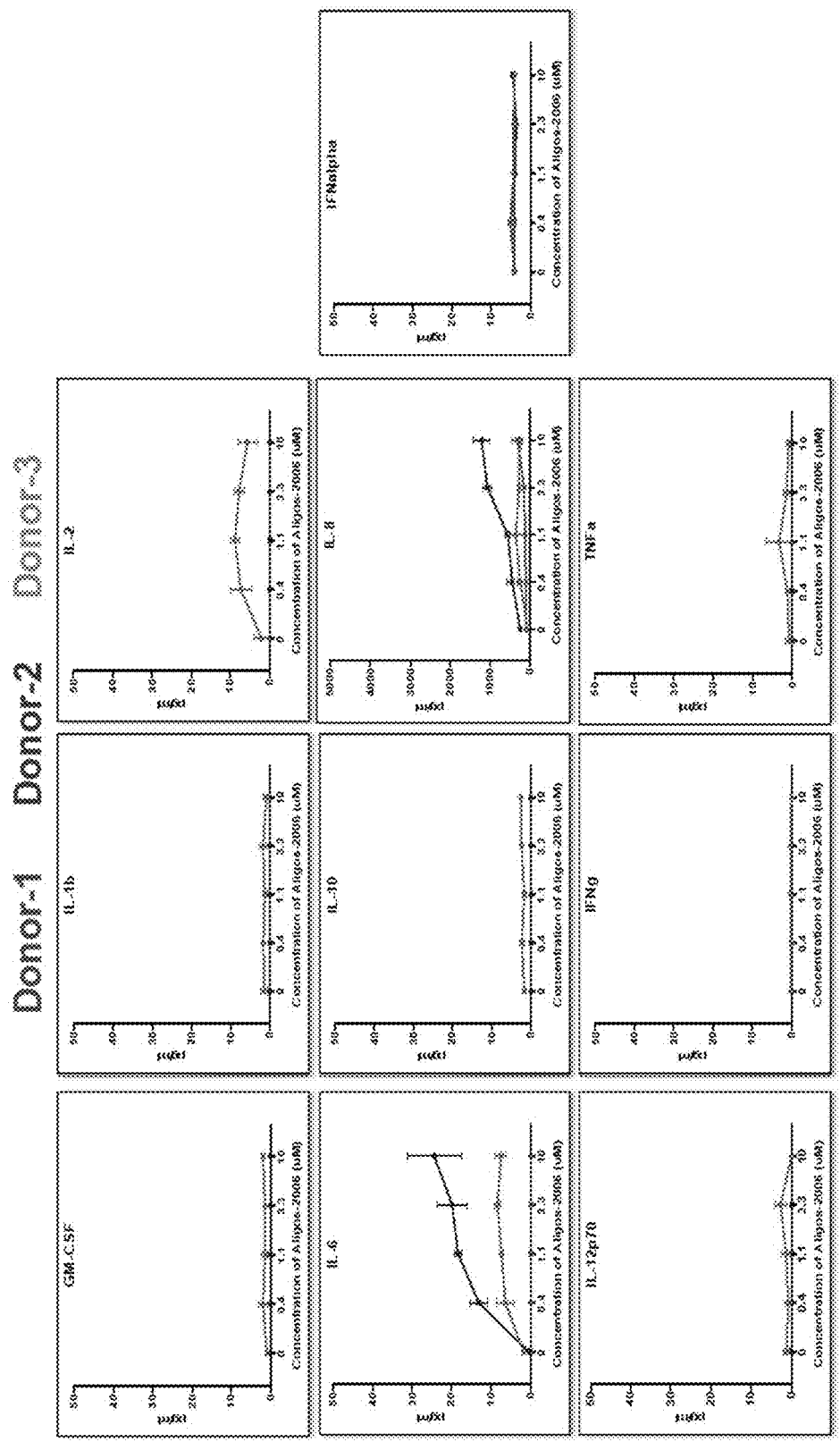
FIG. 14 illustrates PBMC assay results illustrating the immune reaction of embodiments of modified oligonucleotide compounds.
Figure 15:
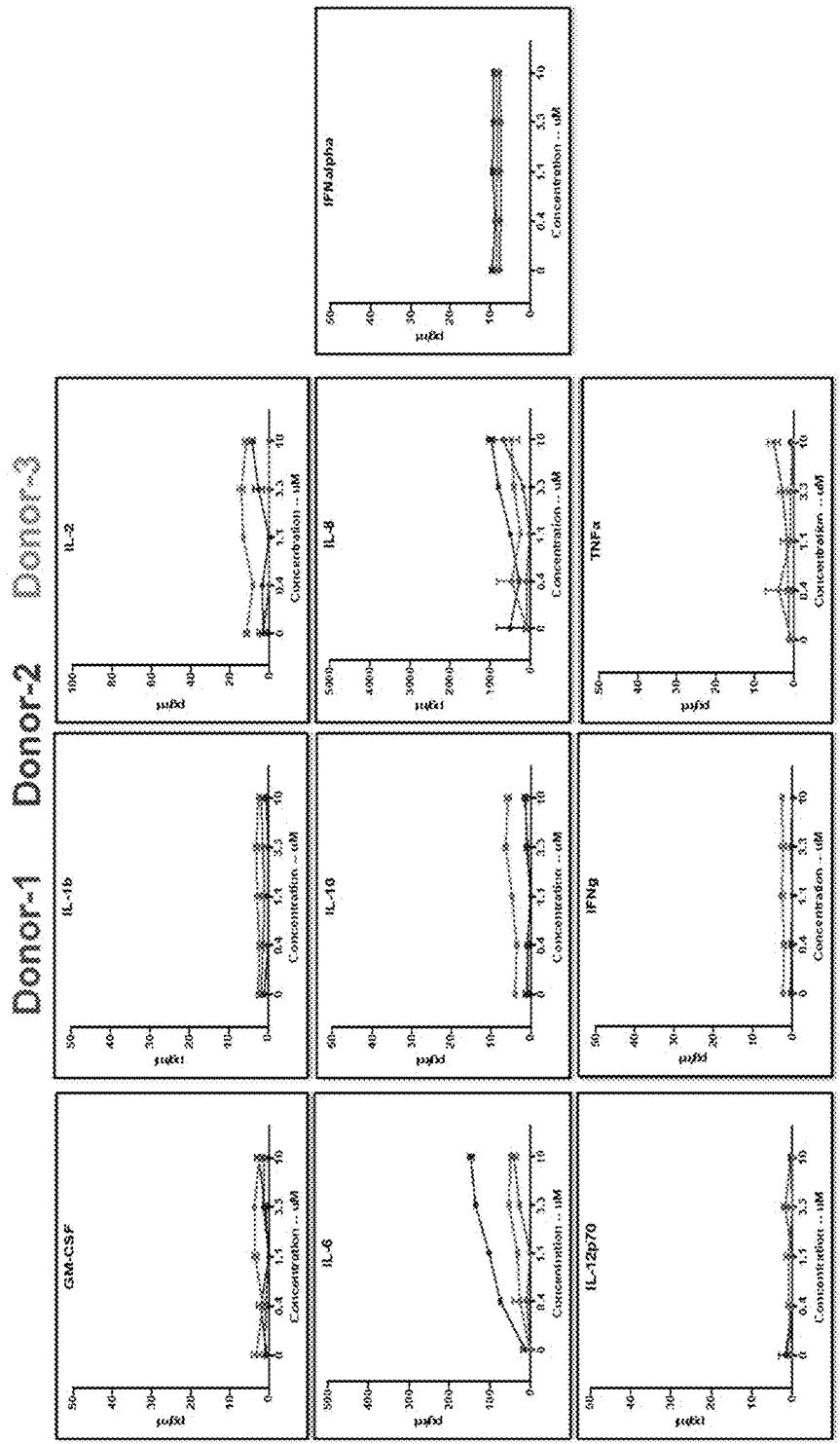
FIG. 15 illustrates PBMC assay results illustrating the immune reaction of embodiments of modified oligonucleotide compounds.
Figure 16:
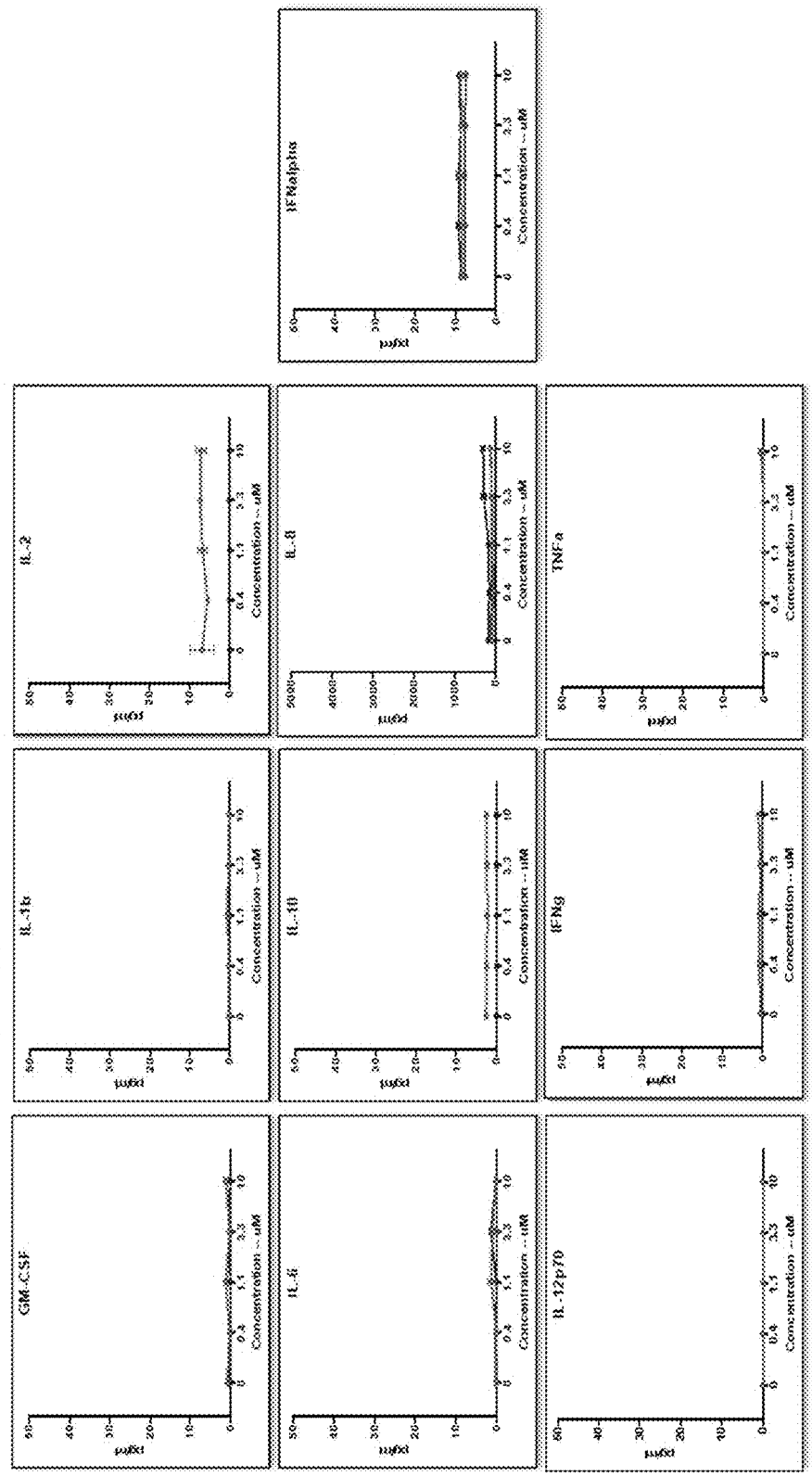
FIG. 16 illustrates PBMC assay results illustrating the immune reaction of embodiments of modified oligonucleotide compounds.
Figure 17:
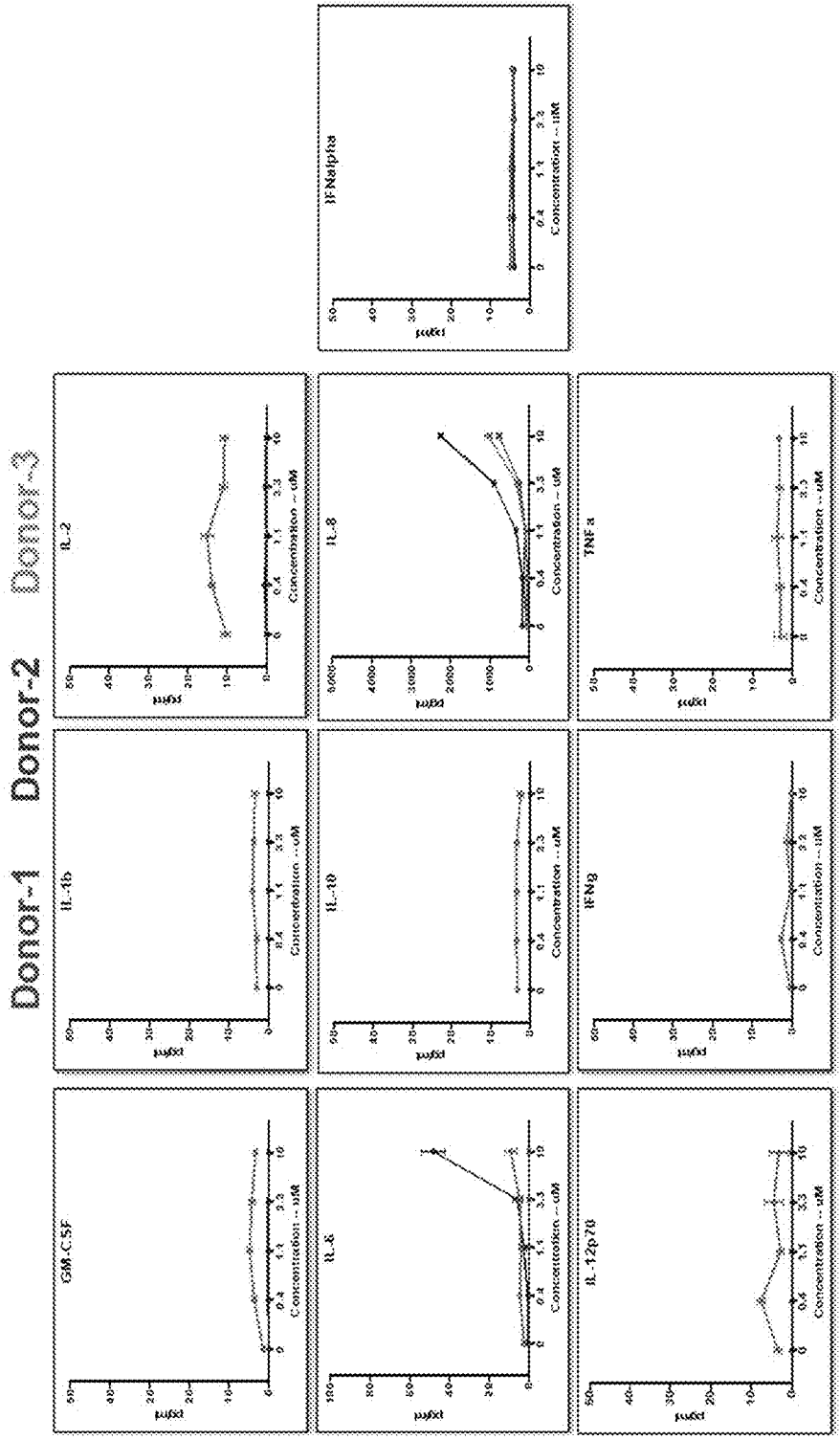
FIG. 17 illustrates PBMC assay results illustrating the immune reaction of embodiments of modified oligonucleotide compounds.
Figure 18:
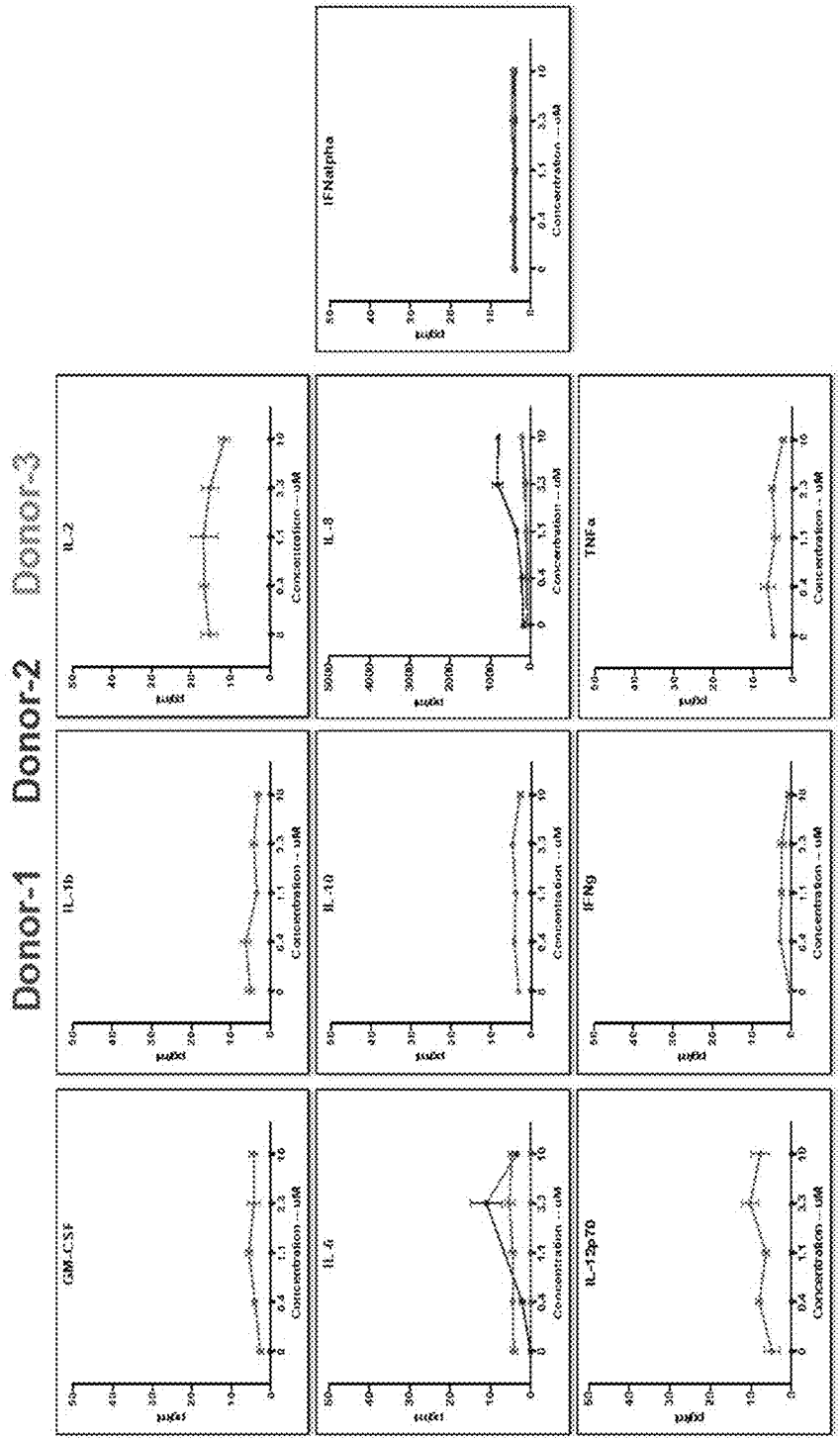
FIG. 18 illustrates PBMC assay results illustrating the immune reaction of embodiments of modified oligonucleotide compounds.
Figure 19:
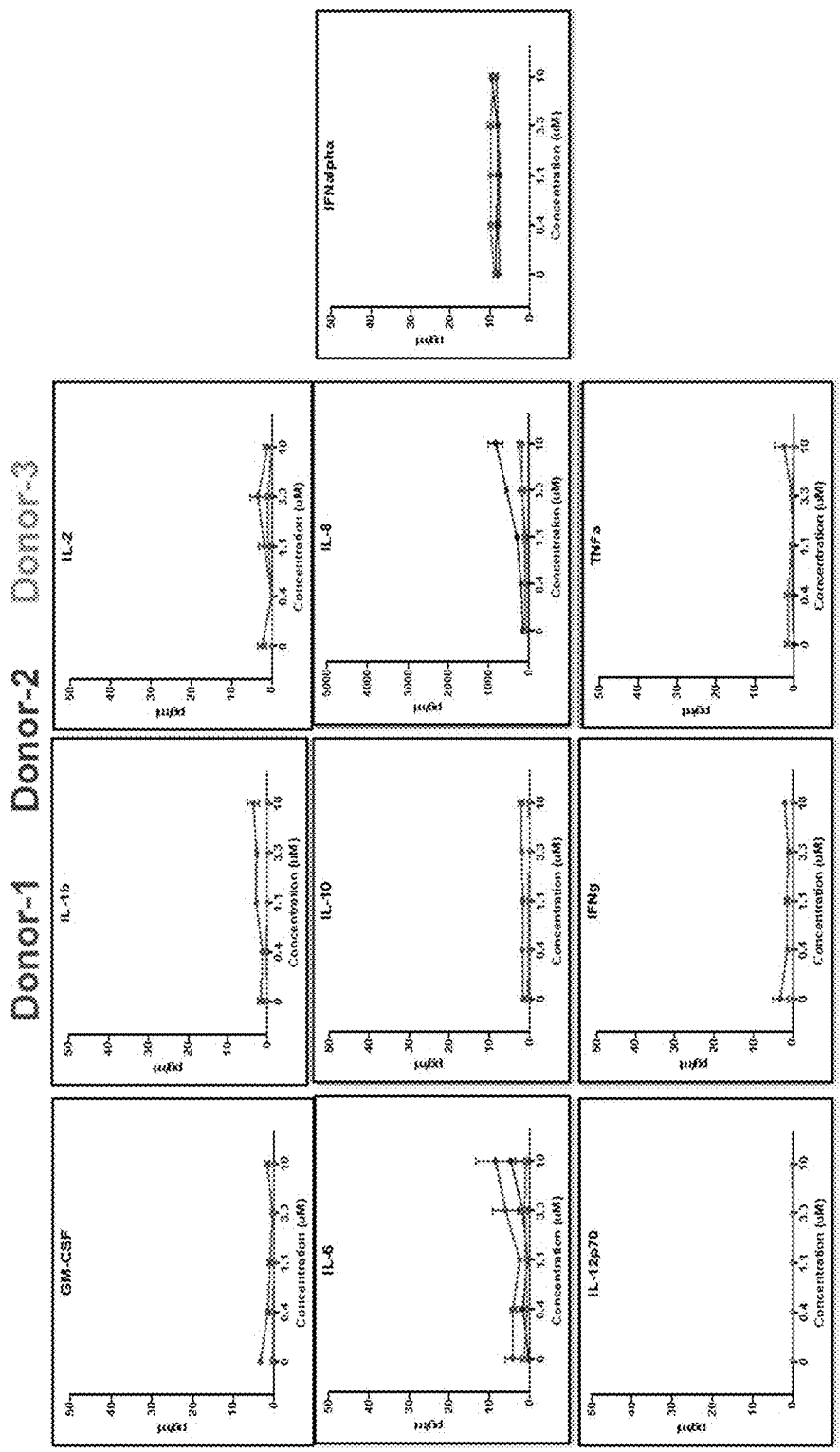
FIG. 19 illustrates PBMC assay results illustrating the immune reaction of embodiments of modified oligonucleotide compounds.
Figure 20:
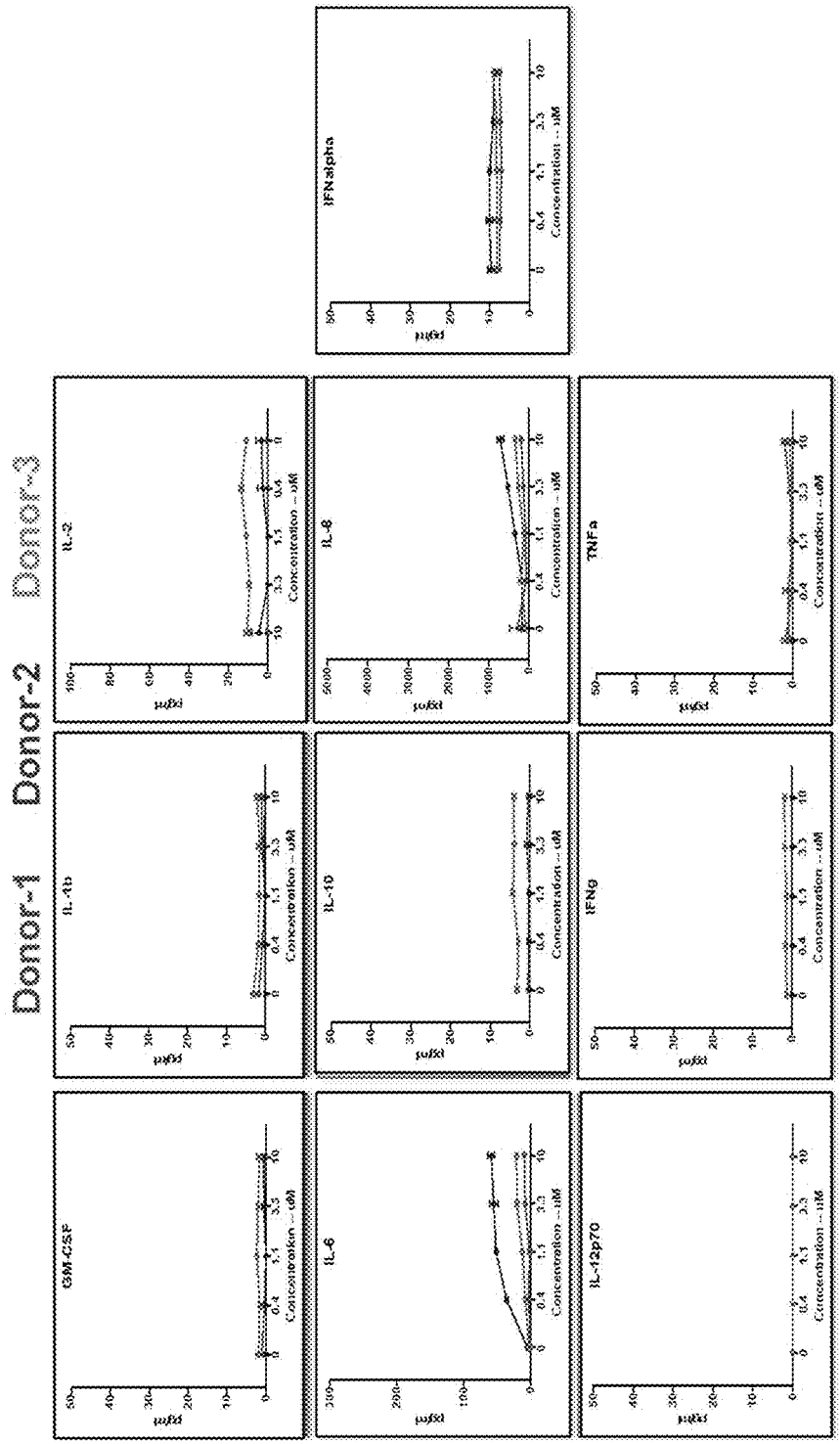
FIG. 20 illustrates PBMC assay results illustrating the immune reaction of embodiments of modified oligonucleotide compounds.
Figure 21:
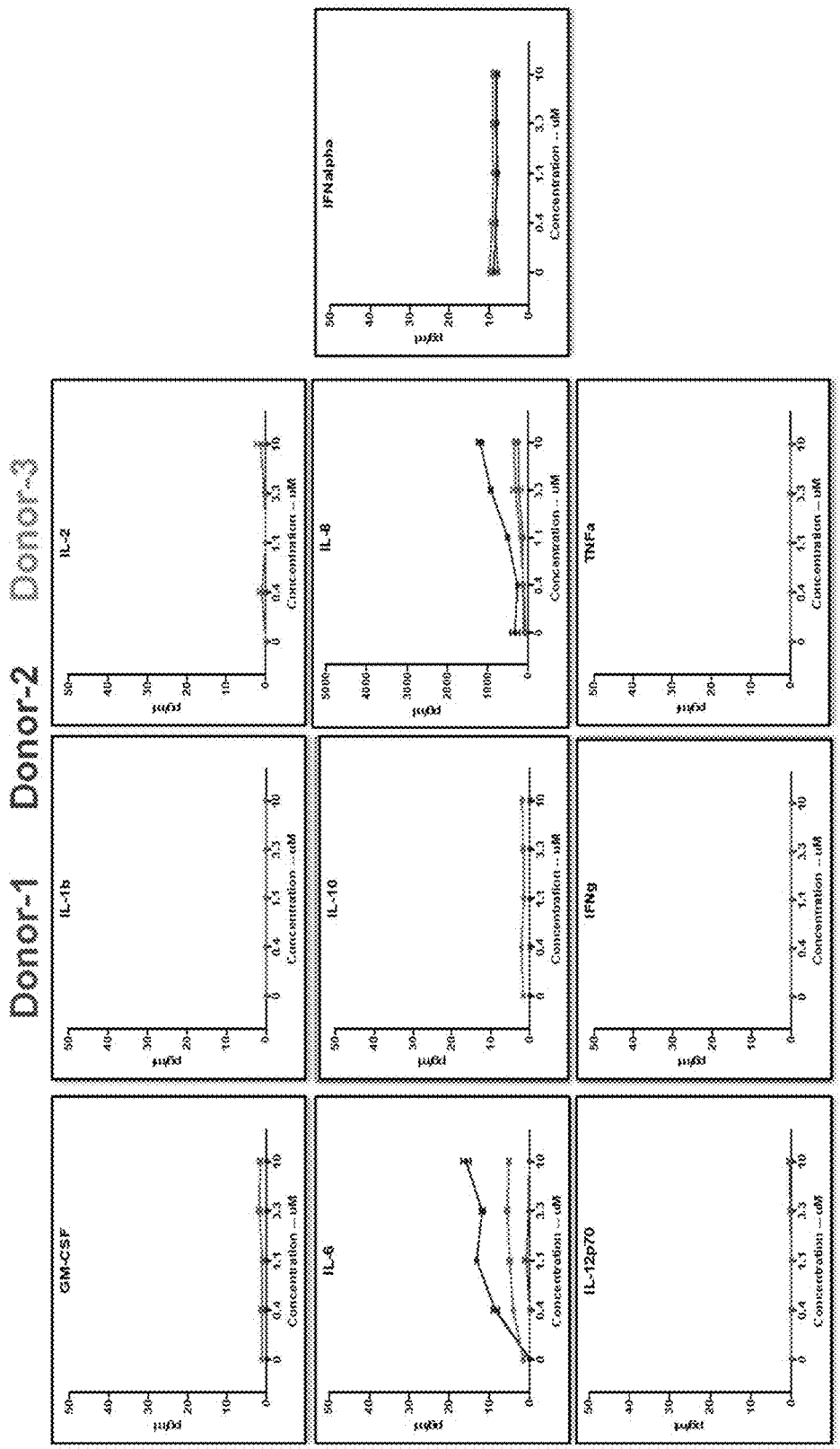
FIG. 21 illustrates PBMC assay results illustrating the immune reaction of embodiments of modified oligonucleotide compounds.
Figure 22:
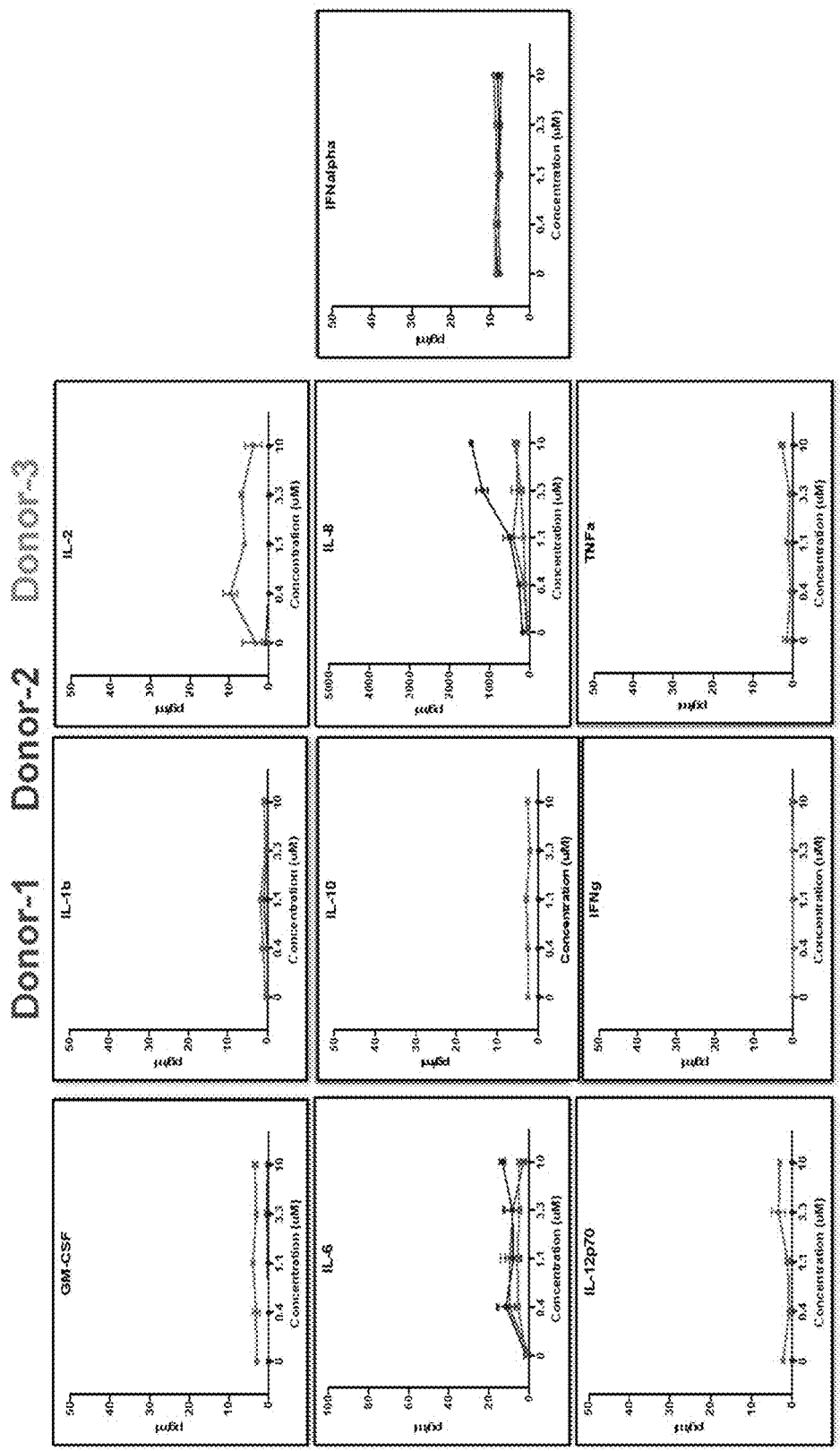
FIG. 22 illustrates PBMC assay results illustrating the immune reaction of embodiments of modified oligonucleotide compounds.

Unexpectedly, as illustrated in FIG. 12 and Example B5 below, it has now been found that liver exposure following subcutaneous administration to non-human primates is much higher than expected based on liver exposure levels resulting from otherwise comparable intravenous dosing. This finding means that embodiments of modified oligonucleotides or complexes thereof as described herein, and particularly embodiments of highly potent STOPS™ compounds or complexes as described herein, can be safely and effectively administered to primates via subcutaneous administration at dosages lower than previously considered likely to be effective. These lower dosages reduce the risk profile (e.g., reduce risk of injection site reactions) and thus provide a clinically acceptable safety profile for human use.

Some embodiments disclosed herein relate to a method of treating a HBV and/or HDV infection that can include contacting a cell infected with the HBV and/or HDV with an effective amount of a modified oligonucleotide or complex thereof as described herein, or a pharmaceutical composition that includes an effective amount of a modified oligonucleotide or complex thereof as described herein. In an embodiment, such a method of treating a HBV and/or HDV infection comprises safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP- 2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Other embodiments described herein relate to using a modified oligonucleotide or complex thereof as described herein in the manufacture of a medicament for treating a HBV and/or HDV infection. Still other embodiments described herein relate to the use of a modified oligonucleotide or complex thereof as described herein, or a pharmaceutical composition that includes an effective amount of a modified oligonucleotide or complex thereof as described herein for treating a HBV and/or HDV infection. In an embodiment, such uses comprise safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Some embodiments disclosed herein relate to a method of inhibiting replication of HBV and/or HDV that can include contacting a cell infected with the HBV and/or HDV with an effective amount of a modified oligonucleotide or complex thereof as described herein, or a pharmaceutical composition that includes an effective amount of a modified oligonucleotide or complex thereof as described herein. In an embodiment, such a method of inhibiting replication of HBV and/or HDV comprises safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Other embodiments described herein relate to using a modified oligonucleotide or complex thereof as described herein in the manufacture of a medicament for inhibiting replication of HBV and/or HDV. Still other embodiments described herein relate to the use of a modified oligonucleotide or complex thereof as described herein, or a pharmaceutical composition that includes an effective amount of a modified oligonucleotide or complex thereof as described herein, for inhibiting replication of HBV and/or HDV. In an embodiment, such uses for inhibiting replication of HBV and/or HDV comprise safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a modified oligonucleotide or complex thereof as described herein, or a pharmaceutical composition that includes an effective amount of a modified oligonucleotide or complex thereof as described herein. In an embodiment, such a method of treating liver cirrhosis that is developed because of a HBV and/or HDV infection comprises safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Other embodiments described herein relate to using a modified oligonucleotide or complex thereof as described herein in the manufacture of a medicament for treating liver cirrhosis that is developed because of a HBV and/or HDV infection, with an effective amount of the modified oligonucleotide(s). Still other embodiments described herein relate to the use of a modified oligonucleotide or complex thereof as described herein, or a pharmaceutical composition that includes an effective amount of a modified oligonucleotide or complex thereof as described herein for treating liver cirrhosis that is developed because of a HBV and/or HDV infection. In an embodiment, such uses for treating liver cirrhosis comprise safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a modified oligonucleotide or complex thereof as described herein, or a pharmaceutical composition that includes an effective amount of a modified oligonucleotide or complex thereof as described herein. In an embodiment, such a method of treating liver cancer (such as hepatocellular carcinoma) that is developed because of a HBV and/or HDV infection comprises safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Other embodiments described herein relate to using a modified oligonucleotide or complex thereof as described herein in the manufacture of a medicament for treating liver cancer (such as hepatocellular carcinoma) that is developed because of a HBV and/or HDV infection. Still other embodiments described herein relate to the use of a modified oligonucleotide or complex thereof as described herein, or a pharmaceutical composition that includes an effective amount of a modified oligonucleotide or complex thereof as described herein for treating liver cancer (such as hepatocellular carcinoma) that is developed because of a HBV and/or HDV infection. In an embodiment, such uses for treating liver cancer (such as hepatocellular carcinoma) comprise safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a modified oligonucleotide or complex thereof as described herein, or a pharmaceutical composition that includes an effective amount of a modified oligonucleotide or complex thereof as described herein. In an embodiment, such a method of treating liver failure that is developed because of a HBV and/or HDV infection comprises safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Other embodiments described herein relate to using a modified oligonucleotide or complex thereof as described herein in the manufacture of a medicament for treating liver failure that is developed because of a HBV and/or HDV infection. Still other embodiments described herein relate to the use of a modified oligonucleotide or complex thereof as described herein, or a pharmaceutical composition that includes an effective amount of a modified oligonucleotide or complex thereof as described herein for treating liver failure that is developed because of a HBV and/or HDV infection. In an embodiment, such uses for treating liver failure comprise safe and effective subcutaneous administration of the modified oligonucleotide or complex thereof to a human at a dosage lower than otherwise expected based on liver levels observed following otherwise comparable intravenous administration. For example, in an embodiment, the modified oligonucleotide or complex thereof is REP-2139 or a complex thereof. In another embodiment, the modified oligonucleotide or complex thereof comprises a highly potent STOPS™ compound or complex thereof as described herein. For example, in an embodiment, the STOPS™ compound or complex thereof is a modified oligonucleotide or complex thereof as described herein, comprising an at least partially phosphorothioated sequence of alternating A and C units, having sequence independent antiviral activity against hepatitis B, as determined by HBsAg Secretion Assay, that is in an "A" activity range of less than 30 nM.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

In some embodiments, an effective amount of a modified oligonucleotide or complex thereof as described herein is an amount that is effective to achieve a sustained virologic response, for example, a sustained viral response 12 month after completion of treatment.

Subjects who are clinically diagnosed with an HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA by hybridization assays). Further examples of subjects include subjects with a HBV and/or HDV infection who are asymptomatic.

In some embodiments, a modified oligonucleotide or complex thereof as described herein can be provided to a treatment failure subject suffering from HBV and/or HDV. In some embodiments, a modified oligonucleotide or complex thereof as described herein can be provided to a non-responder subject suffering from HBV and/or HDV. In some embodiments, a modified oligonucleotide or complex thereof as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include interferons (such as IFN-α and pegylated interferons that include PEG-IFN-α-2a), and nucleosides/nucleotides (such as lamivudine, telbivudine, adefovir dipivoxil, clevudine, entecavir, tenofovir alafenamide and tenofovir disoproxil). However, some of the drawbacks associated with interferon treatment are the adverse side effects, the need for subcutaneous administration and high cost. A drawback with nucleoside/nucleotide treatment can be the development of resistance.

Resistance can be a cause for treatment failure. The term "resistance" as used herein refers to a viral strain displaying a delayed, lessened and/or null response to an anti-viral agent. In some embodiments, a modified oligonucleotide or complex thereof as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide: and tenofovir disoproxil. In some embodiments, development of resistant HBV and/or HDV strains is delayed when a subject is treated with a modified oligonucleotide as described herein compared to the development of HBV and/or HDV strains resistant to other HBV and/or HDV anti-viral agents, such as those described.

Various embodiments provide a treatment for hepatitis B, hepatitis D or both, comprising an effective amount of the modified oligonucleotide or complex thereof as described herein. Some embodiments provide a cross genotypic treatment for hepatitis B, hepatitis D or both, comprising an effective amount of the modified oligonucleotide or complex thereof as described herein. For example, in an embodiment, the modified oligonucleotide or complex thereof is effective to treat viral infections caused by two or more hepatitis B genotypes selected from genotype A, genotype B, genotype C, genotype D, genotype E, genotype F, genotype G, genotype H, genotype I and genotype J. In another embodiment, the modified oligonucleotide or complex thereof is effective to treat viral infections caused by two or more hepatitis B genotypes selected from genotype A, genotype B, genotype C and genotype D. In other embodiments, the modified oligonucleotide or complex thereof is effective to treat viral infections caused by two or more hepatitis D genotypes selected from genotype 1, genotype 2, genotype 3, genotype 4, genotype 5, genotype 6, genotype 7 and genotype 8.

Combination Therapies

In some embodiments, a modified oligonucleotide or complex thereof as described herein can be used in combination with one or more additional agent(s) for treating and/or inhibiting replication HBV and/or HDV. Additional agents include, but are not limited to, an interferon, nucleoside/nucleotide analogs, a capsid assembly modulator, a sequence specific oligonucleotide (such as anti-sense oligonucleotide and/or siRNA), an entry inhibitor and/or a small molecule immunomodulator. For example, in an embodiment, a modified oligonucleotide or complex thereof as described herein can be used as a first treatment in combination with one or more second treatment(s) for HBV, wherein the second treatment comprises a second oligonucleotide having sequence independent antiviral activity against hepatitis B, an siRNA oligonucleotide (or nucleotides), an anti-sense oligonucleotide, a nucleoside, an interferon, an immunomodulator, a capsid assembly modulator, or a combination thereof. Examples of additional agents include recombinant interferon alpha 2b, IFN-α, PEG-IFN-α-2a, lamivudine, telbivudine, adefovir clevudine, entecavir, tenofovir alafenamide, tenofovir disoproxil, JNJ-3989 (ARO-HBV), RG6004, GSK3228836, AB-729, VIR-2218, DCR-HBVS, JNJ-6379, GLS4, ABI-HO731, JNJ-440, NZ-4, RG7907, AB-423, AB-506 and ABI-H2158. In an embodiment, the additional agent is a capsid assembly modulator (CAM). In an embodiment, the additional agent is an anti-sense oligonucleotide (ASO).

In some embodiments, a modified oligonucleotide or complex thereof as described herein can be administered with one or more additional agent(s) together in a single pharmaceutical composition. In some embodiments, a modified oligonucleotide or complex thereof as described herein can be administered with one or more additional agent(s) as two or more separate pharmaceutical compositions. Further, the order of administration of a modified oligonucleotide or complex thereof as described herein with one or more additional agent(s) can vary.

EXAMPLES

Additional embodiments are disclosed in further detail in the following examples, which are not in any way intended to limit the scope of the claims.

Examples 1-116

A series of modified oligonucleotides containing phosphorothioated sequences of alternating A and C units were synthesized on an ABI 394 synthesizer using standard phosphoramidite chemistry. The solid support was controlled pore glass (CPG, 1000A, Glen Research, Sterling Va.) and the building block monomers are described in Tables 4 and 5. The reagent (dimethylamino-methylidene)amino)-3H-1,2,4-dithiazaoline-3-thione (DDTT) was used as the sulfur-transfer agent for the synthesis of oligoribonucleotide phosphorothioates (PS linkages). An extended coupling of 0.1M solution of phosphoramidite in $CH_3CN$ in the presence of 5-(ethylthio)-1H-tetrazole activator to a solid bound oligonucleotide followed by standard capping, oxidation and deprotection afforded modified oligonucleotides. The stepwise coupling efficiency of all modified phosphoramidites was more than 95%. Several modified oligonucleotides containing sequences of alternating A and C units but having phosphodiester (PO) linkages instead of phosphorothioate (PS) linkages were also made.

Deprotection

After completion of synthesis the controlled pore glass (CPG) was transferred to a screw cap vial or screw caps RNase free microfuge tube. The oligonucleotide was cleaved from the support with simultaneous deprotection of base and phosphate groups with 1.0 mL of a mixture of ethanolic ammonia (ammonia:ethanol (3:1)) for 5-15 hr at 55° C. The vial was cooled briefly on ice and then the ethanolic ammonia mixture was transferred to a new microfuge tube. The CPG was washed with 2×0.1 mL portions of deionized water, put in dry ice for 10 min then dried in speed vac.

Quantitation of Crude Oligomer or Raw Analysis

Samples were dissolved in deionized water (1.0 mL) and quantitated as follows: Blanking was first performed with water alone (1 mL). 20 ul of sample and 980 uL of water were mixed well in a microfuge tube, transferred to cuvette and absorbance reading obtained at 260 nm. The crude material is dried down and stored at −20° C.

HPLC Purification of Oligomer

The crude oligomers were analyzed and purified by HPLC (Dionex PA 100). The buffer system is A=Water B=0.25 M Tris-HCl pH 8, C: 0.375 M Sodium per chlorate, flow 5.0 mL/min, wavelength 260 nm. First inject a small amount of material (~5 OD) and analyze by LC-MS. Once the identity of this material is confirmed the crude oligomer can then be purified using a larger amount of material, e.g., 60 OD's per run, flow rate of 5 mL/min. Fractions containing the full-length oligonucleotides are then pooled together, evaporated and finally desalted as described below.

Desalting of Purified Oligomer

The purified dry oligomer was then desalted using Sephadex G-25M (Amersham Biosciences). The cartridge was conditioned with 10 mL of water. The purified oligomer dissolved thoroughly in 2.5 mL RNAse free water was applied to the cartridge with very slow dropwise elution. The salt free oligomer was eluted with 3.5 ml water directly into a screw cap vial.

HPLC Analysis and Electrospray LC/Ms

Approximately 0.2 OD oligomer is first dried down, redissolved in water (50 ul) and then pipetted in special vials for HPLC and LC-MS analysis.

Table 6 summarizes the sequence length, alternating A and C units and whether the backbone is phosphorothioate (PS) or phosphodiester (PO) for the resulting exemplified modified oligonucleotides.

TABLE 6

| No. | Length | A modification | C modification | Backbone |
|---|---|---|---|---|
| 1 | (AC)20 | 2'-OMe | 2'-OMe | PS |
| 2 | (AC)15 | 2'-OMe | 2'-OMe | PS |
| 3 | (AC)25 | 2'-OMe | 2'-OMe | PS |
| 4 | (AC)30 | 2'-OMe | 2'-OMe | PS |
| 5 | (AC)20 | 2'-O-MOE | 2'-O-MOE | PS |
| 6 | (AC)20 | LNA | LNA | PS |
| 7 | (AC)20 | 2'-F | 2'-F | PS |
| 8 | (AC)20 | 2'-O-Propargyl | 2'-O-Propargyl | PS |
| 9 | (AC)20 | 2'-O-butyne | 2'-O-butyne | PS |
| 10 | (AC)20 | 2'-F-Ara | 2'-F-Ara | PS |
| 11 | (AC)20 | UNA | UNA | PS |
| 12 | (AC)20 | ENA | ENA | PS |
| 13 | (AC)20 | 2'-OMe | 2'-O-MOE | PS |
| 14 | (AC)20 | 2'-OMe | LNA | PS |
| 15 | (AC)20 | 2'-OMe | 2'-F | PS |
| 16 | (AC)20 | 2'-OMe | 2'-O-Propargyl | PS |
| 17 | (AC)20 | 2'-OMe | 2'-O-butyne | PS |
| 18 | (AC)20 | 2'-OMe | 2'-F-Ara | PS |
| 19 | (AC)20 | 2'-OMe | UNA | PS |
| 20 | (AC)20 | 2'-OMe | ENA | PS |
| 21 | (AC)20 | 2'-OMe | 2'-$NH_2$ | PS |
| 22 | (AC)20 | 2'-O-MOE | 2'-OMe | PS |
| 23 | (AC)20 | 2'-O-MOE | LNA | PS |
| 24 | (AC)20 | 2'-O-MOE | 2'-F | PS |
| 25 | (AC)20 | 2'-O-MOE | 2'-O-Propargyl | PS |
| 26 | (AC)20 | 2'-O-MOE | 2'-O-butyne | PS |
| 27 | (AC)20 | 2'-O-MOE | 2'-F-Ara | PS |
| 28 | (AC)20 | 2'-O-MOE | UNA | PS |
| 29 | (AC)20 | 2'-O-MOE | ENA | PS |
| 30 | (AC)20 | 2'-O-MOE | 2'-$NH_2$ | PS |
| 31 | (AC)20 | LNA | 2'-OMe | PS |
| 32 | (AC)20 | LNA | 2'-O-MOE | PS |
| 33 | (AC)20 | LNA | 2'-F | PS |
| 34 | (AC)20 | LNA | 2'-O-Propargyl | PS |
| 35 | (AC)20 | LNA | 2'-O-butyne | PS |
| 36 | (AC)20 | LNA | 2'-F-Ara | PS |
| 37 | (AC)20 | LNA | UNA | PS |
| 38 | (AC)20 | LNA | ENA | PS |
| 39 | (AC)20 | LNA | 2'-$NH_2$ | PS |
| 40 | (AC)20 | 2'-F | LNA | PS |
| 41 | (AC)20 | 2'-F | 2'-OMe | PS |
| 42 | (AC)20 | 2'-F | 2'-O-MOE | PS |
| 43 | (AC)20 | 2'-F | 2'-O-Propargyl | PS |
| 44 | (AC)20 | 2'-F | 2'-O-butyne | PS |
| 45 | (AC)20 | 2'-F | 2'-F-Ara | PS |
| 46 | (AC)20 | 2'-F | UNA | PS |
| 47 | (AC)20 | 2'-F | ENA | PS |
| 48 | (AC)20 | 2'-F | 2'-$NH_2$ | PS |
| 49 | (AC)20 | 2'-O-Propargyl | 2'-OMe | PS |
| 50 | (AC)20 | 2'-O-Propargyl | 2'-O-MOE | PS |
| 51 | (AC)20 | 2'-O-Propargyl | LNA | PS |
| 52 | (AC)20 | 2'-O-Propargyl | 2'-F | PS |
| 53 | (AC)20 | 2'-O-Propargyl | 2'-O-butyne | PS |
| 54 | (AC)20 | 2'-O-Propargyl | 2'-F-Ara | PS |
| 55 | (AC)20 | 2'-O-Propargyl | UNA | PS |
| 56 | (AC)20 | 2'-O-Propargyl | ENA | PS |
| 57 | (AC)20 | 2'-O-Propargyl | 2'-$NH_2$ | PS |
| 58 | (AC)20 | 2'-O-butyne | 2'-OMe | PS |
| 59 | (AC)20 | 2'-O-butyne | 2'-O-MOE | PS |
| 60 | (AC)20 | 2'-O-butyne | LNA | PS |
| 61 | (AC)20 | 2'-O-butyne | 2'-F | PS |
| 62 | (AC)20 | 2'-O-butyne | 2'-O-Propargyl | PS |
| 63 | (AC)20 | 2'-O-butyne | 2'-F-Ara | PS |
| 64 | (AC)20 | 2'-O-butyne | UNA | PS |
| 65 | (AC)20 | 2'-O-butyne | ENA | PS |
| 66 | (AC)20 | 2'-O-butyne | 2'-$NH_2$ | PS |
| 67 | (AC)20 | 2'-F-Ara | 2'-OMe | PS |
| 68 | (AC)20 | 2'-F-Ara | 2'-O-MOE | PS |
| 69 | (AC)20 | 2'-F-Ara | LNA | PS |
| 70 | (AC)20 | 2'-F-Ara | 2'-F | PS |
| 71 | (AC)20 | 2'-F-Ara | 2'-O-Propargyl | PS |
| 72 | (AC)20 | 2'-F-Ara | 2'-O-butyne | PS |
| 73 | (AC)20 | 2'-F-Ara | UNA | PS |
| 74 | (AC)20 | 2'-F-Ara | ENA | PS |
| 75 | (AC)20 | 2'-F-Ara | 2'-$NH_2$ | PS |
| 76 | (AC)20 | UNA | 2'-OMe | PS |
| 77 | (AC)20 | UNA | 2'-O-MOE | PS |
| 78 | (AC)20 | UNA | LNA | PS |

TABLE 6-continued

| No. | Length | A modification | C modification | Backbone |
|---|---|---|---|---|
| 79 | (AC)20 | UNA | 2'-F | PS |
| 80 | (AC)20 | UNA | 2'-O-Propargyl | PS |
| 81 | (AC)20 | UNA | 2'-O-butyne | PS |
| 82 | (AC)20 | UNA | 2'-F-Ara | PS |
| 83 | (AC)20 | UNA | ENA | PS |
| 84 | (AC)20 | UNA | 2'-NH$_2$ | PS |
| 85 | (AC)20 | ENA | 2'-OMe | PS |
| 86 | (AC)20 | ENA | 2'-O-MOE | PS |
| 87 | (AC)20 | ENA | LNA | PS |
| 88 | (AC)20 | ENA | 2'-F | PS |
| 89 | (AC)20 | ENA | 2'-O-Propargyl | PS |
| 90 | (AC)20 | ENA | 2'-O-butyne | PS |
| 91 | (AC)20 | ENA | 2'-F-Ara | PS |
| 92 | (AC)20 | ENA | UNA | PS |
| 93 | (AC)20 | ENA | 2'-NH$_2$ | PS |
| 94 | (AC)20 | LNA | 2'-O-MOE | PS |
| 95 | (AC)20 | 2'-F | LNA | PS |
| 96 | (AC)25 | 2'-OMe | 2'-OMe | PO |
| 97 | (AC)25 | 2'-OMe | 2'-OMe | PS |
| 98 | (AC)20 | 2'-F | 2'-OMe | PS |
| 99 | (AC)20 | LNA | 2-O-Me | PS |
| 100 | (AC)20 | 2'-OMe | 2'-F | PS |
| 101 | (AC)20 | 2'-OMe | 2'-OMe | PO |
| 102 | (AC)20 | 2'-F | 2'-O-MOE | PS |
| 103 | (AC)30 | 2'-OMe | 2'-OMe | PS |
| 104 | (AC)15 | 2'-OMe | 2'-OMe | PS |
| 105 | (AC)20 | 2'-OMe | LNA | PS |
| 106 | (AC)20 | LNA | LNA | PS |
| 107 | (AC)20 | 2'-OMe | 2'-O'MOE | PS |
| 108 | (AC)20 | 2'-O-MOE | 2'-OMe | PS |
| 109 | (AC)20 | 2'-OMe | 2'-OMe | PS |
| 110 | (AC)30 | 2'-OMe | 2'-O-butyne | PO |
| 111 | (AC)20 | 2'-F | 2'-F | PS |
| 112 | (AC)20 | 2'-OMe | 2'-OMe | PS |
| 113 | (AC)15 | 2'-OMe | 2'-OMe | PO |
| 114 | (AC)20 | 2'-O-MOE | 2'-O-MOE | PS |
| 115 | (AC)20 | 2'-O-MOE | 2'-F | PS |
| 116 | (AC)20 | LNA | 2'-F | PS |

Examples 117-130

The effect of 5' modification was evaluated by preparing a series of phosphorothioated oligonucleotides in accordance with the methods described above in Examples 1-116. End capped oligonucleotides were made by using a 5'-vinyl phosphonate building block to incorporate 5'-vinyl phosphonate endcaps:

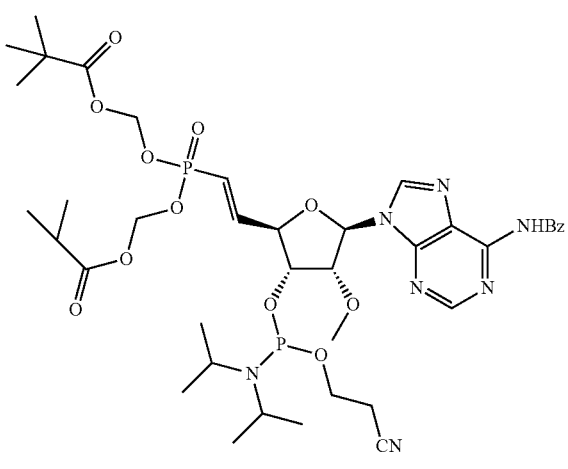

5'-vinyl phosphonate building block (5'-VP)

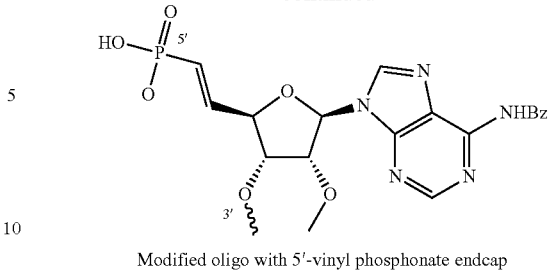

Modified oligo with 5'-vinyl phosphonate endcap

Figure 7:
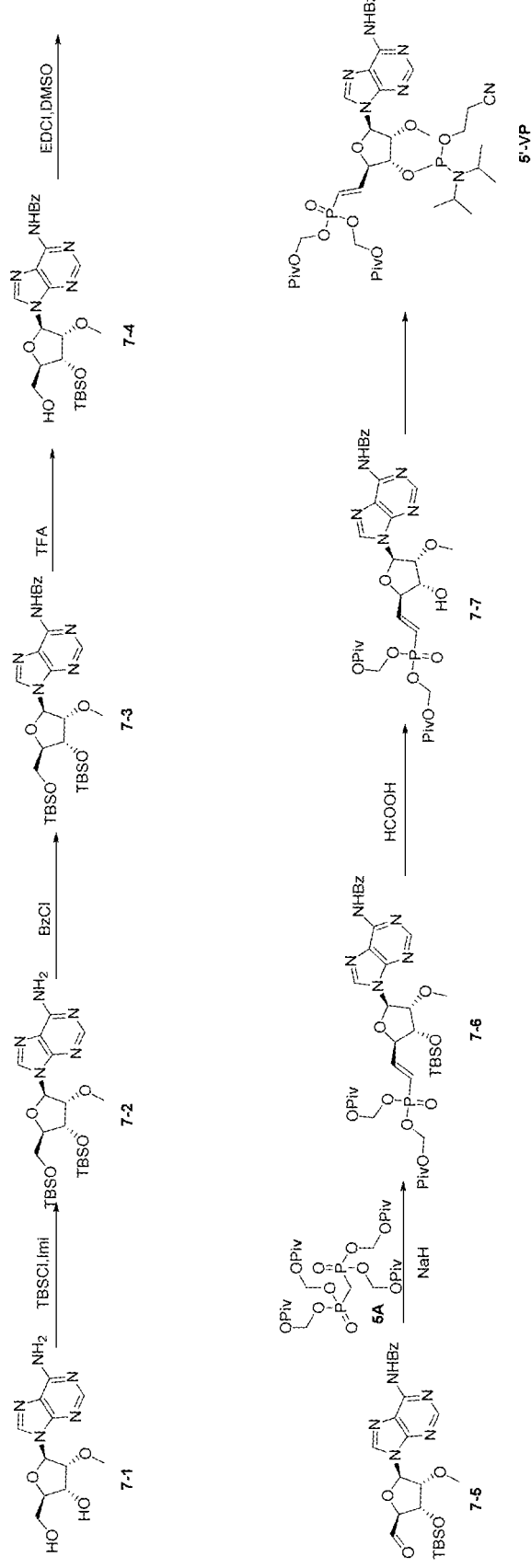
FIG. 7 illustrates an embodiment of a reaction scheme for preparing compound 5'-VP.

With reference to FIG. 7, the 5'-vinyl phosphonate building block (5'-VP) was prepared as follows:

Preparation of compound 7-2: To a solution of 7-1 (15.0 g, 53.3 mmol) in dry pyridine (150 mL) was added TBSCl (20.0 g, 133.3 mmol) and Imidazole (10.8 g, 159.9 mmol). The mixture was stirred at r.t. for 15 h. TLC showed 7-1 was consumed completely. The reaction mixture was concentrated in vacuo to give residue. The residue was quenched with DCM (500 mL). The DCM layer was washed with H$_2$O (1 L*2) 2 times and brine. The DCM layer concentrated in vacuo to give crude 7-2 (27.2 g, 53.3 mmol) as a yellow oil. The crude 7-2 was used in next step directly. ESI-LCMS m/z 510.5 [M+H]$^+$.

Preparation of compound 7-3: To a solution of 7-2 (26.2 g, 51.3 mmol) in pyridine (183 mL) was added dropwise the benzoyl chloride (15.8 g, 113.0 mmol) at 5° C. The reaction mixture was stirred at r.t. for 2 hours. TLC showed the 7-2 was consumed completely. The reaction mixture was quenched with H$_2$O (4 mL). Then NH$_3$.H$_2$O (20 mL) was added to the reaction mixture and stirred at r.t for 30 min. Then the Pyridine was removed from the mixture by concentration under reduced pressure. The residue was added to H$_2$O (100 mL) and extracted with EA (150 mL*3) and the EA layers combined. The EA layer was washed with brine and dried over Na$_2$SO$_4$. Filtered and concentrated to give the crude 7-3 (45.0 g). ESI-LCMS m/z=614.5 [M+H]$^+$.

Preparation of compound 7-4: To a mixture solution of 7-3 (44.0 g, crude) in THF (440 mL) was added the H$_2$O (220 mL) and TFA (220 mL) at 0° C. Then the reaction mixture was stirred at 0° C. for 1.5 h. TLC showed the 7-3 was consumed completely. The reaction mixture pH was adjusted to 7-8 with NH$_3$.H$_2$O. Then the mixture was extracted with EA (300 mL*7). The combined EA layer was washed with brine and concentrated in vacuo to give crude. The crude was purified by column chromatography (EA: PE=1:5~1:1) to give compound 7-4 (15.8 g) as a white solid. $^1$H-NMR (400 MHz, DMSO-d$_6$): δ=11.24 (s, 1H, exchanged with D$_2$O), 8.77 (s, 2H), 8.04-8.06 (m, 2H), 7.64-7.66 (m, 2H), 7.54-7.58 (m, 2H), 6.14-6.16 (d, J=5.9 Hz, 1H), 5.20-5.23 (m, 1H), 4.58-4.60 (m, 1H), 4.52-4.55 (m, 1H), 3.99-4.01 (m, 1H), 3.69-3.75 (m, 1H), 3.57-3.61 (m, 1H), 3.34 (s, 4H), 0.93 (s, 9H), 0.14-0.15 (d, J=1.44 Hz, 6H). ESI-LCMS m/z=500.3 [M+H]$^+$.

Preparation of compound 7-5: To a 500 mL, round-bottom flask was added the DMSO (132 mL) and 7-4 (13.2 g, 26.4 mmol), EDCI (15.19 g, 79.2 mmol) in turn at r.t. Then the Pyridine (2.09 g, 26.4 mmol, 2.1 mL) was added to the reaction mixture. After stirring 5 min, the TFA (1.51 g, 13.2 mmol) was added to the reaction mixture. Then reaction mixture was stirred at r.t for 3 hrs. LC-MS showed the 7-4 was consumed completely. The reaction mixture was added to the ice water (500 mL) and extracted with EA (300 mL*3) 3 times. The combined EA layer was washed with H$_2$O 2 times and brine I time. Dried over Na$_2$SO$_4$ and filtered. The filtrate was concentrated to get crude 7-5 (14.6 g) as a white solid. ESI-LCMS m/z=516.3 [M+H]$^+$.

Preparation of compound 7-6: The 5A (24.4 g, 38.5 mmol) was added to a mixture solution of NaH (2.5 g, 64.3 mmol, 60% purity) in THF (50 mL) at 0° C. After stirring 15 min, the 7-5 (16.0 g, 32.1 mmol) in THF (60 mL) was added to the reaction mixture. Then the reaction mixture was stirred at r.t for 1 hr. LC-MS showed the 7-5 was consumed completely. Then the reaction mixture was quenched with sat. NH$_4$Cl (500 mL) and extracted with EA (400 mL*3) 3 times. The combined EA layer was washed with brine, dried over Na$_2$SO$_4$ and filtered. The filtrate was concentrated in vacuo to get crude. The crude was purified by c.c (EA:PE=1: 5~1:1) to give 7-6 (10.0 g, 12.4 mmol, 38.6% yield) as a white solid. ESI-LCMS m/z=804.4 [M+H]$^+$; $^{31}$P NMR (162 MHz, DMSO-d$_6$) δ 17.01.

Preparation of compound 7-7: To a 500 mL round-bottom flask was added the 7-6 (9.0 g, 11.2 mmol) and H$_2$O (225 mL), HCOOH (225 mL) in turn. The reaction mixture was stirred at 26° C. for 15 h. LC-MS showed the 7-6 was consumed completely. The reaction mixture was adjusted the pH=6-7 with NH$_3$.H$_2$O. Then the mixture was extracted with EA (300 mL*3) 3 times. The combined EA layer was dried over Na$_2$SO$_4$, filtered and filtrate was concentrated to get crude. The crude was purified by column chromatography (DCM/MeOH=100:1~60:1) to give product 7-7 (7.0 g, 10.1 mmol, 90.6% yield). $^1$H-NMR (400 MHz, DMSO-d$_6$): δ=11.11 (s, 1H, exchanged with D$_2$O), 8.71-8.75 (d, J=14.4, 2H), 8.04-8.06 (m, 2H), 7.64-7.65 (m, 1H), 7.54-7.58 (m, 2H), 6.88-7.00 (m, 1H), 6.20-6.22 (d, J=5.4, 2H), 6.06-6.16 (m, 1H), 5.74-5.75 (d, J=5.72, 2H), 5.56-5.64 (m, 4H), 4.64-4.67 (m, 1H), 4.58-4.59 (m, 1H), 4.49-4.52 (m, 1H), 3.37 (s, 3H), 1.09-1.10 (d, J=1.96, 18H). $^{31}$P NMR (162 MHz, DMS O-d$_6$) δ 17.45. ESI-LCMS m/z=690.4 [M+H]$^+$.

Preparation of compound 5'-VP: To a solution of 7-7 (5.5 g, 7.9 mmol) in DCM (55 mL) was added the DCI (750 mg, 6.3 mmol), then CEP[N(iPr)$_2$]$_2$ (3.1 g, 10.3 mmol) was added. The mixture was stirred at r.t. for 2 h. TLC showed 3.5% of 7.7 remained. The reaction mixture was washed with H$_2$O (40 mL*2) and brine (50 mL*2), dried over Na$_2$SO$_4$ and concentrated to give crude. The residue was purified by Flash-Prep-HPLC with the following conditions (IntelFlash-1): Column, C18 silica gel; mobile phase, CH$_3$CN/H$_2$O (0.5% NH$_4$HCO$_3$)=1/5 increasing to CH$_3$CN/H$_2$O (0.5% NH$_4$HCO$_3$)=1/0 within 30 min, the eluted product was collected at CH$_3$CN/H$_2$O (0.5% NH$_4$HCO$_3$)=3/1; Detector, UV 254 nm. The product was concentrated and extracted with EA (50 mL*3). The combined EA layer was washed with brine and dried over Na$_2$SO$_4$, filtered and filtrate was concentrated to get resulting 5'-VP (6.0 g, 98% purity) as a white solid. $^1$H-NMR (400 MHz, DMSO-d$_6$): δ=11.27 (s, 1H, exchanged with D$_2$O), 8.72-8.75 (m, 2H), 8.04-8.06 (m, 2H), 7.54-7.68 (m, 3H), 6.85-7.05 (m, 1H), 6.09-6.26 (m, 2H), 5.57-5.64 (m, 4H), 4.70-4.87 (m, 3H), 3.66-3.88 (m, 4H), 3.37-3.41 (m, 3H), 2.82-2.86 (m, 2H), 1.20-1.21 (m, 12H), 1.08-1.09 (m, 18H). $^{31}$PNMR (162 MHz, DMSO-d$_6$): 149.99, 149.16, 17.05, 16.81. ESI-LCMS m/z=890.8 [M+H]$^+$.

Table 7 summarizes the sequence length, alternating A and C units, and 5' modification for the resulting exemplified modified phosphorothioated oligonucleotides.

TABLE 7

| No. | Length | A | C | 5'-Modification |
|---|---|---|---|---|
| 117 | (AC)17 | LNA-A | LNA-(5m)C | OH |
| 118 | (AC)18 | LNA-A | LNA-(5m)C | OH |
| 119 | (AC)19 | LNA-A | LNA-(5m)C | OH |
| 120 | (AC)17 | LNA-A | LNA-(5m)C | Vinyl-phosphonate-A |
| 121 | (AC)18 | LNA-A | LNA-(5m)C | Vinyl-phosphonate-A |
| 122 | (AC)19 | LNA-A | LNA-(5m)C | Vinyl-phosphonate-A |
| 123 | (AC)20 | LNA-A | LNA-(5m)C | Vinyl-phosphonate-A |
| 124 | (AC)17 | 2'-OMe-A | 2'-OMe-(5m)C | OH |
| 125 | (AC)18 | 2'-OMe-A | 2'-OMe-(5m)C | OH |
| 126 | (AC)19 | 2'-OMe-A | 2'-OMe-(5m)C | OH |
| 127 | (AC)17 | 2'-OMe-A | 2'-OMe-(5m)C | Vinyl-phosphonate-A |
| 128 | (AC)18 | 2'-OMe-A | 2'-OMe-(5m)C | Vinyl-phosphonate-A |
| 129 | (AC)19 | 2'-OMe-A | 2'-OMe-(5m)C | Vinyl-phosphonate-A |
| 130 | (AC)20 | 2'-OMe-A | 2'-OMe-(5m)C | Vinyl-phosphonate-A |

Examples 131-174

The effect of sequence length, LNA incorporation and 5'-modification was evaluated by preparing a series of phosphorothioated oligonucleotides in accordance with the methods described above in Examples 1-116. Table 8 summarizes the sequence length, alternating A and C units, 5' modification, and length and position of LNA units for the resulting exemplified modified phosphorothioated oligonucleotides.

TABLE 8

| No. | Length | A | C | 5'-Modification | LNA Modification |
|---|---|---|---|---|---|
| 131 | (AC)17 | 2'-OMe-A | LNA-(5m)C | OH | |
| 132 | (AC)18 | 2'-OMe-A | LNA-(5m)C | OH | |
| 133 | (AC)19 | 2'-OMe-A | LNA-(5m)C | OH | |
| 134 | (AC)20 | 2'-OMe-A | LNA-(5m)C | OH | |
| 135 | (AC)17 | 2'-OMe-A | LNA-(5m)C | Vinyl-phosphonate-A | |
| 136 | (AC)18 | 2'-OMe-A | LNA-(5m)C | Vinyl-phosphonate-A | |
| 137 | (AC)19 | 2'-OMe-A | LNA-(5m)C | Vinyl-phosphonate-A | |
| 138 | (AC)20 | 2'-OMe-A | LNA-(5m)C | Vinyl-phosphonate-A | |
| 139 | (AC)17 | LNA-A | 2'-OMe-(5m)C | OH | |
| 140 | (AC)18 | LNA-A | 2'-OMe-(5m)C | OH | |
| 141 | (AC)19 | LNA-A | 2'-OMe-(5m)C | OH | |
| 142 | (AC)20 | LNA-A | 2'-OMe-(5m)C | OH | |
| 143 | (AC)17 | LNA-A | 2'-OMe-(5m)C | Vinyl-phosphonate-A | |
| 144 | (AC)18 | LNA-A | 2'-OMe-(5m)C | Vinyl-phosphonate-A | |
| 145 | (AC)19 | LNA-A | 2'-OMe-(5m)C | Vinyl-phosphonate-A | |
| 146 | (AC)20 | LNA-A | 2'-OMe-(5m)C | Vinyl-phosphonate-A | |
| 147 | (AC)17 | UNA-A | LNA-(5m)C | OH | |
| 148 | (AC)18 | UNA-A | LNA-(5m)C | OH | |
| 149 | (AC)19 | UNA-A | LNA-(5m)C | OH | |
| 150 | (AC)20 | UNA-A | LNA-(5m)C | OH | |

TABLE 8-continued

| No. | Length | A | C | 5'-Modification | LNA Modification |
|---|---|---|---|---|---|
| 151 | (AC)17 | UNA-A | LNA-(5m)C | Vinyl-phosphonate-A | |
| 152 | (AC)18 | UNA-A | LNA-(5m)C | Vinyl-phosphonate-A | |
| 153 | (AC)19 | UNA-A | LNA-(5m)C | Vinyl-phosphonate-A | |
| 154 | (AC)20 | UNA-A | LNA-(5m)C | Vinyl-phosphonate-A | |
| 155 | (AC)17 | LNA-A | UNA-(5m)C | OH | |
| 156 | (AC)18 | LNA-A | UNA-(5m)C | OH | |
| 157 | (AC)19 | LNA-A | UNA-(5m)C | OH | |
| 158 | (AC)20 | LNA-A | UNA-(5m)C | OH | |
| 159 | (AC)20 | LNA-A | UNA-(5m)C | OH | Block of 4 LNA |
| 160 | (AC)17 | LNA-A | UNA-(5m)C | Vinyl-phosphonate-A | |
| 161 | (AC)18 | LNA-A | UNA-(5m)C | Vinyl-phosphonate-A | |
| 162 | (AC)19 | LNA-A | UNA-(5m)C | Vinyl-phosphonate-A | |
| 163 | (AC)20 | LNA-A | UNA-(5m)C | Vinyl-phosphonate-A | |
| 164 | (AC)20 | 2'-OMe-A LNA-A | 2'-OMe-(5m)C LNA-(5m)C | OH | Every $3^{rd}$ base is LNA |
| 165 | (AC)20 | 2'-OMe-A LNA-A | 2'-OMe-(5m)C LNA-(5m)C | Vinyl-phosphonate-A | Every $3^{rd}$ base is LNA |
| 166 | (AC)20 | 2'-OMe-A | 2'-OMe-(5m)C LNA-(5m)C | OH | Every 4th base is LNA |
| 167 | (AC)20 | 2'-OMe-A | 2'-OMe-(5m)C LNA-(5m)C | Vinyl-phosphonate-A | Every 4th base is LNA |
| 168 | (AC)17 | 2'-OMe-A | 2'-OMe-(5m)C LNA(5m)C | Vinyl-phosphonate-A | 5 (5m)lnC in the middle |
| 169 | (AC)18 | 2'-OMe-A | 2'-OMe-(5m)C LNA(5m)C | Vinyl-phosphonate-A | 6 lnAps(5m)C in the middle |
| 170 | (AC)19 | 2'-OMe-A | 2'-OMe-(5m)C LNA(5m)C | Vinyl-phosphonate-A | 6 lnAps(5m)C in the middle |
| 171 | (AC)20 | 2'-OMe-A | 2'-OMe-(5m)C LNA(5m)C | OH | 5 (5m)lnC in the middle |
| 172 | (AC)20 | LNA-A 2'-OMe-A | 2'-OMe-(5m)C LNA(5m)C | OH | 10 lnAps(5m)C in the middle |
| 173 | (AC)20 | 2'-OMe-A | 2'-OMe-(5m)C LNA(5m)C | Vinyl-phosphonate-A | 5 (5m)lnC in the middle |
| 174 | (AC)20 | 2'-OMe-A LNA-A | 2'-OMe-(5m)C LNA-(5m)C | Vinyl-phosphonate-A | 10 lnAps(5m)C in the middle |

Examples 175-216

The effect of sequence length, LNA incorporation, stereochemical modification and 5' modification was evaluated by preparing a series of phosphorothioated oligonucleotides in accordance with the methods described above in Examples 1-116, except that the oligonucleotides were prepared by a modified method using a dinucleotide building block consisting of an A unit and a C unit connected by a stereochemically defined phosphorothioate linkage as follows:

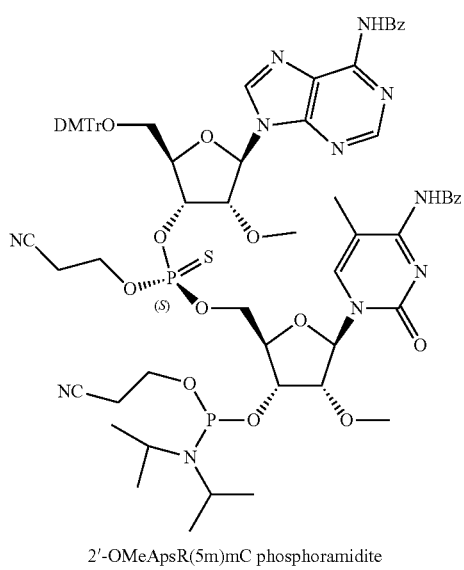

2'-OMeApsR(5m)mC phosphoramidite

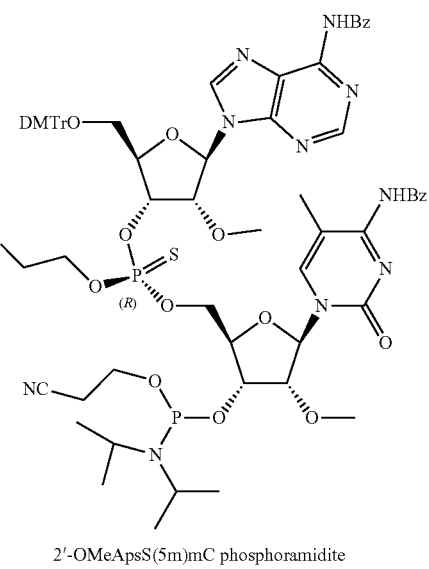

2'-OMeApsS(5m)mC phosphoramidite

Figure 8:
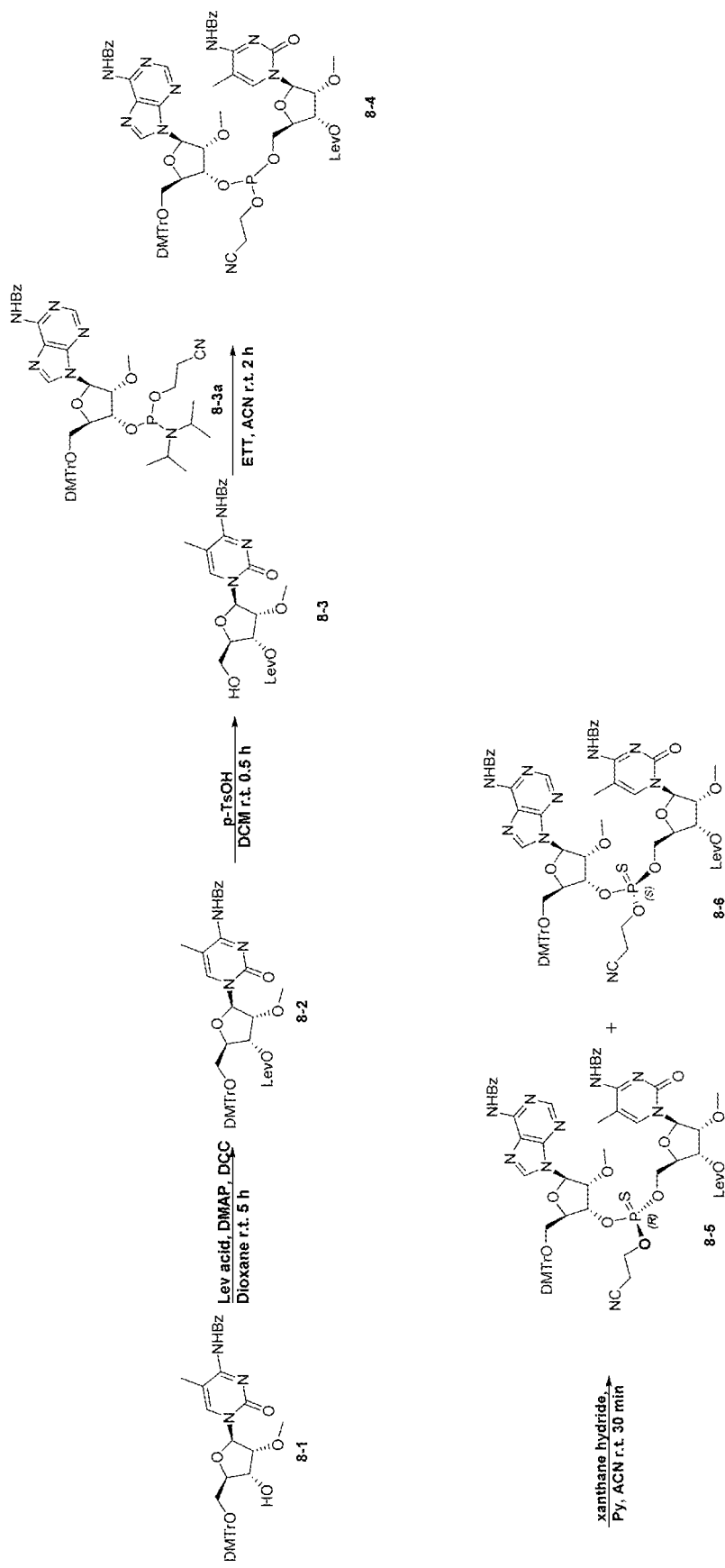
FIG. 8 illustrates an embodiment of a reaction scheme for preparing compounds 8-5 and 8-6.

With reference to FIGS. 8, 9A and 9B, the dinucleotide building blocks 9R and 9S were prepared as follows:

Preparation of compound 8-2: To a solution of 8-1 (300.0 g, 445.1 mmol) in 3000 mL of dry dioxane with an inert atmosphere of nitrogen was added levulinic acid (309.3 g, 2.67 mol) dropwise at room temperature. Then the dicyclohexylcarbodiimide (274.6 g, 1.33 mol) and 4-dimethylaminopyridine (27.1 g, 222.0 mmol) were added in order at room temperature. The resulting solution was stirred at room temperature for 5 h and diluted with 5000 mL of dichloromethane and filtered. The organic phase was washed with 2×3000 mL of 2% aqueous sodium bicarbonate and 1×3000 mL of water respectively. The organic phase was dried over anhydrous sodium sulfate, filtered and concentrated under reduced pressure. 345.0 g (crude) of 8-2 was obtained as a white solid and used for next step without further purification. ESI-LCMS: m/z 774 [M+H]$^+$.

Preparation of compound 8-3: To a solution of 8-2 (345 g, 445.1 mmol) was dissolved in 3000 mL dichloromethane with an inert atmosphere of nitrogen was added p-toluenesulfonic acid (84.6 g, 445.1 mmol) dropwise at 0° C. The resulting solution was stirred at 0° C. for 0.5 h and diluted with 3000 mL of dichloromethane and washed with 2×2000 mL of saturated aqueous sodium bicarbonate and 1×2000 mL of saturated aqueous sodium chloride respectively. The organic phase was dried over anhydrous sodium sulfate, and concentrated under reduced pressure and the residue was purified by silica gel column chromatography (SiO$_2$, dichloromethane:methanol=30:1) to give 8-3 (210.0 g, 90% over two steps) as a white solid. $^1$H-NMR (400 MHz, DMSO-d$_6$) δ=12.88 (s, 1H), 8.17-8.10 (m, 3H), 7.62-7.60 (m, 1H), 7.58-7.48 (m, 2H), 5.97-5.91 (m, 1H), 5.42 (d, J=5.9 Hz, 1H), 5.25 (s, 1H), 4.21-4.08 (m, 2H), 3.78-3.59 (m, 2H), 2.75-2.74 (m, 2H), 2.57 (m, 2H), 2.13 (d, J=2.3 Hz, 3H), 2.02 (s, 3H), 1.81 (m, 1H), 1.77-1.56 (m, 1H), 1.33-0.98 (m, 1H). ESI-LCMS: raiz 474 [M+H]$^+$.

Preparation of compound 8-4: To a solution of 8-3 (210.0 g, 444.9 mmol) in 2000 mL of acetonitrile with an inert atmosphere of nitrogen was added 8-3a (360.0 g, 405.4 mmol) and ETT (58.0 g, 445.9 mmol) in order at 0° C. The resulting solution was stirred for 2 h at room temperature. Then the mixture was filtered and used for next step without further purification. ESI-LCMS: m/z 1258 [M+H]$^+$.

Preparation of compounds 8-5 and 8-6: To a solution of 8-4 (509.9 g, 405.4 mmol) in 2000 mL of acetonitrile with an inert atmosphere of nitrogen was added pyridine (128.0 g, 1.62 mol) and 5-amino-3H-1,2,4-dithiazole-3-thione (121.8 g, 810.9 mmol) in order at room temperature. The reaction solution was stirred for 30 minutes at room temperature. The resulting solution was filtered and concentrated under reduced pressure. The residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in a mixture of 8-5 and 8-6 (430.0 g, 90% over two steps) as a white solid. The fractions were diluted with 3000 mL of dichloromethane. The organic phase was dried over anhydrous sodium sulfate, filtered and concentrated under reduced pressure. The residue was purified by SFC with the following conditions: CHIRALPAK IB N-5(IB50CD-VD008)/SFC 0.46 cm I.D.×25 cm L 10.0 ul Mobile phase: (DCM/EtOAc=80/20(V/V)), Detector, UV 254 nm. The fractions were concentrated until no residual solvent left under reduced pressure. 105.0 g (35.0%) of 8-5 were obtained as a white solid and used to make 9R as described below. $^1$H-NMR (400 MHz, DMSO-d$_6$) δ=12.88 (s, 1H), 11.26 (s, 1H), 8.62 (d, J=8.06 Hz, 2H), 8.18 (m, 2H), 8.05 (d, J=7.2 Hz, 2H), 7.79 (s, 1H), 7.67-7.48 (m, 6H), 7.40 (d, J=7.2 Hz, 2H), 7.28-7.18 (m, 7H), 6.86-6.83 (m, 4H), 6.21 (d, J=6.6 Hz, 1H), 5.91 (d, J=5.0 Hz, 1H), 5.44-5.41 (m, 1H), 5.28-5.26 (m, 1H), 5.06 (m, 1H), 4.45-4.24 (m, 7H), 3.71 (s, 6H), 3.39 (s, 4H), 3.31 (s, 3H), 2.98 (m, 2H), 2.75 (m, 2H), 2.56 (m, 2H), 2.01 (s, 3H). $^{31}$P-NMR (162 MHz, DMSO-d$_6$) δ=67.17. ESI-LCMS: m/z 1292 [M+H]$^+$; 170.0 g (56.6%) of 8-6 were obtained as a white solid and used to make 9S as described below. $^1$H-NMR (400 MHz, DMSO-d$_6$) δ=12.86 (s, 1H), 11.25 (s, 1H), 8.62 (d, J=16.6 Hz, 2H), 8.18 (d, J=7.2 Hz, 2H), 8.05 (m, 2H), 7.78 (s, 1H), 7.67-7.48 (m, 6H), 7.40 (d, J=7.2 Hz, 2H), 7.28-7.18 (m, 7H), 6.87-6.85 (m, 4H), 6.21 (d, J=6.8 Hz, 1H), 5.91 (d, J=5.2 Hz, 1H), 5.43-5.39 (m, 1H), 5.28-5.26 (m, 1H), 5.06 (m, 1H), 4.48-4.21 (m, 7H), 3.72 (s, 6H), 3.36 (s, 4H), 3.26 (s, 3H), 2.95 (m, 2H), 2.73 (m, 2H), 2.55 (m, 2H), 2.04 (s, 3H); $^{31}$P-NMR (162 MHz, DMSO-d$_6$) δ=66.84; ESI-LCMS: m/z 1292 [M+H]$^+$.

Preparation of compound 9-1: To a solution of 8-5 (100.0 g, 77.4 mmol) in 700 mL acetonitrile with an inert atmosphere of nitrogen was added 0.5 M hydrazine hydrate (20.0 g, 0.4 mol) in pyridine/acetic acid (3:2) at 0° C. The resulting solution was stirred for 0.5 h at 0° C. Then the reaction was added 2,4-pentanedione at once, the mixture was allowed to warm to room temperature and stirred for additional 15 min. The solution was diluted with DCM (2000 mL) and washed with sat. aq. NH$_4$Cl twice and washed with brine and dried over Na$_2$SO$_4$. Then the solution was concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in 9-1 (67.0 g, 80%) as a white solid. $^1$H-NMR (400 MHz, DMSO-d$_6$) δ=12.97 (s, 1H), 11.26 (s, 1H), 8.62 (d, J=11.2 Hz, 2H), 8.19 (d, J=7.2 Hz, 2H), 8.05 (m, 2H), 7.74 (s, 1H), 7.67-7.48. (m, 6H), 7.40 (d, J=7.2 Hz, 2H), 7.28-7.18 (m, 7H), 6.85 (m, 4H), 6.21 (m, 1H), 5.90 (d, J=3.2 Hz, 1H), 5.49-5.43 (m, 2H), 5.05 (m, 1H), 4.45 (m, 1H), 4.40-4.30 (m, 4H), 4.18-4.11 (m, 2H), 3.93 (m, 1H), 3.71 (s, 6H), 3.40-3.32 (m, 8H), 2.98 (m, 2H), 2.04 (s, 3H). $^{31}$P-NMR (162 MHz, DMSO-d$_6$) δ=67.30. ESI-LCMS: m/z 1194 [M+H]$^+$.

Preparation of compound 9R: To a solution of 9-1 (58.0 g, 48.6 mmol) in 600 mL of dichloromethane with an inert atmosphere of nitrogen was added CEP[N(iPr)$_2$]$_2$ (18.7 g, 62.1 mmol) and DCI (5.1 g, 43.7 mmol) in order at room temperature. The resulting solution was stirred for 1 hour at room temperature and diluted with 1000 mL dichloromethane and washed with 2×1000 mL of saturated aqueous sodium bicarbonate and 1×1000 mL of saturated aqueous sodium chloride respectively. The organic phase was dried over anhydrous sodium sulfate, filtered and concentrated until no residual solvent left under reduced pressure. The residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in 9R (51.2 g, 70%) as a white solid. $^1$H-NMR (400 MHz, DMSO-d$_6$) δ=12.94 (m, 1H), 11.26 (s, 1H), 8.62 (m, 2H), 8.19 (d, J=7.2 Hz, 2H), 8.05 (m, 2H), 7.77 (m, 1H), 7.69-7.46 (m, 6H), 7.39 (d, J=6.6 Hz, 2H), 7.26-7.20 (m, 7H), 6.84 (m, 4H), 6.20 (m, 1H), 5.90 (m, 1H), 5.43 (m, 1H), 5.06 (s, 1H), 4.46-4.17 (m, 7H), 4.12 (m, 1H), 3.82-3.80 (m, 2H), 3.73-3.66 (s, 6H), 3.64-3.58 (m, 2H), 3.48-3.29 (m, 8H), 2.98 (s, 2H), 2.82-2.77 (m, 2H), 2.03 (s, 3H), 1.24-1.15 (m, 12H). $^{31}$P-NMR (162 MHz, DMSO-d$_6$) δ=149.87, 149.80, 67.43, 67.33. ESI-LCMS: m/z 1394 [M+H]$^+$.

Preparation of compound 9-2: To a solution of 8-6 (110.0 g, 85.1 mmol) in 700 mL acetonitrile with an inert atmosphere of nitrogen was added 0.5 M hydrazine hydrate (21.1 g, 423.6 mmol) in pyridine/acetic acid (3:2) at 0° C. The resulting solution was stirred for 0.5 h at 0° C. Then the reaction was added 2,4-pentanedione at once, the mixture was allowed to warm to room temperature and stirred for additional 15 min, The solution was diluted with DCM (2000 mL) and washed with sat. aq. NH$_4$Cl twice and washed with brine and dried over Na$_2$SO$_4$. Then the solution was concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in 9-2 (72.0 g, 80%) as a white solid. $^1$H-NMR (400 MHz, DMSO-d$_6$) δ=12.94 (s, 1H), 11.24 (s, 1H), 8.61-8.57 (m, 2H), 8.18 (d, J=7.6 Hz, 2H), 8.03 (d, J=7.6 Hz, 2H), 7.74 (s, 1H), 7.66-7.47 (m, 6H), 7.40 (d, J=7.1 Hz, 2H), 7.27-7.20 (m, 7H), 6.86 (m, 4H), 6.20 (d, J=6.6 Hz, 1H), 5.87 (d, J=4.0 Hz, 1H), 5.42 (m, 2H), 5.05 (m, 1H), 4.45 (m, 2H), 4.40-4.24 (m, 1H), 4.22-4.06 (m, 4H), 3.92 (m, 1H), 3.71 (s, 6H), 3.40-3.32 (m, 8H), 2.94 (m, 2H), 2.03 (m, 3H). $^{31}$P-NMR (162 MHz, DMSO-d$_6$) δ=66.87. ESI-LCMS: m/z 1194 [M+H]$^+$.

Preparation of compound 9S: To a solution of 9-2 (62.0 g, 51.9 mmol) in 600 mL of dichloromethane with an inert atmosphere of nitrogen was added CEP[N(iPr)$_2$]$_2$ (19.0 g, 63.1 mmol) and DCI (5.55 g, 47.0 mmol) in order at room temperature. The resulting solution was stirred for 1 hour at room temperature and diluted with 1000 mL dichloromethane and washed with 2×1000 mL of saturated aqueous sodium bicarbonate and 1×1000 mL of saturated aqueous sodium chloride respectively. The organic phase was dried over anhydrous sodium sulfate, filtered and concentrated until no residual solvent left under reduced pressure. The residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in 9S (51.5 g, 70%) as a white solid. $^1$H-NMR (400 MHz, DMSO-d$_6$) δ=12.90 (s, 1H), 11.25 (s, 1H), 8.60 (m, 2H), 8.19 (d, J=6.6 Hz, 2H), 8.04 (m, 2H), 7.77 (s, 1H), 7.67-7.48 (m, 6H), 7.41 (d, J=8.0 Hz, 2H), 7.29-7.19 (m, 7H), 6.85 (m, 4H), 6.21 (d, J=6.8 Hz, 1H), 5.91-5.87 (m, 1H), 5.41 (m, 1H), 5.06 (m, 1H), 4.46-4.21 (m, 7H), 4.10 (m, 1H), 3.83-3.75 (m, 2H), 3.73-3.68 (s, 6H), 3.68-3.59 (m, 2H), 3.40-3.32 (m, 8H), 2.93 (m, 2H), 2.80 (m, 2H), 2.02 (s, 3H), 1.18-1.13 (m, 12H). $^{31}$P-NMR (162 MHz, DMSO-d$_6$) δ=149.96, 149.73, 66.99, 66.86. ESI-LCMS: m/z 1394 [M+H]$^+$.

The modified method also used a longer coupling time (8 min) and a greater number of equivalents of amidites (8 equivalents). Table 9 summarizes the sequence length, alternating A and C units, the number and type (R or S) of stereochemically defined phosphorothioate (PS) linkages, and 5'-modification for the resulting exemplified modified phosphorothioated oligonucleotides.

TABLE 9

| No. | Length | A | C | PS Modification | 5'-Modification |
|---|---|---|---|---|---|
| 175 | (AC)17 | 2'-OMe-A | 2'-OMe-(5m)C | 5 R isomer | OH |
| 176 | (AC)18 | 2'-OMe-A | 2'-OMe-(5m)C | 6 R isomer | OH |
| 177 | (AC)19 | 2'-OMe-A | 2'-OMe-(5m)C | 4 R isomer | OH |
| 178 | (AC)20 | 2'-OMe-A | 2'-OMe-(5m)C | 4 R isomer | OH |
| 179 | (AC)20 | 2'-OMe-A | 2'-OMe-(5m)C | 5 R isomer | OH |
| 180 | (AC)20 | 2'-OMe-A | 2'-OMe-(5m)C | 6 R isomer | OH |
| 181 | (AC)20 | 2'-OMe-A | 2'-OMe-(5m)C | 6 R isomer | Vinyl-phosphonate-A |
| 182 | (AC)20 | 2'-OMe-A | 2'-OMe-(5m)C | 7 R isomer | OH |
| 183 | (AC)20 | 2'-OMe-A | 2'-OMe-(5m)C | 13 R isomer | OH |
| 184 | (AC)20 | 2'-OMe-A | 2'-OMe-(5m)C | 20 R isomer | OH |
| 185 | (AC)20 | 2'-OMe-A | 2'-OMe-(5m)C | 20 R isomer | Vinyl-phosphonate-A |
| 186 | (AC)20 | 2'-OMe-A | 2'-OMe-(5m)C | 19 R isomer | Vinyl-phosphonate-A |
| 187 | (AC)17 | LNA-A | LNA-(5m)C | 5 R isomer | OH |
| 188 | (AC)18 | LNA-A | LNA-(5m)C | 6 R isomer | OH |
| 189 | (AC)19 | LNA-A | LNA-(5m)C | 6 R isomer | OH |
| 190 | (AC)20 | LNA-A | LNA-(5m)C | 4 R isomer | OH |
| 191 | (AC)20 | LNA-A | LNA-(5m)C | 5 R isomer | OH |
| 192 | (AC)20 | LNA-A | LNA-(5m)C | 6 R isomer | OH |
| 193 | (AC)20 | LNA-A | LNA-(5m)C | 6 R isomer, | Vinyl-phosphonate-A |
| 194 | (AC)20 | LNA-A | LNA-(5m)C | 13 R isomer | OH |
| 195 | (AC)20 | LNA-A | LNA-(5m)C | 20 R isomer | OH |
| 196 | (AC)20 | LNA-A | LNA-(5m)C | 20 R isomer | Vinyl-phosphonate-A |
| 197 | (AC)17 | 2'-OMe-A | 2'-OMe-(5m)C | 5 S isomer | OH |
| 198 | (AC)18 | 2'-OMe-A | 2'-OMe-(5m)C | 6 S isomer | OH |
| 199 | (AC)19 | 2'-OMe-A | 2'-OMe-(5m)C | 6 S isomer | OH |
| 200 | (AC)20 | 2'-OMe-A | 2'-OMe-(5m)C | 4 S isomer | OH |
| 201 | (AC)20 | 2'-OMe-A | 2'-OMe-(5m)C | 5 S isomer | OH |
| 202 | (AC)20 | 2'-OMe-A | 2'-OMe-(5m)C | 6 S isomer | OH |
| 203 | (AC)20 | 2'-OMe-A | 2'-OMe-(5m)C | 7 S isomer | OH |
| 204 | (AC)20 | 2'-OMe-A | 2'-OMe-(5m)C | 13 S isomer | OH |
| 205 | (AC)20 | 2'-OMe-A | 2'-OMe-(5m)C | 20 S isomer | OH |
| 206 | (AC)20 | 2'-OMe-A | 2'-OMe-(5m)C | 20 S isomer | Vinyl-phosphonate-A |
| 207 | (AC)17 | LNA-A | LNA-(5m)C | 5 S isomer | OH |
| 208 | (AC)18 | LNA-A | LNA-(5m)C | 6 S isomer | OH |
| 209 | (AC)19 | LNA-A | LNA-(5m)C | 6 S isomer | OH |
| 210 | (AC)20 | LNA-A | LNA-(5m)C | 4 S isomer | OH |
| 211 | (AC)20 | LNA-A | LNA-(5m)C | 5 S isomer | OH |
| 212 | (AC)20 | LNA-A | LNA-(5m)C | 6 S isomer | OH |
| 213 | (AC)20 | LNA-A | LNA-(5m)C | 6 S isomer | Vinyl-phosphonate-A |

TABLE 9-continued

| No. | Length | A | C | PS | Modification | 5'-Modification |
|---|---|---|---|---|---|---|
| 214 | (AC)20 | LNA-A | LNA-(5m)C | 13 | S isomer | OH |
| 215 | (AC)20 | LNA-A | LNA-(5m)C | 20 | S isomer | OH |
| 216 | (AC)20 | LNA-A | LNA-(5m)C | 20 | S isomer | Vinyl-phosphonate-A |

Examples 217-234

The effect of sequence length, LNA incorporation, stereochemical modification and 5' modification was evaluated by preparing a series of phosphorothioated oligonucleotides in accordance with the methods described above in Examples 175-216, except that the oligonucleotides were prepared by a modified method using a dinucleotide building block consisting of an A unit and a C unit connected by a stereochemically defined phosphorothioate linkage as follows:

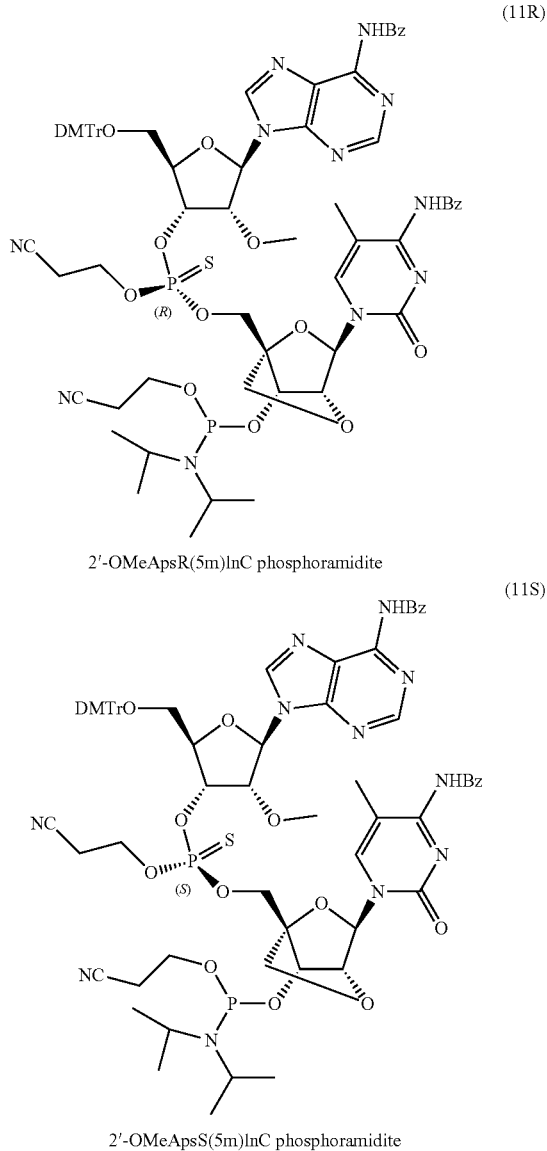

2'-OMeApsR(5m)lnC phosphoramidite (11R)

2'-OMeApsS(5m)lnC phosphoramidite (11S)

Figure 10:
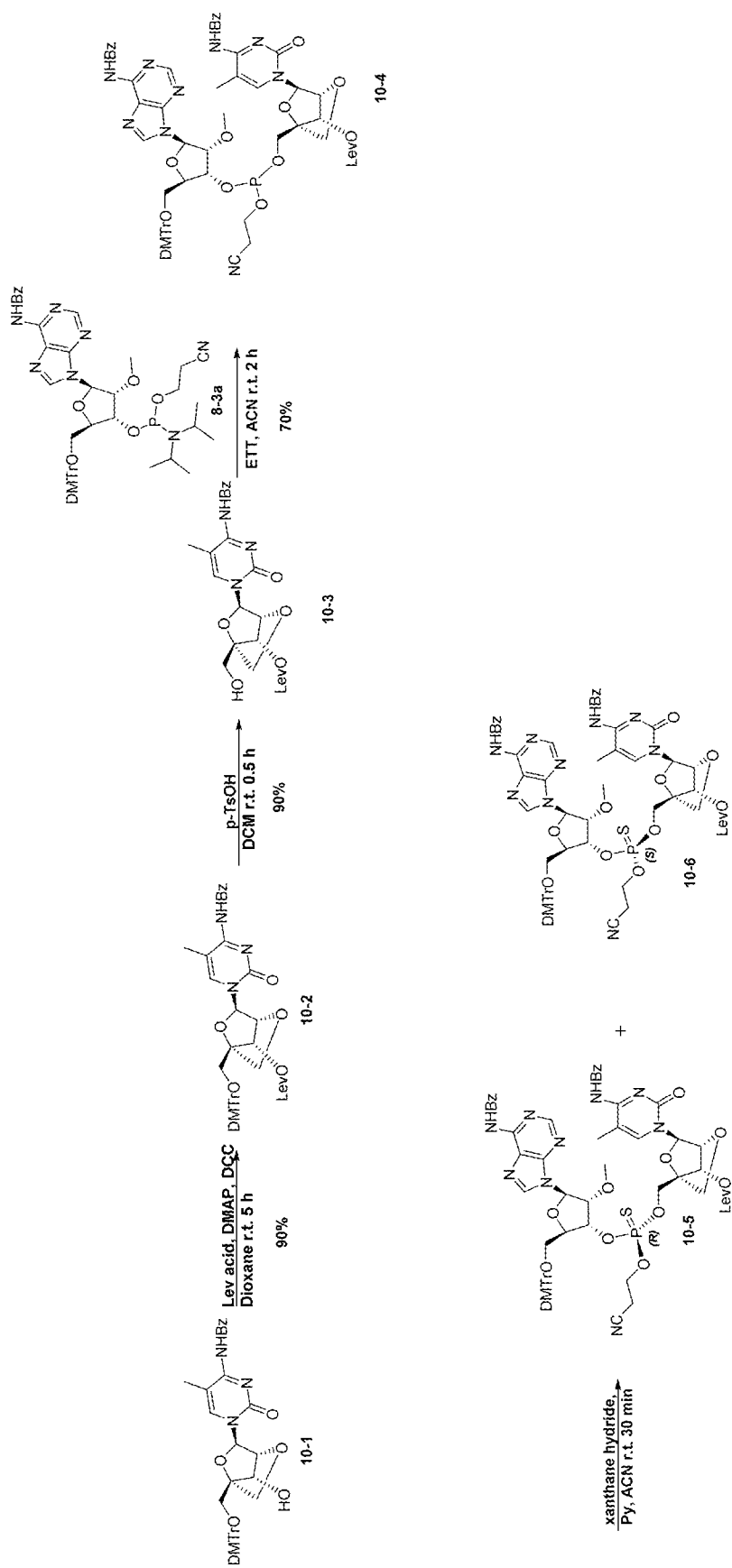
FIG. 10 illustrates an embodiment of a reaction scheme for preparing compounds 10-5 and 10-6.

With reference to FIGS. 10, 11A and 11B, the dinucleotide building blocks 11R and 11S were prepared as follows:

Preparation of compound 10-2: To a solution of 10-1 (50.0 g, 74.0 mmol) in 500 mL of dry dioxane with an inert atmosphere of nitrogen was added levulinic acid (51.5 g, 44.4 mol) dropwise at room temperature. Then the dicyclohexylcarbodiimide (45.7 g, 0.2 mol) and 4-dimethylaminopyridine (4.6 g, 37.0 mmol) were added in order at room temperature. The resulting solution was stirred at room temperature for 5 h and diluted with 3000 mL of dichloromethane and filtered. The organic phase was washed with 2×1000 mL of 2% aqueous sodium bicarbonate and 1×1000 mL of water respectively. The organic phase was dried over anhydrous sodium sulfate, filtered and concentrated under reduced pressure. 52.0 g (crude) of 10-2 was obtained as a white solid and used for next step without further purification. ESI-LCMS: m/z 774 $[M+H]^+$.

Preparation of compound 10-3: To a solution of 10-2 (52.0 g, 67.0 mmol) was dissolved in 400 mL dichloromethane with an inert atmosphere of nitrogen was added p-toluenesulfonic acid (51.5 g, 0.4 mol) dropwise at 0° C. The resulting solution was stirred at 0° C. for 0.5 h and diluted with 2000 mL of dichloromethane and washed with 2×1000 mL of saturated aqueous sodium bicarbonate and 1×1000 mL of saturated aqueous sodium chloride respectively. The organic phase was dried over anhydrous sodium sulfate and concentrated under reduced pressure and the residue was purified by silica gel column chromatography (SiO$_2$, dichloromethane:methanol=30:1) to give 10-3 (32.0 g, 80% over two steps) as a white solid. $^1$H-NMR (400 MHz, DMSO-d$_6$) δ=13.05 (s, 1H), 8.20-7.91 (m, 4H), 7.60-7.49 (m, 4H), 5.57 (m, 2H), 5.32 (d, J=10.8 Hz, 1H), 4.88 (s, 1H), 4.49 (s, 1H), 4.18 (s, 1H), 3.91-3.78 (m, 5H), 2.74-2.69 (m, 4H), 2.59-2.49 (m, 7H), 2.10 (s, 5H), 2.06 (s, 4H), 1.74-1.49 (m, 3H), 1.26-1.02 (m, 3H). ESI-LCMS: m/z 472 $[M+H]^+$.

Preparation of compound 10-4: To a solution of 10-3 (28.0 g, 59.4 mmol) in 300 mL of acetonitrile with an inert atmosphere of nitrogen was added 8-3a (50.0 g, 56.3 mmol) and ETT (7.9 g, 59.4 mmol) in order at 0° C. The resulting solution was stirred for 2 h at room temperature. Then the mixture was filtered and used for next step without further purification. ESI-LCMS: m/z 1258 $[M+H]^+$.

Preparation of compounds 10-5 and 10-6: To a solution of 10-4 (70.9 g, 56.3 mmol) in 300 mL of acetonitrile with an inert atmosphere of nitrogen was added pyridine (17.8 g, 225.2 mmol) and 5-amino-3H-1,2,4-dithiazole-3-thione (16.9 g, 112.6 mmol) in order at room temperature. The reaction solution was stirred for 30 minutes at room temperature. The resulting solution was filtered and concentrated under reduced pressure. The residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in a mixture of 10-5 and 10-6. The fractions were diluted with 3000 mL of dichloromethane. The organic phase was dried over anhydrous sodium sulfate, filtered and concentrated under reduced pressure. The residue was purified by SFC with the following conditions: CHIRAL CEL OD-H/SFC 20 mm*250 mmL Sum (Phase A: $CO_2$; Phase B: 50% ethanol-50% acetonitrile), Detector, UV 220 nm. The fractions were concentrated until no residual solvent left under reduced pressure. 9.0 g (25.7%) of 10-5 were obtained as a white solid and used to make 11R as described below. $^1$H-NMR (400 MHz, DMSO-$d_6$) δ=13.06 (s, 1H), 11.28 (s, 1H), 8.63 (d, J=20 Hz, 2H), 8.20 (m, 2H), 8.05 (d, J=8 Hz, 2H), 7.84 (s, 1H), 7.67-7.39 (m, 8H), 7.28-7.19 (m, 7H), 6.86-6.83 (m, 4H), 6.24 (d, J=6.6 Hz, 1H), 5.66 (s, 2H), 5.45-5.43 (m, 1H), 5.10-5.03 (m, 2H), 4.82-4.76 (m, 1H), 4.60 (s, 1H), 4.50-4.33 (m, 4H), 4.03-3.96 (m, 2H), 3.72 (s, 6H), 3.41-3.35 (m, 7H), 3.03-3.00 (m, 2H), 2.75-2.72 (m, 2H), 2.56-2.53 (m, 2H), 2.08-2.05 (m, 6H). $^{31}$P-NMR (162 MHz, DMSO-$d_6$) δ=67.02. ESI-LCMS: m/z 1290 [M+H]$^+$. 15.0 g (42.8%) of 10-6 were obtained as a white solid and used to make 11S as described below. $^1$H-NMR (400 MHz, DMSO-$d_6$) δ=13.05 (s, 1H), 11.26 (s, 1H), 8.63 (d, J=24 Hz, 2H), 8.-7.96 (m, 4H), 7.76 (s, 1H), 7.67-7.39 (m, 8H), 7.28-7.19 (m, 7H), 6.86 (d, J=7.2 Hz, 4H), 6.24 (d, J=6.4 Hz, 1H), 5.76 (s, 1H), 5.63 (s, 1H), 5.43-5.41 (m, 1H), 5.12 (m, 1H), 4.97 (s, 1H), 4.82-4.79 (m, 1H), 4.57-4.49 (m, 1H), 4.27-4.25 (m, 2H), 4.07-4.03 (m, 2H), 3.72 (s, 6H), 3.44-3.36 (m, 6H), 2.96 (m, 2H), 2.74-2.71 (m, 2H), 2.55-2.53 (m, 2H), 2.08 (s, 3H), 1.94 (s, 3H). $^{31}$P-NMR (162 MHz, DMSO-$d_6$) δ=66.58. ESI-LCMS: m/z 1290 [M+H]$^+$.

Preparation of compound 11-1: To a solution of 10-5 (10.0 g, 7.7 mmol) in 100 mL acetonitrile with an inert atmosphere of nitrogen was added 0.5 M hydrazine hydrate (1.8 g, 37.5 mmol) in pyridine/acetic acid (3:2) at 0° C. The resulting solution was stirred for 0.5 h at 0° C. Then the reaction was added 2,4-pentanedione at once, the mixture was allowed to warm to room temperature and stirred for additional 15 min. The solution was diluted with DCM (500 mL) and washed with sat. aq. NH$_4$Cl twice and washed with brine and dried over Na$_2$SO$_4$. Then the solution was concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in 11-1 (6.0 g, 65%) as a white solid. $^1$H-NMR (400 MHz, DMSO-$d_6$) δ=13.13 (s, 1H), 11.28 (s, 1H), 8.63 (d, J=20 Hz, 2H), 8.21 (d, J=8 Hz, 2H), 8.06-7.95 (m, 3H), 7.80 (s, 1H), 7.67-7.48. (m, 8H), 7.40 (d, J=7.6 Hz, 2H), 7.32-7.19 (m, 10H), 6.85 (m, 5H), 6.24 (d, J=8 Hz, 1H), 6.04 (d, J=4.0 Hz, 1H), 5.57 (s, 2H), 5.44-5.42 (m, 1H), 5.19-5.17 (m, 2H), 5.10-5.08 (m, 1H), 4.80-4.76 (m, 2H), 4.50 (d, J=5.6 Hz, 1H), 4.37-4.32 (m, 4H), 4.06-3.99 (m, 2H), 3.81 (m, 1H), 3.72 (s, 7H), 3.40-3.36 (m, 8H), 3.03-3.00 (m, 2H), 2.05 (m, 3H). $^{31}$P-NMR (162 MHz, DMSO-$d_6$) δ=67.21. ESI-LCMS: m/z 1192 [M+H]$^+$.

Preparation of compound 11R: To a solution of 11-1 (6.0 g, 5.0 mmol) in 60 mL of dichloromethane with an inert atmosphere of nitrogen was added CEP[N(iPr)$_2$]$_2$ (1.9 g, 6.5 mmol) and DCI (0.6 g, 5.0 mmol) in order at room temperature. The resulting solution was stirred for 1 hours at room temperature and diluted with 1000 mL dichloromethane and washed with 2×250 mL of saturated aqueous sodium bicarbonate and 1×250 mL of saturated aqueous sodium chloride respectively. The organic phase was dried over anhydrous sodium sulfate, filtered and concentrated until no residual solvent left under reduced pressure. The residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in 11R (5.0 g, 70%) as a white solid. $^1$H-NMR (400 MHz, DMSO-$d_6$) δ=13.10 (s, 1H), 11.28 (s, 1H), 8.20 (d, J=8.0 Hz, 2H), 8.04 (d, J=7.2 Hz, 2H), 7.79 (d, J=14 Hz, 2H), 7.67-7.48 (m, 6H), 7.39 (d, J=7.2 Hz, 2H), 7.27-7.18 (m, 7H), 6.85-6.82 (m, 4H), 6.23-6.20 (m, 1H), 5.64 (d, J=6.0 Hz, 1H), 5.44-5.41 (m, 1H), 5.08-5.07 (m, 1H), 4.82-4.77 (m, 1H), 4.56-4.46 (m, 3H), 4.36-4.30 (m, 2H), 4.22 (d, J=7.2 Hz, 1H), 3.98 (m, 1H), 3.89 (m, 1H), 3.71 (s, 7H), 3.59-3.55 (m, 2H), 3.40-3.34 (m, 10H), 3.02-2.98 (m, 2H), 2.77-2.72 (m, 2H), 2.08-2.05 (m, 3H), 1.13-1.08 (m, 12H). $^{31}$P-NMR (162 MHz, DMSO-$d_6$) δ=148.71, 148.11, 67.51, 67.44. ESI-LCMS: m/z 1392 [M+H]$^+$.

Preparation of compound 11-2: To a solution of 10-6 (10.0 g, 7.7 mmol) in 100 mL acetonitrile with an inert atmosphere of nitrogen was added 0.5 M hydrazine hydrate (1.8 g, 37.5 mmol) in pyridine/acetic acid (3:2) at 0° C. The resulting solution was stirred for 0.5 h at 0° C. Then the reaction was added 2,4-pentanedione at once, the mixture was allowed to warm to room temperature and stirred for additional 15 min. The solution was diluted with DCM (500 mL) and washed with sat. aq. NH$_4$Cl twice and washed with brine and dried over Na$_2$SO$_4$. Then the solution was concentrated under reduced pressure and the residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in 11-2 (7.5 g, 80%) as a white solid. $^1$H-NMR (400 MHz, DMSO-$d_6$) δ=13.11 (s, 1H), 11.26 (s, 1H), 8.63 (d, J=20 Hz, 2H), 8.20 (d, J=7.2 Hz, 2H), 8.15 (m, 3H), 7.73 (s, 1H), 7.66-7.47. (m, 8H), 7.41 (d, J=7.6 Hz, 2H), 7.32-7.19 (m, 10H), 6.85 (m, 5H), 6.24 (m, 1H), 5.99 (s, 1H), 5.54 (s, H), 5.41 (m, 1H), 5.10 (m, 1H), 4.79-4.75 (m, 1H), 4.57-4.49 (m, 3H), 4.30-4.24 (m, 4H), 4.02 (m, 2H), 3.85 (m, 1H), 3.72 (s, 7H), 3.38-3.35 (m, 7H), 2.95 (m, 2H), 1.98 (m, 3H). $^{31}$P-NMR (162 MHz, DMSO-$d_6$) δ=66.79. ESI-LCMS: m/z 1192 [M+H]$^+$.

Preparation of compound 11S: To a solution of 11-2 (7.0 g, 5.0 mmol) in 70 mL of dichloromethane with an inert atmosphere of nitrogen was added CEP[N(iPr)$_2$]$_2$ (2.0 g, 6.5 mmol) and DCI (0.6 g, 5.0 mmol) in order at room temperature. The resulting solution was stirred for 1 hours at room temperature and diluted with 1000 mL dichloromethane and washed with 2×250 mL of saturated aqueous sodium bicarbonate and 1×250 mL of saturated aqueous sodium chloride respectively. The organic phase was dried over anhydrous sodium sulfate, filtered and concentrated until no residual solvent left under reduced pressure. The residue was purified by Flash-Prep-HPLC with the following conditions (IntelFlash-1): Column, C18 silica gel; mobile phase, CH$_3$CN/H$_2$O (0.5% NH$_4$HCO$_3$)=1/1 increasing to CH$_3$CN/H$_2$O (0.5% NH$_4$HCO$_3$)=1/0 within 20 min, the eluted product was collected at CH$_3$CN/H$_2$O (0.5% NH$_4$HCO$_3$)=1/0; Detector, UV 254 nm. This resulted in 11S (6.3 g, 70%) as a white solid. $^1$H-NMR (400 MHz, DMSO-$d_6$) δ=13.10 (s, 1H), 11.27 (s, 1H), 8.65 (s, 1H), 8.61 (s, 1H), 8.19 (m, 2H), 8.02 (d, J=7.2 Hz, 2H), 7.76-7.73 (m, 1H), 7.66-7.47 (m, 6H), 7.40 (d, J=7.2 Hz, 2H), 7.28-7.19 (m, 7H), 6.86-6.85 (m, 4H), 6.24 (d, J=6.8 Hz, 1H), 5.62 (m, 1H), 5.43-5.41 (m, 1H), 5.10 (s, 1H), 4.84-4.78 (m, 1H), 4.66-4.49 (m, 3H), 4.30-4.18 (m, 3H), 4.04-3.95 (m, 2H), 3.83-3.77 (m, 1H), 3.72 (s, 7H), 3.62-3.54 (m, 2H), 3.44-3.32 (m, 6H), 2.96-2.92 (m, 2H), 2.77-2.72 (m, 2H), 1.98-1.97 (m, 3H), 1.12-1.11 (m, 12H). $^{31}$P-NMR (162 MHz, DMSO-d$_6$) δ=148.53, 148.09, 67.04. ESI-LCMS: m/z 1392 [M+H]$^+$.

As in Examples 175-216, the modified method also used a longer coupling time (8 min) and a greater number of equivalents of amidites (8 equivalents). Table 10 summarizes the sequence length, alternating A and C units, the number and type (R or S) of stereochemically defined phosphorothioate (PS) linkages, and 5' modification for the resulting exemplified modified phosphorothioated oligonucleotides.

TABLE 10

| No. | Length | A | C | PS Modification | 5'-Modification |
|---|---|---|---|---|---|
| 217 | (AC)17 | 2'-OMe-A | 2'-OMe-(5m)C | 5; 2'-OMeApsR(5m)lnC | OH |
| 218 | (AC)18 | 2'-OMe-A | 2'-OMe-(5m)C | 6; 2'-OMeApsR(5m)lnC | OH |
| 219 | (AC)19 | 2'-OMe-A | 2'-OMe-(5m)C | 6; 2'-OMeApsR(5m)lnC | OH |
| 220 | (AC)20 | 2'-OMe-A | 2'-OMe-(5m)C | 6; 2'-OMeApsR(5m)lnC | OH |
| 221 | (AC)20 | 2'-OMe-A | 2'-OMe-(5m)C | 20; 2'-OMeApsR(5m)lnC | OH |
| 222 | (AC)17 | 2'-OMe-A | 2'-OMe-(5m)C | 5; 2'-OMeApsR(5m)lnC | Vinyl-phosphonate-A |
| 223 | (AC)18 | 2'-OMe-A | 2'-OMe-(5m)C | 6; 2'-OMeApsR(5m)lnC | Vinyl-phosphonate-A |
| 224 | (AC)19 | 2'-OMe-A | 2'-OMe-(5m)C | 6; 2'-OMeApsR(5m)lnC | Vinyl-phosphonate-A |
| 225 | (AC)20 | 2'-OMe-A | 2'-OMe-(5m)C | 6; 2'-OMeApsR(5m)lnC | Vinyl-phosphonate-A |
| 226 | (AC)20 | 2'-OMe-A | 2'-OMe-(5m)C | 20; 2'-OMeApsR(5m)lnC | Vinyl-phosphonate-A |
| 227 | (AC)17 | 2'-OMe-A | 2'-OMe-(5m)C | 5; 2'-OMeApsS(5m)lnC | OH |
| 228 | (AC)18 | 2'-OMe-A | 2'-OMe-(5m)C | 6; 2'-OMeApsS(5m)lnC | OH |
| 229 | (AC)19 | 2'-OMe-A | 2'-OMe-(5m)C | 6; 2'-OMeApsS(5m)lnC | OH |
| 230 | (AC)20 | 2'-OMe-A | 2'-OMe-(5m)C | 6; 2'-OMeApsS(5m)lnC | OH |
| 231 | (AC)20 | 2'-OMe-A | 2'-OMe-(5m)C | 20; 2'-OMeApsS(5m)lnC | OH |
| 232 | (AC)17 | 2'-OMe-A | 2'-OMe-(5m)C | 5; 2'-OMeApsS(5m)lnC | Vinyl-phosphonate-A |
| 233 | (AC)18 | 2'-OMe-A | 2'-OMe-(5m)C | 6; 2'-OMeApsS(5m)lnC | Vinyl-phosphonate-A |
| 234 | (AC)19 | 2'-OMe-A | 2'-OMe-(5m)C | 6; 2'-OMeApsS(5m)lnC | Vinyl-phosphonate-A |

Examples 235-240

The effect of branching was evaluated by preparing a series of phosphorothioated oligonucleotides having a branched doubler design in which two of the oligonucleotides are attached to one another via a linking group. An example of a phosphorothioated oligonucleotide having a doubler design is illustrated in FIG. 1. Table 11 summarizes the sequence length, alternating A and C units, and 5' modification for the resulting exemplified phosphorothioated oligonucleotides.

TABLE 11

| No. | Length | A | C | 5'-Modification |
|---|---|---|---|---|
| 235 | (AC)9-(5m)lnC | LNA-A | LNA-(5m)C | 5' OH, 19mer |
| 236 | (AC)15-(5m)lnC | LNA-A | LNA-(5m)C | 5' OH, 31mer |
| 237 | (AC)20-(5m)lnC | LNA-A | LNA-(5m)C | 5' OH, 41mer |
| 238 | (AC)9-(5m)mC | 2'-OMe-A | 2'-OMe-(5m)C | 5' OH, 19mer |
| 239 | (AC)15-(5m)mC | 2'-OMe-A | 2'-OMe-(5m)C | 5' OH, 31mer |
| 240 | (AC)20-(5m)mC | 2'-OMe-A | 2'-OMe-(5m)C | 5' OH, 41mer |

Examples 241-246

The effect of branching was evaluated by preparing a series of phosphorothioated oligonucleotides having a branched trebler design in which three phosphorothioated oligonucleotides are attached to one another via a linking group. An example of a phosphorothioated oligonucleotide having a trebler design is illustrated in FIG. 2. Table 12 summarizes the sequence length, alternating A and C units, and 5' modification for the resulting exemplified phosphorothioated oligonucleotides.

TABLE 12

| No. | Length | A | C | 5'-Modification |
|---|---|---|---|---|
| 241 | (AC)10-TREB-(5m)mC | LNA-A | LNA-(5m)C | 5' OH, 31mer |
| 242 | (AC)13-TREB-(5m)mC | LNA-A | LNA-(5m)C | 5' OH, 40mer |
| 243 | (AC)15-TREB-(5m)mC | LNA-A | LNA-(5m)C | 5' OH, 46mer |
| 244 | (AC)10-TREB-(5m)mC | 2'-OMe-A | 2'-OMe-(5m)C | 5' OH, 31mer |
| 245 | (AC)13-TREB-(5m)mC | 2'-OMe-A | 2'-OMe-(5m)C | 5' OH, 40mer |
| 246 | (AC)15-TREB-(5m)mC | 2'-OMe-A | 2'-OMe-(5m)C | 5' OH, 46mer |

Examples 247-252

The effect of amido-bridge nucleic acid (AmNA-(N-Me)) modification and spirocyclopropylene-bridged nucleic acid (scp-BNA) modification was evaluated by preparing a series of modified phosphorothioated oligonucleotides. The AmNA-N-Me 6-N-benzoyladenosine (A$^{Bz}$), 4-N-benzoyl-5-methyl cytidine were obtained from Luxna Biotech Co, Ltd and scp-BNA phosphoramidite monomers with 6-N-benzoyladenosine (A$^{Bz}$), 4-N-benzoyl-5-methyl cytidine were synthesized by using the procedure described in the references Takao Yamaguchi, Masahiko Horiba and Satoshi Obika; *Chem. Commun.* 2015, 51, 9737-9740, and Masahiko Horiba, Takao Yamaguchi, and Satoshi Obika; *Journal of Organic Chemistry*, 2016, 81, 11000-11008. The monomers were dried in a vacuum desiccator with desiccant (P$_2$O$_5$, at room temperature for 24 hours). For the AmNA and scp-BNA modifications, the synthesis was carried out on a 1 μM scale in a 3' to 5' direction with the phosphoramidite monomers diluted to a concentration of 0.12 M in anhydrous CH$_3$CN in the presence of 0.3 M 5-(benzylthio)-1H-tetrazole activator (coupling time 16-20 min) to a solid bound oligonucleotide followed by modified capping, oxidation and deprotection to afford the modified oligonucleotides. The stepwise coupling efficiency of all modified phosphoramidites was more than 97%. The DDTT (dimethylamino-methylidene) amino)-3H-1, 2, 4-dithiazaoline-3-thione was used as the sulfur-transfer agent for the synthesis of the oligoribonucleotide phosphorothioates. Oligonucleotide-bearing solid supports were washed with 20% DEA solution in acetonitrile for 15 min then the column was washed thoroughly with AcCN. The support was heated at 65° C. with diisopropylamine:water:methanol (1:1:2) for 5 h in a heat block to cleave from the support and deprotect the base labile protecting groups. Table 13 summarizes the sequence length, alternating A and C units, and 5' modification for the resulting exemplified modified phosphorothioated oligonucleotides.

TABLE 13

| No. | Length | A | C | 5'-Modification |
|-----|--------|---|---|-----------------|
| 247 | (AmAps(5m)AmC)20 | AmNA(NMe)-A | AmNA(NMe)-(5m)C | 5' OH, 40mer, All AmNA |
| 248 | (ScpAps(5m)scpC)20 | Scp-BNA-A | Scp-BNA-(5m)C | 5' OH, 40mer, All Scp-BNA |
| 249 | AmAps(5m)mC (AC)19 | 2'-OMe-A | 2'-OMe-(5m)C | One AmNA at 5'-end, 40mer |
| 250 | (AC)19-mAps(5m)AmC | 2'-OMe-A | 2'-OMe-(5m)C | One AmNA at 3'-end, 40mer |
| 251 | ScpAps(5m)mC (AC)19 | 2'-OMe-A | 2'-OMe-(5m)C | One ScpA at 5'-end, 40mer |
| 252 | (AC)19-mAps(5m)ScpC | 2'-OMe-A | 2'-OMe-(5m)C | One ScpC at 3'-end, 40mer |

TABLE 14

| No. | Length | A | C | Targeting Ligand |
|-----|--------|---|---|------------------|
| 253 | Chol-(AC)20 | 2'-OMe-A | 2'-OMe-(5m)C | 5'-Cholesterol, 40mer |
| 254 | (AC)20-Chol | 2'-OMe-A | 2'-OMe-(5m)C | 3'-Cholesterol, 40mer |
| 255 | Toco-(AC)20 | 2'-OMe-A | 2'-OMe-(5m)C | 5'-Tocopherol, 40mer |
| 256 | (AC)20-Toco | 2'-OMe-A | 2'-OMe-(5m)C | 3'-Tocopherol, 40mer |

Examples 253-256

The effect of attaching a targeting ligand was evaluated by preparing a series of modified phosphorothioated oligonucleotides. The targeting ligands, cholesterol and a tocopherol (vitamin E), were attached to phosphorothioated oligonucleotides via an alkylene oxide linking group (tetraethylene glycol, TEG) in accordance with the methods described above in Examples 1-116 except that solid phase synthesis was conducted on cholesterol and tocopherol supports with attachment by a TEG linker for 3'-conjugation while final coupling of the phosphoramidite provided the 5'-conjugated oligonucleotides. FIGS. 3A-D and Table 14 illustrate the structures and summarize the sequence length, alternating A and C units, and targeting ligands for the resulting exemplified modified phosphorothioated oligonucleotides.

Examples 257-268

The effect of attaching a targeting ligand was evaluated by preparing a series of modified phosphorothioated oligonucleotides. N-acetylgalactosamine (GalNac) was attached to phosphorothioated oligonucleotides via various linking groups by reacting with a GalNAc building block as illustrated in FIG. 4A. GalNAc-3 and GalNAc-5 amidites were purchased from AM Chemicals LLC and Glen Research respectively. GalNAc-4 and GalNAc-6 were obtained from AM Chemicals LLC. Table 15 illustrates the structures and summarizes the sequence length, alternating A and C units, and targeting ligands for the resulting exemplified modified phosphorothioated oligonucleotides.

TABLE 15

| No. | Length | A | C | Targeting Ligand |
|-----|--------|---|---|------------------|
| 257 | GalNAc3ps-GalNAc3ps-GalNAc3po-(AC)20 | 2'-OMe-A | 2'-OMe-(5m)C | 5'-GalNAc-3; 40mer |
| 258 | (AC)20-po-GalNAc3ps-GalNAc3ps-GalNAc3 | 2'-OMe-A | 2'-OMe-(5m)C | 3'-GalNAc-3; 40mer |
| 259 | GalNAc3ps-GalNAc3ps-GalNAc3po-(AC)20 | LNA-A | LNA-(5m)C | 5'-GalNAc-3; 40mer |
| 260 | (AC)20-po-GalNAc3ps-GalNAc3ps-GalNAc3 | LNA-A | LNA-(5m)C | 3'-GalNAc-3; 40mer |
| 261 | GalNAc4ps-GalNAc4ps-GalNAc4po-(AC)20 | 2'-OMe-A | 2'-OMe-(5m)C | 5'-GalNAc-4; 40mer |
| 262 | (AC)20-po-GalNAc4ps-GalNAc4ps-GalNAc4 | 2'-OMe-A | 2'-OMe-(5m)C | 3'-GalNAc-4; 40mer |
| 263 | GalNAc4ps-GalNAc4ps-GalNAc4po-(AC)20 | LNA-A | LNA-(5m)C | 5'-GalNAc-4; 40mer |
| 264 | (AC)20-po-GalNAc4ps-GalNAc4ps-GalNAc4 | LNA-A | LNA-(5m)C | 3'-GalNAc-4; 40mer |
| 265 | GalNAc5ps-GalNAc5ps-GalNAc5po-(AC)20 | 2'-OMe-A | 2'-OMe-(5m)C | 5'-GalNAc-5; 40mer |
| 266 | (AC)20-po-GalNAc5ps-GalNAc5ps-GalNAc5 | 2'-OMe-A | 2'-OMe-(5m)C | 3'-GalNAc-5; 40mer |

TABLE 15-continued

| No. | Length | A | C | Targeting Ligand |
|---|---|---|---|---|
| 267 | GalNAc5ps-GalNAc5ps-GalNAc5po-(AC)20 | LNA-A | LNA-(5m)C | 5'-GalNAc-5; 40mer |
| 268 | (AC)20-po-GalNAc5ps-GalNAc5ps-GalNAc5 | LNA-A | LNA-(5m)C | 3'-GalNAc-5; 40mer |

Examples 269-272

The effect of attaching a targeting ligand was evaluated by preparing a series of modified phosphorothioated oligonucleotides. N-acetylgalactosamine (GalNAc) was attached to phosphorothioated oligonucleotides via a linking group by preparing the starting oligonucleotides, forming a precursor by attaching a $C_6$—$NH_2$ linking group at the 5'-terminal, and then reacting the precursor with a GalNAc ester. The sequences were synthesized at 10 μmol scale using universal support (Loading 65 mol/g). The $C_6$—$NH_2$ linker was attached to the 5'-terminal to form the precursor by reacting with 6-(4-monomethoxytritylamino)hexyl-(2-cyanoethyl)-(N, N-diisopropyl)-phosphoramidite in 0.1 M acetonitrile was a coupling time of 10 min. The phosphorothioated oligonucleotide-bearing solid supports were heated at room temperature with aqueous ammonia/methylamine (1:1) solution for 3 h in a shaker to cleave from the support and deprotect the base labile protecting groups.

After IEX purification and desalting, the precursors were dissolved in 0.2 M sodium bicarbonate buffer, pH 8.5 (0.015 mM) and 5-7 mol equivalent of GalNAc ester dissolved in DMSO was added. The structures of the GalNAc esters are illustrated in FIG. 4B. The reaction mixture was stirred at room temperature for 4 h. The sample was analyzed to confirm the absence of precursor. To this aqueous ammonia (28 wt. %) was added (5× reaction volume) and stirred at room temperature for 2-3 h. The reaction mixture was concentrated under reduced pressure and the resulting residue was dissolved in water and purified by HPLC on a strong anion exchange column.

Table 16 illustrates the structures and summarizes the sequence length, alternating A and C units, and targeting ligands for the resulting exemplified modified phosphorothioated oligonucleotides. GalNAc-1 and GalNAc-2 were prepared in accordance with procedures described in *J. Med. Chem.* 2016 59(6) 2718-2733 and WO 2017/021385A1, respectively

TABLE 16

| No. | Length | A | C | Targeting Ligand |
|---|---|---|---|---|
| 269 | GalNAc1-NH-C6-po-(AC)20 | 2'-OMe-A | 2'-OMe-(5m)C | 5'-GalNAc-1; 40mer |
| 270 | GalNAc1-NH-C6-po-(AC)20 | LNA-A | LNA-(5m)C | 5'-GalNAc-1; 40mer |
| 271 | GalNAc2-NH-C6-po-(AC)20 | 2'-OMe-A | 2'-OMe-(5m)C | 5'-GalNAc-2; 40mer |
| 272 | GalNAc2-NH-C6-po-(AC)20 | LNA-A | LNA-(5m)C | 5'-GalNAc-2; 40mer |

Examples 273-281

The effect of 5' modification was evaluated by preparing a series of phosphorothioated oligonucleotides in accordance with the methods described above, except that the following 5'-ethyl phosphonate (EP) building block was utilized to incorporate 5'-ethyl phosphonate endcaps:

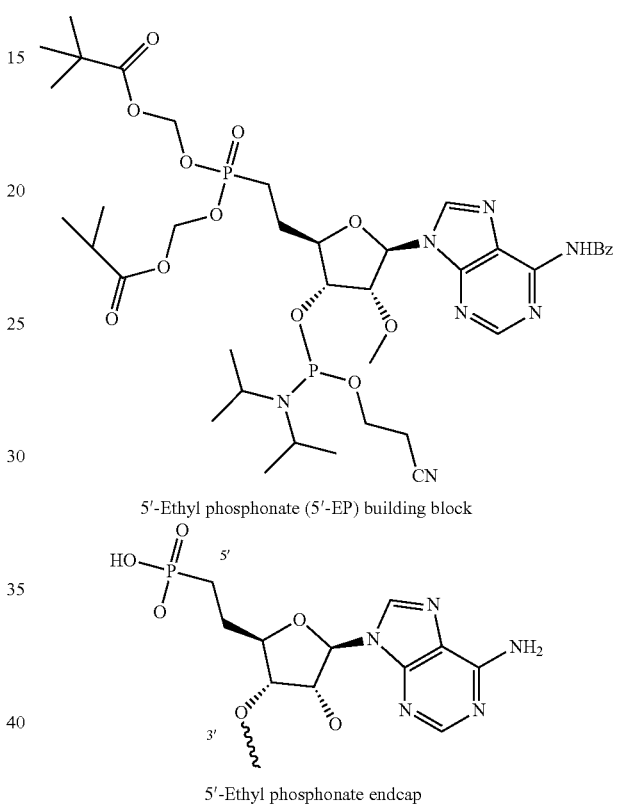

5'-Ethyl phosphonate (5'-EP) building block

5'-Ethyl phosphonate endcap

Figure 5:
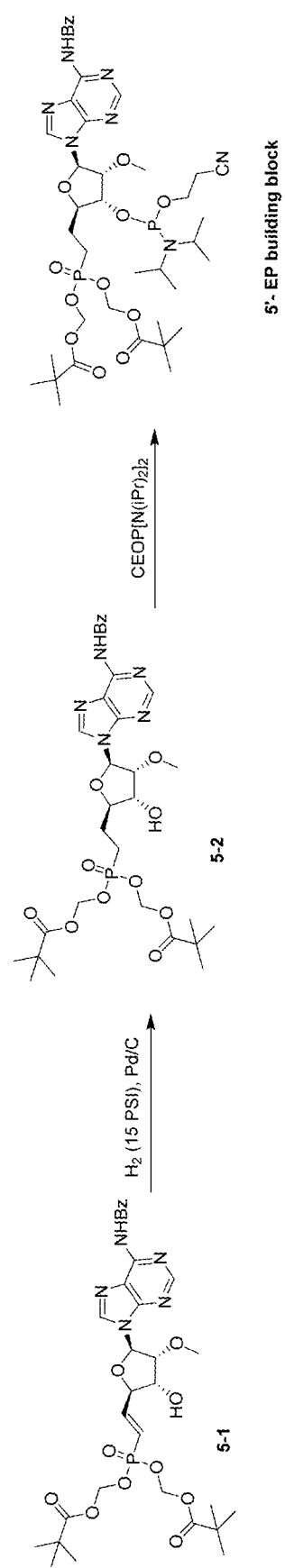
FIG. 5 illustrates an embodiment of a reaction scheme for preparing a 5'-EP building block.

With reference to FIG. 5, the 5'-Ethyl phosphonate building block was prepared as follows:

To a mixture of 5-1 (3.0 g, 4.35 mmol, 1 eq) in MeOH (5 mL) was added Pd/C (900 mg, 72.50 umol, 10% purity) under $N_2$. The suspension was degassed under vacuum and purged with $H_2$ for several times. The mixture was stirred under $H_2$ (15 psi) at 20° C. for 12 hr. $^1$H NMR and $^{31}$P NMR showed 5-1 was consumed completely to form desired product. The reaction mixture was filtered and concentrated to give [2-[(2R,3R,4R,5R)-5-(6-benzamidopurin-9-yl)-3-hydroxy-4-methoxy-tetrahydrofuran-2-yl]ethyl-(2,2-dimethylpropanoyloxymethoxy)phosphoryl]oxymethyl 2,2-dimethylpropanoate, compound 5-2, (2.8 g, 4.05 mmol, 93.06% yield) as a white solid. $^1$H NMR (400 MHz, $CD_3OD$) δ=8.75 (s, 1H), 8.53 (s, 1H), 8.08 (d, J=7.5 Hz, 2H), 7.68-7.61 (m, 1H), 7.59-7.50 (m, 2H), 7.23-7.17 (m, 1H), 7.15-7.10 (m, 1H), 6.15 (d, J=4.2 Hz, 1H), 5.71-5.61 (m, 4H), 4.57 (t, J=4.7 Hz, 1H), 4.41 (t, J=5.3 Hz, 1H), 4.09-3.99 (m, 1H), 3.49 (s, 3H), 2.16-1.97 (m, 4H), 1.17 (d, J=3.5 Hz, 18H); $^{31}$P NMR (162 MHz, $CD_3CN$) δ=32.91 (s, 1P).

To a solution of 5-2 (2.3 g, 3.33 mmol, 1 eq) in DCM (30 mL) was added 1H-imidazole-4,5-dicarbonitrile (589.06 mg, 4.99 mmol, 1.5 eq) followed by 3-bis(diisopropylamino)phosphanyloxypropanenitrile (2.00 g, 6.65 mmol, 2.11 mL, 2.0 eq), and the mixture was stirred at 25° C. for 2 hr. TLC indicated that majority of 5-2 was consumed and one major new spot was formed. The reaction mixture was washed with $H_2O$ (50 mL*2) and brine (50 mL*2), dried over $Na_2SO_4$, and concentrated to give a residue. The residue was purified by Flash-C-18 column using the following conditions: Column, C18 silica gel; mobile phase, water and acetonitrile (0%-70% acetonitrile) to give [2-[(2R,3R,4R,5R)-5-(6-benzamidopurin-9-yl)-3-[2-cyanoethoxy-(diisopropylamino)phosphanyl]oxy-4-methoxy-tetrahydrofuran-2-yl]ethyl-(2,2-dimethylpropanoyloxymethoxy)phosphoryl]oxymethyl 2,2-dimethylpropanoate, (5'-EP building block), (1.4 g, 1.53 mmol, 45.88% yield, 97.2% purity) as a light yellow solid. LCMS (ESI): RT=3.785 min, m/z calcd. for $C_{40}H_{60}N_7O_{12}P_2$ 892.37 $[M+H]^+$, found 892.0. HPLC: Mobile Phase: 10 mMol NH4Ac in water (solvent C) and acetonitrile (solvent D), sing the elution gradient 80%-100% (solvent D) over 10 minutes and holding at 100% for 5 minutes at a flow rate of 1.0 mL/minute; Column30: Waters Xbridge C18 3.5 um, 150*4.6 mm; $^1$H NMR (400 MHz, $CD_3CN$) δ=δ=9.40 (s, 1H), 8.67 (s, 1H), 8.27 (d, J=1.8 Hz, 1H), 8.01 (d, J=7.5 Hz, 2H), 7.68-7.60 (m, 1H), 7.58-7.52 (m, 2H), 6.05 (dd, J=5.1, 8.4 Hz, 1H), 5.62-5.54 (m, 4H), 4.68 (t, J=1.8, 5.0 Hz, 1H), 4.64-4.55 (m, 1H), 4.25-4.11 (m, 1H), 3.93-3.66 (m, 4H), 3.40 (d, J=19.2 Hz, 3H), 2.75-2.67 (m, 2H), 2.14-1.95 (m, 4H), 1.25-1.20 (m, 12H), 1.15-1.11 (m, 18H); $^{31}$P NMR (162 MHz, $CD_3CN$) δ=149.95, 149.27, 32.29, 32.05.

Table 17 summarizes the sequence length, alternating A and C units, the number and type (R or S) of stereochemically defined phosphorothioate (PS) linkages and LNA modification for the resulting exemplified 5'-EP endcapped modified phosphorothioated oligonucleotides.

TABLE 17

| No. | Length | A | C | PS Modification | Comments |
|---|---|---|---|---|---|
| 273 | (AC)20 | 2'0-Me-A | 2'-OMe-(5m)C | PS | 40mer |
| 274 | (AC)20 | LNA-A | LNA-(5m)C | PS | 40mer |
| 275 | (AC)20 | 2'-OMe-A | 2'-OMe-(5m)C | 20; 2'-OMeApsR(5m)lnC | 20 R isomer, 41mer |
| 276 | (AC)20 | 2'-OMe-A | 2'-OMe-(5m)C | 19; 2'-OMeApsR(5m)lnC | 19 R isomer, 40mer |
| 277 | (AC)20 | 2'-OMe-A | LNA-(5m)C | PS | 40mer Alternate 2'-OMe/LNA |
| 278 | (AC)20 | 2'-OMe-A LNA-A | 2'-OMe-(5m)C LNA-(5m)C | PS | Every 3rd base is LNA |
| 279 | (AC)20 | 2'-OMe-A | 2'-OMe-(5m)C LNA-(5m)C | PS | Every 4th base is LNA |
| 280 | (AC)20 | 2'-OMe-A | 2'-OMe-(5m)C LNA-(5m)C | PS | 5 LNA in the middle |
| 281 | (AC)20 | 2'-OMe-A LNA-A | 2'-OMe-(5m)C LNA-(5m)C | PS | 10 LNA in the middle |

Examples 282-298

FIG. 6A describes compound nos. 282-295, which were prepared in accordance with the methods described above.

Examples 296-304

The effect of sequence length, LNA incorporation, and RNA incorporation was evaluated by preparing a series of phosphorothioated oligonucleotides in accordance with the methods described above. The results are summarized in Table 18.

TABLE 18

| No. | Length | A | C | RNA Modification |
|---|---|---|---|---|
| 296 | (AC)20 | 2'-OMe-A | LNA-(5m)C | 5 RNA |
| 297 | (AC)20 | 2'-OMe-A | 2'-OMe-(5m)C | 7 RNA |
| 298 | (AC)20 | 2'-OMe-A | 2'-OMe-(5m)C | 14 RNA |
| 299 | (AC)15 | 2'-OMe-A | 2'-OMe-(5m)C | 5 RNA |
| 300 | (AC)15 | 2'-OMe-A | 2'-OMe-(5m)C | 10 RNA |
| 301 | (AC)20 | LNA-A | LNA-(5m)C | 7 RNA |
| 302 | (AC)20 | LNA-A | LNA-(5m)C | 14 RNA |
| 303 | (AC)15 | LNA-A | LNA-(5m)C | 5 RNA |
| 304 | (AC)15 | LNA-A | LNA-(5m)C | 10 RNA |

Examples 305-313

The effect of sequence length, LNA incorporation, and backbone was evaluated by preparing a series of phosphorothioated oligonucleotides in accordance with the methods described above. The results are summarized in Table 19.

TABLE 19

| No. | Length | A | C | Backbone |
|---|---|---|---|---|
| 305 | (AC)20 | LNA-A | LNA-(5m)C | 40mer; 20 PO; 19 PS |
| 306 | (AC)20 | LNA-A | LNA-(5m)C | 40mer; 7 PO; 32 PS |
| 307 | (AC)20 | LNA-A | LNA-(5m)C | 40mer; 14 PO; 25 PS |
| 308 | (AC)15 | LNA-A | LNA-(5m)C | 30mer; 5 PO; 24 PS |
| 309 | (AC)15 | LNA-A | LNA-(5m)C | 30mer; 10 PO; 19 PS |
| 310 | (AC)20 | 2'-OMe-A | 2'-OMe-(5m)C | 40mer; 7 PO; 32 PS |
| 311 | (AC)20 | 2'-OMe-A | 2'-OMe-(5m)C | 40mer; 14 PO; 25 PS |
| 312 | (AC)15 | 2'-OMe-A | 2'-OMe-(5m)C | 30mer; 5 PO; 24 PS |
| 313 | (AC)15 | 2'-OMe-A | 2'-OMe-(5m)C | 30mer; 10 PO; 19 PS |

Examples 314-322

The effect of sequence length, LNA incorporation, and ethyl phosphonate endcap was evaluated by preparing a series of phosphorothioated oligonucleotides in accordance with the methods described above. The results are summarized in Table 20.

TABLE 20

| No. | Length | A | C | Modification |
|---|---|---|---|---|
| 314 | (AC)20 | 2'-OMe-A | LNA-(5m)C | Ethyl-phosphonate-A |
| 315 | (AC)20 | 2'-OMe-A | 2'-OMe-(5m)C | 19 R dimer block; Ethyl-phosphonate-A |
| 316 | (AC)20 | 2'-OMe-A | 2'-OMe-(5m)C | 5 LNA, Ethyl-phosphonate-A |
| 317 | (AC)20 | 2'-OMe-A | 2'-OMe-(5m)C LNA-(5m)C | 40mer; Every 4$^{th}$ base is LNA Ethyl-phosphonate-A |
| 318 | (AC)20 | 2'-OMe-A | 2'-OMe-(5m)C LNA-(5m)C | 40mer; Every 3rd base is LNA Ethyl-phosphonate-A |
| 319 | (AC)20 | 2'-OMe-A | 2'-OMe-(5m)C | 40mer; Ethyl-phosphonate-A |
| 320 | (AC)18 | 2'-OMe-A | LNA-(5m)C | 36mer; Alternate 2'-OMe and LNA |
| 321 | (AC)20 | 2'-OMe-A LNA-A | 2'-OMe-(5m)C LNA-(5m)C | 36mer; Every 3rd base is LNA |
| 322 | (AC)20 | 2'-OMe-A | LNA-(5m)C | 36mer; Every 4$^{th}$ base is LNA |

Examples 323-324

The effect of LNA incorporation and phosphate endcap was evaluated by preparing phosphorothioated oligonucleotides in accordance with the methods described above. The results are summarized in Table 21.

TABLE 21

| No. | Length | A | C | Endcap |
|---|---|---|---|---|
| 323 | (AC)20 | LNA-A | LNA-(5m)C | 5'-Phosphate |
| 324 | (AC)20 | 2'-OMe-A | 2'-OMe-(5m)C | 5'-Phosphate |

Examples 325-338

The effect of level of LNA incorporation was evaluated by preparing a series of phosphorothioated oligonucleotides in accordance with the methods described above. The results are summarized in Table 22.

TABLE 22

| No. | Length | A | C | Modification |
|---|---|---|---|---|
| 325 | (AC)20 | 2'-OMe-A LNA-A | 2'-OMe-(5m)C LNA-(5m)C | 40mer; 75% 2'-OMe, 25% LNA |
| 326 | (AC)20 | 2'-OMe-A LNA-A | 2'-OMe-(5m)C LNA-(5m)C | 40mer; 67.5% 2'-OMe 37.5% LNA |
| 327 | (AC)20 | 2'-O-MOE-A LNA-A | 2'-O-MOE-(5m)C LNA-(5m)C | 40mer; 75% 2'-O-MOE, 25% LNA |
| 328 | (AC)20 | 2'-O-MOE-A LNA-A | 2'-O-MOE-(5m)C LNA-(5m)C | 40mer; 67.5% 2'-O-MOE 37.5% LNA |
| 329 | (AC)20 | 2'-OMe-A LNA-A | 2'-OMe-(5m)C LNA-(5m)C | 40mer; 75% LNA, 25% 2'-OMe (10mer block) |
| 330 | (AC)20 | 2'-OMe-A LNA-A | 2'-OMe-(5m)C LNA-(5m)C | 40mer; 50% LNA; 50% 2'-OMe(20mer block) |
| 331 | (AC)20 | 2'-O-OE-A LNA-A | 2'-O-MOE-(5m)C LNA-(5m)C | 40mer; 75% LNA, 25% 2'-O-MOE (10mer block) |
| 332 | (AC)20 | 2'-O-MOE-A LNA-A | 2'-O-MOE-(5m)C LNA-(5m)C | 40mer; 50% LNA; 50% 2'-O-MOE (20mer block) |
| 333 | (AC)20 | LNA-A DNA-A | LNA-(5m)C DNA-(5m)C | 40mer; 7 DNA |
| 334 | (AC)20 | LNA-A DNA-A | LNA-(5m)C DNA-(5m)C | 40mer; 14 DNA |
| 335 | (AC)20 | LNA-A DNA-A | LNA-(5m)C DNA-(5m)C | 30mer; 5 DNA |
| 336 | (AC)20 | LNA-A DNA-A | LNA-(5m)C DNA-(5m)C | 30mer; 10 DNA |
| 337 | (AC)20 | LNA-A DNA-A | LNA-(5m)C DNA-(5m)C | 40mer; 50% LNA; 50% DNA (10mer DNA block) |
| 338 | (AC)20 | LNA-A DNA-A | LNA-(5m)C DNA-(5m)C | 40mer; 50% LNA; 50% DNA (20mer DNA block) |

Examples 339-340

The effect of ScpA and AmNA incorporation was evaluated by preparing phosphorothioated oligonucleotides in accordance with the methods described above. The results are summarized in Table 23.

TABLE 23

| No. | Length | A | C | Modification |
|---|---|---|---|---|
| 339 | (AC)20 | 2'-OMe-A | LNA-(5m)C | One ScpA at 3'-end, 40mer |
| 340 | (AC)20 | 2'-OMe-A | LNA-(5m)C | One AmNA at 3'-end, 40mer |

Examples 341-346

The effect of GNA and UNA incorporation was evaluated by preparing a series of phosphorothioated oligonucleotides in accordance with the methods described above. The results are summarized in Table 24.

TABLE 24

| No. | Length | A | C |
|---|---|---|---|
| 341 | (AC)20 | LNA-A | GNA-(5m)C |
| 342 | (AC)20 | GNA-A | 2'-OMe-(5m)C |
| 343 | (AC)20 | 2'-OMe-A | GNA-(5m)C |
| 345 | (AC)20 | UNA-A | UNA-(5m)C |
| 346 | (AC)20 | UNA-A | UNA-(5m)C |

Examples 347-350

The effect of attaching a targeting ligand was evaluated by preparing a series of modified phosphorothioated oligonucleotides in accordance with the methods described above. The results are summarized in Table 25.

TABLE 25

| No. | Length | A | C | Modification |
|---|---|---|---|---|
| 347 | GalNAc5ps-GalNAc5ps-GalNAc5po-(AC)20 | 2'-OMe-A | LNA-(5m)C | 40mer, alternate 2'-OMe-LNA; 5'-GalNac |
| 348 | GalNAc5ps-GalNAc5ps-GalNAc5po-(AC)20 | 2'-OMe-A | 2'-OMe-(5m)C LNA-(5m)C | 40mer, every 4th base is LNA; 5'-GalNac |
| 349 | GalNAc5ps-GalNAc5ps-GalNAc5po-(AC)20 | 2'-OMe-A | 2'-OMe-(5m)C LNA-A | 40mer, 5 LNA; 5'-GalNac |
| 350 | GalNAc5ps-GalNAc5ps-GalNAc5po-(AC)20 | 2'-OMe-A | LNA-(5m)C | 40mer, alternate 2'-OMe-LNA 5 RNA; 5'-GalNac |

Examples 351-355

The effect of attaching a cholesterol or tocopherol targeting ligand was evaluated by preparing a series of modified phosphorothioated oligonucleotides in accordance with the methods described above. The results are summarized in Table 26.

TABLE 26

| No. | Length | A | C | Targeting Ligand |
|---|---|---|---|---|
| 351 | Chol-(AC)20 | 2'-OMe-A | (5m)-Propargyl-C | 3'-Cholesterol, 40mer |
| 352 | (AC)20-Chol | 2'-OMe-A | (5m)-Propargyl-C | 3'-Palmitoyl, 40mer |
| 353 | (AC)20 | 3'-OMe-A | 3'-OMe-(5m)C | 3'-OMe, 40mer |
| 354 | (AC)20-Chol | 3'-OMe-A | 3'-OMe-(5m)C | 3'-cholesterol, 40mer |
| 355 | (AC)20-Toco | 3'-OMe-A | 3'-OMe-(5m)C | 3'-Tocopherol, 40mer |

Examples 356-358

The effect of endcap structure (methyl, allyl, cytosine) was evaluated by preparing phosphorothioated oligonucleotides in accordance with the methods described above. The results are summarized in Table 27.

TABLE 27

| No. | Length | A | C | Endcap |
|---|---|---|---|---|
| 356 | (AC)20 | 2'-OMe-A | LNA-(5m)C | 40mer, 4'-Me at 5'end |
| 357 | (AC)20 | 2'-OMe-A 3'-C-allyl-A | LNA-A LNA-(5m)C | 40mer, 5 3'-C-allyl-A |
| 358 | (AC)20 | LNA-A | LNA-(5m)C | 40mer, Cy-5 at 3'-end |

Examples 359-362

The effect of including G and U bases was evaluated by preparing phosphorothioated oligonucleotides in accordance with the methods described above. The compounds are summarized in Table 28.

TABLE 28

| No. | Length | Base 1 | Base 2 | Modification |
|---|---|---|---|---|
| 359 | (AG)20 | 2'-OMe-A | 2'-OMe-G | AG repeat |
| 360 | (GA)20 | 2'-OMe-G | 2'-OMe-A | GA repeat |
| 361 | (CA)20 | 2'-OMe-(5m)C | 2'-OMe-A | CA repeat |
| 362 | (AU)20 | 2'-OMe-A | 2'-OMe-U | AU repeat |

Examples 363-376

The effect of sequence length was evaluated by preparing a series of phosphorothioated oligonucleotides in accordance with the methods described above. The compounds are summarized in Table 29.

TABLE 29

| No. | Length | A | C | Modification |
|---|---|---|---|---|
| 363 | (AC)14 | 2'-OMe-A | 2'-OMe-C | 28mer |
| 364 | (AC)15-A | 2'-OMe-A | 2'-OMe-(5m)C | 31mer |
| 365 | (AC)17 | 2'-OMe-A | 2'-OMe-(5m)C | 34mer |
| 366 | (AC)18-A | 2'-OMe-A | 2'-OMe-(5m)C | 37mer |
| 367 | (AC)20 | 2'-OMe-A | 2'-OMe-C | 20mer |
| 368 | (AC)9 | 2'-OMe-A | 2'-OMe-(5m)C | 18mer |
| 369 | (AC)9-A | 2'-OMe-A | 2'-OMe-(5m)C | 19mer |
| 370 | (AC)10 | 2'-OMe-A | 2'-OMe-(5m)C | 20mer |
| 371 | (AC)9-A | LNA-A | LNA-(5m)C | 19mer |
| 372 | (AC)9 | LNA-A | LNA-(5m)C | 18mer |
| 373 | (AC)15 | LNA-A | LNA-(5m)C | 30mer |
| 374 | (AC)12-A | 2'-OMe-A | 2'-OMe-(5m)C | 25mer |
| 375 | (AC)20 | 2'-OMe-A | 2'-OMe-(5m)C | 40mer, 5 S isomers |
| 376 | (AC)10 | LNA-A | LNA-(5m)C | 20mer |

Examples 377-380 and 384

The effect of RNA incorporation was evaluated by preparing a series of phosphorothioated oligonucleotides in accordance with the methods described above. The results are summarized in Table 30.

TABLE 30

| No. | Length | A | C | Modification |
|---|---|---|---|---|
| 377 | (AC)20 | 2'-OMe-A Ribo-A | LNA-(5m)C | 40mer, 4 RNA |
| 378 | (AC)20 | 2'-OMe-A Ribo-A | LNA-(5m)C | 40mer, 3 RNA |
| 379 | (AC)20 | 2'-OMe-A Ribo-A | LNA-(5m)C | 40mer, 2 RNA |
| 380 | (AC)20 | 2'-OMe-A UNA-A | 2'-OMe-(5m)C UNA-(5m)C | 40mer, 4mer blocks of 2'-OMe and UNA |
| 384 | (AC)20 | 2'-OMe-A Ribo-A | LNA-(5m)C | 40mer, 1 RNA |

Examples 381-383

The effect of 4etl (4-ethyl-LNA) incorporation was evaluated by preparing a series of phosphorothioated oligonucleotides in accordance with the methods described above. The 4etl monomers were prepared in accordance with known methods (Seth, P. P., J. Org. Chem. 2010, 75, (5), 1569-1581). The results are summarized in Table 31.

TABLE 31

| No. | Length | A | C | Modification |
|---|---|---|---|---|
| 381 | (AC)20 | 4etl-A | 4etl-(5m)C | 40mer, 100% 4etl |
| 382 | (AC)20 | 2'-OMe-A | 4etl-(5m)C | 40mer, 50% 4etl |
| 383 | (AC)20 | 2'-OMe-A | 2'-OMe-(5m)C 4etl-(5m)C | 40mer, 25% 4etl |

Examples 385-389

The effect of nmLNA (N-methyl LNA) A and C incorporation was evaluated by preparing a series of phosphorothioated oligonucleotides in accordance with the methods described above. The nmLNA monomers were obtained from commercial sources (Bio-Synthesis Inc., Lewisville, Tex.). The results are summarized in Table 32.

TABLE 32

| No. | Length | A | C | Modification |
|---|---|---|---|---|
| 385 | (AC)20 | 2'-OMe-A nmLNA-A | LNA-(5m)C | 40mer, 1 nmLNA |
| 386 | (AC)20 | 2'-OMe-A nmLNA-A | LNA-(5m)C | 40mer, 3 nmLNA |
| 387 | (AC)20 | 2'-OMe-A nmLNA-A | LNA-(5m)C nmLNA (5m)-C | 40mer, 3 nmLNA |
| 388 | (AC)20 | 2'-OMe-A | LNA-(5m)C nmLNA (5m)-C | 40mer, 3 nmLNA |
| 389 | (AC)20 | 2'-OMe-A nmLNA-A | LNA-(5m)C nmLNA (5m)-C | 40mer, 4 nmLNA |

Examples 390-392

The effect of AmNA and Scp-BNA A and C incorporation was evaluated by preparing a series of phosphorothioated oligonucleotides in accordance with the methods described above. The results are summarized in Table 33 (also see Table 23).

TABLE 33

| No. | Length | A | C | Modification |
|---|---|---|---|---|
| 390 | (AC)20 | 2'-OMe-A | AmNA-(5m)C | 40mer, 20 AmNA(50%) |
| 391 | (AC)20 | 2'-OMe-A | 2'-OMe-(5m)C Scp-(5m)C | 40mer, 10 scp-BNA (25%) |
| 392 | (AC)20 | 2'-OMe-A Scp-A | 2'-OMe-(5m)C | 40mer, 5 scp-BNA (12.5%) |

Example B1

HBsAg Secretion Assay and Cytotoxicity Assay

Figure 6B:
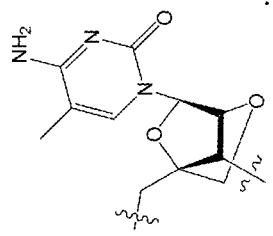
FIG. 6B illustrates embodiments of modified oligonucleotides and corresponding values of sequence independent antiviral activity against hepatitis B (as determined by HBsAg Secretion Assay) and cytotoxicity.

The sequence independent antiviral activity against hepatitis B (as determined by HBsAg Secretion Assay) and the cytotoxicity of a number of exemplified modified oligonucleotide compounds was determined as described below and summarized in Tables 34-35 and FIGS. 6A and 6B.

HBsAg Release Assay Protocol

Cell Culture

HepG2.2.15 cells were maintained in DMEM medium with 10% fetal bovine serum (FBS) and 1% penicillin/streptomycin, 1% Glutamine, 1% non-essential amino acids, 1% Sodium Pyruvate and 380 ug/ml G418. Cells were maintained at 37° C. in a 5% $CO_2$ atmosphere.

HBsAg Secretion Assay

HepG2.2.15 cells were grown in DMEM medium as described above. Cells were plated at a concentration of 45,000 cells/well in collagen-I coated 96 well plates. Immediately after addition of the cells, test compounds are added.

Selected compounds may also be tested following Lipofectamine® RNAiMAX transfection. Lipofectamine® RNAiMAX Transfection Reagent (Thermo Fisher) is used following the manufacturer's instructions.

The 50% inhibitory concentration ($EC_{50}$) and 50% cytotoxic concentration ($CC_{50}$; below) were assessed by solubilizing in 1×PBS to 100× the desired final testing concentration. Each compound was then serially diluted (1:3) up to 8 distinct concentrations to 10× the desired final testing concentration in DMEM medium with 10% FBS. A 10 μL sample of the 10× compounds in cell culture media was used to treat the HepG2.2.15 cells in a 96-well format. Cells were initially incubated with compounds for 3 days at 37° C. in a 5% $CO_2$ atmosphere.

Three days post compound addition/transfection replace media and compound with fresh media/compound with RNAiMax and incubate for a further 3 days for a total incubation time of 6 days. Collect both the cellular supernatant and cell lysate (see below) for quantification of HBsAg.

Secreted HBsAg was measured quantitatively using HBsAg ELISA kit (Autobio-CL0310).

The $EC_{50}$, the concentration of the drug required for reducing HBsAg secretion by 50% in relation to the untreated cell control value was calculated from the plot of the percentage reduction of the HBsAg level against the drug concentrations using Microsoft Excel (forecast function).

Set up a parallel set of plates that are to be used for testing compound induced cellular cytotoxicity (see below).

Cytotoxicity Assay

HepG2.2.15 cells were cultured and treated as above. At Day 6, cellular cytotoxicity was assessed using a cell proliferation assay (CellTiter-Glo Luminescent Cell Viability Assay; Promega) according to the manufacturer's instructions or a suitable alternative.

The $CC_{50}$, the concentration of the drug required for reducing cell viability by 50% in relation to the untreated cell control value was calculated from the plot of the percentage reduction of viable cells against the drug concentrations using Microsoft Excel (forecast function).

TABLE 34

POTENCY AND CYTOTOXICITY

| Compound No. | $EC_{50}$ (µM) | $CC_{50}$ (µM) |
|---|---|---|
| 3 | B | A |
| 6 | A | B |
| 8 | B | A |
| 9 | A | A |
| 10 | A | A |
| 12 | A | A |
| 13 | B | A |
| 18 | C | A |
| 20 | B | B |
| 23 | B | B |
| 26 | C | A |
| 34 | B | A |
| 36 | B | A |
| 38 | A | A |
| 39 | B | C |
| 44 | A | A |
| 45 | A | A |
| 63 | B | A |
| 97 | B | A |
| 98 | B | A |
| 99 | B | A |
| 105 | B | A |
| 106 | B | A |
| 120 | C | A |
| 121 | B | A |
| 122 | B | A |
| 127 | B | A |
| 128 | D | A |
| 129 | D | A |
| 130 | B | A |
| 134 | A | A |
| 142 | C | A |
| 147 | D | A |
| 148 | D | A |
| 149 | B | A |
| 150 | A | A |
| 151 | D | A |
| 152 | D | A |
| 153 | B | A |
| 158 | B | A |
| 159 | C | A |
| 178 | A | A |
| 179 | A | A |
| 180 | A | A |
| 182 | A | A |
| 183 | A | A |
| 184 | A | A |
| 190 | B | A |
| 191 | B | A |
| 192 | A | A |
| 199 | B | A |
| 200 | C | A |
| 201 | B | A |
| 202 | B | A |
| 204 | B | A |
| 205 | B | A |
| 220 | C | A |
| 221 | A | A |
| 223 | C | A |
| 235 | D | B |
| 236 | D | B |
| 237 | A | B |
| 238 | D | A |
| 239 | D | A |
| 240 | B | A |

TABLE 34-continued

POTENCY AND CYTOTOXICITY

| Compound No. | $EC_{50}$ (µM) | $CC_{50}$ (µM) |
|---|---|---|
| 241 | B | A |
| 242 | A | A |
| 243 | A | A |
| 244 | C | A |
| 245 | D | A |

Potency: A: ≥5-fold higher than (2'-OMe-A; 2'-OMe-C); B: ≥2-fold higher than (2'-OMe-A; 2'-OMe-C) and <5-fold higher than (2'-OMe-A; 2'-OMe-C); C: higher than or equal to (2'-OMe-A; 2'-OMe-C) and <2-fold higher than (2'-OMe-A; 2'-OMe-C); D: lower than (2'-OMe-A; 2'-OMe-C).

Cytotoxicity: A: ≥2 µM; B: <2 µM

TABLE 35

POTENCY AND CYTOTOXICITY

| Compound No.[1] | $EC_{50}$ | $CC_{50}$ |
|---|---|---|
| 6, 274, 283 | A | B |
| 376 | D | A |
| 371 | D | A |
| 372 | D | A |
| 273, 282 | D | A |
| 367 | C | A |
| 368 | D | A |
| 369 | D | A |
| 370 | D | A |
| 345 | B | A |
| 346 | A | A |
| 351 | D | B |
| 352 | D | B |
| 373 | B | B |
| 308 | C | A |
| 239 | D | A |
| 235 | D | B |
| 236 | D | B |
| 237 | A | B |
| 301 | A | B |
| 303 | B | B |
| 305 | C | A |
| 315 | C | A |
| 309 | D | B |
| 297 | C | A |
| 298 | D | A |
| 300 | D | A |
| 312 | D | A |
| 313 | D | A |
| 299 | D | A |
| 304 | D | A |
| 302 | D | A |
| 307 | D | A |
| 375 | B | A |
| 201 | C | A |
| 202 | C | A |
| 203 | B | A |
| 204 | D | A |
| 205 | D | A |
| 353 | B | A |
| 351 | D | A |
| 352 | D | A |
| 178 | A | A |
| 179 | A | A |
| 180 | C | A |
| 182 | A | A |
| 183 | D | A |
| 184, 290 | A | A |
| 177 | B | A |
| 374 | D | A |
| 363 | D | A |
| 364 | D | A |
| 365 | D | A |
| 366 | D | A |

TABLE 35-continued

POTENCY AND CYTOTOXICITY

| Compound No.[1] | $EC_{50}$ | $CC_{50}$ |
|---|---|---|
| 238 | D | A |
| 240 | B | A |
| 241 | B | A |
| 242 | A | A |
| 243 | A | A |
| 130 | A | A |
| 380 | D | A |
| 310 | D | A |
| 311 | D | A |
| 254 | D | A |
| 325 | D | A |
| 326 | D | A |
| 327 | D | A |
| 328 | D | A |
| 158 | B | A |
| 150 | A | A |
| 159 | C | A |
| 341 | D | A |
| 342 | B | A |
| 244 | C | A |
| 245 | C | A |
| 343 | B | A |
| 329 | C | A |
| 330 | B | B |
| 331 | D | A |
| 332 | D | A |
| 333 | B | A |
| 334 | B | A |
| 335 | C | A |
| 336 | C | A |
| 337 | A | B |
| 338 | B | B |
| 117 | B | A |
| 118 | B | A |
| 134, 277, 284 | A | A |
| 142 | C | A |
| 190 | B | A |
| 191 | B | A |
| 192 | B | A |
| 210 | B | A |
| 211 | B | A |
| 212 | B | A |
| 218 | C | A |
| 223 | C | A |
| 221 | A | A |
| 127 | D | A |
| 128 | C | A |
| 129 | C | A |
| 120 | B | A |
| 121 | B | A |
| 122 | A | A |
| 181 | C | A |
| 147 | D | A |
| 148 | D | A |
| 149 | B | A |
| 151 | D | A |
| 152 | D | A |
| 153 | B | A |
| 294 | B | A |
| 276, 291 | A | A |
| 275, 295 | A | B |
| 173, 293 | A | A |
| 165, 287 | B | A |
| 167, 289 | B | A |
| 164, 286 | C | A |
| 166, 288 | A | A |
| 171, 280, 292 | B | A |
| 314 | A | B |
| 281, 316 | A | A |
| 296 | A | A |
| 285 | A | B |
| 251 | A | A |
| 356 | A | A |
| 320 | A | A |
| 321 | A | B |
| 322 | B | A |
| 317 | A | B |
| 318 | B | B |
| 319 | A | B |
| 357 | A | A |
| 339 | A | A |
| 252 | A | A |
| 340 | A | A |
| 250 | A | A |
| 359 | D | A |
| 360 | D | A |
| 361 | D | A |
| 362 | D | A |
| 12 | A | A |
| 20 | B | A |
| 38 | A | A |
| 385 | A | A |
| 386 | A | A |
| 387 | A | A |
| 388 | A | A |
| 389 | A | A |
| 376 | A | A |
| 377 | A | A |
| 378 | A | A |
| 379 | A | A |
| 384 | A | A |
| 381 | A | A |
| 382 | A | A |
| 383 | B | A |
| 390 | A | B |
| 391 | A | B |
| 392 | B | B |

[1]A number of compounds described herein are referred to by more than a single compound no. as indicated here and elsewhere throughout the disclosure.
Potency: A: $EC_{50}$ < 30 nM; B: $EC_{50}$ ≥ 30 nM and $EC_{50}$ < 100 nM; C: $EC_{50}$ ≥ 100 nM and $EC_{50}$ < 300 nM; D: $EC_{50}$ > 300 nM.
Cytotoxicity: A: $CC_{50}$ ≥ 1000 nM; B: $CC_{50}$ < 1000 nM Example B2

Live Infection Assay

HepG2-NTCP cells were maintained in DMEM/F12 medium with 10% fetal bovine serum (FBS) and 1% penicillin/streptomycin, 1% Glutamine, 1% non-essential amino acids, 1% Sodium Pyruvate. Cells were maintained at 37° C. in a 5% $CO_2$ atmosphere.

HepG2-NTCP cells were resuspended with above mentioned medium and plated at a concentration of 15,000 cells/well in collagen-I coated 96 well plates. On the second day (day 0), the cells were infected with HBV (purified HBV from HepAD38 cells) at 200 moi (ge) in the presence of 4% PEG8000 and 2% DMSO and incubated at 37° C. overnight. The inoculum was vacuumed and cells were washed three times with DMEM/F12 with 2% FBS before replacing with the HepG2-NTCP culture medium.

Treat the cells on day 5. On Day 5, the test compounds were diluted 3-fold with Opti-MEM I media and mixed with Lipofectamine® RNAiMAX transfection reagent following the manufacturer's instructions. After media replacement on Day 8, the test compounds were transfected as described. After incubation for an additional 3 days, the supernatant was harvested and HBsAg was measured by ELISA (Diasino). The cell viability was measured with CellTiter-Glo (Promega).

The EC50, the concentration of the drug required for reducing HBsAg secretion by 50% in relation to the untreated cell control value, was calculated from the plot of the percent reduction of the HBsAg level against the drug concentrations using the Microsoft Excel forecast function or GraphPad Prism and summarized in Table 36.

TABLE 36

POTENCY AND CYTOTOXICITY

| Compound No. | $EC_{50}$ | $CC_{50}$ |
|---|---|---|
| 6, 274, 283 | A | A |
| 273, 282 | C | A |
| 315 | D | A |
| 290 | A | A |
| 184 | | |
| 134, 277, 284 | A | A |
| 192 | A | A |
| 221 | A | A |
| 294 | C | A |
| 291 | A | A |
| 276 | | |
| 295 | B | A |
| 275 | | |
| 173, 293 | B | A |
| 165, 287 | A | A |
| 167, 289 | B | A |
| 164, 286 | B | A |
| 166, 288 | B | A |
| 171, 280, 292 | B | A |
| 314 | A | A |
| 281, 316 | C | A |
| 296 | A | A |
| 285 | A | A |
| 251 | B | A |
| 356 | A | A |
| 320 | A | A |

Potency: A: $EC_{50} < 30$ nM; B: $EC_{50} \geq 30$ nM and $EC_{50} < 100$ nM; C: $EC_{50} \geq 100$ nM and $EC_{50} < 300$ nM; D: $EC_{50} > 300$ nM.
Cytotoxicity: A: $CC_{50} \geq 1000$ nM; B: $CC_{50} < 1000$ nM Example B3

HBsAg Secretion Assay for Combinations

Figure 23:
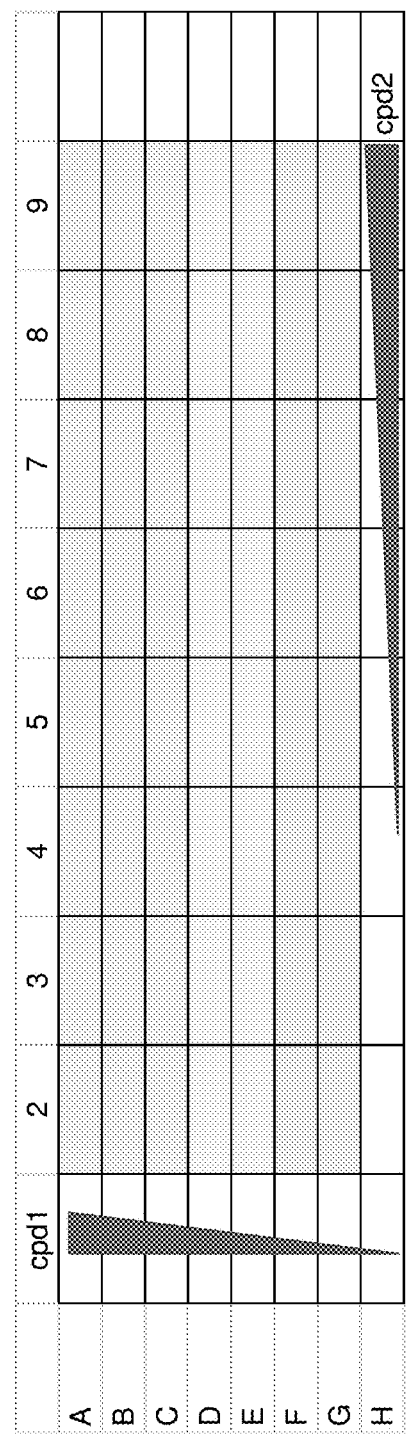
FIG. 23 illustrates a graph that is utilized in connection with the HBsAg Secretion Assays described in Examples B3 and B4.

The sequence independent antiviral activity against hepatitis B (as determined by HBsAg Secretion Assay) of exemplified modified oligonucleotide compounds in combination with antisense oligonucleotides (ASOs) was determined as described below and summarized in Table 37.
Cell Culture
HepG2.2.15 cells were maintained in DMEM/F12 medium with 10% fetal bovine serum (FBS) and 1% penicillin/streptomycin, 1% Glutamine, 1% non-essential amino acids, 1% Sodium Pyruvate. Cells were maintained at 37° C. in a 5% $CO_2$ atmosphere.
HBsAg Secretion Assay
HepG2.2.15 cells were grown in DMEM/F12 medium as described above. Cells were seeded at a concentration of 35,000 cells/well in collagen-I coated 96-well plates. Immediately after addition of the cells, add test compounds. Do double transfections on day 0 and 3.
Transfection Method
Lipofectamine® RNAiMAX transfection. Lipofectamine® RNAiMAX Transfection Reagent (Thermo Fisher, cat #: 13778-150) is used following the manufacturer's instructions.
A: mix RNAiMAX (0.3 ul/well for 96-well plate) with Opti-MEM I (make 20% extra), incubate for 5 min at RT.
B: dilute combinations of ASOs and modified oligonucleotides in Opti-MEM I to make 40× final concentration (8-point, 3-fold dilution, include concentration 0 nM). The top concentration is about 100-200 folds of $EC_{50}$ value. Then mix equal volume dilutions from both compound 1 and compound 2 at opposite direction as indicated in the graph shown in FIG. 23.

Mix A and B at equal volume (make 20% extra volume), incubate another 5-10 min. Then add mixture of A and B at 1/10 of the final culture volume to each well, swirl the plates for 10 seconds by hand. There should be at least triplicate for the plates. Incubate at 37° C. for 3 days, refresh medium, repeat the transfection process. On day 6 upon treatment, harvest supernatant for ELISA assay, measure cell viability with CellTiter-Glo (Promega).
Data Analysis
To analyze the synergism, the percentage of HBsAg (or DNA) reduction is calculated for each well. Percentage of reduction=(1-well/average of no drug control)*100. These numbers are input to MacSynergy II software and the synergism/antagonism volume is obtained following the instruction of the software.

Synergy volume <25 indicates no synergism/antagonism.

Synergy volume 25-50 indicates minor synergism/antagonism.

Synergy volume 50-100 indicates moderate synergism/antagonism.

Synergy volume >100 indicates strong synergism/antagonism.

Synergy volume >1,000 indicates possible errors, check the data.

Percentage of cell viability=(well/average of no drug control)*100.

Monitor cytotoxicity as previously described.
HBsAg Quantification
Secreted HBsAg was measured quantitatively using HBsAg ELISA kit (Autobio-CL0310). Synergy values for combinations of modified oligonucleotides with ASOs are provided in Table 37.

TABLE 37

SYNERGY OF COMBINATIONS

| Compound No. | ASO[1] | HBsAg 95% Synergy Volume |
|---|---|---|
| 166, 288 | ASO-1 | 335.08 |
| 134, 277, 284 | ASO-2 | 52.98 |
| 296 | ASO-2 | 43.05 |

[1]ASO-1 is an unconjugated HBV ASO SSO-1 as disclosed in in Javanbakht, H. et al. Molecular Therapy: Nucleic Acids Vol. 11 June 2018, having the following structure: 5-lnApslnGpsln(5m)CpsGpsApsApsGpsTpsGps(5m)CpsAps(5m)CpsApsln(5m) CpslnGpslnG-3. ASO-2 is an ASO having a structure as described for the ASO referred to as Sequence #9 in U.S. application Ser. No. 62/855,793, which is hereby incorporated herein by reference and particularly for the purpose of describing the structure of the Sequence #9.

Example B4

HBsAg Secretion Assay for Combinations

The sequence independent antiviral activity against hepatitis B (as determined by HBsAg Secretion Assay) of exemplified modified oligonucleotide compounds in combination with an ASO, capsid assembly modulators (CAM compound 1 or CAM compound 2), or nucleoside analog (Entecavir, ETV) was determined as described below and summarized in Table 38.
Cell Culture
The following assay procedure describes the HBV antiviral assay. This assay uses HepG2.2.15 cells, which have been transfected with HBV genome, and extracellular HBV DNA quantification as endpoint. Cell viability is assessed in parallel by measuring the intracellular ATP content using the CellTiter-Glo® reagent from Promega.

HBsAg Secretion Assay

HepG2.2.15 cells were grown in DMEM/F12 medium as described above. Cells were seeded at a concentration of 35,000 cells/well in collagen-I coated 96-well plates. Immediately after addition of the cells, add test compounds. Do double transfections on day 0 and 3.

HBV DNA Quantification Assay

Extracellular DNA was isolated with QIAamp 96 DNA Blood Kit per the manufacturer's manual. HBV DNA was then quantified by qPCR with HBV specific primers and probes as specified below using the FastStart Universal MasterMix from Roche on an ABI-7900HT. The PCR cycle program consisted of 95° C. for 10 min, followed by 40 cycles at 95° C. for 15 sec and 60° C. for 1 min.

| Items | Name | Sequence (5'→3') |
|---|---|---|
| HBV Primer | HBV-forward | GTGTCTGCGGCGTTTTATCA |
| | HBV-reverse | GACAAACGGGCAACATACCTT |
| HBV Probe | HBV probe | FAM-CCTCTKCATCCTGCTGCTATGCCTCATC-TAMRA |

Transfection Method

Lipofectamine® RNAiMAX transfection. Lipofectamine® RNAiMAX Transfection Reagent (Thermo Fisher, cat #: 13778-150) is used following the manufacturer's instructions.

A: mix RNAiMAX (0.3 ul/well for 96-well plate) with Opti-MEM I (make 20% extra), incubate for 5 min at RT B: dilute combinations of a CAM, ASO or ETV with modified oligonucleotides in Opti-MEM I to make 40× of final concentration (8-point, 3-fold dilution, include concentration 0 nM). The top concentration is about 100-200 folds of $EC_{50}$ value. Then mix equal volume dilutions from both compound 1 and compound 2 at opposite direction as indicated in the graph shown in FIG. 23.

Mix A and B at equal volume (make 20% extra volume), incubate another 5-10 min. Then add mixture of A and B at ¹⁄₁₀ of the final culture volume to each well, swirl the plates for 10 seconds by hands. There should be at least triplicate for the plates. Incubate at 37° C. for 4-hrs before adding the ASO, ETV or CAMs to let the cells recover from transfection. On day 3 upon treatment, harvest supernatant for ELISA assay, measure cell viability with CellTiter-Glo (Promega).

Data Analysis

The synergism data was analyzed as described in Example B3 above.

HBsAg Quantification

Secreted HBsAg was measured quantitatively using HBsAg ELISA kit (Autobio-CL0310). Synergy values for combinations of modified oligonucleotides with ASOs are provided in Table 38.

TABLE 38

SYNERGY OF COMBINATIONS

| Compound No. | ASO, CAM or ETV[1] | HBV DNA | HBV DNA 95% Synergy Volume |
|---|---|---|---|
| 166, 288 | ASO-1 | Additive | 23.99 |
| 134, 277, 284 | ETV | Synergy | 25.91 |

TABLE 38-continued

SYNERGY OF COMBINATIONS

| Compound No. | ASO, CAM or ETV[1] | HBV DNA | HBV DNA 95% Synergy Volume |
|---|---|---|---|
| 134, 277, 284 | CAM compound 1 | Additive | 1.35 |
| 134, 277, 284 | CAM compound 2 | Synergy | 41.86 |

[1]CAM compound 1 is a CAM having a structure as described for the CAM compound referred to as compound 3 in WO2017/181141, which is hereby incorporated herein by reference and particularly for the purpose of describing the structure of the compound 3. CAM compound 2 is a CAM having a structure as described for the CAM compound referred to as compound 1 in U.S. Ser. No. 62/805,725, which is hereby incorporated herein by reference and particularly for the purpose of describing the structure of the compound 1. ASO-1 is as described above for Table 37.

Example B5

Liver Exposure in Non-Human Primates

Terminal liver exposures in non-human primates were evaluated by dosing exemplified modified oligonucleotide compounds to female cynomolgus monkeys by either the intravenous (IV) or subcutaneous (SC) route. For the IV route, the compound was administered in sterile phosphate-buffered saline (PBS) vehicle and infused over a 2-hr period at 1 mL/kg. For subcutaneous dosing, the vehicle was also sterile PBS and the compound was administered as a single bolus at 1 mL/kg. There were two animals per dose group, and the data shown is the average of the two animals. Liver levels were determined at the 24-hour timepoint. The doses utilized for this study and the data obtained is shown in FIG. 12. Unexpectedly, liver exposure following subcutaneous administration to non-human primates is much higher than expected based on liver exposure levels resulting from otherwise comparable intravenous dosing.

Example B6

PBMC Assay

The effect of exemplified modified oligonucleotide compounds on the release of cytokines from peripheral blood mononuclear cells (PBMC) was evaluated as described below and summarized in Table 39 and FIGS. 13-22.

Buffy coats (N=3) were obtained from Stanford Blood Center and processed to isolate PBMC as per Aragen's standard protocol using Ficoll density gradient centrifugation. PBMC (1 million/mL) were suspended in complete culture (RPMI supplemented with 10% heat inactivated-low IgG FBS and PSG) and plated at 100 µL/well in a 96-well round bottom plate. PBMC were treated with test articles (list on next slide) (concentration range: 10 µM to 0 µM-3 fold dilution) and PHA and Poly IC (concentration range: 10 µg/mL to 0 µg/mL-3 fold dilution). All was set up in triplicates. After 24 hours incubation at 37° C./5% $CO_2$ humidified standard cell culture incubator, supernatants were harvested and stored at −80° C. until assayed for cytokines. Cytokines (GM-CSF, IL-1b, IL-2, IL-6, IL-10, IL-8, IL-12p70, IFNg, TNFa) were tested on Intellicyt iQue Screener and analyzed using ForeCyt analysis software. Cytokine (IFNa) was tested by standard ELISA. Results are expressed as pg/ml calculated based on the standard curve.

TABLE 39

| Compound No. | FIG. No. | Immune Reaction[1] |
|---|---|---|
| PHA Control | 13 | Strong |
| REP-2139 | 14 | Weak |

TABLE 39-continued

| Compound No. | FIG. No. | Immune Reaction[1] |
|---|---|---|
| 171, 280, 292 | 15 | Weak |
| 296 | 16 | None |
| 134, 277, 284 | 17 | Weak |
| 166, 288 | 18 | None |
| 167, 289 | 19 | None |
| 281, 316 | 20 | None |
| 294 | 21 | Weak |
| 276, 291 | 22 | Weak |

[1]Strong: significant induction observed in more than two types of cytokines in the panel tested; Weak: induction observed in one or two types of cytokines in the panel tested; None: no induction observed in any cytokine in the panel tested.

Example B7

Cross-Genotype Activities of Modified Oligonucleotides in Hbv HBsAg Release Inhibition The cross-genotype activities of the compound of Example 296 and REP-2139 were evaluated as described below and summarized in Table 40.

Testing in Stable Cell Line

For HBV Genotype D: The HepG2.2.15 cell line (Sells M A, Chen M, Acs G. Production of hepatitis B virus particles in Hep G2 cells transfected with cloned hepatitis B virus DNA. Proc Nat Acad Sci USA 1987; 84:1005-1009), which contains 2 head-to-tail integrated copies of the HBV genome and produces infectious HBV particles, was used as an in vitro model of HBV infection. The cell line was licensed and obtained from the Fox Chase Cancer Center (Philadelphia, Pa.). HepG2.2.15 cells were maintained in DMEM/F12 (Catalog 10-092-CM, Corning) with 10% fetal bovine serum, 1% penicillin and streptomycin, 2 mM glutamine, 1% non-essential amino acids, and 1% sodium pyruvate. To prepare the HepG2.2.15 for assay, the cells were trypsinized at 37° C. and diluted to $0.35 \times 10^6$/mL with maintenance medium.

The transfection mixture was prepared as follows: First, a master mixture was prepared by combining RNAiMAX (Catalog 13778-150, Thermo Fisher; 0.3 μL/well for a 96-well plate) with Opti-MEM I (5.2 μL/well), which was then vortexed and incubated for 5 minutes at room temperature. At least a 20% excess volume of the master mixture was prepared. Next, serial dilutions of the test compounds (3-fold) were made with Opti-MEM I at 20× of final concentration (8-point dose response), which was mixed with equal volumes of master mixture and then incubated for another 5-10 minutes.

The resulting test compound/RNAiMAX mixtures were added to 96-well plates at a volume of 11 μL per well and then 100 μL of HepG2.2.15 cells per well were added. The plates were swirled for 10 seconds by hand then incubated at 37° C. for 3 days. After 3 days, the medium was refreshed, and the same test compound and RNAiMAX transfection mixture was added a second time, swirled for 10 seconds by hand, then incubated at 37° C. for another 3 days.

On Day 6, the supernatant was harvested for HBsAg quantitation and the cells were assayed for viability. The HBsAg was measured with an ELISA kit (Catalog DS187701, Diasino) and cell viability was measured with the CellTiter-Glo (Promega) assay kit according to the manufacturer's instructions.

The HepG2-GtA and HepG2-GtB cell lines were established at Aligos Therapeutics, Inc. These cell lines contain 1.3×HBV genomes (AB246338.1 genotype A and AB246341 genotype B) and produce HBV viral products continuously. Otherwise the protocol was the same as HepG2.2.15.

Live HBV-Infected HepG2-NTCP

HepG2-NTCP cells contain an over-expressed NTCP receptor in the HepG2 cell line and have been shown to be a robust cell culture system supporting the complete life cycle of HBV (see Michailidis E, Pabon J, Xiang K, et al. A robust cell culture system supporting the complete life cycle of hepatitis B virus. Sci Rep 2017; 7(1):16616. doi:10.1038/s41598-017-16882-5). The cell line was licensed and obtained from the Fox Chase Cancer Center (Philadelphia, Pa.). HepG2-NTCP cells were maintained in DMEM/F12 (Catalog 10-092-CM, Corning) with 10% fetal bovine serum, 1% penicillin and streptomycin, 2 mM glutamine, 1% non-essential amino acids and 1% sodium pyruvate. The cells were trypsinized at 37° C. and diluted to $0.15 \times 10^6$/mL with maintenance medium. Briefly, the cells were seeded at 20,000/well in a 96-well plate on Day −2 and infected with HBV at a multiplicity of infection of 500 on Day 0. Infectious HBV particles (Genotype D) were harvested and concentrated from the supernatant of HepG2.2.15 cells (see Sells et. al. 1987), also licensed from the Fox Chase Cancer Center. Genotype B HBV (GenBank Accession No. JN406371) and Genotype C HBV (GenBank Accession No. AB246345) clinical isolates were purified from the supernatant of cultured HepG2 cells that had been transfected with plasmid DNA containing the corresponding HBV genomes.

The infected cells were transfected with test compounds on Days 5 and 8. The HBsAg was measured in the supernatant on Day 11 and the remaining cells were measured for cell viability.

The transfection mixture was prepared as follows: First, a master mixture was prepared by combining RNAiMAX (Catalog 13778-150, Thermo Fisher; 0.3 μL/well for a 96-well plate) with Opti-MEM I (5.2 μL/well), which was then vortexed and incubated for 5 minutes at room temperature. At least a 20% excess volume of master mixture was prepared. Next, serial dilutions of the test compounds (3-fold) were made with Opti-MEM I at 20× of final concentration (8-point dose response), which was then mixed with equal volumes of the master mixture and then incubated for another 5-10 minutes.

The above test compound/RNAiMAX mixtures were added to 96-well plates containing HBV-infected HepG2-NTCP cells in a volume of 11 μL per well. The plates were swirled for 10 seconds by hand and then incubated at 37° C. for 3 days. After 3 days, the medium was refreshed, and the same test compound and RNAiMAX transfection mixture was added for a second time, swirled for 10 seconds by hand, then incubated at 37° C. for an additional 3 days.

Three days after the second compound treatment, the supernatant was harvested for HBsAg detection. HBsAg was measured with an ELISA kit (Catalog DS187701, Diasino) and cell viability was measured with the CellTiter-Glo (Promega) assay kit according to the manufacturer's instructions.

The results are summarized in Table 40 below and demonstrate that the modified oligonucleotide (Example 296) demonstrated greater potency than REP-2139. The compound of Example 296 also demonstrated enhanced cross genotypic activity, inhibiting the HBsAg release in cells containing HBV genotype A, B, C and D viruses with $EC_{50}$ values of 7.9, 9.25, 0.72 and 3.9 nM, respectively.

TABLE 40

| HBV Genotype | Compound | Activity (EC$_{50}$) in Stable Cell Lines (nM) | Activity (EC$_{50}$) in Live HBV-Infected HepG2-NTCP (nM) |
|---|---|---|---|
| A | Example 296 | 7.6 ± 2.0 | — |
|   | REP-2139 | 71.7 ± 15.6 | — |
| B | Example 296 | 18.24 ± 8.1 | 9.25 ± 1.26 |
|   | REP-2139 | >10,000 | 71.89 ± 10.74 |
| C | Example 296 | — | 0.72 ± 0.03 |
|   | REP-2139 | — | 71.04 ± 15.69 |
| D | Example 296 | 4.8 ± 1.1 | 2.7 ± 0.9 |
|   | REP-2139 | 260.3 ± 98 | 320.7 ± 110 |

What is claimed is:

1. A modified oligonucleotide or complex thereof, wherein the modified oligonucleotide is represented by the following formula:

5'mApsln(5m)CpsmApsln(5m)CpsmApsln(5m)CpsmApsln(5m)CpsmApsln(5m) CpsrApsln(5m)CpsmApsln(5m)CpsmApsln(5m)CpsrApsln(5m)CpsmApsln(5m) CpsmApsln(5m)CpsrApsln(5m) CpsmApsln(5m)CpsmApsln(5m)CpsrApsln(5m) CpsmApsln(5m)CpsmApsln(5m)CpsrApsln(5m)CpsmApsln(5m)CpsmApsln(5m) C 3' (SEQ ID NO: 146), wherein mA is 2'-O-methyladenosine, ps is phosphorothioate, ln(5m)C is locked 5-methylcytidine, and rA is ribo-adenosine.

2. The complex of the modified oligonucleotide of claim 1, wherein the complex is a chelate complex.

3. The complex of the modified oligonucleotide of claim 1, wherein the complex is a monovalent counterion complex.

4. The complex of claim 3, wherein the complex is a lithium, sodium or potassium complex of the modified oligonucleotide.

5. A pharmaceutical composition, comprising an amount of the modified oligonucleotide or complex thereof of claim 1, that is effective for treating a subject infected with hepatitis B and/or hepatitis D; and a pharmaceutically acceptable carrier.

6. The pharmaceutical composition of claim 5, wherein the pharmaceutical composition is formulated for subcutaneous delivery.

* * * * *

SEQUENCE LISTING

```
<160> NUMBER OF SEQ ID NOS: 169

<210> SEQ ID NO 1
<211> LENGTH: 18
<212> TYPE: DNA
<213> ORGANISM: Artificial Sequence
<220> FEATURE:
<223> OTHER INFORMATION: Modified Oligonucleotide

<400> SEQUENCE: 1
acacacacac acacacac                                                 18

<210> SEQ ID NO 2
<211> LENGTH: 18
<212> TYPE: DNA
<213> ORGANISM: Artificial Sequence
<220> FEATURE:
<223> OTHER INFORMATION: Modified Oligonucleotide

<400> SEQUENCE: 2
acacacacac acacacac                                                 18

<210> SEQ ID NO 3
<211> LENGTH: 18
<212> TYPE: DNA
<213> ORGANISM: Artificial Sequence
<220> FEATURE:
<223> OTHER INFORMATION: Modified Oligonucleotide

<400> SEQUENCE: 3
acacacacaa cacacaca                                                 18

<210> SEQ ID NO 4
<211> LENGTH: 18
<212> TYPE: DNA
<213> ORGANISM: Artificial Sequence
<220> FEATURE:
<223> OTHER INFORMATION: Modified Oligonucleotide

<400> SEQUENCE: 4
acacacacaa cacacaca                                                 18

<210> SEQ ID NO 5
<211> LENGTH: 19
<212> TYPE: DNA
<213> ORGANISM: Artificial Sequence
<220> FEATURE:
<223> OTHER INFORMATION: Modified Oligonucleotide

<400> SEQUENCE: 5
acacacacac acacacaca                                                19

<210> SEQ ID NO 6
<211> LENGTH: 19
```

```
<212> TYPE: DNA
<213> ORGANISM: Artificial Sequence
<220> FEATURE:
<223> OTHER INFORMATION: Modified Oligonucleotide

<400> SEQUENCE: 6
acacacacac acacacaca                                                  19

<210> SEQ ID NO 7
<211> LENGTH: 20
<212> TYPE: DNA
<213> ORGANISM: Artificial Sequence
<220> FEATURE:
<223> OTHER INFORMATION: Modified Oligonucleotide

<400> SEQUENCE: 7
acacacacac acacacacac                                                 20

<210> SEQ ID NO 8
<211> LENGTH: 20
<212> TYPE: DNA
<213> ORGANISM: Artificial Sequence
<220> FEATURE:
<223> OTHER INFORMATION: Modified Oligonucleotide

<400> SEQUENCE: 8
acacacacac acacacacac                                                 20

<210> SEQ ID NO 9
<211> LENGTH: 25
<212> TYPE: DNA
<213> ORGANISM: Artificial Sequence
<220> FEATURE:
<223> OTHER INFORMATION: Modified Oligonucleotide

<400> SEQUENCE: 9
acacacacac acacacacac acaca                                           25

<210> SEQ ID NO 10
<211> LENGTH: 28
<212> TYPE: DNA
<213> ORGANISM: Artificial Sequence
<220> FEATURE:
<223> OTHER INFORMATION: Modified Oligonucleotide

<400> SEQUENCE: 10
acacacacac acacacacac acacacac                                        28

<210> SEQ ID NO 11
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 11
acacacacac acacacacac acacacacac                                      30

<210> SEQ ID NO 12
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 12
```
acacacacac acacacacac acacacacac                                    30

<210> SEQ ID NO 13
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 13
acacacacac acacacacac acacacacac                                    30

<210> SEQ ID NO 14
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 14
acacacacac acacacacac acacacacac                                    30

<210> SEQ ID NO 15
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 15
acacacacac acacacacac acacacacac                                    30

<210> SEQ ID NO 16
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 16
acacacacac acacacacac acacacacac                                    30

<210> SEQ ID NO 17
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 17
acacacacac acacacacac acacacacac                                    30

<210> SEQ ID NO 18
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 18
acacacacac acacacacac acacacacac                                    30

<210> SEQ ID NO 19
<211> LENGTH: 30
<212> TYPE: DNA
<213> ORGANISM: Artificial Sequence

```
<220> FEATURE:
<223> OTHER INFORMATION: Modified Oligonucleotide

<400> SEQUENCE: 19
acacacacac acacacacac acacacacac                                    30

<210> SEQ ID NO 20
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 20
acacacacac acacacacac acacacacac                                    30

<210> SEQ ID NO 21
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 21
acacacacac acacacacac acacacacac                                    30

<210> SEQ ID NO 22
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 22
acacacacac acacaacaca cacacacaca                                    30

<210> SEQ ID NO 23
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 23
acacacacac acacaacaca cacacacaca                                    30

<210> SEQ ID NO 24
<211> LENGTH: 31
<212> TYPE: DNA
<213> ORGANISM: Artificial Sequence
<220> FEATURE:
<223> OTHER INFORMATION: Modified Oligonucleotide

<400> SEQUENCE: 24
acacacacac acacacacac acacacacac a                                  31

<210> SEQ ID NO 25
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 25
acacacacac acacacacac acacacacac                                    30
```

<210> SEQ ID NO 26
<211> LENGTH: 30
<212> TYPE: DNA
<213> ORGANISM: Artificial Sequence
<220> FEATURE:
<223> OTHER INFORMATION: Modified Oligonucleotide

<400> SEQUENCE: 26
acacacacac acacacacac acacacacac                                      30

<210> SEQ ID NO 27
<211> LENGTH: 34
<212> TYPE: DNA
<213> ORGANISM: Artificial Sequence
<220> FEATURE:
<223> OTHER INFORMATION: Modified Oligonucleotide

<400> SEQUENCE: 27
acacacacac acacacacac acacacacac acac                                 34

<210> SEQ ID NO 28
<211> LENGTH: 34
<212> TYPE: DNA
<213> ORGANISM: Artificial Sequence
<220> FEATURE:
<223> OTHER INFORMATION: Modified Oligonucleotide

<400> SEQUENCE: 28
acacacacac acacacacac acacacacac acac                                 34

<210> SEQ ID NO 29
<211> LENGTH: 34
<212> TYPE: DNA
<213> ORGANISM: Artificial Sequence
<220> FEATURE:
<223> OTHER INFORMATION: Modified Oligonucleotide

<400> SEQUENCE: 29
acacacacac acacacacac acacacacac acac                                 34

<210> SEQ ID NO 30
<211> LENGTH: 34
<212> TYPE: DNA
<213> ORGANISM: Artificial Sequence
<220> FEATURE:
<223> OTHER INFORMATION: Modified Oligonucleotide

<400> SEQUENCE: 30
acacacacac acacacacac acacacacac acac                                 34

<210> SEQ ID NO 31
<211> LENGTH: 34
<212> TYPE: DNA
<213> ORGANISM: Artificial Sequence
<220> FEATURE:
<223> OTHER INFORMATION: Modified Oligonucleotide

<400> SEQUENCE: 31
acacacacac acacacacac acacacacac acac                                 34

<210> SEQ ID NO 32
<211> LENGTH: 34
<212> TYPE: DNA
<213> ORGANISM: Artificial Sequence
<220> FEATURE:
<223> OTHER INFORMATION: Modified Oligonucleotide

```
<400> SEQUENCE: 32
acacacacac acacacacac acacacacac acac                              34

<210> SEQ ID NO 33
<211> LENGTH: 34
<212> TYPE: DNA
<213> ORGANISM: Artificial Sequence
<220> FEATURE:
<223> OTHER INFORMATION: Modified Oligonucleotide

<400> SEQUENCE: 33
acacacacac acacacacac acacacacac acac                              34

<210> SEQ ID NO 34
<211> LENGTH: 36
<212> TYPE: DNA
<213> ORGANISM: Artificial Sequence
<220> FEATURE:
<223> OTHER INFORMATION: Modified Oligonucleotide

<400> SEQUENCE: 34
acacacacac acacacacac acacacacac acacac                            36

<210> SEQ ID NO 35
<211> LENGTH: 36
<212> TYPE: DNA
<213> ORGANISM: Artificial Sequence
<220> FEATURE:
<223> OTHER INFORMATION: Modified Oligonucleotide

<400> SEQUENCE: 35
acacacacac acacacacac acacacacac acacac                            36

<210> SEQ ID NO 36
<211> LENGTH: 36
<212> TYPE: DNA
<213> ORGANISM: Artificial Sequence
<220> FEATURE:
<223> OTHER INFORMATION: Modified Oligonucleotide

<400> SEQUENCE: 36
acacacacac acacacacac acacacacac acacac                            36

<210> SEQ ID NO 37
<211> LENGTH: 36
<212> TYPE: DNA
<213> ORGANISM: Artificial Sequence
<220> FEATURE:
<223> OTHER INFORMATION: Modified Oligonucleotide

<400> SEQUENCE: 37
acacacacac acacacacac acacacacac acacac                            36

<210> SEQ ID NO 38
<211> LENGTH: 36
<212> TYPE: DNA
<213> ORGANISM: Artificial Sequence
<220> FEATURE:
<223> OTHER INFORMATION: Modified Oligonucleotide

<400> SEQUENCE: 38
acacacacac acacacacac acacacacac acacac                            36

<210> SEQ ID NO 39
```

```
<211> LENGTH: 36
<212> TYPE: DNA
<213> ORGANISM: Artificial Sequence
<220> FEATURE:
<223> OTHER INFORMATION: Modified Oligonucleotide

<400> SEQUENCE: 39
acacacacac acacacacac acacacacac acacac                                 36

<210> SEQ ID NO 40
<211> LENGTH: 36
<212> TYPE: DNA
<213> ORGANISM: Artificial Sequence
<220> FEATURE:
<223> OTHER INFORMATION: Modified Oligonucleotide

<400> SEQUENCE: 40
acacacacac acacacacac acacacacac acacac                                 36

<210> SEQ ID NO 41
<211> LENGTH: 36
<212> TYPE: DNA
<213> ORGANISM: Artificial Sequence
<220> FEATURE:
<223> OTHER INFORMATION: Modified Oligonucleotide

<400> SEQUENCE: 41
acacacacac acacacacac acacacacac acacac                                 36

<210> SEQ ID NO 42
<211> LENGTH: 37
<212> TYPE: DNA
<213> ORGANISM: Artificial Sequence
<220> FEATURE:
<223> OTHER INFORMATION: Modified Oligonucleotide

<400> SEQUENCE: 42
acacacacac acacacacac acacacacac acacaca                                37

<210> SEQ ID NO 43
<211> LENGTH: 37
<212> TYPE: DNA
<213> ORGANISM: Artificial Sequence
<220> FEATURE:
<223> OTHER INFORMATION: Modified Oligonucleotide

<400> SEQUENCE: 43
acacacacac acacacacac acacacacac acacaca                                37

<210> SEQ ID NO 44
<211> LENGTH: 38
<212> TYPE: DNA
<213> ORGANISM: Artificial Sequence
<220> FEATURE:
<223> OTHER INFORMATION: Modified Oligonucleotide

<400> SEQUENCE: 44
acacacacac acacacacac acacacacac acacacac                               38

<210> SEQ ID NO 45
<211> LENGTH: 38
<212> TYPE: DNA
<213> ORGANISM: Artificial Sequence
<220> FEATURE:
<223> OTHER INFORMATION: Modified Oligonucleotide

<400> SEQUENCE: 45
```
acacacacac acacacacac acacacacac acacacac         38

<210> SEQ ID NO 46
<211> LENGTH: 38
<212> TYPE: DNA
<213> ORGANISM: Artificial Sequence
<220> FEATURE:
<223> OTHER INFORMATION: Modified Oligonucleotide

<400> SEQUENCE: 46
acacacacac acacacacac acacacacac acacacac         38

<210> SEQ ID NO 47
<211> LENGTH: 38
<212> TYPE: DNA
<213> ORGANISM: Artificial Sequence
<220> FEATURE:
<223> OTHER INFORMATION: Modified Oligonucleotide

<400> SEQUENCE: 47
acacacacac acacacacac acacacacac acacacac         38

<210> SEQ ID NO 48
<211> LENGTH: 38
<212> TYPE: DNA
<213> ORGANISM: Artificial Sequence
<220> FEATURE:
<223> OTHER INFORMATION: Modified Oligonucleotide

<400> SEQUENCE: 48
acacacacac acacacacac acacacacac acacacac         38

<210> SEQ ID NO 49
<211> LENGTH: 38
<212> TYPE: DNA
<213> ORGANISM: Artificial Sequence
<220> FEATURE:
<223> OTHER INFORMATION: Modified Oligonucleotide

<400> SEQUENCE: 49
acacacacac acacacacac acacacacac acacacac         38

<210> SEQ ID NO 50
<211> LENGTH: 38
<212> TYPE: DNA
<213> ORGANISM: Artificial Sequence
<220> FEATURE:
<223> OTHER INFORMATION: Modified Oligonucleotide

<400> SEQUENCE: 50
acacacacac acacacacac acacacacac acacacac         38

<210> SEQ ID NO 51
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 51
acacacacac acacacacac acacacacac acacacacac        40

<210> SEQ ID NO 52
<211> LENGTH: 40
<212> TYPE: DNA

```
<213> ORGANISM: Artificial Sequence
<220> FEATURE:
<223> OTHER INFORMATION: Modified Oligonucleotide

<400> SEQUENCE: 52
acacacacac acacacacac acacacacac acacacacac                                40

<210> SEQ ID NO 53
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 53
acacacacac acacacacac acacacacac acacacacac                                40

<210> SEQ ID NO 54
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 54
acacacacac acacacacac acacacacac acacacacac                                40

<210> SEQ ID NO 55
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 55
acacacacac acacacacac acacacacac acacacacac                                40

<210> SEQ ID NO 56
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 56
acacacacac acacacacac acacacacac acacacacac                                40

<210> SEQ ID NO 57
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 57
acacacacac acacacacac acacacacac acacacacac                                40

<210> SEQ ID NO 58
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 58
acacacacac acacacacac acacacacac acacacacac                                40
```

<210> SEQ ID NO 59
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 59
acacacacac acacacacac acacacacac acacacacac                            40

<210> SEQ ID NO 60
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 60
acacacacac acacacacac acacacacac acacacacac                            40

<210> SEQ ID NO 61
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 61
acacacacac acacacacac acacacacac acacacacac                            40

<210> SEQ ID NO 62
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 62
acacacacac acacacacac acacacacac acacacacac                            40

<210> SEQ ID NO 63
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 63
acacacacac acacacacac acacacacac acacacacac                            40

<210> SEQ ID NO 64
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 64
acacacacac acacacacac acacacacac acacacacac                            40

<210> SEQ ID NO 65
<211> LENGTH: 40
<212> TYPE: DNA
<213> ORGANISM: Artificial Sequence
<220> FEATURE:

<223> OTHER INFORMATION: Modified Oligonucleotide

<400> SEQUENCE: 65
acacacacac acacacacac acacacacac acacacacac                                40

<210> SEQ ID NO 66
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 66
acacacacac acacacacac acacacacac acacacacac                                40

<210> SEQ ID NO 67
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 67
acacacacac acacacacac acacacacac acacacacac                                40

<210> SEQ ID NO 68
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 68
acacacacac acacacacac acacacacac acacacacac                                40

<210> SEQ ID NO 69
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 69
acacacacac acacacacac acacacacac acacacacac                                40

<210> SEQ ID NO 70
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 70
acacacacac acacacacac acacacacac acacacacac                                40

<210> SEQ ID NO 71
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 71
acacacacac acacacacac acacacacac acacacacac                                40

```
<210> SEQ ID NO 72
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 72
acacacacac acacacacac acacacacac acacacacac                          40

<210> SEQ ID NO 73
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 73
acacacacac acacacacac acacacacac acacacacac                          40

<210> SEQ ID NO 74
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 74
acacacacac acacacacac acacacacac acacacacac                          40

<210> SEQ ID NO 75
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 75
acacacacac acacacacac acacacacac acacacacac                          40

<210> SEQ ID NO 76
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 76
acacacacac acacacacac acacacacac acacacacac                          40

<210> SEQ ID NO 77
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 77
acacacacac acacacacac acacacacac acacacacac                          40

<210> SEQ ID NO 78
<211> LENGTH: 40
<212> TYPE: DNA
<213> ORGANISM: Artificial Sequence
<220> FEATURE:
<223> OTHER INFORMATION: Modified Oligonucleotide
```

```
<400> SEQUENCE: 78
acacacacac acacacacac acacacacac acacacacac                    40

<210> SEQ ID NO 79
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 79
acacacacac acacacacac acacacacac acacacacac                    40

<210> SEQ ID NO 80
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 80
acacacacac acacacacac acacacacac acacacacac                    40

<210> SEQ ID NO 81
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 81
acacacacac acacacacac acacacacac acacacacac                    40

<210> SEQ ID NO 82
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 82
acacacacac acacacacac acacacacac acacacacac                    40

<210> SEQ ID NO 83
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 83
acacacacac acacacacac acacacacac acacacacac                    40

<210> SEQ ID NO 84
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 84
acacacacac acacacacac acacacacac acacacacac                    40

<210> SEQ ID NO 85
<211> LENGTH: 40
```

-continued

```
<212> TYPE: DNA
<213> ORGANISM: Artificial Sequence
<220> FEATURE:
<223> OTHER INFORMATION: Modified Oligonucleotide

<400> SEQUENCE: 85
acacacacac acacacacac acacacacac acacacacac                             40

<210> SEQ ID NO 86
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 86
acacacacac acacacacac acacacacac acacacacac                             40

<210> SEQ ID NO 87
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 87
acacacacac acacacacac acacacacac acacacacac                             40

<210> SEQ ID NO 88
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 88
acacacacac acacacacac acacacacac acacacacac                             40

<210> SEQ ID NO 89
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 89
acacacacac acacacacac acacacacac acacacacac                             40

<210> SEQ ID NO 90
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 90
acacacacac acacacacac acacacacac acacacacac                             40

<210> SEQ ID NO 91
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 91
```

-continued acacacacac acacacacac acacacacac acacacacac        40

<210> SEQ ID NO 92
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 92
acacacacac acacacacac acacacacac acacacacac        40

<210> SEQ ID NO 93
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 93
acacacacac acacacacac acacacacac acacacacac        40

<210> SEQ ID NO 94
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 94
acacacacac acacacacac acacacacac acacacacac        40

<210> SEQ ID NO 95
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 95
acacacacac acacacacac acacacacac acacacacac        40

<210> SEQ ID NO 96
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 96
acacacacac acacacacac acacacacac acacacacac        40

<210> SEQ ID NO 97
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 97
acacacacac acacacacac acacacacac acacacacac        40

<210> SEQ ID NO 98
<211> LENGTH: 40
<212> TYPE: DNA
<213> ORGANISM: Artificial Sequence -continued

```
<220> FEATURE:
<223> OTHER INFORMATION: Modified Oligonucleotide

<400> SEQUENCE: 98
acacacacac acacacacac acacacacac acacacacac                            40

<210> SEQ ID NO 99
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 99
acacacacac acacacacac acacacacac acacacacac                            40

<210> SEQ ID NO 100
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 100
acacacacac acacacacac acacacacac acacacacac                            40

<210> SEQ ID NO 101
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 101
acacacacac acacacacac acacacacac acacacacac                            40

<210> SEQ ID NO 102
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 102
acacacacac acacacacac acacacacac acacacacac                            40

<210> SEQ ID NO 103
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 103
acacacacac acacacacac acacacacac acacacacac                            40

<210> SEQ ID NO 104
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 104
acacacacac acacacacac acacacacac acacacacac                            40
```

<210> SEQ ID NO 105
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 105
acacacacac acacacacac acacacacac acacacacac                              40

<210> SEQ ID NO 106
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 106
acacacacac acacacacac acacacacac acacacacac                              40

<210> SEQ ID NO 107
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 107
acacacacac acacacacac acacacacac acacacacac                              40

<210> SEQ ID NO 108
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 108
acacacacac acacacacac acacacacac acacacacac                              40

<210> SEQ ID NO 109
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 109
acacacacac acacacacac acacacacac acacacacac                              40

<210> SEQ ID NO 110
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 110
acacacacac acacacacac acacacacac acacacacac                              40

<210> SEQ ID NO 111
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 111
acacacacac acacacacac acacacacac acacacacac                                40

<210> SEQ ID NO 112
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 112
acacacacac acacacacac acacacacac acacacacac                                40

<210> SEQ ID NO 113
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 113
acacacacac acacacacac acacacacac acacacacac                                40

<210> SEQ ID NO 114
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 114
acacacacac acacacacac acacacacac acacacacac                                40

<210> SEQ ID NO 115
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 115
acacacacac acacacacac acacacacac acacacacac                                40

<210> SEQ ID NO 116
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 116
acacacacac acacacacac acacacacac acacacacac                                40

<210> SEQ ID NO 117
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 117
acacacacac acacacacac acacacacac acacacacac                                40

<210> SEQ ID NO 118

<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 118
acacacacac acacacacac acacacacac acacacacac        40

<210> SEQ ID NO 119
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 119
acacacacac acacacacac acacacacac acacacacac        40

<210> SEQ ID NO 120
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 120
acacacacac acacacacac acacacacac acacacacac        40

<210> SEQ ID NO 121
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 121
acacacacac acacacacac acacacacac acacacacac        40

<210> SEQ ID NO 122
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 122
acacacacac acacacacac acacacacac acacacacac        40

<210> SEQ ID NO 123
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 123
acacacacac acacacacac acacacacac acacacacac        40

<210> SEQ ID NO 124
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 124
acacacacac acacacacac acacacacac acacacacac                                40

<210> SEQ ID NO 125
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 125
acacacacac acacacacac acacacacac acacacacac                                40

<210> SEQ ID NO 126
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 126
acacacacac acacacacac acacacacac acacacacac                                40

<210> SEQ ID NO 127
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 127
acacacacac acacacacac acacacacac acacacacac                                40

<210> SEQ ID NO 128
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 128
acacacacac acacacacac acacacacac acacacacac                                40

<210> SEQ ID NO 129
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 129
acacacacac acacacacac acacacacac acacacacac                                40

<210> SEQ ID NO 130
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 130
acacacacac acacacacac acacacacac acacacacac                                40

<210> SEQ ID NO 131
<211> LENGTH: 40
<212> TYPE: DNA

<213> ORGANISM: Artificial Sequence
<220> FEATURE:
<223> OTHER INFORMATION: Modified Oligonucleotide

<400> SEQUENCE: 131
acacacacac acacacacac acacacacac acacacacac                    40

<210> SEQ ID NO 132
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 132
acacacacac acacacacac acacacacac acacacacac                    40

<210> SEQ ID NO 133
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 133
acacacacac acacacacac acacacacac acacacacac                    40

<210> SEQ ID NO 134
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 134
acacacacac acacacacac acacacacac acacacacac                    40

<210> SEQ ID NO 135
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 135
acacacacac acacacacac acacacacac acacacacac                    40

<210> SEQ ID NO 136
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 136
acacacacac acacacacac acacacacac acacacacac                    40

<210> SEQ ID NO 137
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 137
acacacacac acacacacac acacacacac acacacacac                    40

<210> SEQ ID NO 138
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 138
acacacacac acacacacac acacacacac acacacacac                              40

<210> SEQ ID NO 139
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 139
acacacacac acacacacac acacacacac acacacacac                              40

<210> SEQ ID NO 140
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 140
acacacacac acacacacac acacacacac acacacacac                              40

<210> SEQ ID NO 141
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 141
acacacacac acacacacac acacacacac acacacacac                              40

<210> SEQ ID NO 142
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 142
acacacacac acacacacac acacacacac acacacacac                              40

<210> SEQ ID NO 143
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 143
acacacacac acacacacac acacacacac acacacacac                              40

<210> SEQ ID NO 144
<211> LENGTH: 40
<212> TYPE: DNA
<213> ORGANISM: Artificial Sequence
<220> FEATURE:

```
<223> OTHER INFORMATION: Modified Oligonucleotide

<400> SEQUENCE: 144
acacacacac acacacacac acacacacac acacacacac                             40

<210> SEQ ID NO 145
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 145
acacacacac acacacacac acacacacac acacacacac                             40

<210> SEQ ID NO 146
<211> LENGTH: 40
<212> TYPE: DNA
<213> ORGANISM: Artificial Sequence
<220> FEATURE:
<223> OTHER INFORMATION: Modified Oligonucleotide
<220> FEATURE:
<221> NAME/KEY: modified_base
<222> LOCATION: (1)...(40)
<223> OTHER INFORMATION: Phosphorothioate linkage
<220> FEATURE:
<221> NAME/KEY: modified_base
<222> LOCATION: (1)...(1)
<223> OTHER INFORMATION: 2'-OMe-nucleotide
<220> FEATURE:
<221> NAME/KEY: modified_base
<222> LOCATION: (2)...(2)
<223> OTHER INFORMATION: locked 5-methyl-nucleotide
<220> FEATURE:
<221> NAME/KEY: modified_base
<222> LOCATION: (3)...(3)
<223> OTHER INFORMATION: 2'-OMe-nucleotide
<220> FEATURE:
<221> NAME/KEY: modified_base
<222> LOCATION: (4)...(4)
<223> OTHER INFORMATION: locked 5-methyl-nucleotide
<220> FEATURE:
<221> NAME/KEY: modified_base
<222> LOCATION: (5)...(5)
<223> OTHER INFORMATION: 2'-OMe-nucleotide
<220> FEATURE:
<221> NAME/KEY: modified_base
<222> LOCATION: (6)...(6)
<223> OTHER INFORMATION: locked 5-methyl-nucleotide
<220> FEATURE:
<221> NAME/KEY: modified_base
<222> LOCATION: (7)...(7)
<223> OTHER INFORMATION: 2'-OMe-nucleotide
<220> FEATURE:
<221> NAME/KEY: modified_base
<222> LOCATION: (8)...(8)
<223> OTHER INFORMATION: locked 5-methyl-nucleotide
<220> FEATURE:
<221> NAME/KEY: modified_base
<222> LOCATION: (9)...(9)
<223> OTHER INFORMATION: 2'-OMe-nucleotide
<220> FEATURE:
<221> NAME/KEY: modified_base
<222> LOCATION: (10)...(10)
<223> OTHER INFORMATION: locked 5-methyl-nucleotide
<220> FEATURE:
<221> NAME/KEY: modified_base
<222> LOCATION: (11)...(11)
<223> OTHER INFORMATION: ribo-nucleotide
<220> FEATURE:
<221> NAME/KEY: modified_base
<222> LOCATION: (12)...(12)
<223> OTHER INFORMATION: locked 5-methyl-nucleotide
<220> FEATURE:
<221> NAME/KEY: modified_base
```

```
<222> LOCATION: (13)...(13)
<223> OTHER INFORMATION: 2'-OMe-nucleotide
<220> FEATURE:
<221> NAME/KEY: modified_base
<222> LOCATION: (14)...(14)
<223> OTHER INFORMATION: locked 5-methyl-nucleotide
<220> FEATURE:
<221> NAME/KEY: modified_base
<222> LOCATION: (15)...(15)
<223> OTHER INFORMATION: 2'-OMe-nucleotide
<220> FEATURE:
<221> NAME/KEY: modified_base
<222> LOCATION: (16)...(16)
<223> OTHER INFORMATION: locked 5-methyl-nucleotide
<220> FEATURE:
<221> NAME/KEY: modified_base
<222> LOCATION: (17)...(17)
<223> OTHER INFORMATION: ribo-nucleotide
<220> FEATURE:
<221> NAME/KEY: modified_base
<222> LOCATION: (18)...(18)
<223> OTHER INFORMATION: locked 5-methyl-nucleotide
<220> FEATURE:
<221> NAME/KEY: modified_base
<222> LOCATION: (19)...(19)
<223> OTHER INFORMATION: 2'-OMe-nucleotide
<220> FEATURE:
<221> NAME/KEY: modified_base
<222> LOCATION: (20)...(20)
<223> OTHER INFORMATION: locked 5-methyl-nucleotide
<220> FEATURE:
<221> NAME/KEY: modified_base
<222> LOCATION: (21)...(21)
<223> OTHER INFORMATION: 2'-OMe-nucleotide
<220> FEATURE:
<221> NAME/KEY: modified_base
<222> LOCATION: (22)...(22)
<223> OTHER INFORMATION: locked 5-methyl-nucleotide
<220> FEATURE:
<221> NAME/KEY: modified_base
<222> LOCATION: (23)...(23)
<223> OTHER INFORMATION: ribo-nucleotide
<220> FEATURE:
<221> NAME/KEY: modified_base
<222> LOCATION: (24)...(24)
<223> OTHER INFORMATION: locked 5-methyl-nucleotide
<220> FEATURE:
<221> NAME/KEY: modified_base
<222> LOCATION: (25)...(25)
<223> OTHER INFORMATION: 2'-OMe-nucleotide
<220> FEATURE:
<221> NAME/KEY: modified_base
<222> LOCATION: (26)...(26)
<223> OTHER INFORMATION: locked 5-methyl-nucleotide
<220> FEATURE:
<221> NAME/KEY: modified_base
<222> LOCATION: (27)...(27)
<223> OTHER INFORMATION: 2'-OMe-nucleotide
<220> FEATURE:
<221> NAME/KEY: modified_base
<222> LOCATION: (28)...(28)
<223> OTHER INFORMATION: locked 5-methyl-nucleotide
<220> FEATURE:
<221> NAME/KEY: modified_base
<222> LOCATION: (29)...(29)
<223> OTHER INFORMATION: ribo-nucleotide
<220> FEATURE:
<221> NAME/KEY: modified_base
<222> LOCATION: (30)...(30)
<223> OTHER INFORMATION: locked 5-methyl-nucleotide
<220> FEATURE:
<221> NAME/KEY: modified_base
<222> LOCATION: (31)...(31)
<223> OTHER INFORMATION: 2'-OMe-nucleotide
<220> FEATURE:
<221> NAME/KEY: modified_base
<222> LOCATION: (32)...(32)
<223> OTHER INFORMATION: locked 5-methyl-nucleotide
<220> FEATURE:
```

```
<221> NAME/KEY: modified_base
<222> LOCATION: (33)...(33)
<223> OTHER INFORMATION: 2'-OMe-nucleotide
<220> FEATURE:
<221> NAME/KEY: modified_base
<222> LOCATION: (34)...(34)
<223> OTHER INFORMATION: locked 5-methyl-nucleotide
<220> FEATURE:
<221> NAME/KEY: modified_base
<222> LOCATION: (35)...(35)
<223> OTHER INFORMATION: ribo-nucleotide
<220> FEATURE:
<221> NAME/KEY: modified_base
<222> LOCATION: (36)...(36)
<223> OTHER INFORMATION: locked 5-methyl-nucleotide
<220> FEATURE:
<221> NAME/KEY: modified_base
<222> LOCATION: (37)...(37)
<223> OTHER INFORMATION: 2'-OMe-nucleotide
<220> FEATURE:
<221> NAME/KEY: modified_base
<222> LOCATION: (38)...(38)
<223> OTHER INFORMATION: locked 5-methyl-nucleotide
<220> FEATURE:
<221> NAME/KEY: modified_base
<222> LOCATION: (39)...(39)
<223> OTHER INFORMATION: 2'-OMe-nucleotide
<220> FEATURE:
<221> NAME/KEY: modified_base
<222> LOCATION: (40)...(40)
<223> OTHER INFORMATION: locked 5-methyl-nucleotide

<400> SEQUENCE: 146
acacacacac acacacacac acacacacac acacacacac                            40

<210> SEQ ID NO 147
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 147
acacacacac acacacacac acacacacac acacacacac                            40

<210> SEQ ID NO 148
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 148
acacacacac acacacacac acacacacac acacacacac                            40

<210> SEQ ID NO 149
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 149
acacacacac acacacacac acacacacac acacacacac                            40

<210> SEQ ID NO 150
<211> LENGTH: 40
<212> TYPE: DNA
<213> ORGANISM: Artificial Sequence
<220> FEATURE:
<223> OTHER INFORMATION: Modified Oligonucleotide
```

-continued

```
<400> SEQUENCE: 150
acacacacac acacacacac acacacacac acacacacac                40

<210> SEQ ID NO 151
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 151
acacacacac acacacacac acacacacac acacacacac                40

<210> SEQ ID NO 152
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 152
acacacacac acacacacac acacacacac acacacacac                40

<210> SEQ ID NO 153
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 153
acacacacac acacacacac acacacacac acacacacac                40

<210> SEQ ID NO 154
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 154
acacacacac acacacacac acacacacac acacacacac                40

<210> SEQ ID NO 155
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 155
acacacacac acacacacac acacacacac acacacacac                40

<210> SEQ ID NO 156
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 156
acacacacac acacacacac acacacacac acacacacac                40

<210> SEQ ID NO 157
```

```
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 157
acacacacac acacacacac acacacacac acacacacac                        40

<210> SEQ ID NO 158
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 158
acacacacac acacacacac acacacacac acacacacac                        40

<210> SEQ ID NO 159
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 159
agagagagag agagagagag agagagagag agagagagag                        40

<210> SEQ ID NO 160
<211> LENGTH: 40
<212> TYPE: RNA
<213> ORGANISM: Artificial Sequence
<220> FEATURE:
<223> OTHER INFORMATION: Modified Oligonucleotide

<400> SEQUENCE: 160
auauauauau auauauauau auauauauau auauauauau                        40

<210> SEQ ID NO 161
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 161
cacacacaca cacacacaca cacacacaca cacacacaca                        40

<210> SEQ ID NO 162
<211> LENGTH: 40
<212> TYPE: RNA
<213> ORGANISM: Artificial Sequence
<220> FEATURE:
<223> OTHER INFORMATION: Modified Oligonucleotide

<400> SEQUENCE: 162
gagagagaga gagagagaga gagagagaga gagagagaga                        40

<210> SEQ ID NO 163
<211> LENGTH: 41
<212> TYPE: DNA
<213> ORGANISM: Artificial Sequence
<220> FEATURE:
<223> OTHER INFORMATION: Modified Oligonucleotide

<400> SEQUENCE: 163
```
aacacacaca cacacacaca cacacacaca cacacacaca c                     41

<210> SEQ ID NO 164
<211> LENGTH: 39
<212> TYPE: DNA
<213> ORGANISM: Artificial Sequence
<220> FEATURE:
<223> OTHER INFORMATION: Modified Oligonucleotide

<400> SEQUENCE: 164
acacacacac acaacacaca cacacaacac acacacaca                       39

<210> SEQ ID NO 165
<211> LENGTH: 39
<212> TYPE: DNA
<213> ORGANISM: Artificial Sequence
<220> FEATURE:
<223> OTHER INFORMATION: Modified Oligonucleotide

<400> SEQUENCE: 165
acacacacac acaacacaca cacacaacac acacacaca                       39

<210> SEQ ID NO 166
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 166
acacacacac acacacacac acacacacac acacacacac                      40

<210> SEQ ID NO 167
<211> LENGTH: 40
<212> TYPE: DNA
<213> ORGANISM: Artificial Sequence
<220> FEATURE:
<223> OTHER INFORMATION: Modified Oligonucleotide

<400> SEQUENCE: 167
acacacacac acacacacac acacacacac acacacacac                      40

<210> SEQ ID NO 168
<211> LENGTH: 46
<212> TYPE: DNA
<213> ORGANISM: Artificial Sequence
<220> FEATURE:
<223> OTHER INFORMATION: Modified Oligonucleotide

<400> SEQUENCE: 168
acacacacac acacacacac acacacacac acacacacac acacac              46

<210> SEQ ID NO 169
<211> LENGTH: 45
<212> TYPE: DNA
<213> ORGANISM: Artificial Sequence
<220> FEATURE:
<223> OTHER INFORMATION: Modified Oligonucleotide

<400> SEQUENCE: 169
acacacacac acaacacaca cacacacaca acacacacac acaca               45